US006551809B2

(12) United States Patent
Yan et al.

(10) Patent No.: US 6,551,809 B2
(45) Date of Patent: Apr. 22, 2003

(54) ISOLATED HUMAN PHOSPHATASE PROTEINS, NUCLEIC ACID MOLECULES ENCODING HUMAN PHOPHATASE PROTEINS, AND USES THEREOF

(75) Inventors: Chunhua Yan, Boyds, MD (US); Weiniu Gan, Gaithersburg, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 46 days.

(21) Appl. No.: 09/811,469

(22) Filed: Mar. 20, 2001

(65) Prior Publication Data
US 2003/0049824 A1 Mar. 13, 2003

(51) Int. Cl.[7] .............................. C12N 9/12; C12N 1/20; C12N 15/00; C07H 21/04; C07K 1/00
(52) U.S. Cl. ................. 435/194; 435/252.3; 435/320.1; 536/23.2; 530/350
(58) Field of Search ................. 435/194, 252.3, 435/320.1; 536/23.2; 530/350

(56) References Cited

PUBLICATIONS

Blast alignment of SEQ ID No:2 against Derwent and NCBI Protein Patent Databases; Sep. 16, 2002; pp. 1–2, pertaining to Accession Nos.: AAB73227, ABB97942, ABG17947, AAM78500, AAM79484, ABB69333, ABG17946.

Primary Examiner—Tekchand Saidha
(74) Attorney, Agent, or Firm—Celera Genomics; Lin Sun-Hoffman

(57) ABSTRACT

The present invention provides amino acid sequences of peptides that are encoded by genes within the human genome, the phosphatase peptides of the present invention. The present invention specifically provides isolated peptide and nucleic acid molecules, methods of identifying orthologs and paralogs of the phosphatase peptides, and methods of identifying modulators of the phosphatase peptides.

9 Claims, 54 Drawing Sheets

```
   1 GAGAGCTTTA CGCCCGGAGG CGTCGGCGCT GCCACTGGCC CGCGACGGGA
  51 ACGGGGCGAA AAGGCGGCGG CACCATGTTC TCCCTCAAGC CGCCCAAACC
 101 CACCTTCAGG TCCTACCTCC TGCCACCGCC CCAGACTGAC GATAAGATCA
 151 ATTCGGAACC GAAGATTAAA AAACTGGAGC CAGTCCTTTT GCCAGGAGAA
 201 ATTGTCGTAA ATGAAGTCAA TTTTGTGAGA AAATGCATTG CAACAGACAC
 251 AAGCCAGTAC GATTTGTGGG GAAAGCTGAT ATGCAGTAAC TTCAAAATCT
 301 CCTTTATTAC AGATGACCCA ATGCCATTAC AGAAATTCCA TTACAGAAAC
 351 CTTCTTCTTG GTGAACACGA TGTCCCTTTA ACATGTATTG AACAAATTGT
 401 CACAGTAAAC GACCACAAGA GGAAGCAGAA AGTCCTAGGC CCCAACCAGA
 451 AACTGAAATT TAATCCAACA GAGTTAATTA TTTATTGTAA AGATTTCAGA
 501 ATTGTCAGAT TTCGCTTTGA TGAATCAGGT CCCGAAAGTG CTAAAAAGGT
 551 ATGCCTTGCA ATAGCTCATT ATTCCCAGCC AACAGACCTC CAGCTACTCT
 601 TTGCATTTGA ATATGTTGGG AAAAAATACC ACAATTCAGC AAACAAAATT
 651 AATGGAATTC CCTCAGGAGA TGGAGGAGGA GGAGGAGGAG GAGGTAATGG
 701 AGCTGGTGGT GGCAGCAGCC AGAAAACTCC ACTCTTTGAA ACTTACTCGG
 751 ATTGGGACAG AGAAATCAAG AGGACAGGTG CTTCCGGGTG GAGAGTTTGT
 801 TCTATTAACG AGGGTTACAT GATATCCACT TGCCTTCCAG AATACATTGT
 851 AGTGCCAAGT TCTTTAGCAG ACCAAGATCT AAAGATCTTT TCCCATTCTT
 901 TTGTTGGGAG AAGGATGCCA CTCTGGTGCT GGAGCCACTC TAACGGCAGT
 951 GCTCTTGTGC GAATGGCCCT CATCAAAGAC GTGCTGCAGC AGAGGAAGAT
1001 TGACCAGAGG ATTTGTAATG CAATAACTAA AAGTCACCCA CAGAGAAGTG
1051 ATGTTTACAA ATCAGATTTG GATAAGACCT TGCCTAATAT TCAAGAAGTA
1101 CAGGCAGCAT TTGTAAAACT GAAGCAGCTA TGCGTTAATG AGCCTTTTGA
1151 AGAAACTGAA GAGAAATGGT TATCTTCACT GGAAAATACT CGATGGTTAG
1201 AATATGTAAG GGCATTCCTT AAGCATTCAG CAGAACTTGT ATACATGCTA
1251 GAAAGCAAAC ATCTCTCTGT AGTCCTACAA GAGGAGGAAG GAAGAGACTT
1301 GAGCTGTTGT GTAGCTTCTC TTGTTCAAGT GATGCTGGAT CCCTATTTTA
1351 GGACAATTAC TGGATTTCAG AGTCTGATAC AGAAGGAGTG GGTCATGGCA
1401 GGATATCAGT TTCTAGACAG ATGCAACCAT CTAAAGAGAT CAGAGAAAGA
1451 GTCTCCTTTA TTTTTGCTAT TCTTGGATGC CACCTGGCAG CTGTTAGAAC
1501 AATATCCTGC AGCTTTTGAG TTCTCCGAAA CCTACCTGGC AGTGTTGTAT
1551 GACAGCACCC GGATCTCACT GTTTGGCACC TTCCTGTTCA ACTCCCCTCA
1601 CCAGCGAGTG AAGCAAAGCA CGGAATTTGC TATAAGCAAA AACATCCAAT
1651 TGGGTGATGA GAAGGGCTTA AAATTCCCCT CTGTTTGGGA CTGGTCTCTC
1701 CAGTTTACAG CAAAGGATCG CACCCTTTTC CATAACCCCT TCTACATTGG
1751 AAAGAGCACA CCTTGTATAC AGAATGGCTC CGTGAAGTCT TTTAAACGGA
1801 CAAAGAAAAG CTACAGCTCC ACACTAAGAG GAATGCCGTC TGCCTTAAAG
1851 AATGGAATCA TCAGTGACCA AGAATTACTT CCAAGGAGAA ATTCATTGAT
1901 ATTAAAACCA AAGCCAGATC CAGCTCAGCA AACCGACAGC CAGAACAGTG
1951 ATACGGAGCA GTATTTTAGA GAATGGTTTT CCAAACCCGC CAACCTGCAC
2001 GGTGTTATTC TGCCACGTGT CTCTGGAACA CACATAAAAC TGTGGAAACT
2051 GTGCTACTTC CGCTGGGTTC CCGAGGCCCA GATCAGCCTG GGTGGCTCCA
2101 TCACAGCCTT TCACAAGCTC TCCCTCCTGG CTGATGAAGT CGACGTACTG
2151 AGCAGGATGC TGCGGCAACA GCGCAGTGGC CCCCTGGAGG CCTGCTATGG
2201 GGAGCTGGGC CAGAGCAGGA TGTACTTCAA CGCCAGCGGC CCTCACCACA
2251 CCGACACCCTC GGGGACACCG GAGTTTCTCT CCTCCTCATT TCCATTTTCT
2301 CCTGTAGGGA ATCTGTGCAG ACGAAGCATT TTAGGAACAC CATTAAGCAA
2351 ATTTTTAAGT GGGGCCAAAA TATGGTTGTC TACTGAGACA TTAGCAAATG
2401 AAGACTAAAA TAGGGTGTTT TCTGAACATT TTGAGGGAAG CTGTCAACTT
2451 TTTTCCTCTG AATTAACATT GCTAACCTAG GCGTTTGAAT CTCTAATAAC
2501 TTTATATGTA AGAATAATAG TTGGAATTTG CACTAATATT TAAAAACATG
2551 TTGAATCATG CTTCTTTCAC ACTTATTTTA AGAGAGATGT AAATTTTGTT
2601 CCTGTCCTCT TTCTGTCATT ACAGGTCTGG CTCTTGTAAC CGTGATCAAA
2651 CTGTTCATGT TGTCTGCTAC ATTTTTGTCT CCATCCATTT TTCCTACCAC
2701 CTCCTGAAGG CTATCTGATA GTCAGTCACA TTAGCAGCCC CAGGCAGCAG
2751 ACAACAGGAA AGTTAGGAAA TTTGTGTTTC GTGTCATTTT TAGGAGCATC
2801 TGATAAAACC TCCAGCAGGT TTTAGGAAGT ATTCATGTAT TTTTCTGGTT
2851 ACTTTCTGTC ATCTCTAATT GAACTCACCT GATGAAGGTT CAGTGTTCTG
2901 GGGCCAGAAT TTATGATTTT AGATCACCTT CTTTGGAACC TTAGATCACT
2951 GTGTTTTGAA ATCATGAGTT TGCTTTTAAC TTCATAGGGT CAACTTTAAA
3001 ATGATATGCA CTGTTAATTT TAAAGCATTT GCTGCAGATA ATTAAACTTA
3051 GAAGTGCCTT TGACTTTAGG ATACAAATAT TACAGAAGAA AATATAATTT
3101 CACTTTTTAA AATTGGGGTG GGAAAATCCC ATTGCATATT TGAAATAGGC
3151 TTTTCATACT AAGCTTCATA GCCAGGAGTC CCCAGAGTCT TGTTCCTCTG
3201 AAAGCCACTG GGGAGTGGCC TCTGGGGTGC TGATTCCACA GAGGTGTATG
3251 CTGTAGACAG GAGAGTGCCA TCTATGCCAA AACTCGCCCT CAAAAACAAA
3301 CAAGGCTTGC TGGGAGGCGT GCTGGGCTTG GCCATCAGTA TTTCCAGTGT
3351 GGTAAACTAT TGCTGGCACT TCCCCCTGGA AATAACTAAT GAGGTTACGA
```

FIGURE 1A

```
3401 GTTGGGCACC TGCACAGATG TCCTTCTCTC ATAGTTCCTA ATGCTTAGGA
3451 ATAGAGGAGA AATAAAAAAA TGGATTCTCT CAAAACACTG CCATTTGAAT
3501 AGCGACAGAA GTGCTCCCCC AGCCCCCAAC TTTGGACAGC AAAGTTGAGG
3551 AGAATGAGCA GACACAGTTG TTTGCTTGAT CTGAATCTCT CTAAAGTAAA
3601 GTATTTCCAA ACTGTGTGAC AAGAGCCTAC CTACCACTGT AGCGGTCAAA
3651 GCTGAAGCTT CTTACAGCAG TGAAACGGGG CACCACCTCC CCCACACTCC
3701 TCATTCCCCG CTTAAAACAT GGATACTTTC AAATTTGACT GTTTCTTAAA
3751 CTGCCATCCT AAGATATGGA AAATTTTTAT AGTAAAGTGT CTAGTTAGCT
3801 TATTTCCTTT TCTAAAACAA GTGTTTTCAA GATAACTGTA TTTTACCTTT
3851 ATATGTACTG AATAGCTGTT TCTTTTTGAA TTATTTGCCT TTTAAAATTT
3901 GATAATGTCT CTGGATATAA CAGGACAGGA GTTCTTAAAA AATATCTTAA
3951 GAAATTCACT TTATGGGTAA ACCCAAGGTT TTTGCCAACT TGTTGCCTAG
4001 AAAATAAGGG CTAGTTTCAG TTTATACAAA TAGAATTATT AAACATTTTA
4051 CAGTCCTTGA TTAGAAACCA GACCCAATCT CCTTATAACA CCACAGCGTA
4101 TCCTGCCATT GACAGTGTAA TCACAATTCT CCCTTTTTCA TTTAGCTGCT
4151 TTTTTATTAT TACTAAATGT TTTGGATTGA GCATTTTTCC CTCTGTAATT
4201 TTCTTCCTTC ACGTTTATTT TATTTTAACT CTTGTAGTAT TTTATTGTTG
4251 TTAATTTACA AGTTTAAAAA TATTTAGGTAC TATTAATAAT GGTTAAAAAT
4301 AGAAAAATGC ATATTTTTGT ATGATAATCA AATGTAAAAT ACTTTTATTT
4351 TTGCTGGACA GTTGTTATAT CATGATTATT GTGCTACAGT TTATTGTGCA
4401 TAATATGAAA AACAACTATG ACAGCCTTCA GTCGGGCCAG GGTGAAGCTG
4451 CTTATACC  (SEQ ID NO:1)
```

FEATURES:
5'UTR:          1-74
Start Codon:    75
Stop Codon:     2406
3'UTR:          2409

Homologous proteins:
Top 10 BLAST Hits

```
                                                                          Score   E
CRA|335001098689405 /altid=gi|11433679 /def=ref|XP_007769.1| hy...         987    0.0
CRA|66000019403732  /altid=gi|8923297  /def=ref|NP_060232.1| hypo...       899    0.0
CRA|113000085275835 /altid=gi|12697909 /def=dbj|BAB21773.1| (AB...         441    e-122
CRA|66000019403839  /altid=gi|9506679  /def=ref|NP_061934.1| hypo...       291    2e-77
CRA|89000000195580  /altid=gi|7293003  /def=gb|AAF48390.1| (AE003...       269    1e-70
CRA|1000682317637   /altid=gi|7705564  /def=ref|NP_057240.1| KIAA1...      167    5e-40
CRA|108000024650128 /altid=gi|12735904 /def=ref|XP_011954.1| si...         167    5e-40
CRA|108000024650126 /altid=gi|12735902 /def=ref|XP_005992.2| si...         167    5e-40
CRA|66000019403815  /altid=gi|7661582  /def=ref|NP_056273.1| DKFZ...       161    3e-38
CRA|335001098685012 /altid=gi|11425780 /def=ref|XP_005213.1| DK...         161    3e-38
```

BLAST dbEST hits:

```
                                             Score   E
gi|12907851 /dataset=dbest /taxon=960...     1657    0.0
gi|12950044 /dataset=dbest /taxon=960...     1243    0.0
gi|7143189  /dataset=dbest /taxon=9606...     918    0.0
gi|7114815  /dataset=dbest /taxon=9606...     918    0.0
gi|4073139  /dataset=dbest /taxon=9606 ...    908    0.0
gi|8060283  /dataset=dbest /taxon=960...       904    0.0
gi|11511187 /dataset=dbest /taxon=96...        864    0.0
gi|2841819  /dataset=dbest /taxon=9606 ...    852    0.0
gi|9512988  /dataset=dbest /taxon=9606...      831    0.0
gi|1445380  /dataset=dbest /taxon=9606 ...    821    0.0
```

EXPRESSION INFORMATION FOR MODULATORY USE:
library source:
From BLAST dbEST hits:
gi|12907851 B cell Burkitt's lymphoma
gi|12950044 B cell Burkitt's lymphoma
gi|7143189  Lymph germinal center B cell
gi|7114815  Lymph germinal center B cell
gi|4073139  Fetal lung
gi|8060283  Neural tissue normal
gi|11511187 Breast invasive ductal carcinoma

FIGURE 1B

```
gi|2841819  Parathyroid tumor
gi|9512988  Lung- carcinoid
gi|1445380  Fetal liver spleen
```

From PCR-based tissue screening panels:
whole liver

FIGURE 1C

```
  1 MFSLKPPKPT FRSYLLPPPQ TDDKINSEPK IKKLEPVLLP GEIVVNEVNF
 51 VRKCIATDTS QYDLWGKLIC SNFKISFITD DPMPLQKFHY RNLLLGEHDV
101 PLTCIEQIVT VNDHKRKQKV LGPNQKLKFN PTELIIYCKD FRIVRFRFDE
151 SGPESAKKVC LAIAHYSQPT DLQLLFAFEY VGKKYHNSAN KINGIPSGDG
201 GGGGGGGNGA GGGSSQKTPL FETYSDWDRE IKRTGASGWR VCSINEGYMI
251 STCLPEYIVV PSSLADQDLK IFSHSFVGRR MPLWCWSHSN GSALVRMALI
301 KDVLQQRKID QRICNAITKS HPQRSDVYKS DLDKTLPNIQ EVQAAFVKLK
351 QLCVNEPFEE TEEKWLSSLE NTRWLEYVRA FLKHSAELVY MLESKHLSVV
401 LQEEEGRDLS CCVASLVQVM LDPYFRTITG FQSLIQKEWV MAGYQFLDRC
451 NHLKRSEKES PLFLLFLDAT WQLLEQYPAA FEFSETYLAV LYDSTRISLF
501 GTFLFNSPHQ RVKQSTEFAI SKNIQLGDEK GLKFPSVWDW SLQFTAKDRT
551 LFHNPFYIGK STPCIQNGSV KSFKRTKKSY SSTLRGMPSA LKNGIISDQE
601 LLPRRNSLIL KPKPDPAQQT DSQNSDTEQY FREWFSKPAN LHGVILPRVS
651 GTHIKLWKLC YFRWVPEAQI SLGGSITAFH KLSLLADEVD VLSRMLRQQR
701 SGPLEACYGE LGQSRMYFNA SGPHHTDTSG TPEFLSSSFP FSPVGNLCRR
751 SILGTPLSKF LSGAKIWLST ETLANED   (SEQ ID NO:2)
```

FEATURES:
Functional domains and key regions:
[1] PDOC00001 PS00001 ASN_GLYCOSYLATION
N-glycosylation site Number of matches: 3
    1    290-293 NGSA
    2    567-570 NGSV
    3    719-722 NASG

[2] PDOC00004 PS00004 CAMP_PHOSPHO_SITE
cAMP- and cGMP-dependent protein kinase phosphorylation site 604-607 RRNS

[3] PDOC00005 PS00005 PKC_PHOSPHO_SITE
Protein kinase C phosphorylation site

Number of matches: 11
    1      3-5 SLK
    2     10-12 TFR
    3    155-157 SAK
    4    215-217 SQK
    5    456-458 SEK
    6    494-496 STR
    7    545-547 TAK
    8    569-571 SVK
    9    572-574 SFK
   10    576-578 TKK
   11    583-585 TLR

FIGURE 2A

[4] PDOC00006 PS00006 CK2_PHOSPHO_SITE
Casein kinase II phosphorylation site

Number of matches: 15
```
    1      60-63  SQYD
    2     103-106 TCIE
    3     110-113 TVND
    4     151-154 SGPE
    5     223-226 TYSD
    6     225-228 SDWD
    7     243-246 SINE
    8     263-266 SLAD
    9     330-333 SDLD
   10     367-370 SSLE
   11     456-459 SEKE
   12     536-539 SVWD
   13     545-548 TAKD
   14     597-600 SDQE
   15     625-628 SDTE
```

[5] PDOC00007 PS00007 TYR_PHOSPHO_SITE
Tyrosine kinase phosphorylation site

```
         383-390 KHSAELVY
```

[6] PDOC00008 PS00008 MYRISTYL
N-myristoylation site

Number of matches: 16
```
    1     194-199 GIPSGD
    2     200-205 GGGGGG
    3     201-206 GGGGGG
    4     202-207 GGGGGG
    5     200-205 GGGGGG
    6     201-206 GGGGGG
    7     202-207 GGGGGG
    8     200-205 GGGGGG
    9     201-206 GGGGGG
   10     202-207 GGGGGG
   11     203-208 GGGGGN
   12     204-209 GGGGNG
   13     205-210 GGGNGA
   14     206-211 GGNGAG
   15     207-212 GNGAGG
   16     209-214 GAGGGS
```

[7] PDOC00009 PS00009 AMIDATION
Amidation site

Number of matches: 2
```
    1     181-184 VGKK
    2     277-280 VGRR
```

Membrane spanning structure and domains:
```
 Helix Begin    End   Score Certainty
   1    246     266   0.714 Putative
   2    728     748   0.683 Putative
```

FIGURE 2B

BLAST Alignment to Top Hit:
>CRA|335001098689405 /altid=gi|11433679 /def=ref|XP_007769.1|
        hypothetical protein FLJ20313 [Homo sapiens] /org=Homo
        sapiens /taxon=9606 /dataset=nraa /length=497
        Length = 497

Score =  987 bits (2524), Expect = 0.0
 Identities = 476/476 (100%), Positives = 476/476 (100%)

```
Query:  41 GEIVVNEVNFVRKCIATDTSQYDLWGKLICSNFKISFITDDPMPLQKFHYRNLLLGEHDV 100
           GEIVVNEVNFVRKCIATDTSQYDLWGKLICSNFKISFITDDPMPLQKFHYRNLLLGEHDV
Sbjct:   5 GEIVVNEVNFVRKCIATDTSQYDLWGKLICSNFKISFITDDPMPLQKFHYRNLLLGEHDV 64

Query: 101 PLTCIEQIVTVNDHKRKQKVLGPNQKLKFNPTELIIYCKDFRIVRFRFDESGPESAKKVC 160
           PLTCIEQIVTVNDHKRKQKVLGPNQKLKFNPTELIIYCKDFRIVRFRFDESGPESAKKVC
Sbjct:  65 PLTCIEQIVTVNDHKRKQKVLGPNQKLKFNPTELIIYCKDFRIVRFRFDESGPESAKKVC 124

Query: 161 LAIAHYSQPTDLQLLFAFEYVGKKYHNSANKINGIPSGDGGGGGGGGNGAGGGSSQKTPL 220
           LAIAHYSQPTDLQLLFAFEYVGKKYHNSANKINGIPSGDGGGGGGGGNGAGGGSSQKTPL
Sbjct: 125 LAIAHYSQPTDLQLLFAFEYVGKKYHNSANKINGIPSGDGGGGGGGGNGAGGGSSQKTPL 184

Query: 221 FETYSDWDREIKRTGASGWRVCSINEGYMISTCLPEYIVVPSSLADQDLKIFSHSFVGRR 280
           FETYSDWDREIKRTGASGWRVCSINEGYMISTCLPEYIVVPSSLADQDLKIFSHSFVGRR
Sbjct: 185 FETYSDWDREIKRTGASGWRVCSINEGYMISTCLPEYIVVPSSLADQDLKIFSHSFVGRR 244

Query: 281 MPLWCWSHSNGSALVRMALIKDVLQQRKIDQRICNAITKSHPQRSDVYKSDLDKTLPNIQ 340
           MPLWCWSHSNGSALVRMALIKDVLQQRKIDQRICNAITKSHPQRSDVYKSDLDKTLPNIQ
Sbjct: 245 MPLWCWSHSNGSALVRMALIKDVLQQRKIDQRICNAITKSHPQRSDVYKSDLDKTLPNIQ 304

Query: 341 EVQAAFVKLKQLCVNEPFEETEEKWLSSLENTRWLEYVRAFLKHSAELVYMLESKHLSVV 400
           EVQAAFVKLKQLCVNEPFEETEEKWLSSLENTRWLEYVRAFLKHSAELVYMLESKHLSVV
Sbjct: 305 EVQAAFVKLKQLCVNEPFEETEEKWLSSLENTRWLEYVRAFLKHSAELVYMLESKHLSVV 364

Query: 401 LQEEEGRDLSCCVASLVQVMLDPYFRTITGFQSLIQKEWVMAGYQFLDRCNHLKRSEKES 460
           LQEEEGRDLSCCVASLVQVMLDPYFRTITGFQSLIQKEWVMAGYQFLDRCNHLKRSEKES
Sbjct: 365 LQEEEGRDLSCCVASLVQVMLDPYFRTITGFQSLIQKEWVMAGYQFLDRCNHLKRSEKES 424

Query: 461 PLFLLFLDATWQLLEQYPAAFEFSETYLAVLYDSTRISLFGTFLFNSPHQRVKQST 516
           PLFLLFLDATWQLLEQYPAAFEFSETYLAVLYDSTRISLFGTFLFNSPHQRVKQST
Sbjct: 425 PLFLLFLDATWQLLEQYPAAFEFSETYLAVLYDSTRISLFGTFLFNSPHQRVKQST 480  (SEQ
ID NO:4)
```

>CRA|66000019403732 /altid=gi|8923297 /def=ref|NP_060232.1|
        hypothetical protein FLJ20313 [Homo sapiens] /org=Homo
        sapiens /taxon=9606 /dataset=nraa /length=451
        Length = 451

Score =  899 bits (2299), Expect = 0.0
 Identities = 434/434 (100%), Positives = 434/434 (100%)

```
Query:  83 MPLQKFHYRNLLLGEHDVPLTCIEQIVTVNDHKRKQKVLGPNQKLKFNPTELIIYCKDFR 142
           MPLQKFHYRNLLLGEHDVPLTCIEQIVTVNDHKRKQKVLGPNQKLKFNPTELIIYCKDFR
Sbjct:   1 MPLQKFHYRNLLLGEHDVPLTCIEQIVTVNDHKRKQKVLGPNQKLKFNPTELIIYCKDFR 60

Query: 143 IVRFRFDESGPESAKKVCLAIAHYSQPTDLQLLFAFEYVGKKYHNSANKINGIPSGDGGG 202
           IVRFRFDESGPESAKKVCLAIAHYSQPTDLQLLFAFEYVGKKYHNSANKINGIPSGDGGG
Sbjct:  61 IVRFRFDESGPESAKKVCLAIAHYSQPTDLQLLFAFEYVGKKYHNSANKINGIPSGDGGG 120

Query: 203 GGGGNGAGGGSSQKTPLFETYSDWDREIKRTGASGWRVCSINEGYMISTCLPEYIVVPS 262
           GGGGNGAGGGSSQKTPLFETYSDWDREIKRTGASGWRVCSINEGYMISTCLPEYIVVPS
Sbjct: 121 GGGGNGAGGGSSQKTPLFETYSDWDREIKRTGASGWRVCSINEGYMISTCLPEYIVVPS 180

Query: 263 SLADQDLKIFSHSFVGRRMPLWCWSHSNGSALVRMALIKDVLQQRKIDQRICNAITKSHP 322
           SLADQDLKIFSHSFVGRRMPLWCWSHSNGSALVRMALIKDVLQQRKIDQRICNAITKSHP
Sbjct: 181 SLADQDLKIFSHSFVGRRMPLWCWSHSNGSALVRMALIKDVLQQRKIDQRICNAITKSHP 240

Query: 323 QRSDVYKSDLDKTLPNIQEVQAAFVKLKQLCVNEPFEETEEKWLSSLENTRWLEYVRAFL 382
```

FIGURE 2C

```
              QRSDVYKSDLDKTLPNIQEVQAAFVKLKQLCVNEPFEETEEKWLSSLENTRWLEYVRAFL
Sbjct:  241   QRSDVYKSDLDKTLPNIQEVQAAFVKLKQLCVNEPFEETEEKWLSSLENTRWLEYVRAFL  300

Query:  383   KHSAELVYMLESKHLSVVLQEEEGRDLSCCVASLVQVMLDPYFRTITGFQSLIQKEWVMA  442
              KHSAELVYMLESKHLSVVLQEEEGRDLSCCVASLVQVMLDPYFRTITGFQSLIQKEWVMA
Sbjct:  301   KHSAELVYMLESKHLSVVLQEEEGRDLSCCVASLVQVMLDPYFRTITGFQSLIQKEWVMA  360

Query:  443   GYQFLDRCNHLKRSEKESPLFLLFLDATWQLLEQYPAAFEFSETYLAVLYDSTRISLFGT  502
              GYQFLDRCNHLKRSEKESPLFLLFLDATWQLLEQYPAAFEFSETYLAVLYDSTRISLFGT
Sbjct:  361   GYQFLDRCNHLKRSEKESPLFLLFLDATWQLLEQYPAAFEFSETYLAVLYDSTRISLFGT  420

Query:  503   FLFNSPHQRVKQST  516
              FLFNSPHQRVKQST
Sbjct:  421   FLFNSPHQRVKQST  434    (SEQ ID NO:5)

>CRA|113000085275835 /altid=gi|12697909 /def=dbj|BAB21773.1|
        (AB051469) KIAA1682 protein [Homo sapiens] /org=Homo
        sapiens /taxon=9606 /dataset=nraa /length=775
        Length = 775

Score =  441 bits (1123), Expect = e-122
  Identities = 265/718 (36%), Positives = 405/718 (55%), Gaps = 73/718 (10%)

Query:    5   KPPKPTFRSYLLPPP-QTDDKINSEPKIKKLEPVLLPGEIVVNEVNFVRKCIATDTSQYD   63
              K PKP+F SY+ P      T++K +E K++   LLPGE ++ E + VK + D+ Q+
Sbjct:   42   KAPKPSFVSYVRPEEIHTNEKEVTE---KEVTLHLLPGEQLLCEASTVLKYVQEDSCQHG   98

Query:   64   LWGKLICSNFKISFITDDPMPLQ--KFHYRNLLLGEHDVPLTCIEQIVTVNDHKRKQKVL  121
              ++G+L+C++FKI+F+ DD    L   + ++N ++GE+D+ L C++QI   V D K+K  +
Sbjct:   99   VYGRLVCTDFKIAFLGDDESALDNDETQFKNKVIGENDITLHCVDQIYGVFDEKKKT-LF  157

Query:  122   GPNQKLKFNPTELIIYCKDFRIVRFRFDESGPESAKKVCLAIAHYSQ-PTDLQLLFAFEY  180
              G    +LK  P +LII+CKD R+   +F   E   K++  I H++Q P L+ LF F Y
Sbjct:  158   G---QLKKYPEKLIIHCKDLRVFQFCLRYTKEEEVKRIVSGIIHHTQAPKLLKRLFLFSY  214

Query:  181   VGKKYHNSANKINGIPSGDGGGGGGGGNGAGGGSSQKTPLFETYSDWDREIKRT-GASGW  239
                  +N+                        T +F+T DW E++RT G  +
Sbjct:  215   ATAAQNNTVTD-------------------PKNHTVMFDTLKDWCWELERTKGNMKY    252

Query:  240   RVCSINEGYMISTCLPEYIVVPSSLADQDLKIFSHSFVGRRMPLWCWSHSNGSALVRM-A  298
              +  S+NEGY +   LP Y VVP+ L +++++  F   G +P+WCWS  NGSAL++M A
Sbjct:  253   KAVSVNEGYKVCERLPAYFVVPTPLPEENVQRFQ----GHGIPIWCWSCHNGSALLKMSA  308

Query:  299   LIKD----VLQQRKIDQRICNAITKS--HPQRSDVYKSDLDKTLPNIQEVQAAFVKLKQL  352
              L K+    +LQ    I +    + I K+   P    V  DL     ++QE+Q A+ K KQL
Sbjct:  309   LPKEQDDGILQ---IQKSFLDGIYKTIHRPPYEIVKTEDLSSNFLSLQEIQTAYSKFKQL  365

Query:  353   CV---NEPFEETEEKWLSSLENTRWLEYVRAFLKHSAELVYMLESKHLSVVLQEEEGRDL  409
               +    +  F +T+ KW S LE++ WL +R LK + E+  +E+++++V+L EE    DL
Sbjct:  366   FLIDNSTEFWDTDIKWFSLLESSSWLDIIRRCLKKAIEITECMEAQNMNVLLLEENASDL  425

Query:  410   SCCVASLVQVMLDPYFRTITGFQSLIQKEWVMAGYQFLDRCNHLKRSEKES-PLFLLFLD  468
               C ++SLVQ+M+DP+ RT  GFQSLIQKEWVM G+  FLDRCNHL++++KE  P+FLLFLD
Sbjct:  426   CCLISSLVQLMMDPHCRTRIGFQSLIQKEWVMGGHCFLDRCNHLRQNDKEEVPVFLLFLD  485

Query:  469   ATWQLLEQYPAAFEFSETYLAVLYDSTRISLFGTFLFNSPHQRVKQSTEFAISKNIQLGD  528
                WQL+ Q+P AFEF+ETYL VL DS I +F TF FNSPHQ+        +   ++ Q
Sbjct:  486   CVWQLVHQHPPAFEFTETYLTVLSDSLYIPIFSTFFFNSPHQK-----DTNMGREGQDTQ  540

Query:  529   EKGLKFPSVWDWSLQFTAKDRTLFHNPFYIGKSTPCIQNGSVKSFK-RTKKSYSSTLRGM  587
                K L  +VWDWS+QF  K  TL NP Y+ K  P + G K  + ++  S  L
Sbjct:  541   SKPLNLLTVWDWSVQFEPKAQTLLKNPLYVEK--PKLDKGQRKGMRFKHQRQLSLPLTQS  598

Query:  588   PSALKNGIISDQ------ELLPRRNSLILKPKPDPAQQTDSQNSDTEQYFREWFSKPANL  641
               S+  K G  ++         LL +R S ++      +D    +  +++ W SK +
Sbjct:  599   KSSPKRGFFREETDHLIKNLLGKRISKLI-------NSSDELQDNFREFYDSWHSKSTDY  651
```

FIGURE 2D

```
Query: 642 HGVILPRVSGTHIKLWKLCYFRWVPEAQISLGGSITAFHKLSLLADEVDVLSRMLRQQ 699
            HG++LP + G  IK+W   Y RW+PEAQI GG +   KL  + +EV L   + ++
Sbjct: 652 HGLLLPHIEGPEIKVWAQRYLRWIPEAQILGGGQVATLSKLLEMMEEVQSLQEKIDER 709   (SEQ
ID NO:6)

>CRA|66000019403839 /altid=gi|9506679 /def=ref|NP_061934.1|
    hypothetical protein [Homo sapiens] /org=Homo sapiens
    /taxon=9606 /dataset=nraa /length=637
    Length = 637

Score =  291 bits (738), Expect = 2e-77
 Identities = 194/548 (35%), Positives = 299/548 (54%), Gaps = 55/548 (10%)

Query:   5 KPPKPTFRSYLLPPP-QTDDKINSEPKIKKLEPVLLPGEIVVNEVNFVRKCIATDTSQYD  63
           K PKP+F SY+ P    T++K +E K++   LLPGE ++ E + V K + D+ Q+
Sbjct:  14 KAPKPSFVSYVRPEEIHTNEKEVTE---KEVTLHLLPGEQLLCEASTVLKYVQEDSCQHG  70

Query:  64 LWGKLICSNFKISFITDDPMPLQ--KFHYRNLLLGEHDVPLTCIEQIVTVNDHKRKQKVL 121
           ++G+L+C++FKI+F+ DD  L    + ++N ++GE+D+ L C++QI  V D K+K  +
Sbjct:  71 VYGRLVCTDFKIAFLGDDESALDNDETQFKNKVIGENDITLHCVDQIYGVFDEKKKT-LF 129

Query: 122 GPNQKLKFNPTELIIYCKDFRIVRFRFDESGPESAKKVCLAIAHYSQ-PTDLQLLFAFEY 180
           G  +LK  P +LII+CKD R+ +F     E   K++   I H++Q P L+ LF F Y
Sbjct: 130 G---QLKKYPEKLIIHCKDLRVFQFCLRYTKEEEVKRIVSGIIHHTQAPKLLKRLFLFSY 186

Query: 181 VGKKYHNSANKINGIPSGDGGGGGGGNGAGGGSSQKTPLFETYSDWDREIKRT-GASGW 239
             +N+    +P                      T +F+T DW E++RT G  +
Sbjct: 187 ATAAQNNTVT----VPKNH----------------TVMFDTLKDWCWELERTKGNMKY 224

Query: 240 RVCSINEGYMISTCLPEYIVVPSSLADQDLKIFSHSFVGRRMPLWCWSHSNGSALVRM-A 298
           + S+NEGY +   LP Y VVP+ L +++++ F     G  +P+WCWS  NGSAL++M A
Sbjct: 225 KAVSVNEGYKVCERLPAYFVVPTPLPEENVQRFQ----GHGIPIWCWSCHNGSALLKMSA 280

Query: 299 LIKD----VLQQRKIDQRICNAITKS--HPQRSDVYKSDLDKTLPNIQEVQAAFVKLKQL 352
           L K+    +LQ    I +    + I K+   P  V DL    ++QE+Q A+ K KQL
Sbjct: 281 LPKEQDDGILQ---IQKSFLDGIYKTIHRPPYEIVKTEDLSSNFLSLQEIQTAYSKFKQL 337

Query: 353 CV---NEPFEETEEKWLSSLENTRWLEYVRAFLKHSAELVYMLESKHLSVVLQEEEGRDL 409
            +    +  F +T+ KW S LE++  WL+ +R  LK + E+  +E+++++V+L EE    DL
Sbjct: 338 FLIDNSTEFWDTDIKWFSLLESSSWLDIIRRCLKKAIEITECMEAQNMNVLLLEENASDL 397

Query: 410 SCCVASLVQVMLDPYFRTITGFQSLIQKEWVMAGYQFLDRCNHLKRSEKESPLFLLFLDA 469
              C  ++SLVQ+M+DP+ RT  GFQSLIQKEWVM G+  FLDRCNHL++++KE    L L
Sbjct: 398 CCLISSLVQLMMDPHCRTRIGFQSLIQKEWVMGGHCFLDRCNHLRQNDKEEHQRQLSLPL 457

Query: 470 TWQLLEQYPAAFEFSETYLAVLYDSTRISLFGTFLFNSPHQRVKQSTEFAISKNIQLGDE 529
           T       F   +L  RIS   L NS +    EF S + D
Sbjct: 458 TQSKSSPKRGFFREETDHLIKNLLGKRISK----LINSSDELQDNFREFYDSWHSKSTDY 513

Query: 530 KGLKFPSV 537
            GL  P +
Sbjct: 514 HGLLLPHI 521   (SEQ ID NO:7)

Score = 66.0 bits (158), Expect = 2e-09
 Identities = 27/80 (33%), Positives = 44/80 (54%)

Query: 620 TDSQNSDTEQYFREWFSKPANLHGVILPRVSGTHIKLWKLCYFRWVPEAQISLGGSITAF 679
           +D   + +++  W SK  + HG++LP + G  IK+W   Y RW+PEAQI GG +
Sbjct: 492 SDELQDNFREFYDSWHSKSTDYHGLLLPHIEGPEIKVWAQRYLRWIPEAQILGGGQVATL 551

Query: 680 HKLSLLADEVDVLSRMLRQQ 699
             KL  + +EV L   + ++
Sbjct: 552 SKLLEMMEEVQSLQEKIDER 571   (SEQ ID NO:8)

>CRA|89000000195580 /altid=gi|7293003 /def=gb|AAF48390.1| (AE003497)
```

FIGURE 2E

```
CG14411 gene product [Drosophila melanogaster]
/org=Drosophila melanogaster /taxon=7227 /dataset=nraa
/length=843
Length = 843

Score =  269 bits (680), Expect = 1e-70
 Identities = 202/708 (28%), Positives = 321/708 (44%), Gaps = 127/708 (17%)

Query:  65  WGKLICSNFKISFITDDPM-------PLQKFHYRNLLLGEHDVPLTCIEQIVTVNDHKRK 117
            +G L  +NFK++F+          PL   + N  LG +++ L  I+ I T+ +  R
Sbjct: 114  FGLLSVTNFKLAFVPLHEKRNQAITAPLIDLYQENTYLGRNEITLNNIDHIYTITELGRA 173

Query: 118  QKVL-----------GPNQKLKFNPTE----------LIIYCKDFRIVRFRFDES------ 151
             L           G +++ K  P +          L I CK+FR+++F  F  +
Sbjct: 174  ASALQAARGMASHAGMSRRKKLEPFKQQNISGRIAALHIVCKNFRLLKFAFQQQDSKMFG 233

Query: 152  GPESAKKVCLAIAHYSQPTDLQLLFAFEYVGKKYHNSANKINGIPSGDGGGGGGGGNGAG 211
              + K + A+ ++ P   L FA+ +  + Y+++                         GA
Sbjct: 234  ASDQGKLIASALVRFAYPMRHDLSFAYAH-REPYYSTL-----------------GAS 273

Query: 212  GGSSQKTPLFETYSDWDREIKRTGASGWRVCSINEGYMISTCL-------PEYIVVPSSL 264
            G      T ++ T +DW RE+ R GA+ W+V S    ++       L       P + V+P S
Sbjct: 274  G-----TSMYATKNDWARELIRCGATEWQVVSCASVQLLQNPLQAGKYTVPPHFVIPKSC 328

Query: 265  ADQDLKIFSHSFVGRRMPLWCWSHSNGSALVRMALIKDVLQQRKIDQRICNAITKSHPQR 324
            +          S +F    R   W +S+ + + +ALVR+A ++    QQ     + +  + +
Sbjct: 329  SVDRFLDLSRAFCDSRAAFWVYSYGSSAALVRLAELQPAAQQDTKSENVMLELVRKCDAG 388

Query: 325  SDVYKSDLDKTLPNIQEVQAAFVKLKQLCVNEPFEE---TEEKWLSSLENTRWLEYVRAF 381
             +      L    LP+IQ+V  A+  KL++LC  E    E+      +++K+L  LE T WL YV
Sbjct: 389  RQLKLLQLTDRLPSIQDVLRAYQKLRRLCTPETPEKFMLQDDKYLGLLEKTNWLFYVSLC 448

Query: 382  LKHSAELVYMLESKHLSVVLQEEEGRDLSCCVASLVQVMLDPYFRTITGFQSLIQKEWVM 441
            L++++E    L S  ++ VLQE  GRDL C  ++SL Q++LDP+FRTI GFQSL+QKEWV
Sbjct: 449  LRYASEASATLRSG-VTCVLQESNGRDLCCVISSLAQLLLDPHFRTIDGFQSLVQKEWVA 507

Query: 442  AGYQFLDRCNHLKRSE-----------KESPLFLLFLDATWQLLEQYPAAFEFSETYLAV 490
             + F R  H+ ++             ++SP+FLLFLD WQLL+Q+P  FEF++TYL
Sbjct: 508  LEHPFQRRLGHVYPAQPAGGNAELFDSEQSPVFLLFLDCVWQLLQQFPDEFEFTQTYLTT 567

Query: 491  LYDSTRISLFGTFLFNSPHQRVKQSTEFAISKNIQLGDEKGLKFPSVWDWSLQFTAKDRT 550
            L+DS + +F TF F++   QR+K  T           +  L    VWDW  QF+ KD+
Sbjct: 568  LWDSCFMPIFDTFQFDTQAQRLKAVT-----------DSQLVLRPVWDWGEQFSDKDKM 615

Query: 551  LFHNPFYIGKSTPCIQNGSVKSFKRTKKSYSSTLRGMPSALKNGIISDQELLPRRNSLIL 610
             F NP Y  +         +    +R+   S   G S +
Sbjct: 616  FFSNPLYQRQRGDLGAQAAVAHRRSLAVGSKGAHGAASGV------------------ 656

Query: 611  KPKPDPAQQTDSQNSDTEQYFREWFSKPANLHGVILPRVSGTHIKLWKLCYFRWVPEAQI 670
                   T S+N+   Q F    SP + + P    +++W CY+RW+P    I
Sbjct: 657  --------TPSRNTINPQLFATASSVPQDRY--LQPAHRIFDLQVWDQCYYRWLPILDI 705

Query: 671  SLGG--SITAFHKLSLLADEVDVLSRMLRQQRSGPLEACYGEL-GQSR 715
             GG   +  +H+  LL  +   + RL Q    L  Y E G+SR
Sbjct: 706  RGGGQPQVDLYHR--LLLSNIAKVQRCLDYQNFDDLPDAYYEFAGESR 751   (SEQ ID NO:9)

>CRA|1000682317637 /altid=gi|7705564 /def=ref|NP_057240.1| KIAA1073
     protein [Homo sapiens] /org=Homo sapiens /taxon=9606
     /dataset=nraa /length=643
     Length = 643

Score =  167 bits (418), Expect = 5e-40
 Identities = 144/521 (27%), Positives = 228/521 (43%), Gaps = 103/521 (19%)

Query:  35  EPVLLPGEIV---VNEVNFVRKCIATDTSQYDLWGKLICSNFKISFITDDPMPLQKFHYR  91
            EP LLPGE +   +V ++  C T +     G L +N+++ F +
Sbjct:  75  EPPLLPGENIKDMAKDVTYI--CPFTGAVR----GTLTVTNYRLYFKSM----------  117
```

FIGURE 2F

```
Query: 92  NLLLGEHDVPLTCIEQIVTVNDHKRKQKVLGPNQKLKFNPTELIIYCKDFRIVRFRFDES 151
              E D P      + +N   R +K+ G + + +N   L   CKD R +RF
Sbjct: 118 -----ERDPPFVLDASLGVIN---RVEKIGGASSRGE-NSYGLETVCKDIRNLRFAHKPE 168

Query: 152 GPESAKKVCLAIAHYSQPTDLQL-LFAFEYVGKKYHNSANKINGIPSGDGGGGGGGGNGA 210
              G + + +   + Y+ P    L LFAFEY      N
Sbjct: 169 G-RTRRSIFENLMKYAFPVSNNLPLFAFEYKEVFPEN---------------------- 204

Query: 211 GGGSSQKTPLFETYSDWDREIKRTGA--SGWRVCSINEGYMISTCLPEYIVVPSSLADQD 268
              G   PL E         +R G   WR+  INE Y +    P +VVP+++ D++
Sbjct: 205 --GWKLYDPLLE--------YRRQGIPNESWRITKINERYELCDTYPALLVVPANIPDEE 254

Query: 269 LKIFSHSFVGRRMPLWCWSHSNGSALV---RMALIKDVLQQRKIDQRICNAITKSHPQRS 325
              LK +      R+P+  W H    A +      ++    ++ K D++    AI  S+ Q
Sbjct: 255 LKRVASFRSRGRIPVLSWIHPESQATITRCSQPMVGVSGKRSKEDEKYLQAIMDSNAQSH 314

Query: 326 DVYKSDLDKT--------------------------LPNIQEVQAAFVKLKQLCVNEP 357
              ++  D  +                            + NI  ++ +   KLK++ V
Sbjct: 315 KIFIFDARPSVNAVANKAKGGGYESEDAYQNAELVFLDIHNIHVMRESLRKLKEI-VYPN 373

Query: 358 FEETEEKWLSSLENTRWLEYVRAFLKHSAELVYMLESKHLSVVLQEEEGRDLSCCVASLV 417
              EET     WLS+LE+T WLE+++   L  +  +  +ES  SVV+    +G D +  + SL
Sbjct: 374 IEETH--WLSNLESTHWLEHIKLILAGALRIADKVESGKTSVVVHCSDGWDRTAQLTSLA 431

Query: 418 QVMLDPYFRTITGFQSLIQKEWVMAGYQFLDRCNHLKRSEKE---SPLFLLFLDATWQLL 474
              +MLD Y+RTI GF+ L++KEW+  G++F  R  H  ++ +     SP+FL F+D WQ+
Sbjct: 432 MLMLDGYYRTIRGFEVLVKEKEWLSFGHRFQLRVGHGDKNHADADRSPVFLQFIDCWQMT 491

Query: 475 EQYPAAFEFSETYLAVLYDSTRISLFGTFLFNSPHQRVKQS 515
              Q+P AFEF+E +L  + D      LFGTFL NS  QR K++
Sbjct: 492 RQFPTAFEFNEYFLITILDHLYSCLFGTFLCNSEQQRGKEN 532    (SEQ ID NO:10)

>CRA|108000024650128 /altid=gi|12735904 /def=ref|XP_011954.1|
    similar to myotubularin related protein 2 (H. sapiens)
    [Homo sapiens] /org=Homo sapiens /taxon=9606
    /dataset=nraa /length=619
          Length = 619

Score =  167 bits (418), Expect = 5e-40
 Identities = 144/521 (27%), Positives = 228/521 (43%), Gaps = 103/521 (19%)

Query: 35  EPVLLPGEIV---VNEVNFVRKCIATDTSQYDLWGKLICSNFKISFITDDPMPLQKFHYR 91
             EP LLPGE +    +V ++    C T +     G L +N+++   F +
Sbjct: 51  EPPLLPGENIKDMAKDVTYI--CPFTGAVR----GTLTVTNYRLYFKSM----------- 93

Query: 92  NLLLGEHDVPLTCIEQIVTVNDHKRKQKVLGPNQKLKFNPTELIIYCKDFRIVRFRFDES 151
              E D P      + +N   R +K+ G + + +N   L   CKD R +RF
Sbjct: 94  -----ERDPPFVLDASLGVIN---RVEKIGGASSRGE-NSYGLETVCKDIRNLRFAHKPE 144

Query: 152 GPESAKKVCLAIAHYSQPTDLQL-LFAFEYVGKKYHNSANKINGIPSGDGGGGGGGGNGA 210
              G + + +   + Y+ P    L LFAFEY      N
Sbjct: 145 G-RTRRSIFENLMKYAFPVSNNLPLFAFEYKEVFPEN---------------------- 180

Query: 211 GGGSSQKTPLFETYSDWDREIKRTGA--SGWRVCSINEGYMISTCLPEYIVVPSSLADQD 268
              G   PL E         +R G   WR+  INE Y +    P +VVP+++ D++
Sbjct: 181 --GWKLYDPLLE--------YRRQGIPNESWRITKINERYELCDTYPALLVVPANIPDEE 230

Query: 269 LKIFSHSFVGRRMPLWCWSHSNGSALV---RMALIKDVLQQRKIDQRICNAITKSHPQRS 325
              LK +      R+P+  W H    A +      ++    ++ K D++    AI  S+ Q
Sbjct: 231 LKRVASFRSRGRIPVLSWIHPESQATITRCSQPMVGVSGKRSKEDEKYLQAIMDSNAQSH 290

Query: 326 DVYKSDLDKT--------------------------LPNIQEVQAAFVKLKQLCVNEP 357
              ++  D  +                            + NI  ++ +   KLK++ V
Sbjct: 291 KIFIFDARPSVNAVANKAKGGGYESEDAYQNAELVFLDIHNIHVMRESLRKLKEI-VYPN 349

Query: 358 FEETEEKWLSSLENTRWLEYVRAFLKHSAELVYMLESKHLSVVLQEEEGRDLSCCVASLV 417
```

FIGURE 2G

```
                EET    WLS+LE+T WLE+++    L   +   +   +ES      SVV+     +G D  +  + SL
Sbjct:  350 IEETH--WLSNLESTHWLEHIKLILAGALRIADKVESGKTSVVVHCSDGWDRTAQLTSLA 407

Query:  418 QVMLDPYFRTITGFQSLIQKEWVMAGYQFLDRCNHLKRSEKE---SPLFLLFLDATWQLL 474
            +MLD Y+RTI GF+ L++KEW+  G++F  R  H  ++   +      SP+FL F+D WQ+
Sbjct:  408 MLMLDGYYRTIRGFEVLVEKEWLSFGHRFQLRVGHGDKNHADADRSPVFLQFIDCWQMT 467

Query:  475 EQYPAAFEFSETYLAVLYDSTRISLFGTFLFNSPHQRVKQS 515
            Q+P AFEF+E +L  + D      LFGTFL NS  QR K++
Sbjct:  468 RQFPTAFEFNEYFLITILDHLYSCLFGTFLCNSEQQRGKEN 508   (SEQ ID NO:11)
```

FIGURE 2H

```
   1 AAAAACAGAA AAATGGGTGA AGCAGGACAA AACAGTGACA TTAGAGCCAA
  51 AAGCAGGGGG TAGGCAATAA CACCAAACAT ACAGCGTAGT CAAGGGCATC
 101 AGGGTCTGAG AAGAGGTTAT AAAACTAGTT CTACGGACTG AATTGTGTTC
 151 CTCCAAAATG CTAATGTTGA AACCCTAACC CCTGGTATGG CTACATTTGG
 201 AGATTTTAGG AGGTAATTAA AGTTAAATAA GGTAGTAAGA GTGGGGCTCT
 251 AATCTGATAG GATTAGCGTC CTTACAAGAA GAGACATCAA GAGATCCCAG
 301 AGAGCATGTT ATATACCCTC CCCGCACTGT GTGAGGACAT GGTGAGATGG
 351 CAGCCATCTG CAAATCCGGC AGAGAGCCCT CACCTGTCTG CCTGCCACAA
 401 GTTAGGCAGA TCCCTACCTT GCCAACACCT GGATCTTGGA CTTCCTATAC
 451 TCCAGAATTG TGAGAAATTA ATGTCTGCTC TTTAAGCCAT CAACCTGTGG
 501 TATTTTGTTA TGGCAGCCTG AGCAGACTAA TACAACCAGA TATTTGGGAA
 551 ATGCCATAAA ATTTAGTGTT AAGACAATAA TAAATGCTGG AAATAGAGTT
 601 TTTCCACTTT TCAGTTGTAT GGTCACATAT TAGAATTGCA GATCCTAAGA
 651 AAACCTGTAC AGAAAAACCC AAATCACAGA GTCATTTAAG TGTAAAGAAA
 701 AAGCCAATTA TTGCTTAAAG AGTATTTGTA GAAAATATCC GTTGAATATA
 751 GAGGAATAAC AGCATATTCA TAAAAATTTT TTAAAAAGTG TGCACGACAG
 801 TGATTTTAAC ACTTCTAATC CAATGGAACT AACATTTTAA AGTACAATTA
 851 TGGCCAGGCA CGGTGCCTCA TGCCCATAGT CCCGGCTACT TGAGAGGCTA
 901 AGGCACGTGG ATCACTTGAG CCCAGGAGGT GGAGGCAGCA GTGAGCCCTG
 951 ATCATGCCAC TGCACTTCAG CCCAGGTGAT GGTGTGAGAC CCTGACTCTA
1001 AAAAATACAA TTATGGTTAC GGTTCTTGGG CAGAGTGGAA TTCAAACAGG
1051 TTAACCTGAA AGATCAGTAG GGTTCTAAAT CCAGGATAAA TTATTTTCAG
1101 AAAAAGAATA ACTTTTTGAA TCTTTATTTA AATTGTTAAA TGTTCCTGTG
1151 AGTAACACTC ATCAGCGTGA TTGTGACTGG TATGGCTGCA TGGAAGCTTC
1201 CCTGTGGCAT TAATCATAAA ATGCTGGATT GGGGTTTGAT TCTTCAAGGT
1251 ATAAGAAGGA CCTAGTCTCA AGTAATAGAT TCACCAAAAT GTAACACCAC
1301 TAGCCCCCTC CCACCAAAAT CTGCTCCAGT CAGAATTACC GTAAGAGCTC
1351 AGAAGTGACC TGTGCTTGGC GGCACCGGCC CACTTTCCCA GTGCCGGTTC
1401 CTCGCATCCT GGGCGCAGAC GGGGTGACCG CCTGACCCCT GGACCCGAGT
1451 CACCTTTCCC TGCCCTGAGC TCCTCCTTGA GAGCTTCAAA ACAATGCTCG
1501 CCCAGGCCGG AGGGCGAAGT CGGCCCATGT GTAAGTCAAG GGAACTGTCC
1551 CAGGACTGCA GCCCGGCCAG AAGACGCCCC GCGCCGCCGT CCCAGGCAGC
1601 CACCGCTGCC GCCATGGCCC CCGCAGGCCG CCGTAGGCCC CCGCGGGCCG
1651 CCTGACCCCT GCGGGCCGCC GTAGAAGGAC CCTCCAGAGG CCGCGCTCTT
1701 GAGATGGCCG TCGGGCTCCG CTCCCCGCGG GGCCCCGGCT GAGGGCCCGC
1751 CAGCGGGCAC CTGGCGCCAC CGCTGCGTTC CGGCACTAGC ACGGGACACG
1801 GTCAGGGAGC GGCGGGCCGC GGCCTTGCGC GCGCCGTCTC TCGGGGCGGG
1851 GCACCGGGCC CCTTCCGGGG ATGGGCCCCG CGCCCGCGT CGGCCTGGCT
1901 GTGCCCGGCC CCTCCCCGCT CGGGCGGGCG CTGCGCCGTA TCCCCGCCCG
1951 TCAGTCCGCC CGGCTCGGCT GGCCGCAGAA AGGGCCTGGG CGGCCGCACT
2001 GAGAGCTTTA CGCCCGGAGG CGTCGGCGCT GCCACTGGCC CGCGACGGGA
2051 ACGGGGCGAA AAGCGGCGG CACCATGTTC TCCCTCAAGC CGCCCAAACC
2101 CACCTTCAGG TCCTACCTCC TGCCACCGCC CCAGGTAAAC AACCCCTCCC
2151 CGCGAGCGCC CGACTCTCCT CTGCGCTTCC GTGGAGCCTC CAGGCCGACC
2201 CCCGGGAACT GGAGGACCCC AGGAGGCTGC GCGCGTCTCC CTGCCCACAG
2251 CAGCGCGGCT GCCTGATTCC CGGCGCCGCG AAATGCGCCT TCTCGGGAGC
2301 CCCCACTGGC TCGGCGAAAA CTTGTAAAAC TCTTCTGCAG CCATTCTCTG
2351 CCCGAAGTTC TGTCGTCCGT AGTTTTGCGG AGTGTTGAGG CCCAGGGGAG
2401 CCTTGGGAGC TGGGGTTTTC TTTAGTTTCC AACCCATCGA CCCTCCCTCC
2451 TATGACCGCC AGCATGATTG CAGCACCTGG GGTCACTGGT CGAGGCGGTT
2501 ACCCGTCTGT CATAAATGTG AACACCTGGA AGCGACACTG GCAGTTTAAA
2551 CATTTTTTAT TATTAGGCTT CCAAGTCGAT AATGAGCAGA TCTTAAAAAC
2601 AGCTCAGTTA ATATGCGAAA GAATTTAAAT GGGGGGCTGT GTGTCTTTCG
2651 CATGTGTCAT CACTTAGAAA ACAACATTTG CTGTAGCATT TTACGGAGGG
2701 TGGGGGATT GAGATTTTGA TTTATTTTGC TAATGTATTT CAGACTGACG
2751 ATAAGATCAA TTCGGAACCG AAGATTAAAA AACTGGAGCC AGTCCTTTTG
2801 CCAGGTAAAC ATTAGTTAGG ATTCTAACAG ATACTTTAGC AACGTATTTT
2851 GGTTTAAGAT TATTCTGCCG ACTAGTATCA TGTGGTTAAC TTCCCTTCTC
2901 TCATTAAACT TTCTCCAGTT AAAAGTCTAG TGACTGAGAG GAGAAAAAGG
2951 AACTGTCAAG AATGTCATTA CCTCATTTCC TTTTTTGTCT CCCGAATTTC
3001 TTTTTGAAAA GATGTATATG TTTAATTGCT TGGGTAGTAA AAGTACTCTT
3051 TGCTGACGTG TTTGCCACTT ATTGCATTAA TGATTAATCA TTTTAATGCA
3101 TTTTGATAGT ATAAAAAGAC GCCTTTATTA TGTGTGTGTC TCTATACCAA
3151 TAACAGAGCT TAGTGAACTT TGAATTACTT GCTTGGCAAT TGTTTTTTGA
3201 AGTTGTCAGC TGTATTTGCA AATTTGCTTG TTTCAGTTTA GAACCAGGCT
3251 TTTCCCAGCA GAGACACTTA ATTGACATTT GGGGCCAGAT AATTCATAGT
3301 TGGACGGGCA GGCTGTCCTG TGTATAGCAA CAAAGATGGC CTCCACCCAC
3351 TAGATGCCAG TAGTAGTACC CTTATCCCCC ACCACCTAGT TGCGACCTAG
```

FIGURE 3A

```
3401 TTGCCACACC AAAATGCCAC CAGTCATTGC CAATTTTTTT TTGTCCCCTA
3451 CCTCTGGGGG ACAAAAATCT CACAGTTGAG AATCACTGCT TTAGAACAAA
3501 ATTTGCTATA GGTGACCTTA GAGATGGAAG TAGGGATTGG TGGTAGAAAG
3551 GGGTTTGTTT TAGAGCATAC AGAATATTGG TATGGTATTT TGAATTGTAT
3601 AACAATTGTA TAATAATTAG GAAAAGTCAG TTGTTTAATG CGATTATTAG
3651 GGGAAGTAGC CAGATACTTA GGAAAGCCTG TTTTAAACCT GAAATCGGCC
3701 GGGCACGGTG GCTCATGCCT GTAATCCCAG CACTTTGGGA GGCCGAGGCG
3751 GGTGGATCAC GTGGTCAAGA GACCGAGACC ATCCTGGCTA ACACGGTGAA
3801 ACCCCGTCTC TACTAAAAAT ACAAAAAAAA TTAGCCAGGC ATGGTGGCGG
3851 GCGCCTGTAG TCCCAGCTAC TCGGGAGGCT GAGGCAGGAG AATGGCATGA
3901 ACTCGGGAGG CGGAGCTTGC AGTGAGCCGA GATCCTGCCA CTGCAGTCCA
3951 GCCTGGGCGG CAGAGTGAGA CACCGTCTCA AAAAAAAAAA AAAACCTGAA
4001 ATCAAATACT AGTTTGTGTG GCTACTATCA GCATTGTAAA ATCTGACTCA
4051 TTACTTAAAG CCAAATCGGT AAAATAATTA GAATTTTGTA GGTAAAAATT
4101 GAACAAATGT GGAAACTTTA AAATTTTAAA TATTATATAG GGACAAAATA
4151 TTAAAAACAC CAAACTTTGG TTCCATATGA AAGTTTAAAA AGTGTTTTTT
4201 AAACTTTACT ATGGGAGTCA TAAATATTTT CCCTTGATTT TGTTAGTGCT
4251 TTTCACTCAA CAGTGTGTAC TAATTAATCA TTTGTACTTT TCCTCAGAGT
4301 GAACAGTAGA ATTACTAAGT AACCCTTGCT CCCTGTGTGC TCTGTTTTAG
4351 TCTTAGTCAC TCTGAGCATT TAAAATGCAG GGACGAGGAA ACAGTACTCA
4401 TCTTGAATGA GTGCCATGA GCTATTGAAC TTTGACTTCG TTTACTCTGA
4451 ACAGGCCTGG TTCTTAGGCT TTGATTCCTC CACTCTGCAT ACTATGATTT
4501 CACACTCAGA AACAACATGG TCTTAGCTGT AAATGTCAGT GCTTGCTTTT
4551 TAATTTTTTA AAATTTTTTT TAAATTTTTT TTTTTTTTTT TTTGAGACAG
4601 AGTCTCACTC TTACTTGGGC TGGAGTGCAG TGGCGTGATC TCGGCTCACT
4651 GCAACCTCTG CCTCCCAGGT TCAAGCGATT CTCCTGCCTC TGTCTCCCAA
4701 GTAGCTGGGA TTACAGGAGC CCACCACCAC ACCTGGCTAA TTTTTCGTAT
4751 TTTTAGTAGA AATGGGGTTT CTCCATGTTG GCCAGGCTGG TCTTGAACTC
4801 CTGCCCTCAG GTGATCCGCC CGCCTTGGCC TCCCAAAGTG CTGGGATTAC
4851 AGGCGTGAGC CACTGGCGCC TGGCCACTTT TTTAAAATTA GCTTTTAAAT
4901 TTAAGATATG TGCTAAGAAA AGGTGTTACT AAGTATGCAT AAACTTGAAG
4951 AACTTTCTCA CTGAGGGTTA TCAATTCTAT AAAATGGCTA AAAGTCAGAG
5001 TTTTCTGGGG AAGTTGTAAA CCAAGTTTCT GACTGTGCTT TTCTTGTCCC
5051 AGAAATGGCA GCTAAATTCC GTATTATTTT TAGAGAAATT CTAAAAGAGC
5101 TGTAACACTA AGTCTGAACC TTTTAGTTGC CCATTAAGGA ATTCTCTGAC
5151 CTGTGTTAAT TTTTATTGCA TTGGCGGCCA AATCATAGCT GAAATCTGTA
5201 CATGCATACA TGACGGCTCT ATCACCCAGC ATTCTGTTTG TACCTGACTT
5251 ATCCTTACCC AACATTTAGC CGGTCCTGAA TTAGGATGTC TTTTGCCCCC
5301 TTCCTCTCCC CTTCTGTTCT TACCCTCTCA TTCTGGCCTT CCTGCACCCA
5351 TCCTGGCTGT GTTCTGTCTG GCTGCCCTGT TGTGGTCTCT GTTTCCTGCT
5401 TTACCTCGCC TGTCACATCT CTCACTGCTA CCATTTGCTC TTTGTTGGCC
5451 TGTAGCCTAC TGCTCTACCC ATGAAATCTG GAAGACAAGT GGAAAGTTAC
5501 CGAACTATTG GTGATCTAAA GACCTAGACT AGGCTAGAGC TTTTACTAAG
5551 AGGGAGTGAA TAATATAGTT CTTGCCTTTG TGACTATCAG AATCAATAGA
5601 AAACCTGGCC ACATCACNNN NNNNNNNNN NNNNNNNNN NNNNNNNNNN
5651 NNNNNNNNNN NNNNNNNNNN NNNNNNNNNN NNNNNNNNNN NNNNNNNNNN
5701 NNNNNNNNNN NNNNNNNNNN NNNNNNNNNN NNNNNNNNNN NNNNNNNNNN
5751 NNNNNNNNNN NNNNNNNNNN NNNNNNNNNN NNNNNNNNNN NNNNNNNNNN
5801 NNNNNNNNNN NNNNNNNNNN NNNNNNNNNN NNNNNNNNNN NNNNNNNNNN
5851 NNNTGTTGGG GGTGGGGGAT GAGGGAAGGG AGAGCATTAG GACAAATACC
5901 TAATGCGTGC GGGGCTTGAA ATTCCCGGCG TCATCCCTAA AGACGGGGTT
5951 GATGGGTGCA GCAAACCAGC ATGGCACGTA TATACCTATG TAACAAACCT
6001 GCACATTCTG CACATGTATC CCAGAACTTA AAAAAAAAAA TAAAAAAAGA
6051 ATTAATTGTT AGAGATATGG TATTGCATGC TTTGCTTTGG CATAATGCCT
6101 TGGGTCCAAG GGTATCCTAC TTCAGTTGCC CAAAGTTTGA ACTTCTAATT
6151 CAATAAGCAG ATGAAAATTA GAACACAAAA TGAGTTGTTT ATTTGTGTGC
6201 TGTCACCATG TGCACTGTTG GAACTTAAGC CTAATTTCAA AATGATCCTC
6251 ATCTTTTATT AAGTAAAGAA AACAGAAGAA AATGACTAGT AATTTAATTT
6301 AGATTGTGGT TTATGTTAGT AATTTTCAGC TTTCCTGATA CATGAAACTC
6351 TGAGATGGGT ATTGTGCCTA CTTCAACTTT GTGGTCTTGA TGTCTCACAA
6401 AGTGCCAGGA ATGTGGTAGA CACTGAGATG TTTACTGAGG GACTGAACGA
6451 AAGGACCTCT CAGACCACCT GGCTTAAACT GTTACCTTAC CCAGGCACAC
6501 ACACAGACTA ACTTTCAGAT TTAGGAGTAA AGGGAAGACT GTGTTATTTT
6551 ATGCCAGACA TTTCAAGAGA TTTATGTCGG AGCCTGGAAT TGAAATAGAG
6601 TACTCTGTCA AAGTAGTCAG CTTTTGTGTA GGCTTTCTCT TTATCTTCCT
6651 CTCATTATGT GAATTTCATT CTTTCAGTGA TTATATTGTA TATGTGTAAA
6701 ATCACTCCAA TACTTGAAAA CTGAGTTTGA CTTTTAAAGT GTGTGTGTGT
6751 ATATATGTTT GTGTTCCAGT ATATATTTGT TAAGAGCATG TAATGCCAGA
```

FIGURE 3B

```
6801 CTCTGTCCTG TTTAGCTGCT GGACTGGTGG ATCGGTTCGG TGAGGATGTG
6851 AGTATCTCCT GGGTGCCAGG TCTGTCCTGG ATAGCGAGAA TGCTGGAGGT
6901 GTCATGTGCC TGTATCGCAG AAAGGCGTGG GGTGAGCCCT AAGCTGCCTG
6951 TTGACAAGGT AGAAGACTGT GACCTGGATC ACTGGTACCC AGATTCCAGC
7001 CAGGGCCTGG TATCAGATTT GGATGAAGTT TTTACCAGCC CTTGGTCAAA
7051 GTGAGAAAAT TAAGAAAAGT GCAGTTTTCT TTAATAAAGA TAAATTTATT
7101 TGATTTAAAA GATTGTCTTT TATTCTGAGA TTATGTTCTT CTAACTTACT
7151 TGGAATAGAT ACTTTTTTTG TTAAATGTTG GTGATAATAG CTGTAGCTTT
7201 AAAAAAGTTT TTAAGTTAAC AAAATTAAAA AGTTAAAAAC TCTTTATTGG
7251 TCCTTTAAAT TAGTTTTGCA CTATACCTGG TTTGAATCT AAACTAGAAC
7301 CTACTAGATG AGATTATTAT AATACTATAG ATACAATTTT GTGAGCACTC
7351 ACACAGAGAA CATTAATTAT TTTGTCTGCC TAGGAGTACT GCCATTTTTT
7401 TGTTTGTGTT TTGAGACAGG GTCTCGCTCT GTCACCCAGT TTGGACTGTA
7451 GTGGTGTGAT CACGGCTTAC TGCAGCTTCA ACCTCCTGGG CTCGAGTGAT
7501 CCTCACAGCT CAGCCTCCCA AGTAGCTAGG ACTACAGACG TGCGCCACCA
7551 CACCTGGCTA ATTTTTGTAT TTTTTGTGGA GATGGGGTCC AACTATATTG
7601 CCCAGGCTGG TTTCGAACTC CTGGGCTCAA GCAATTGGCT CACCTTGGCC
7651 TCCCAAAGTG TTGGGATTAT AGCCGTGAGC CACCACACCC AGCCCCCTTC
7701 CACCATCCTC TGAAAAATGC ATCCTCCCTC TTTTGACAAA TTATCCTTTC
7751 CTGACTAACT CCACCCAACC TTGGGTTCCA GTGTGGCCAG CAAGGTTAAT
7801 AACCCACCCT GGACTGCAAG CATGAACACA GGTCTGCCTC TGGATGTTGT
7851 TAGGTTGGTA CTAAGGGAAG AGGTCCTCTT TGGTAATGCT GCAAGTGGCC
7901 ACAGTTCCAG AAGAATCTGT TGAAAAGAGT GAAGAACCCC AAGGAAGTGC
7951 ACTAATGTGT GTTGAAGTCC CTGGGTTTCA TTGTCCTTGC AGGCCAGGT
8001 ACACAAAAGC CTTGTATTCT TCTTTTTGCT AAGCTATTAC CAGGCATGTT
8051 TCTGAACATA CTTTGAACGA GGATCCTTAA CTAATATAGC TTGCAGATTA
8101 ATCATCATAA CAGTCTTGTC AGCTAGGATA CCAGTTTATC TCCATTTGAC
8151 AGATGTGAAA ACTATAGTTT GCTGAGGTTA AGTAACTTGC CCAGTGTCAC
8201 ACAGCTAGCA AGGCAGAGCC AGAGTTCTCT GTCCAGCTCC CAGGCTGTGC
8251 CACTAACTGC TAAGTAGCAC GGCCCACCTG GCTGCACTGG TGACACTAGG
8301 GTACAGATTT ATGCTTTGGA ACTGTTGGGG AGTAGATTGG ATGTCAGCCT
8351 AGAGGGAGTT CTCTAGTGAA GTAAAAAGAG CTCTGTCCTT GTCTTTGCCC
8401 TTTTCACAAC AGTGACAGAT TTTGACCCAG CGTGCAGAAG AACTTTCAGA
8451 GAATTTCAGC TGCCAGAAAA TGGAATGTCT TAGGGAGGTA GTGGACTTCC
8501 TGTTGCTGGC TGTGCCGAAG CACAGTCTGG TGAAATGCCA GCAGCTTTGT
8551 ATTGAGGATG TAAGATTTGC AGTGAGTGGG GCTTGATGGC CTTTGCTCTC
8601 TTCTCACCCC AGGGCATGCT CTTTTTTAAG GGAGAAGAGT TGAAATGCCA
8651 AGACTAACGA TAATGAATTT GTTCTGCAGG TATTGAGTGT GTGCTTGATG
8701 CAGTTTGGCA GAAGGGTAAA ATGCTGAGGA GATGGGATCC TGTTCTTAGA
8751 CAGTTTCAGT TCACTGGAGA GATGCTTCAG TAGAGGAGAG AAAAAGTAGT
8801 AAGAGCTCAG AGGAAGGTCA CCTAAGCCAG ATTTGGAGTA GGGCAGGGGT
8851 GTCAAGAAAG ATCTCTGGAA ACAAATGCTT GTGCTCTGAA TCTTGAGTGC
8901 CCGTTGAGCC TGGGCCCCTG TGCTGAGGCT GTGCGTCAGC TCAGTTCTTT
8951 CCCCTGTTCG CATCTACAGT GCTCACAGCA CTTTCATTCT TGAGATTAAC
9001 TATTAGATAA TGAATGCAGT GATTGTCAGA GTCTTTTGTA ATCGGATCAG
9051 AAAAGCATAC AACCATGGGC CATCTGGGAA ATGAAAATAG CCATTGTTGT
9101 ATAGATGTCT TGTTTATTTT TTACAAGCTC ACTGGCCCGT ACTGTTCTTG
9151 TTTTCTGTCT CACCATACGT CTTATTTCCT CAGTTGGGTT GTTAATTCCT
9201 TAAAGGCAAA GACTTTATCT TTCAAGTGTT TTATGTAATT CCTTTTTGTA
9251 GGTAGGCTTC ATAAATGATT GTAGACTGAT TTTTGTAGTA TTTTAATTTG
9301 TGAATGCATT GTTTTTGAAA GACCAAAGGA CTTGTAACAC ACCCTCAGAA
9351 CAGTGAACAG TGTAACTGTA CTATCTTAGC ATTAGCTTTA TACCTTACCC
9401 GTAGAGCCTT AGGAATGTTT GGAGCTGTCC ATTCCTTAGG CTTTTGCTGC
9451 AGTACCTTAG GCCAGCATTT TCTTACCCCT CCAAACTACT CACTATCGTT
9501 GTCAACACCG TTCATGAACC TCCATAAATA AAATCCTACT TAAGCAGGAT
9551 AAAATCCAAA TTCTTTAACC TTGTAATTTG CTAACACTGT ACCTCACTGA
9601 CTTCATTTCT CAGTATTTCC CAATATTGAT ATTTGCTTCA ATCATGCCGC
9651 TTCCTTGGTC TCTTCCAGAT GCCTTATTCC TTATTTAGGA CCTTGTTACT
9701 GTTATTATCA CACATTCTCT ACTATCTCAA TGCTCTTTCTT CCTTCAAGAT
9751 TTCATTCTAC AATTTTTCCT GAGATCGGCA CTATACCCTT CCTCCTGCCC
9801 CATCCTATCC TGAGTGCTAC TCACTGGACT TGGTACTTGC TTTTTTTACAT
9851 TGTGTGTTAG TACCAGCATT AAAGATTTGT GTTTATCTTC CACATAGTTT
9901 CAATTTCCTG TGATAACTTT TGAGCCACTT TAATTCCTGA ATTTACCTAA
9951 AGCTAGGGTG ACCAGCTTGT CCCAGTTTGC TTGAGACTGT CCTGGTTTTA
10001 GTGCTAAAAA TACCACATCC CAGGGAAACC CCTCTGTCCC AGACAAACTG
10051 GGGCAGTCAC CCTACTGTTA AAAGCCCAAG TTAAGTTATG CTTTTGGCCT
10101 CTACACATCC CACAGGTTAA TTAGCACGT GTGCCGTGAG ACTTTGCCTT
10151 AAACTGTGTT CCAACCTAAA ATGTATGGGA AACATTATTT CTGTCCATCA
```

FIGURE 3C

```
10201 AACGTGATGA ATTTCTAAAT GTATAAGGTG TTAGGAAAGA TAATACAACA
10251 TGGTTTTGAG GTCCTCAGGG AGTTAAAAAC TTTCCTAGCC ATATCATTTG
10301 GAGGTTTATT AACTGTAATT GCATTTCCCT TCTTATTTAT ATTTACAGAT
10351 GAAAGGGTCT TGAGAAAATA AACTTGGATT TCTTGATTTC TTCCCAGGTG
10401 TTAGTAGAAA CCTTTGGCTC ATCATCCTCT AATTTAGAAG GTTTTTGCTT
10451 ACCGCACACT GAAGCTAATT TCCTGCTTTT TCTGGCTTCA TGAGGCTTCC
10501 TTGTGGCATC CTGGGAAGTG CTTGGTGCTG TAAATGGTCC CACCGTGGCT
10551 GATGGCATAG CACAGAGCTG GGAGAGAGGA GTCTGGTGGG TTCTCACAAG
10601 CAGGCCAGCC AGCCGTCTCT AGCACACCAC CCTTTTACTG CATAAAAAGC
10651 ACAGGCGTAT AGTCTCCCTG AAAACTTCAG ATCCTCTAGA GCTTTGAAGC
10701 TTTTATTCGG AGTTTTCTCT TCAAGGTCAC TTAATTTAAC ATGTGAACAA
10751 GAGCAGTCTC AGTACCTTCT TTTTATATAT CCTATCTGGG AAGAGGCCAC
10801 TTTGTGTCTT CTTTTTCTTC CCTGTGTATA AGCTAGTTTT CTGGCCCACA
10851 GTGTTTCAGT GCATGGCAGG AGCTTATGAC AGCTCCTTCT CAGCATTCCT
10901 TTTTTTTAAA ATTATGAACA AATGACTTAC GTGAGCAGAC AGCTGTGCTA
10951 CATGATCCAA ATATTTTAAA GACTGGTTCT GCATGAACAA AATTTAGCAT
11001 TATCAAATAA AACTCATGTC ACTAACTCGA CACTTAATTA TTGTAATAGG
11051 AAGACCCAAT TGTAGCATAT CCTCAGAAGT GCCCTTCTTT TCTTTCTTCT
11101 TCCCCTGTAT CCCTCTGTAC TTCTGTTCTT TGCTCTCTTC CAAGGGCTCA
11151 TTTCCATTCT GTAAGAAAAG GCTGTGTGGC GCTTAAAAGA CCCTGGCCCA
11201 GAGAGTCCTT CTTTCACTTT TTTTTTCTTT TTTCTTTTTT TTGGCTGTTG
11251 TTAATGTTGT GTCTCTTGTT TATTTTCTTC TTTAGTAGTT TTATTTTGGA
11301 ATGAATTTGA ATTTGTAAGA GTTGTACAAA AGAGGATAGA GTTAATGTGA
11351 ACTCTTCAGC CAGCTTCCGC TAATGTTAAT AGCTTATGTA ACCTTGGTGA
11401 ATTTAGCTCA ACTGAGAAAC CAACAATACT ATTAGCTAAA CTGCAGGTTT
11451 TATTCGTATT TCCCTAGTTT TTCCACAAAT GTTCTTTACC TGTTTCAGGT
11501 TCACATCCAG GATACTACAT AGCATTTAGT TGTCGTGTCT CCTTATTCTC
11551 AATGTCTCAG TCTGTGACAG CTTTTTCATC TCATCTTTCA AGACCTTGAC
11601 GTGTTTTTTT CTATTGAATT TGATTTTCTT TTTTTTCTTT TTCTTTTCTT
11651 TTTTTTTTTG AGATGGAGTC TTGTTCTGTC ACCCAGGCTG GAGTGCAGTG
11701 GCGTGATCTC CGCTCACCGC AACCTCCAGC TCCCGAGTTT GAGCGATTCT
11751 CCTGCCTCAG CCTGTTGAGT AGCTGGGAGT ACAGGTGCGC ACCACCAGGC
11801 CCAGCTAATT TTTTGTGTTT TTAGTAGAGA CGGGGTTTTA CCATGTTGGC
11851 CAGGCTGGTT TCGAACTCCT GACCTCAAGT GATCTGCCTG CCTCAGCCTC
11901 CCAAAGTGCT AAGATTACAG GCATGAGAAT GAGATTTTTA TTTTGCCTCA
11951 AATAATACAT ATTAAAGCTC TTTAAACATA GAAATATACT ACTACAAAAG
12001 GAAAAATTTT ATAATTACTA GATTTCTGTT CTAACAAACC ACCCCCTAGA
12051 AACGTCATCA AATTGACTTA AAAATGTAGA CGTAATTTCA GACTTAGAGA
12101 AAAGTTGCAA ATAACAGAAG AATCTGTGGA TACCCTTTCC TTAGATTCCC
12151 CAATAAAACC TTGACGCTTT GGAAGATTAT TATTCAGGTA GTGTCTTGTA
12201 GTATGCCTCT TGGTTTGGAT TTGTCCGATG TTTTCTTTTG ATTAAGCAGA
12251 GGTTATGGAT TTTGGGAAAG ACCCACAGAG GTGGTATCCT TTGCCCTTGT
12301 GTCATGTGAG CAGGCACAAG ACATCAACAT GATTGGTTAT TGGTGAGGTT
12351 AACCTCGATC ACTTCAGGTT AAAGTGATAT CTGTCAGGTT TCTCCTCTAG
12401 AAAGTGACTG TTTTTCCTTT TCTGTACTGT TTGTTAGAAA CAAATCACTA
12451 AGTGCAGCCC ACATTCAAGG GATTGGGAAT TAAGCTCCAC TTCCTGGAGA
12501 GAGGAGAATC ACGAATTTAT GGGCATACCT TAAAACTACC ACAGTAATTA
12551 GTCAATACTT TTGGGAAGAT AGCTTTGTGC TTATACAAAT AACCTGTTTC
12601 TCCTTAAAGT TTGGCTCTCT GAATTTAGCA TTCATCAATG CATGTTGCAC
12651 ACAGCAGTCA TTCAGTCTAT GACATTGAGT CCATGATAGT TTCTTGATCT
12701 TTACTGTAAT GTTCTAATCA TGATTTTGTT TCCTTATTCC TCCTACATTT
12751 ATTAATTGGA ATTCTTCTGT GAGGAAGATT TGTCTCTTCT CCGCATTTA
12801 TTTATTTATT ATTCAGTCAT CTGTTGACAA CAGTATGGAT TCACAGATAC
12851 TTTTTAATTT ACTTTCTAAT CCGGCATTTT TGTTATTTCT TTTGTTGCTC
12901 AGATTGTTCC AGCTTTGGCC ATTGAGAGTT ATTTCATCTT GGCTCTTGTA
12951 TCCTTTGGAA ATGCCGTCCC CCCGCTTTTC TTCACCCCCA CTTCCATATT
13001 TTCTGGTATT CTGGCATTAC CAGAGGCTAC AGACTCATCT TCTGTTTCCC
13051 CTGCCCCAGC CTTGGAATCA GCCATTTCTC TAAAGAGCCC TAGTTCTTTT
13101 TATTGGAAAA TGGTATTTTA AAAGCAAGAG CTGGGTACTG AGTGTGTATG
13151 TTGTTGCTGG AGCGTCACTG CTTTTAGCAC TTTCAGAGGG CAGAGCTAGA
13201 AAACATACAC ACATGTACCA ACCCAGGTGT ACACACATCT GTTACTGCAT
13251 GTCTATTTGT ATATTTATTA AGGCAAGCAT AAGTTCATTC TGCTATCTCA
13301 AACTCTTAAT CTAGCCCCTC GGGGTTCATT TCCAAATTCT TGCTTTTGCT
13351 TTTTGTTGAT GGAGTATGGG CAGTACAGCA GTTAAACCTG GTTTCCATAT
13401 TTACTTTCTG CTGAGTGCTG TAGCTCATTG GTGAGAAAGG GATCTTTTGA
13451 CTTGACTTGC ATGGACACAT TCTAGTAGGA AGGTTGTCTG TCCTCATCAC
13501 TCCTGTGAGT GGTCCTCTAG AGCTCTTTGA AATGGCTACA ACATTGCAGA
13551 TCAAAAACAC CTGCTTTTCA GGTGCTTCAC TTCTCACCTT TCAGATGGGA
```

FIGURE 3D

```
13601 CATGCCCAGT TGTGTCTTCT AAACCTTGTT TCAGATAATT TTAAGAGTTG
13651 TCGCTTCAGT AACTATCTCT AACACAGGGA TCAGCAAACC TTTTCTGTGA
13701 AGTGCAGTAA ATATTTTAGG CTTTGCGGAC CATAAGGTAT TTGTTTCAAG
13751 TACTCAGCTC TGTCTTTGTC CTGTGAAAGC AGCCATAGAT GGCACATGAA
13801 CAAATGAGTA TGGCTATGTC TTACTAAAAT TTCATTTACA AAAACAAGGT
13851 TTTGTATTTG GCCCGTGGGC CATGGTTTAC CATCCGTTGG ACCCATTAAG
13901 TATATTCTCC TCCTCTTCTT TGTCTCATTC TCACTGCGTT CATAGGCTTG
13951 ATACGTTAAC ATTCGTGCAT CAGTAAAAGA ATCTGGCTTC TAGAGAAGAA
14001 GGGCTGTCCA TGGGCGTTTG ACTCCTAAAT ACAGTTTGTT TATGGTACTA
14051 GTGTGGCCAC AAGGCTCTGC CACACAAGCT CTGTCTCTTC CTTCCTGTTA
14101 TTACTTCTGC TTCCCTTCTC AGGAACCTGA AATCATATGG TAGTTTGTTT
14151 GTTTAAGTGA TTTTTTTTTT TGAGATGGAG TCTAGCTCTG TTGCCCAGTC
14201 TGGAGTGCAC TGCAACCTCC ACCTCCTGGG TTCAAGCAGT TCTCCTGCCT
14251 CAGCCTCCCA AGTAGCTGGG GCTACAGGTG CGCACCACCA CGCCTGGCGC
14301 ACCACCACGC CTGGCTAAAT TTTTTTTTTT TTTAATAGAG ATGGGTTTCA
14351 CCATGTTGGC TCAGGTGGTC TCAAACTGAC TTCAGGTGAT CCACCCGCCT
14401 CAGCCAAAGT GTTGGGATTA TAGATGTGAG CCACCACGCC CAGCCTTTAA
14451 GTGAATTTTT ATTTGAGTAT AACATGCATA ACAAGTTTGT GTGGATCATA
14501 AGTCTTAGAA GTGGATGAAT TTTTGTAGCA AGGTTTGAAG AGTCTGTTTT
14551 TAGATGAGTT TGCTAAGGTG GCACAGTATG TGATGATTCC GTGTAAAGAA
14601 GTCATTGTTA CAGGGCTGTG TCCTCTATCT GAACTGGCAT GGTTAGTTTA
14651 GTTGTTTAAA TTGAGGGCCT GCTTACAATT CATATCTAAG ATTTACTGGA
14701 GAGGAGAAAG GGTTGAGTAT TCAGTGGCCC AGAATCTGAT ATGGGAATTG
14751 GTAAGGTTTA TGTTCAAGGA GCCAAAGAAG ATTTAAATTT TATGTATTTG
14801 AATTACTCAG TGCGTCTATA TATATATATA TTTGGTCATC TTAAATTTTT
14851 TTTCTCGTTA GAATTCAGTT AAGGCCAATA TTTGAACTTT AATAAGTTTT
14901 GGTACTTGCT ACACTGCAGT ACATTTAATT GTATGTAATT ATAGGGAAAG
14951 ACTATGGGAA TTGAAGTCAG AACACTTGGT TATAAGTGCG AAGTCCACTA
15001 CTTCTTTTTA AGATCTTAGG AAAGTGATTT AACCTCTTTG GGTGCAAATC
15051 CTTTATCTGT GTATTAAGGA AACCATCTGC CTTCCTCACC TTACAGGTTG
15101 TTGAAAGAAT CAGACAGGAC AGATGTCCTA TTTATAGCTC TTTAATGCAT
15151 ATGTAGGCAA GCAGTGGCAG TTCTGTGACT CTTCTCTAAC TTACATATCA
15201 TTTACCCAAA CAGCCCTTAT CTTCCAGCCA GCTTGGCTGC TTAGCCATAT
15251 TGAATTACTA GTTTCTCTTA TCTAGAACAA CTTCTGCCCA ACTCATGGTG
15301 GACAGAACCA AGTGTCATGA AGTGATTTTA TTCATTCTTG CATTCAGCAC
15351 TCTTTTCACA GGCACCTACC CTGTGCCAGA CACTGTTCTA GGCACTAACA
15401 TTTCAGCAGT GAATAAAGTC AGTCCATCTT CTACCCTCAT GGAGCATATA
15451 ATCCTGAGGG TAATGCAGGC ATTAATTTAA AAATATATAA ATATAATTGT
15501 AGCTATCATG AGTGCTGGAA ATACAATGCT TCGATATGTG AATGTAAACT
15551 AGATAGGAAG ATTTTTTTAA AGAGGCATTC CCTAGACAGT GGTTGGACTA
15601 AGGTAGAAGA AAAGAATATT CCATGAAATG GGAAGAAGCA TGGTCCCATG
15651 AGGGATTAAT AGGCCACCAC TGTGGGCAGA GCAGTGAGGG TGAGGAAGGC
15701 TGGTAGCTGG CTGGGTATGC AGGGCTCCCA GCCATGAGAG GGAGGCTTGT
15751 CTTCAAAGTG GAAGTTAACT CAAGCTGTTG GCACTGTGAA TTTGACATGA
15801 GCAGATTTTA GGTAAATGTT AAGGGGCAGT TACTAAAACT AGCCTTGTAC
15851 ATTTTTAAGA ACTTCGAATA AAAGTTATTG CAGCTCAAAT TTGTTATAAC
15901 CTATTTGTTA AAGAGAGGAT TGTTTTGAGA CTATAGTTCC ATTCTTCATG
15951 AATTGGTAGG AGTTTGGAGT TTGTCAGCAA ACATTCTATC GGGCTAAAGG
16001 TTTTTTATAAT GAAAGAAATA GGCAAAGTGG ATCAGTACAC TCACTTTTCT
16051 ACCATTGACA CTGGAGACAG ATGGCTTAAA ATGTTCTGCG TCTAGTTGAC
16101 TTTTAGATCT TGAAATTAAG GTTAATGAT GACCAAGCTT TAAATAAATT
16151 GTAGAAAAGT ATTCTTTCAA AAGTACATTA TAACTTTTAT ATTGGTTTCT
16201 TATATTTATT TCTTTTAATC TTTTCTTTTA ACTCAAACTA CGTTTTAAGG
16251 TTTTGTTGCC TACTAAGTTA TAATCTGAGT GCAGAAGGAA ACTTGATTTG
16301 GCTTTATGGA ATACATTTTA CATTCAGTGA AGCTGAGCTC TGTTTCTCAT
16351 TCCTTACAAA AGGAATCAAA GGCATTGGTT TGAGAGATCA AGTCATGTGT
16401 TAATAACACA CAAATATTCC ATCAAGTAAT ACTCTGAAGG AGCAGGTGTA
16451 GTTTATTTCT TCTCCAGAAA GTCTTCCAGC AGATAAATAA TGAGAGGTAG
16501 TATGGCATAG GAAAAAAGTA CACTGAAGTC AGCCTTTCTG GTTCAACCAG
16551 CTCAGACCCC TGAGCTATTT TTGCCTCAGT TTTACGCCTT GGAGAACAAT
16601 GCCTTGTCAT TACTATTCAC TTTATGACCA TACAGTGCCT GGCACCTGGT
16651 GGGCAATTGG TGAATGTTTT CACTATCCTC ATCCTTGCCC TCATGAAACA
16701 CTCCTTCTAG GTCCCACAAA GACCGTTGGT ATTTTATGAC AAAGTACCTT
16751 ACAAATATTT TTCTTTTTTT AAAGGAGAAA TTGTCGTAAA TGAAGTCAAT
16801 TTTGTGAGAA AATGCATTGC AACAGACACA AGCCAGTACG ATTTGTGGGG
16851 AAAGCTGATA TGCAGTAACT TCAAAATCTC CTTTATTACA GATGACCCAA
16901 TGCCATTACA GGTGTGTTTT ATTAGTACAC TGTTTCATTC TATCAGGCTT
16951 TCAACTCTAA GTGGTACATA TTATTATATA AAACATAGGT ATGGAAAAGT
```

FIGURE 3E

```
17001 TATAGTAGAA GTATTAGGTA ATGCAATGTT TGGGATAAAT TATATTAAGA
17051 TTTAAAGTAA AGTTTAAGAA GAATGTTGGA ACTTGCTAGA GGAGTATTAG
17101 TGAGAGGATT GTAAGTCACC TTGCTTTATT TATCCTCTGT GATCGTTCAT
17151 TATATGTCCT TTTCATTAAG GAAGTTATTC CCTCTGTTGC AGATCTTTTA
17201 ACCTGCTTAT AAAAATGACA TAAAGAGAAA AGGTTGTTTG CTAAATGATT
17251 TTATAAATGC CACACATTTT AGTGATTTCA TAGGTTTTTT TGTTGTTGGG
17301 TTTTTGATTT TTTTGTTTTG AGCCTGGATC TCGCTCTGTC TTGTCTCCCA
17351 GGCTGGAGTG CAGTGGCATG ATGTCGGCTC ACTGCAACCT CTGTCTGCTT
17401 CCTGGGCTCA AGCTATCCTG CCACCTCAGC CTCCTGAGTA GCTGGGACTA
17451 CAGGTGCATG CCACCACTCC CGGCTAACTG TTGTATTTTT TTGTAGAGAT
17501 GGGGTTTTGT TATGATGCCC GGATTGGTCT TGAACTTCTG AGCCCAAGCA
17551 ATCTGCCTGC CTCCCCCTCC CAAAGTGCCA GAGTACAGGC CACTGCACCC
17601 AGCTACCTTT TTTTTTTTTT TTTAAACTAA TTAGAGTTAT TTTCCTAAAA
17651 AGTTAAATTC TAATTTCTAG GAAGAGTGAA GAATAGTATC GATTTAAAAA
17701 TTTTCAGTAG CCCTCTTGCT ATTTTATGTT CTTACTGGAA AGTAATAGTT
17751 CCATGTAATT TTGGTTTTTA GAAGTTCAGG CATTCATTTG ATTAACTTAA
17801 AAACCCTGGA CTTTTCTGTC AGCCATTTTG TATTTTGTTT TATAAAGTAT
17851 TATACACACT TACCCCTAGA TCTTTCTTTA TAGTAATTGT TCTTTAATGA
17901 AATATTGGTA TATGAACTGT AAACTTTTAA ATTTAAGGAT CTAATAGTTT
17951 AGTGTAAGTA TATTTCATGT AGTCACTCAC TAATTTACCA TAATTATTAT
18001 ACTGTACAAA TATTTATTGT ACTGTATATT TGTGTGTTCA TTACAGTCTT
18051 ATGTAGGTAT ATTTAGACTA AATTTAAGGC ACTTAAAGAT ACCCACTGTG
18101 TAGGGACAGT AGCTTATTTG GATATAGGCT TGTGTGTTTC TCTTTGTTTT
18151 TAGCTTCATA ATGATCATTG GCCCCAGACT TCACTGTAAA TGAGAAGCAG
18201 ATACCTGGAA CAGCTTAAAT CCAGTACCAC TATTAGGAAA AAGTAAACCA
18251 GTGCCCTACT GACAGCAGAT TGATAGTGTT AACTACGTCC TTAGTTTGAA
18301 CATGCAAAAC CTTTTCTAAT GGTTTTTATT TCTAGTAGAC TTTGTGCTTT
18351 AAAAAGATAG TTATTTTGCA CTTTAAAATC TTCAGTGTGA AAATCAAACA
18401 TGATTTTACC CACTTAAAAT CTGATGACCT AAGAGCCCTT TTTTCTTTAA
18451 TATGTTGTGG CCAGCTTATC CAGATCTAGA CATGCAAATG CTTGCTGGTA
18501 AGGTGATTGA TGATATTCCC TATCTTAGGT ATTATAATAA GATTGTTGTG
18551 TACATTTTAA CCTAATTTCT ATCTGTCAAC ATTGGAATGG CCCTAGCTAC
18601 CTAGACAAAA GCTTTTTGTG CTTTTTAGAG ATAACTGTCA CAGTTTATCA
18651 TCACAGTTTA AGGCTTATAC TACCATTGTG AGATTATTGG GAAAAGAATT
18701 AATATGAACA TAATTTTTTA TTCCAGAAAT TCCATTACAG AAACCTTCTT
18751 CTTGGTGAAC ACGATGTCCC TTTAACATGT ATTGAACAAA TTGTCACAGG
18801 TACGTAGTAT TCCGTACATA TCTAAAAGT CAATTCCACT CTGGAAGTAT
18851 TATTTGAAAA GTCATACCTC TCAAAATACT TGGATTGGCG TTTTATTTCT
18901 GTAAGTTTAC TTTTGCCGTT TTTTTGAGTC CCGGGAACAT AAAGAGGGAT
18951 ATGTTAATAA ATTATTTTAA AAGGAAGATA TAAAATGTAT AACTTTTCAT
19001 AGTTTCTAGG TTTTTTGTCC TCTTTTTAAT TAAAATTAAT CATTAAATGT
19051 ATCTAGATGG TGGTTTTATG CAAATAATCA TTTAAAATAT CTTCCAAAGC
19101 AAAGTTAAAA CCAACCCCCA AGTTCTAGGA ATTACAAGTA TGAAACATTC
19151 TAGACAAGCA GAGCTCAAAT GTTGGGTGAC CTTCCAATTA TTTTCACTAA
19201 GAATTTGTAT TAAAGGGTGA GTAACAAATA ACTGTTACGC ATTTTATTTT
19251 CTCTATTTTT TTTTCTTTTT TAGTAAACGA CCACAAGAGG AAGCAGAAAG
19301 TCCTAGGCCC CAACCAGAAA CTGAAATTTA ATCCAACAGA GTTAATTATT
19351 TATTGTAAAG ATTTCAGAAT TGTCAGATTT CGCTTTGATG AATCAGGTCC
19401 CGAAAGTGCT AAAAAGGTAA TACTGTTAAG GTTTATCAAG TTCTGGGTTC
19451 TGTACTGTGT TTACTGATTT CAATTCCGTA TGGCAGTTTT CATTTCTCAA
19501 TTGCTCAGAT GTTTTTTAGG GGAAGTTATC AGACATCTTC TTAAGTAAAG
19551 TCAAAGCCAA GAATATTAAT AGAACTATTT TCTTGGATTG GTTTATGGCT
19601 GTTTTAAAGT GTTCTATATA ACTTTTTATC AGCTTCTCAA ATATTAAAGA
19651 CTCTTACGTG GAAATTAGCA TTTTTTTACA TAAAGATCAT TACTTGTCAG
19701 TTTCTTGGTT AAAAGGTTGA AAAGTTGGTG ATATACTGTA ATTAAGGTTT
19751 GGTTAGGCTT TTAATTCAGT ACTGCAGAAC TTTACCAACA AACTGTAAGC
19801 TAGACTTATG TTACATAAGA TTTAGGTAAA TATATAATTA CGGGAAAGGC
19851 CTAGTAATTA TTAGTGGTTT AAAGAAATAT TATGAATTGA GTGACACTCA
19901 ACAGGGGCAA CACAAAGCTA GTAACTTTTT AACTGCCTTA TTTTTCCACG
19951 GCCTTCCAGA TAATGACTTA TTACCCTACT TGTAAGAGTC AAGGGCATGT
20001 TTTCCATGTT TTGCTTTGCC AGAGGAGTGA AGCTGGTAGA CCTAATATGG
20051 CCCCCGTTCC AGTCTGTGCT GCAGCAAATG CAGAGTCACA GACTTTCCAG
20101 TAGGAAGCTT GCGCGTGTGT ATGGGAATAG GGCAACAGTA TCTTAGTATA
20151 ATAGGACGTG GCTTTCTCTC AGAATGGAGG CAGTCTTTGC ACCACCAAGC
20201 AATGAGTGCC TTTGTTTTCC ATGGTTAGTC AACTGACTGC AGTAAATCTT
20251 CTGTTGATAC CAAAACAAGG CTGGCAAAAA TACTGTAAGG CAGCTGTCTT
20301 CATATACTTT GGTGAAGAGG TGGTAGATTT GTTTTTAGAT TGAGAACCAA
20351 CAGTTTCTTC ACAGGAAGGC AAGCAGGAGA TGAATATATG AAAATACATC
```

FIGURE 3F

```
20401 TGAAAATATG TGACTGTCTA GCAGAGTAGA GTGGTTGTAG GCTCCTCTAT
20451 GGGTAAAAGT TTTCAAATGG TCTGTATAAC CATCTCTCAG CAAGCTGCAT
20501 TATTGAAAAT TCAACTAGAT AACTCTTAAA GCCTCTTTCA CCTGTTCGAT
20551 TGTGCTGTTT GTGATTTTGG CATTTTACTA ATTTAAAGTG CCTATTATAT
20601 AGAAGGACTT TAGAATTCAT GATGTATTAG ACTGTACATA AAATATTTCA
20651 GACAGGTTAA TTCCTCAAGC TTATTTATAT TTGTAATTTA ATTGATCAAA
20701 GCATCAAAGA CCTGCTTATG AAAACCTTAA GATGTGTAGC ATCTCAAGAT
20751 TAGGGACATC ACAGAACTTG CTAGATTGAG TTAGGACAGC ATATTCCTAA
20801 GGAAGAAATT GATGCAATTG ACCGGATCTC TTTCGGAAAG TTCAATTCTC
20851 CCTCTTTTAC TGTATTTTTC AGTTTACACT ATTTTAATGA GTGGAAATAA
20901 TAATTATTTG GCCTAGTTCT TGAACCATCT GTAGTACTTG TTGGTCATTT
20951 TTCATGTTGA GGCAGTGTGC TAAATTTTGC AAGTAGAAAG AAGGGTAAGA
21001 TGCAGTTTCT TGCCCTAGAG AACTTAAATC TAGTGAAGAA GATAAAGCAT
21051 GAACAAATGA AAAGTAATGG TACAAAGTGG CAGCATAAAA TCAACTACAC
21101 AAATAGTTGA TTTCCAGATG AACAGAGCAT AATAAGTGCT GTGGAAATTC
21151 AGAATATCCC CTATGTGTTG TGCTGCTGGT TCATGAAGAG GGCCTTACTA
21201 AACCGTCTGC ACAAAACAAG CCAGTCCCTC ATATGCCCTT TCCTAAGACC
21251 AAGTTTCAGA CAAAAATCTT TTCCCCAGTA TCCTAAAATA TAAAAAGCAT
21301 GTGAGTCTCT GTCTTTTGTA TAGCCACGGG GGTTGCAGGG CAGGGGAGGG
21351 TGCAGGAAAA AAAAATAGAT GCAATGAGAA TATAAATAGT TTTTTTGGGA
21401 TTTACGCATT TCAAACAGGG TTAAGTTGTA TATGGCTACC AAAGCTTGAC
21451 GGCTTTGTGA GTTAAAAACA AAAATTATGG CATATTCTTT TATTTCAAGT
21501 GAAAAGTTTT CATCTAAAAT TCGGTAGCAG TTAGGAAATT ATGGCTCATT
21551 TTTACCTCCT GGAAGCTTGG AATACTGTTT TCTCTGGAAA ATGCTTTGCT
21601 ATTTTATCAG TTGCTTTAAA ATGATGAAAT GCATGTTTGG AGTTCTCTGG
21651 TGGGTAAACC GTTGATTCAT TTTGAAATAC CTAAGCCATT TATGTTTTTG
21701 TTTTGAAAAA TGAAATTCAA GAATACTAAA TTGGTTCACA TTTTGTTAAA
21751 TGTTCTGAAC CCTTCTGGTT GTCTTGTTGG TGTTGTTTCA ATTGTATTAT
21801 GACAAAATTA GATTGCTTTG GGCACTTGTA CTCATTAATA TTCATCCTCA
21851 TTATCCTCGA GCTGTCACAG GAAAATAGTG ATATTTGGGA AAGGTCTGTA
21901 TAAAGAAAGA AGGAATTTGA TGGTGCAGAA TTGGACATCT AACCTCATAG
21951 CAACTTAGAA CCACCATTTT CTTTTGCAGA ACCTTTGCTC AAAAACTGAAG
22001 GGCAAATAAA TAAAGGTTGT TTTTAATGAT TTATCTATAT ATCTGTCTGT
22051 GTAGATAAAG ATAAATATAT AGATACACAT GAGTGACAAG TGAAATACAT
22101 GCCTTTTGTC TCCACTTTGT TCTCTGATTA GTGGGTTGTG AATCACTTCT
22151 TCAGGAATAC TTTATAGAAG TGAATTCCAT TCATCTGATT AAGGAACAAG
22201 TTGGCCTTTT CATGAACTGT CATTTTTGAC TTGAATCTGG TACTGTTTTT
22251 TGGTGGCTTT CAGGCCACAG AAATAAACCA CTTTTGTTTG CAAATGAGAT
22301 AGAACTTAAT GAGGTTTGAG TGTTTCCTGG ATTTGAGTTT CTTCAGTACT
22351 GCACCCCAGG TGATCTTAGG AAAGAAACCA TCCACTGTGG GTACTTCTGG
22401 CTTCTGTCCA GAGAAGATTA TCAGCTTTGG TCCAAAAATT GATTTAAAAG
22451 TAGTTTACTT CTTTTTCTCC AATAAAATAT TTGCCATAAT TTAATGTCTT
22501 TAATACCAAC ATTTTCTTCA TTTCCTGTGG TAGCCAGGAC AAATGAAGTA
22551 TTTCAGATCT TTCAAAAACT CTTAGGATGA AAGGTAGGAA TTTGGACTTA
22601 GGTTTTTAAA ATAGTGTGTA TGTAAAAGTG CAAAGAATGG GGCCCTGGCT
22651 TTCTCTTCTC GGAGTGTTCC ACAGTAACAA CATGAAGACA ATCCAGGTAC
22701 ACAAGTTTGT ATGTGCCTTA GTCTGTGTGT CCAAAGAGGC CTCTTACTTA
22751 GGTCATATGA ACATAAGTTA TACACTTGAA ATTCACTACT GAAAAACAAT
22801 GTATTTAGTT CGAGTTCTGC CACCCCAAAA AAATCAACGA GTAATTCAAC
22851 TGACTTGCAG TTTTACAATA TTTTTATAGA CTTCTTTCAG CGTAGATGCT
22901 TTTGGACATA CTCATTTGTT TCCTAACCTG ATGTGATATT GTGCTATTTT
22951 TAAGGGGCTT TTAAAAAATA CGCTGTGTTG GGTTTTGCCT TGAAAATAGG
23001 CTTTATTTCT TTTTTGCCTC ATGGCCACAA AAAAGGATG TCCATGATCA
23051 ATGATCTGTG AATTTCTTTT CTGTAAACAG AAAGAGCATG TAACTGCTTT
23101 CTAATTGTTT TGGAGAATGT GATAGACATT AGTATTATTA TTATTGGCTT
23151 GGAGCATTTT CCTTAATATG TTGGTAACTA CTTTTGTCAG TGAATATTAG
23201 TGTAGCCACT GTTGGACACA GAGCACCGTC AGAAAGCTAC TGAAGTGGTG
23251 CTGCAAAGTG CAGACATCTT CAGATCTTTA CTCAAGTCTG TGCAGAGAGG
23301 TCTTTCTTGG TCTCCTTCTC TACTTTTTAG CCTGTCTCCC TCTTCTCACT
23351 GTAACACTTC ATATTCCCCT TCCCTGCTCT ATTATTTTTC TCTTTTAGCA
23401 TTCATAGTTA TCTAACTTTC TGTATTTTTT CTCTTTATCT TGTTTAGTGT
23451 CTGTCTTCCC ACTAGAATGT AAGCTTCATG AGGACAGGGA TTAGTGTCTG
23501 TTTTGTTCAC TGCATCTCTA GGGCTTACAA CATTGTAGGT ACTCAGTAAA
23551 TATTTGTTAA ATCAATGTGA AATGTGTCAT TTATCCTTAA GGAATTGACC
23601 TTCATGGTAG AAGTGTAACA GAACCACCTA TATCCTACTT TTCATCCACA
23651 TCATAACTAT TATGTGAATA CCTTGGAAGT AAAGCAAAAT AAGCACTTAA
23701 CTAAAGAGAC GCTTTATATT GAAACTGTTG TTCTGGGTTT CTGGAATTAG
23751 TACTCTGAAA TTGGCTCCCT CTAGGAAGGC TTGTGAAGAG AGTAGTGTTG
```

FIGURE 3G

```
23801 AACAGACATG ACAGTTTCCA AGAAAGCATA GTTGGCTAAG AGGAGTAGGA
23851 TTTTCCAAGC AAAGAGTGTG ACAGTGGAGA TGGCTGGGGC TAAGTCAGGC
23901 AGAATGTGTT CAAACCTGTT TTTCTCTGAC CTGAGATTGC GGAGGGAATA
23951 TTGGGAAGGT ATAGTTACCT GGTGAGGAGA GCCAGTTTTG TGAAGAATCA
24001 AGAATGAGGA GATTTAATTT GTTATGCAGA TGTCTGGGAA CCACAGCAGA
24051 TTATCAGGAG AGCAAAATTG TTAGTCAGAA TTACATCGTT AGAAGGTAAT
24101 CCTTAAGTTT TGTAGATTTC TAGAATGTAA GGAAGCTCTC AGAGGTGCCA
24151 TAAGGTGAGT ATGGCCTAAG GATGTGGCTA TGGCAGTGTA GCAAAATGGA
24201 CAACTATGAA AAATGTCTAG AGAAAAGTGC AACATAGCTT ATCAACGGTG
24251 CCCAAACAAA TAGGAAGGAT GAGAACTTTT TCAAGCTACA GATTTCAGTA
24301 GTTTTGCTGC TAGAAATGCT TTAAGGAAAA CTGTTAAAAA GATTAGGAAT
24351 GGGAATATAG ATAACCGGCT CCTAAATTTT GCAAGTGGGA CCGTCATAGA
24401 AAGCTCTCCT ATAGGTATTG AGAAATCGAG ATACCACGTA AGTTTCAAGA
24451 AGCAGTTTTT TTTTTCTTTT TGGTCAAAAC TAATGACAAA TTCTGTCCCC
24501 TTGTTTGTAT ATTTTAACTT AGTGAGACAG GAAACATTTA TTCTATAGAA
24551 GACTTTTAAA ATGTAGTTTA AACAGTTGA CACATGCTTA CTGGTTAATG
24601 AAATGTGCAT CAACCCACTC CAAACACCAC TAATTTGACA TGAACTAACA
24651 ATTAACTTTT CTTACTCACT GTCAAAAGTA TATCATTCTG CCTTAACTTA
24701 ACGCTTTACC TTCTAAATAA AATTTAATCT TTTAAATAAG TTTTTCTGCT
24751 ATGTTTTCCT TGCATATGTC TTAAATTTCT TCTTTCGTCT TTGCTCACTG
24801 AAGAGCATTT TCTCCCACAT TCTAGTGACT ACCAGGGTTT GTAAGCCTAG
24851 AGCACCATCC TTCATTCTAT CTAGCAGCAG TTGAGAATAA TAACAGCCAT
24901 ATTTCTATAT ATGGAGCTCC TCCAAAGGCC TAGCCTGCAT TAAGCTTGTT
24951 AATTCTTACC ACAGCCTAGG TATTACTTTT GTTTTACAAG TGAGCAAACT
25001 GAGGCTAGAA AAGAGGAAAT GACTTCACAC ATGTTATGTA GCAAGTACTT
25051 GACAGAGCTA GGATTCAAGC CCCCTGATCT GTTTGATTCT AAAGCCCGCA
25101 CGTTTTCCAC CACAGGGCAC ACAGTCCCAA ACCATTTTAC TTAAACACAG
25151 TTTGTGTGTG TGTGTGTGTG TGTGTGTGTG TGTGTGTGTG TGTGTGTTGT
25201 TTTTTTGATG TACCTCTTTG AGCCACCCAT GCATTTTTGG AGTTTCTTGC
25251 TAATTTTAAT TTTTTGTAAT TATGTTTCTC TATTTAGATG TTTAAATCCA
25301 TGAGGCGTAA ACTTTAAAGT TTCATGCCTT ATATTAATCC TTTATAGTCC
25351 ACCAAAAATG AAACTTTTTT CTTCCTTTTT TGGAGTGGAC ATGTAGTCAC
25401 TGCCTTTTTG GAGAATGCTT CTTTAGTTTG AAGCTTTCTT TATTGGACTA
25451 AAATTACTTT CCAATTAAAA TTTAACTCAG CAAATACTTA CTGAATACTT
25501 GCCATGTGCT AGCTAAAGAT AAACAATGTC TTGAGGGCAT GAAAGTGAAT
25551 GAGATACCTG GCCTTAAGGA GCTCTTTTAT ATTCTAGGTC AACAGAAAAA
25601 CATGTAAATA GTATCTATAA TCACTGCCCC AAGATGATGC TCCCAGTGCC
25651 CAAGGCCTTA TTGTACATTT CATTTAACTA AGTGTGTTAA AATCAAATTC
25701 TAAATGTAGA ATTTTTCCTA GGTATGCCTT GCAATAGCTC ATTATTCCCA
25751 GCCAACAGAC CTCCAGCTAC TCTTTGCATT TGAATATGTT GGGAAAAAAT
25801 ACCACAATTC AGGTAAATAT GAAAATATTA AATATTGTGA CTAATTTTAC
25851 ATGTGTAAAT TTTACTCTTA TGTTTACCGG AAGCCTCCAA GTACATGAGC
25901 TTTAATGATT GTAGAATTAC TAGCTTCATA CCTTAGAGAA GTAAGCACTA
25951 CATGCTAAAA GAGCCAATAG TTTGTCAGAT TATTTCTTGA CAAGTTACCA
26001 GGAAGAACCT TTAATGCTAT GAATATGGGC TTATAAGTTA TGTCAGATAT
26051 TTAATCTCCA GTCACTGGCT TGTATTTTAT GATGAAGAAT ATATAACCCA
26101 CCCTTTTTAA TTGATAGCTT GAGTTAAAGT AATCTTATCT TTTAAGAAAA
26151 CTGGCAGAAA ACTAAAGAT ATATTAAAAG CATAATCTTT TCTGGCAAGG
26201 TGTGATTTCA TGCAAAAGCT AAAGTGATTA AAAACTTTTT GTGGACTTCA
26251 TTAAGATTCT CAGAATACTG AGTTTCTATT TCTGAGTAAT ACTGATGAAA
26301 GGAAGATGAG CATTTTTCCA AGGACAAGTA TATTACTAGA CAGCTTTTGT
26351 GAAAGTAAAT AGTTTTGTCT ATATATCTGA CAGTCATGAC ATGACCAGGG
26401 AAGATTCCAG ATGATCATGC AANNNNNNNN NNNNNNNNNN NNNNNNNNNN
26451 NNNNNNNNNN NNNNNNNNNN NNNNNNNNNN NNNNNNNNNN NNNNNNNNNN
26501 NNNNNNNNNN NNNNNNNNNN NNNNNNNNNN NNNNNNNNNN NNNNNNNNNN
26551 NNNNNNNNNN NNNNNNNNNN NNNNNNNNNN NNNNNNNNNN NNNNNNNNNN
26601 NNNNNNNNNN NNNNNNNNNN NNNNNNNNNN NNNNNNNNNN NNNNNNNNNN
26651 NNNNNNNNNN NNNNNNNNNN NNNNNNNNNN NNNNNNNNNN NNNNNNNNNN
26701 NNNNNNNNNN NNNNNNNNNN NNNNNNNNNN NNNNNNNNNN NNNNNNNNNN
26751 NNNNNNNNNN NNNNNNNNNN NNNNNNNNNN NNNNNNNNNN NNNNNNNNNN
26801 NNNNNNNNNN NNNNNNNNNN NNNNNNNNNN NNNNNNNNNN NNNNNNNNNN
26851 NNNNNNNNNN NNNNNNNNNN NNNNNNNNNN NNNNNNNNNN NNNNNNNNNN
26901 NNNNNNNNNN NNNNNNNNNN NNNNNNNNNN NNNNNNNNNN NNNNNNNNNN
26951 NNNNNNNNNN NNNNNNNNNN NNNNNNNNNN NNNNNNNNNN NNNNNNNNNN
27001 NNNNNNNNNN NNNNNNNNNN NNNNNNNNNN NNNNNNNNNN NNNNNNNNNN
27051 NNNNNNNNNN NNNNNNNNNN NNNNNNNNNN NNNNNNNNNN NNNNNNNNNN
27101 NNNNNNNNNN NNNNNNNNNN NNNNNNNNNN NNNNNNNNNN NNNNNNNNNN
27151 NNNNNNNNNN NNNNNNNNNN NNNNNNNNNN NNNNNNNNNN NNNNNNNNNN
```

FIGURE 3H

```
27201 NNNNNNNNNN NNNNNNNNNN NNNNNNNNNN NNNNNNNNNN NNNNNNNNNN
27251 NNNNNNNNNN NNNNNNNNNN NNNNNNNNNN NNNNNNNNNN NNNNNNNNNN
27301 NNNNNNNNNN NNNNNNNNNN NNNNNNNNNN NNNNNNNNNN NNNNNNNNNN
27351 NNNNNNNNNN NNNNNNNNNN NNNNNNNNNN NNNNNNNNNN NNNNNNNNNN
27401 NNNNNNNNNN NNNNNNNNNN NNNNNNNNNN NNNNNNNNNN NNNNNNNNNN
27451 NNNNNNNNNN NNNNNNNNNN NNNNNNNNNN NNNNNNNNNN NNNNNNNNNN
27501 NNNNNNNNNN NNNNNNNNNN NNNNNNNNNN NNNNNNNNNN NNNNNNNNNN
27551 NNNNNNNNNN NNNNNNNNNN NNNNNNNNNN NNNNNNNNNN NNNNNNNNNN
27601 NNNNNNNNNN NNNNNNNNNN NNNNNNNNNN NNNNNNNNNN NNNNNNNNNN
27651 NNNNNNNNNN NNNNNNNNNN NNNNNNNNNN NNNNNNNNNN NNNNNNNNNN
27701 NNNNNNNNNN NNNNNNNNNN NNNNNNNNNN NNNNNNNNNN NNNNNNNNNN
27751 NNNNNNNNNN NNNNNNNNNN NNNNNNNNNN NNNNNNNNNN NNNNNNNNNN
27801 NNNNNNNNNN NNNNNNNNNN NNNNNNNNNN NNNNNNNNNN NNNNNNNNNN
27851 NNNNNNNNNN NNNNNNNNNN NNNNNNNNNN NNNNNNNNNN NNNNNNNNNN
27901 NNNNNNNNNN NNNNNNNNNN NNNNNNNNNN NNNNNNNNNN NNNNNNNNNN
27951 NNNNNNNNNN NNNNNNNNNN NNNNNNNNNN NNNNNNNNNN NNNNNNNNNN
28001 NNNNNNNNNN NNNNNNNNNN NNNNNNNNNN NNNNNNNNNN NNNNNNNNNN
28051 NNNNNNNNNN NNNNNNNNNN NNNNNNNNNN NNNNNNNNNN NNNNNNNNNN
28101 NNNNNNNNNN NNNNNNNNNN NNNNNNNNNN NNNNNNNNNN NNNNNNNNNN
28151 NNNNNNNNNN NNNNNNNNNN NNNNNNNNNN NNNNNNNNNN NNNNNNNNNN
28201 NNNNNNNNNN NNNNNNNNNN NNNNNNNNNN NNNNNNNNNN NNNNNNNNNN
28251 NNNNNNNNNN NNNNNNNNNN NNNNNNNNNN NNNNNNNNNN NNNNNNNNNN
28301 NNNNNNNNNN NNNNNNNNNN NNNNNNNNNN NNNNNNNNNN NNNNNNNNNN
28351 NNNNNNNNNN NNNNNNNNNN NNNNNNNNNN NNNNNNNNNN NNNNNNNNNN
28401 NNNNNNNNNN NNNNNNNNNN NNNNNNNNNN NNNNNNNNNN NNNNNNNNNN
28451 NNNNNNNNNN NNNNNNNNNN NNNNNNNNNN NNNNNNNNNN NNNNNNNNNN
28501 NNNNNNNNNN NNNNNNNNNN NNNNNNNNNN NNNNNNNNNN NNNNNNNNNN
28551 NNNNNNNNNN NNNNNNNNNN NNNNNNNNNN NNNNNNNNNN NNNNNNNNNN
28601 NNNNNNNNNN NNNNNNNNNN NNNNNNNNNN NNNNNNNNNN NNNNNNNNNN
28651 NNNNNNNNNN NNNNNNNNNN NNNNNNNNNN NNNNNNNNNN NNNNNNNNNN
28701 NNNNNNNNNN NNNNNNNNNN NNNNNNNNNN NNNNNNNNNN NNNNNNNNNN
28751 NNNNNNNNNN NNNNNNNNNN NNNNNNNNNN NNNNNNNNNN NNNNNNNNNN
28801 NNNNNNNNNN NNNNNNNNNN NNNNNNNNNN NNNNNNNNNN NNNNNNNNNN
28851 NNNNNNNNNN NNNNNNNNNN NNNNNNNNNN NNNNNNNNNN NNNNNNNNNN
28901 NNNNNNNNNN NNNNNNNNNN NNNNNNNNNN NNNNNNNNNN NNNNNNNNNN
28951 NNNNNNNNNN NNNNNNNNNN NNNNNNNNNN NNNNNNNNNN NNNNNNNNNN
29001 NNNNNNNNNN NNNNNNNNNN NNNNNNNNNN NNNNNNNNNN NNNNNNNNNN
29051 NNNNNNNNNN NNNNNNNNNN NNNNNNNNNN NNNNNNNNNN NNNNNNNNNN
29101 NNNNNNNNNN NNNNNNNNNN NNNNNNNNNN NNNNNNNNNN NNNNNNNNNN
29151 NNNNNNNNNN NNNNNNNNNN NNNNNNNNNN NNNNNNNNNN NNNNNNNNNN
29201 NNNNNNNNNN NNNNNNNNNN NNNNNNNNNN NNNNNNNNNN NNNNNNNNNN
29251 NNNNNNNNNN NNNNNNNNNN NNNNNNNNNN NNNNNNNNNN NNNNNNNNNN
29301 NNNNNNNNNN NNNNNNNNNN NNNNNNNNNN NNNNNNNNNN NNNNNNNNNN
29351 NNNNNNNNNN NNNNNNNNNN NNNNNNNNNN NNNNNNNNNN NNNNNNNNNN
29401 NNNNNNNNNN NNNNNNNNNN NNNNNNNNNN NNNNNNNNNN NNNNNNNNNN
29451 NNNNNNNNNN NNNNNNNNNN NNNNNNNNNN NNNNNNNNNN NNNNNNNNNN
29501 NNNNNNNNNN NNNNNNNNNN NNNNNNNNNN NNNNNNNNNN NNNNNNNNNN
29551 NNNNNNNNNN NNNNNNNNNN NNNNNNNNNN NNNNNNNNNN NNNNNNNNNN
29601 NNNNNNNNNN NNNNNNNNNN NNNNNNNNNN NNNNNNNNNN NNNNNNNNNN
29651 NNNNNNNNNN NNNNNNNNNN NNNNNNNNNN NNNNNNNNNN NNNNNNNNNN
29701 NNNNNNNNNN NNNNNNNNNN NNNNNNNNNN NNNNNNNNNN NNNNNNNNNN
29751 NNNNNNNNNN NNNNNNNNNN NNNNNNNNNN NNNNNNNNNN NNNNNNNNNN
29801 NNNNNNNNNN NNNNNNNNNN NNNNNNNNNN NNNNNNNNNN NNNNNNNNNN
29851 NNNNNNNNNN NNNNNNNNNN NNNNNNNNNN NNNNNNNNNN NNNNNNNNNN
29901 NNNNNNNNNN NNNNNNNNNN NNNNNNNNNN NNNNNNNNNN NNNNNNNNNN
29951 NNNNNNNNNN NNNNNNNNNN NNNNNNNNNN NNNNNNNNNN NNNNNNNNNN
30001 NNNNNNNNNN NNNNNNNNNN NNNNNNNNNN NNNNNNNNNN NNNNNNNNNN
30051 NNNNNNNNNN NNNNNNNNNN NNNNNNNNNN NNNNNNNNNN NNNNNNNNNN
30101 NNNNNNNNNN NNNNNNNNNN NNNNNNNNNN NNNNNNNNNN NNNNNNNNNN
30151 NNNNNNNNNN NNNNNNNNNN NNNNNNNNNN NNNNNNNNNN NNNNNNNNNN
30201 NNNNNNNNNN NNNNNNNNNN NNNNNNNNNN NNNNNNNNNN NNNNNNNNNN
30251 NNNNNNNNNN NNNNNNNNNN NNNNNNNNNN NNNNNNNNNN NNNNNNNNNN
30301 NNNNNNNNNN NNNNNNNNNN NNNNNNNNNN NNNNNNNNNN NNNNNNNNNN
30351 NNNNNNNNNN NNNNNNNNNN NNNNNNNNNN NNNNNNNNNN NNNNNNNNNN
30401 NNNNNNNNNN NNNNNNNNNN NNNNNNNNNN NNNNNNNNNN NNNNNNNNNN
30451 NNNNNNNNNN NNNNNNNNNN NNNNNNNNNN NNNNNNNNNN NNNNNNNNNN
30501 NNNNNNNNNN NNNNNNNNNN NNNNNNNNNN NNNNNNNNNN NNNNNNNNNN
30551 NNNNNNNNNN NNNNNNNNNN NNNNNNNNNN NNNNNCAGTG ATGGAAAGTA
```

FIGURE 3I

```
30601 GGGCAGCCCA CTAGAAGCCA CTAGCCACAT GTGGCTGTTA AGTACTTGAA
30651 ATGTGGCTAG TGCAAACTGA TGGACTGAAT TTTTAATTTT ATTTAATTTT
30701 CATTTCAGTT TAAATTTAAA TGGGCTTGTG TGGCTAGAAG TTACGTTTTT
30751 GGGAAACATA CTAGAGTCTA GGCCCTATTT GATTTCCCGC CTCTCTTCCA
30801 CCACCTGTTG AATCCCTATG CTCTAGCTGT ATTTAGTTAC TTGATATTAT
30851 ACAGTTATAC CATCTTTTTA AAGTTCTTCT CTGTCTAGCA TGCCTACCTC
30901 CTCCTCACCA GCTACCTGGC AACTTTTGAC TTGTTCCTTA GAACTCTCTT
30951 TAGTTGTGGT CAAGTCATGA AGCTTTTCCT GCCCCGGCCT CTCTCTGCAG
31001 CGAGAGTTAG GGGACTTCTC TTTTGCATCT TCATTGCACT CAGACATCTG
31051 GTACTCTGTG ATTATCACAC TTATTAATGC TCTCAAGATA GAGATAAAAT
31101 CTTATTCATC TTTTTGCTCT CAGGCATTAG CACATGGGGA GTTCTCAGAA
31151 AATACCTGTC TTATACCAGG AATTAATGAA TAATCAGTAG GAATGAGCAT
31201 GACATGTTCA TGGGACGTTG GAGGGTAGTG CATGGCTGCA GAGGAGAATG
31251 GGAAATGAAG GTCAGATAAG TTACGTGAGG GATCTCTAAG GCCAAGAGAA
31301 GCCATTTAGG TTTGATTTGG TTGGAAAATG AGCTTATTGA AAGTTTAAGG
31351 CAAGGGACTA GCATCATGAA CACATCTTTT TAGGGAAGTG TGTCTTGTGG
31401 TAAGCTGCTG GCTGGTTTAA ATGCAGCAGA ATATTCCATT GGGGATGCCA
31451 GCTGGGAGAC TTGCCACAGT TGCAGCCTGC AGCAGAAAGA CCCTGGGCCA
31501 GAATGGGTTG TGCCATCTGT CACCAGATAT TGCCAAGGTA GATCTGGCTG
31551 ACTTTGTGGG ACAGCTTGTT TCTCAATAAT CACTTTGCAG GCACTCTTGA
31601 GGCTGTGAGC ATGCTCCCAG AAGATAGCAT TACTTCTCTC TCAGAGCAGG
31651 CTCCTTTCTA AGGAAATGCA AGTCTAGGCC TGCCCTGCTG TAATCTTCAT
31701 GTGGAAACAG CACTCTAGCA AAGAACAAGG AACCTGATGA GCTTTTCAAA
31751 GGAAAATCGA GTAGATACAG GAAACCAAGA ATTTTCTAAT GAGCAGATAG
31801 AAAAGAGCAG GTAGGTGAGA AGTTGGTATT AGAAAAATTA AAGATTTGAA
31851 GGGCTTGAGG ACAGAGATGA TTGTTGGATG TTTCATTTTT CCAGGCAAAA
31901 TATGTGGAGC AAATAATCAA ATGACATGGA CTTACCCCAC AATTAGGGAC
31951 GGAGATGAGG AAGGGTTAGG AATAGTTTCT GTTAGAATGG TAGGGATGGA
32001 AGACAATTGA AAATTAAAGA GAAAATAAAT GGAGAGGAAA TCTAGGCAGC
32051 AGCCATTCTT CATTCTGGGG GAAGGTGGTC AGGAAAAGGA AGGAAGAAAA
32101 ATGTATAGCA TAGTAGCTAG AGTGGTCCGG CGTGATCAAA GTGTTTTCAA
32151 TATCATGTTG ACTGACCTGT TTACGTTTGA AGGCAGAGAA GATAGAGCCA
32201 GTAGAAGGAG AGAAAAATCA AAGCTGTTTT ACGGAGTTGT GAAAGAGCTG
32251 GATAAGGACA AGACTAAATG AGTTATTTTT AGGCCAGGCA TGGTGGCTCA
32301 TGCCTGTAAT CCCAGCACTT TGGGAGGCCA AGGCAGGTGG GGCACCTGAG
32351 GTCAGGAGTT CAAGAGCAGC CTGGCCAACA TGGTGAAACC CTGTCTCTAT
32401 TAAAAATACA AAAATTAGCT GGACATGGTG CATGGTGGCA GGTGCCTGTA
32451 ATCCCAGCTA CTCAAGAGGC TGAGGCAGGA GAATAGCTTG AACCCGGGGG
32501 GCGGAGGTTG CAGTCAGCCG AGATCATGCC AGTGCATTCC AGCCTGGGCG
32551 ACAGAACGAG ACTCCGTCAA AAAAAAAAAA AGGAGTTATT TTTAAATGGA
32601 AAGGGCAAGA CAGTTACTCG GAGAGACTTG GAAGGTGAAG CAGGTTAGAG
32651 ACAGCACATC AGAGTATGCA TGTGACAGGA GGCTCAGAGA AGAGGGAATG
32701 CTGGGGAAAA TGTGACTGTT AAAATTCATA ATGTTGCTTT TTCCTACAGC
32751 AAACAAAATT AATGGAATTC CCTCAGGAGA TGGAGGAGGA GGAGGAGGAG
32801 GAGGTAATGG AGCTGGTGGT GGCAGCAGCC AGAAAACTCC ACTCTTTGAA
32851 ACTTACTCGG ATTGGGACAG AGAAATCAAG AGGACAGGTG CTTCCGGGTG
32901 GAGAGTTTGT TCTATTAACG AGGGTTACAT GATATCCACT TGGTAAGTAC
32951 AATTTTAGCA ATGTTATATA TGGCTGGAAG TCACTTCCCT ATGAATAATC
33001 ATCAAACTCT GTTGTCATTG ATGACTTTCA AGTTGTGGTT AATGGAATAT
33051 TTGTTTTTAA TAATGTTTTA ATAAATATTT TATTTTAAAG ATCAAGGCTT
33101 ATTAATATAA ATTACGGTAT CCCTTAAAAG AAGTTGATAG TAATTCCTTA
33151 CTGTCATCAG TAGTCAGTGT TTATTGCATT ATATCTTGTA ACTGGTGTTT
33201 TACAGTTGGT TTGTTCATAT CAGGATCTAA AGTCTTCACA TTGAATTTGC
33251 TTAATATGTC TCTTAGGCCT TTTAATCTAC AACAGTCTCC TCCCACCTCT
33301 TTTTTACCTA CTATTTGTTG ACAAACCAGG TCATTGTTTC CCTAGAATTT
33351 TCCACATTGT AGATATTGCT TGTTTTATCC CCAGGGTGTC CCGTAATGTG
33401 TTCCTCTGTC TCTAATATTT CCTTTAAAAT GTTAGCAACA GAGGCTTAAT
33451 CGGATTCAGG TTCAGTACTT TTGGCAAGAA TGTTTCATTA GGTGGTTCTG
33501 TGTTCTCCTG TGGAGTCACA TCCCATCTCA GGCTGGCTGG CTGTGTCTCT
33551 CTCATTGTAA TCCTGACGAC CAGTGGGCTT AGAGGGTGTC AACCTGATCC
33601 ACCCAGTAAA AGTTCCCCTC TTATATCATG GTTTGAGCTC CCAAAAATAG
33651 TTTTGCACTG GGAGGGAGGA TCATTGCTCA GATCGTTATT TCACTAAGGA
33701 TTGCTATTGT TCACCTTCTA ATTCTATCAT CTTTCTGCTT TTATCGAACT
33751 TTTCTCTCAC CAGCTCTTTA GTGCCCTGTA ACACAGTTCG TACAAGAAAA
33801 GCAATATAAA TATCTACATT TTCTCCTTTA CTTAACATTT TTCCAAATAG
33851 TGAGCTGGTT CCCTAGGGGA TCTTTCTAGA AGTGACTAGG AATTTGTTTT
33901 TTTAATTTGT TTAATGTCAT TTAGTTATTA TGAATTTTTT GGAATGCCTT
33951 ATTTTAAGGT CATTGAAGTC CTCATTAGTT CACGCACATA AGCAGCTTTT
```

FIGURE 3J

```
34001 TAGAAAAAGG AAGAAAAGCA CTACTGTGTT ATTACTGGTT AATCCAGTAC
34051 CAGGAACTTC TAGTACAGTT CTAGAAAGGT GCTTTGCAGC ATGTAGCTTG
34101 TATGCTTTTG CTTCCCCTGG AATTTAAGCT TCAAGGCCAG CACACTCTGG
34151 TATATGTGCT GAGAAACATG TGATGGGGCT GCCNNNNNNN NNNNNNNNNN
34201 NNNNNNNNNN NNNNNNNNNN NNNNNNNNNN NNNNNNNNNN NNNNNNNNNN
34251 NNNNNNNNNN NNNNNNNNNN NNNNNNNNNN NNNNNNNNNN NNNNNNNNNN
34301 NNNNNNNNNN NNNNNNNNNN NNNNNNNNNN NNNNNNNNNN NNNNNNNNNN
34351 NNNNNNNNNN NNNNNNNNNN NNNNNNNNNN NNNNNNNNNN NNNNNNNNNN
34401 NNNNNNNNNN NNNNNNNNNN NNNNNNNNNN NNNNNNNNNN NNNNNNNNNN
34451 NNNNNNNNNN NNNNNNNNNN NNNNNNNNNN NNNNNNNNNN NNNNNNNNNN
34501 NNNNNNNNNN NNNNNNNNNN NNNNNNNNNN NNNNNNNNNN NNNNNNNNNN
34551 NNNNNNNNNN NNNNNNNNNN NNNNNNNNNN NNNNNNNNNN NNNNNNNNNN
34601 NNNNNNNNNN NNNNNNNNNN NNNNNNNNNN NNNNNNNNNN NNNNNNNNNN
34651 NNNNNNNNNN NNNNNNNNNN NNNNNNNNNN NNNNNNNNNN NNNNNNNNNN
34701 NNNNNNNNNN NNNNNNNNNN NNNNNNNNNN NNNNNNNNNN NNNNNNNNNN
34751 NNNNNNNNNN NNNNNNNNNN NNNNNNNNNN NNNNNNNNNN NNNNNNNNNN
34801 NNNNNNNNNN NNNNNNNNNN NNNNNNNNNN NNNNNNNNNN NNNNNNNNNN
34851 NNNNNNNNNN NNNNNNNNNN NNNNNNNNNN NNNNNNNNNN NNNNNNNNNN
34901 NNNNNNNNNN NNNNNNNNNN NNNNNNNNNN NNNNNNNNNN NNNNNNNNNN
34951 NNNNNNNNNN NNNNNNNNNN NNNNNNNNNN NNNNNNNNNN NNNNNNNNNN
35001 NNNNNNNNNN NNNNNNNNNN NNNNNNNNNN NNNNNNNNNN TGGTAAAACC
35051 CCGCCTCTAC TAAAAATACA AAAATTTAGC CAGGTGTGGT GGCGGGTGCC
35101 TGTAATCCCA ACTACTCGGG AGGGTGAGGC AGGAGAATCG CTTGAACCCG
35151 GGAGGGGGAG GTTGCAGTGA GCCGAGATGG TGCCACTGCA CTCCAGCCTG
35201 GGCGACAGTA TGAGACTCCG TCTCAAAAAG AAAAAGAAGG AAATGATCTA
35251 ATTTGTTCTG TGCACTGCAC GTGGGGGTGG CAGTGAGGTG AATGGCAGCA
35301 TTCTGCAGTA GTCAAAGCCA GATGGGTGGG AGAAGTTGGG TGCTAAGAGG
35351 GAAACAAAGT TTACCTGTCT TCTCCTTGAT TTCACTCTCA GTTTTATGAG
35401 AATACAGAAA AATCATGCAG AGAAACCTGA TGGAATAGTC TCTAAAACTA
35451 AAAAATAAGA TAAGCAATGG TTCTGTCTTA AAAAAAAAAA AGTAAACTCC
35501 ATGAAGGCAG AGACCTTACC TGTCTCATTC CTCTCTCTAT CCCCTGGTCT
35551 ATAGTAAGGG TTAAATAAAT ATATGCTGAA ATGAATGAGT AATGACTAAA
35601 GTATTTTTGT CTTTATTAGG ATTTGTAATG CAATAACTAA AAGTCACCCA
35651 CAGAGAAGTG ATGTTTACAA ATCAGATTTG GATAAGCCCT TGCCTAATAT
35701 TCANNNNNNN NNNNNNNNNN NNNNNNNNNN NNNNNNNNNN NNNNNNNNNN
35751 NNNNNNNNNN NNNNNNNNNN NNNNNNNNNN NNNNNNNNNN NNNNNNNNNN
35801 NNCAGCTCAA ATTTGTTATA ACCTATTTGT TAAAGAGAGG ATTGTTTTGA
35851 GACTATAGTT CCATTCTTCA TGAATTGGTA GGAGTTTGGA GTTTGTCAGC
35901 AAACATTCTA TCGGGCTAAA GGTTTTTATA ATGAAAGAAA TAGGCAAAGT
35951 GGATCAGTAC ACTCACTTTT CTACCATTGA CCCTGGGAGC AGATGGCTTA
36001 AAATGTTCTG CGTCTAGTTG ACTTTTAGAT CTTGAAATTA AGGTTTAATG
36051 ATGACCAAGC TTTAAATAAA TTGTAGAAAA GTATTCTTTC AAAAGTACAT
36101 TATAACTTTT ATATTGGTTT CTTATATTTA TTTCTTTTAA TCTTTTCTTT
36151 TAACACAAAC TACGTTTTAA GGTTTTGTTG CCTACTAAGT TATAATCTGA
36201 GTGCAGAGG AAACTTGATT TGGCTTTATG GAATACATTT TACATTCAGT
36251 GAAGCTGAGC TCTGTTTCTC ATTCCTTACA AAAGGAATCA AAGGCATTGG
36301 TTTGAGAGAT CAAGTCATGT GTTAATAAAA CACAAATATT CCATCAAGTA
36351 ATACTCTGAA GGAGCAGGTG TAGTTTATTT CTTCTCCAGA AAGTCTTCCA
36401 GCAGATAAAT AATGAGAGGT AGTATGGCAT AGGAAAAAAG TACACTGAAG
36451 TCAGCCTTTC TGGTTCAACC AGCTCAGACC CCTGAGCTAT TTTTGCCTCA
36501 GTTTTACGCC TTGGAGAACA ATGCCTTGTC ATTACTATTC ACTTTATGAC
36551 CATACAGTGC CTGGCACCTG GTGGGCAATT GGTGAATGTT TTCACTATCC
36601 TCATCCTTGC CCTCATGAAA CACTCCTTCT AGGTCCCACA AAGACCGTTG
36651 GTATTTTATG ACAAAGTACC TTACAAATAT TTTTCTTTTT TTAAAGGAGA
36701 AATTGTCGTA AATGAAGTCA ATTTTGTGAG AAAATGCATT GCAACAGACA
36751 CAAGCCAGTA CGATTTGTGG GGAAAGCTGA TATGCAGTAA CTTCAAAATC
36801 TCCTTTATTA CAGATGACCC AATGCCATTA CAGGTGTGTT TTATTAGTAC
36851 ACTGTTTCAT TCTATCAGGC TTTCAACTCT AAGTGGTACA TATTATTATA
36901 TAAAACATAG GTATGGAAAA GTTATAGTAG AAGTATTAGG TAATGCAATG
36951 TTTGGGATAA ATTATATTAA GATTTAAAGT AAAGTTTAAG AAGAATGTTG
37001 GAACTTGCTA GAGGAGTATT AGTGAGAGGA TTGTAAGTCA CCTTGCTTTA
37051 TTTATCCTCT GTGATCGTTC ATTATATGTC CTTTTCATTA AGGAAGTTAT
37101 TCCCTCTGTT GCAGATCTTT TAACCTGCTT ATAAAAATGA CATAAAGAGA
37151 AAAGGTTGTT TGCTAAATGA TTTTATAAAT GCCACACATT TTAGTGATTT
37201 CATAGGTTTT TTTGTTGTTG GGTTTTTGAT TTTTTTGTTT TGAGCCTGGA
37251 TCTCGCTCTG TCTTGTCTCC CAGGCTGGAG TGCAGTGGCA TGATGTCGGC
37301 TCACTGCAAC CTCTGTCTGC TTCCTGGGCT CAAGCTATCC TGCCACCTCA
37351 GCCTCCTGAG TAGCTGGGAC TACAGGTGCA TGCCACCACT CCCGGCTAAC
```

FIGURE 3K

```
37401 TGTTGTATTT TTTTGTAGAG ATGGGGTTTT GTTATGATGC CCGGATTGGT
37451 CTTGAACTTC TGAGCCCAAG CAATCTGCCT GCCTCCCCCT CCCAAAGTGC
37501 CAGAGTACAG GCCACTGCAC CCAGCTACCT TTTTTTTTTT TTTTTAAACT
37551 AATTAGTGTT ATTTTCCTAA AAAGTTAAAT TCTAATTTCT AGGAAGAGTG
37601 AAGAATAGTA TCGATTTAAA AATTTTCAGT AGCCCTCTTG CTATTTTATG
37651 TTCTTACTGG AAAGTAATAG TTCCATGTAA TTTTGGTTTT TAGAAGTTCA
37701 GGCATTCATT TGATTAACTT AAAAACCCTG GACTTTTCTG TCAGCCATTT
37751 TGTATTTTGT TTTATAAAGT ATTATACACA CTTACCCCTA GATCTTTCTT
37801 TATAGTAATT GTTCTTTAAT GAAATATTGG TATATGAACT GTAAACTTTT
37851 AAATTTAAGG ATCTAATAGT TTAGTGTAAG TATATTTCAT GTAGTCACTC
37901 ACTAATTTAC CATAATTATT ATACTGTACA AATATTTATT GTACTGTATA
37951 TTTGTGTGTT CATTACAGTC TTATGTAGGT ATATTTAGAC TAAATTTAAG
38001 GCACTTAAAG ATACCCACTG TGTAGGGACA GTAGCTTATT TGGATATAGG
38051 CTTGTGTGTT TCTCTTTGTT TTTAGCTTCA TAATGATCAT TGGCCCCAGA
38101 CTTCACTGTA AATGAGAAGC AGATACCTGG AACAGCTTAA ATCCAGTACC
38151 ACTATTAGGA AAAAGTAAAC CAGTGCCCTA CTGACAGCAG ATTGATAGTG
38201 TTAACTACGT CCTTAGTTTG AACATGCAAA ACCTTTTCTA ATGGTTTTTA
38251 TTTCTAGTAG ACTTTGTGCT TTAAAAAGAT AGTTATTTTG CACTTTAAAA
38301 TCTTCAGTGT GAAAATCAAA CATGATTTTA CCCACTTAAA ATCTGATGAC
38351 CTAAGAGCCC TTTTTTCTTT AATATGTTGT GGCCAGCTTA TCCAGATCTA
38401 GACATGCAAA TGCTTGCTGG TAAGGTGATT GATGATATTC CCTATCTTAG
38451 GTATTATAAT AAGATTGTTG TGTACATTTT AACCTAATTT CTATCTGTCA
38501 ACATTGGAAT GGCCCTAGCT ACCTAGACAA AAGCTTTTTG TGCTTTTTAG
38551 AGATAACTGT CACAGTTTAT CATCACAGTT TAAGGCTTAT ACTACCATTG
38601 TGAGATTATT GGGAAAAGAA TTAATATGAA CATAATTTTT TATTCCAGAA
38651 ATTCCATTAC AGAAACCTTC TTCTTGGTGA ACACGATGTC CCTTTAACAT
38701 GTATTGAGCA AATTGTCACA GGTACGTAGT ATTCCGTACA TACTCTAAAA
38751 GTCAATTCCA CTCTGGAAGT ATTATTTGAA AAGTCATACC TCTCAAAATA
38801 CTTGGATTGG CGTTTTATTT CTGTAAGTTT ACTTTTGCCG TTTTTTTGAG
38851 TCCCGGGAAC ATAAAGAGGG ATATGTTAAT AAATTATTTT AAAAGGAAGA
38901 TATAAAATGT ATAACTTTTC ATAGTTTCTA GGTTTTTTGT CCTCTTTTTA
38951 ATTAAAATTA ATCATTAAAT GTGTCTAGAT GGTGGTTTTA TGCAAATAAT
39001 CATTTAAAAT ATCTTCCAAA GCAAAGTTAA AACCAACCCC CAAGTTCTAG
39051 GAATTACAAG TATGAAACAT TCTAGACAAG CAGAGCTCAA ATGTTGGGTG
39101 ACCTTCCAAT TATTTTCACT AAGAATTTGT ATTAAAGGGT GAGTAACAAA
39151 TAACTGTTAC GCATTTTATT TTCTCTATTT TTTTTTCTTT TTTAGTAAAC
39201 GACCACAAGA GGAAGCAGAA AGTCCTAGGC CCCAACCAGA AACTGAAATT
39251 TAATCCAACA GAGTTAATTA TTTATTGTAA AGATTTCAGA ATTGTCAGAT
39301 TTCGCTTTGA TGAATCAGGT CCCGAAAGTG CTAAAAAGGT AATACTGTTA
39351 AGGTTTATCA AGTTCTGGGT TCTGTACTGT GTTACTGAT TTCAATTCCG
39401 TATGGCAGTT TTCATTTCTC AATTGCTCAG ATGTTTTTTA GGGGAAGTTA
39451 TCAGACATCT TCTTAAGTAA AGTCAAAGCC AAGAATATTA ATAGAACTAT
39501 TTTCTTGGAT TGGTTTATGG CTGTTTTAAA GTGTTCTATA TAACTTTTTA
39551 TCAGCTTCTC AAATATTAAA GACTCTTACG TGGAAATTAG CATTTTTTTA
39601 CATAAAGATC ATTACTTGTC AGTTTCTTGG TTAAAAGGTT GAAAAGTTGG
39651 TGATATACTG TAATTAAGGT TTGGTTAGGC TTTTAATTCA GTACTGCAGA
39701 ACTTTACCAA CAAACTGTAA GCTAGACTTA TGTTACATAA GATTTAGGTA
39751 AATATATAAT TACGGGAAAG GCCTAGTAAT TATTAGTGGT TTAAAGAAAT
39801 ATTATGAATT GAGTGACACT CAACAGGGGC AACACAAAGC TAGTAACTTT
39851 TTAACTGCCT TATTTTTCCA CGGCCTTCCA GATAATGACT TATTACCCTA
39901 CTTGTAAGAG TCAAGGGCAT GTTTTCCATG TTTTGCTTTG CCAGAGGAGT
39951 GAAGCTGGTA GACCTAATAT GGCCCCCGTT CCAGTCTGTG CTGCAGCAAA
40001 TGCAGAGTCA CAGACTTTCC AGTAGGAAGC TTGCGCGTGT GTATGGGAAT
40051 AGGGCAACAG TATCTTAGTA TAATAGGACG TGGCTTTCTC TCAGAATGGA
40101 GGCAGTCTTT GCACCACCAA GCAATGAGTG CCTTTGTTTT CCATGGTTAG
40151 TCAACTGACT GCAGTAAATC TTCTGTTGAT ACCAAAACAA GGCTGGCAAA
40201 AATACTGTAA GGCAGCTGTC TTCATATACT TTGGTGAAGA GGTGGTAGAT
40251 TTGTTTTTAG ATTGAGAACC AACAGTTTCT TCACAGGAAG GCAAGCAGGA
40301 GATGAATATA TGAAAATACA TCTGAAAATA TGTGACTGTC TAGCAGAGTA
40351 GAGTGGTTGT AGGCTCCTCT ATGGGTAAAA GTTTTCAAAT GGTCTGTATA
40401 ACCATCTCTC AGCAAGCTGC ATTATTGAAA ATTCAACTAG ATAACTCTTA
40451 AAGCCTCTTT CACCTGTTCG ATTGTGCTGT TTGTGATTTT GGCATTTTAC
40501 TAATTTAAAG TGCCTATTAT ATAGAAGGAC TTTAGAATTC ATGATGTATT
40551 AGACTGTACA TAAAATATTT CAGACAGGTT AATTCCTCAA GCTTATTTAT
40601 ATTTGTAATT TAATTGATCA AAGCATCAAA GACCTGCTTA TGAAAACCTT
40651 AAGATGTGTA GCATCTCAAG ATTAGGGACA TCACAGAACT TGCTAGATTG
40701 AGTTAGGACA GCATATTCCT AAGGAAGAAA TTGATGCAAT TGACCGGATC
40751 TCTTTCGGAA AGTTCAATTC TCCCTCTTTT ACTGTATTTT TCAGTTTACA
```

FIGURE 3L

```
40801 CTATTTTAAT GAGTGGAAAT AATAATTATT TGGCCTAGTT CTTGAACCAT
40851 CTGTAGTACT TGTTGGTCAT TTTTCATGTT GAGGCAGTGT GCTAAATTTT
40901 GCAAGTAGAA AGAAGGGTAA GATGCATTTT CTTGCCCTAG AGAACTTAAA
40951 TCTAGTGAAG AAGATAAAGC ATGAACAAAT GAAAAGTAAT GGTACAAAGT
41001 GGCAGCATAA AATCAACTAC ACAAATAGTT GATTTCCAGA TGAACAGAGC
41051 ATAATAAGTG CTGTGGAAAT TCAGAATATC CCCTATGTGT TGTGCTGCTG
41101 GTTCATGAAG AGGGCCTTAC TAAACCGTCT GCACAAAACA AGCCAGTCCC
41151 TCATATGCCC TTTCCTAAGA CCAAGTTTCA GACAAAAATC TTTTCCCCAG
41201 TATCCTAAAA TATAAAAAGC ATGTGAGTCT CTGTCTTTTG TATAGCCACG
41251 GGGGTTGCAG GGCAGGGGAG GGTGCAGGAA AAAAAAATAG ATGCAATGAG
41301 AATATAAATA GTTTTTTTGG GATTTACGCA TTTCAAACAG GGTTAAGTTG
41351 TATATGGCTA CCAAAGCTTG ACGGCTTTGT GAGTTAAAAA CAAAAATTAT
41401 GGCATATTCT TTTATTTCAA GTGAAAAGTT TTCATCTAAA ATTCGGTAGC
41451 AGTTAGGAAA TTATGGCTCA TTTTTACCTC CTGGAAGCTT GGAATACTGT
41501 TTTCTCTGGA AAATGCTTTG CTATTTTATC AGTTGCTTTA AAATGATGAA
41551 ATGCATGTTT GGAGTTCTCT GGTGGGTAAA CCGTTGATTC ATTTTGAAAT
41601 ACCTAAGCCA TTTATGTTTT TGTTTTGAAA AATGAAATTC AAGAATACTA
41651 AATTGGTTCA CATTTTGTTA AATGTTCTGA ACCCTTCTGG TTGTCTTGTT
41701 GGTGTTGTTT CAATTGTATT ATGACAAAAT TAGATTGCTT TGGGCACTTG
41751 TACTCATTAA TATTCATCCT CATTATCCTC GAGCTGTCAC AGGAAAATAG
41801 TGATATTTGG GAAAGGTCTG TATAAAGAAA GAAGGAATTT GATGGTGCAG
41851 AATTGGACAT CTAACCTCAT AGCAACTTAG AACCACCATT TTCTTTTGCA
41901 GAACCTTTGC TCAAAACTGA AGGGCAAAAT AATAAAGGTT GTTTTTAATG
41951 ATTTATCTAT ATATCTGTCT GTGTAGATAA AGATAAATAT ATAGATACAC
42001 ATGAGTGACA AGTGAAATAC ATGCCTTTTG TCTCCACTTT GTTCTCTGAT
42051 TAGTGGGTTG TGAATCACTT CTTCAGGAAT ACTTTATAGA AGTGAATTCC
42101 ATTCATCTGA TTAAGGAACA AGTTGGCCTT TTCATGAACT GTCATTTTTG
42151 ACTTGAATCT GGTACTGTTT TTTGGTGGCT TTCAGGCCAC AGAAATAAAC
42201 CACTTTTGTT TGCAAATGAG ATAGAACTTA ATGAGGTTTG AGTGTTTCCT
42251 GGATTTGAGT TTCTTCAGTA CTGCACCCCA GGTGATCTTA GGAAAGAAAC
42301 CATCCACTGT GGGTACTTCT GGCTTCTGTC CAGAGAAGAT TATCAGCTTT
42351 GGTCCAAAAA TTGATTTAAA AGTAGTTTAC TTCTTTTTCT CCAATAAAAT
42401 ATTTGCCATA ATTTAATGTC TTTAATACCA ACATTTTCTT CATTTCCTGT
42451 GGTAGCCAGG ACAAATGAAG TATTTCAGAT CTTTCAAAAA CTCTTAGGAT
42501 GAAAGGTAGG AATTTGGACT TAGGTTTTTA AAATAGTGTG TATGTAAAAG
42551 TGCAAAGAAT GGGGCCCTGG CTTTCTCTTC TCGGAGTGTT CCACAGTAAC
42601 AACATGAAGA CAATCCAGGT ACACAAGTTT GTATGTGCCT TAGTCTGTGT
42651 GTCCAAAGAG GCCTCTTACT TAGGTCATAT GAACATAAGT TATACACTTG
42701 AAATTCACTA CTGAAAAACA ATGTATTTAG TTCGAGTTCT GCCACCCCAA
42751 AAAAATCAAC GAGTAATTCA ACTGACTTGC AGTTTACAA TATTTTTATA
42801 GACTTCTTTC AGCGTAGATG CTTTTGGACA TACTCATTTG TTTCCTAACC
42851 TGATGTGATA TTGTGCTATT TTTAAGGGGC TTTTAAAAAA TACGCTGTGT
42901 TGGGTTTTGC CTTGAAAATA GGCTTTATTT CTTTTTTGCC TCATGGCCAC
42951 AAAAAAAGGA TGTCCATGAT CAATGATCTG TGAATTTCTT TTCTGTAAAC
43001 AGAAAGAGCA TGTAACTGCT TTCTAATTGT TTTGGAGAAT GTGATAGACA
43051 TTAGTATTAT TATTATTGGC TTGGAGCATT TTCCTTAATA TGTTGGTAAC
43101 TACTTTTGTC AGTGAATATT AGTGTAGCCA CTGTTGGACA CAGAGCACCG
43151 TCAGAAAGCT ACTGAAGTGG TGCTGCAAAG TGCAGACATC TTCAGATCTT
43201 TACTCAAGTC TGTGCAGAGA GGTCTTTCTT GGTCTCCTTC TCTACTTTTT
43251 AGCCTGTCTC CCTCTTCTCA CTGTAACACT TCATATTCCC CTTCCCTGCT
43301 CTATTATTTT TCTCTTTTAG CATTCATAGT TATCTAACTT TCTGTATTTT
43351 TTCTCTTTAT CTTGTTTAGT GTCTGTCTTC CCACTAGAAT GTAAGCTTCA
43401 TGAGGACAGG GATTAGTGTC TGTTTTGTTC ACTGCATCTC TAGGGCTTAC
43451 AACATTGTAG GTACTCAGTA AATATTTGTT AAATCAATGT GAAATGTGTC
43501 ATTTATCCTT AAGGAATTGA CCTTCATGGT AGAAGTGTAA CAGAACCACC
43551 TATATCCTAC TTTTCATCCA CATCATAACT ATTATGTGAA TACCTTGGAA
43601 GTAAAGCAAA ATAAGCACTT AACTAAAGAG ACGCTTTATA TTGAAACTGT
43651 TGTTCTGGGT TTCTGGAATT AGTACTCTGA AATTGGCTCC CTCTAGGAAG
43701 GCTTGTGAAG AGAGTAGTGT TGAACAGACA TGACAGTTTC CAAGAAAGCA
43751 TAGTTGGCTA AGAGGAGTAG GATTTTCCAA GCAAAGAGTG TGACAGTGGA
43801 GATGGCTGGG GCTAAGTCAG GCAGAATGTG TTCAAACCTG TTTTTCTCTG
43851 ACCTGAGATT GCGGAGGGAA TATTGGGAAG GTATAGTTAC CTGGTGAGGA
43901 GAGCCAGTTT TGTGAAGAAT CAAGAATGAG GAGATTTAAT TTGTTATGCA
43951 GATGTCTGGG AACCACAGCA GATTATCAGG AGAGCAAAAT TGTTAGTCAG
44001 AATTACATCG TTAGAAGGTA ATCCTTAAGT TTTGTAGATT TCTAGAATGT
44051 AAGGAAGCTC TCAGAGGTGC CATAAGGTGA GTATGGCCTA AGGATGTGGC
44101 TATGGCAGTG TAGCAAAATG GACAACTATG AAAAATGTCT AGAGAAAAGT
44151 GCAACATAGC TTATCAACGG TGCCCAAACA AATAGGAAGG ATGAGAACTT
```

FIGURE 3M

```
44201 TTTCAAGCTA CAGATTTCAG TAGTTTTGCT GCTAGAAATG CTTTAAGGAA
44251 AACTGTTAAA AAGATTAGGA ATGGGAATAT AGATAACCGG CTCCTAAATT
44301 TTGCAAGTGG GACCGTCATA GAAAGCTCTC CTATAGGTAT TGAGAAATCG
44351 AGATACCACG TAAGTTTCAA GAAGCAGTTT TTTTTTTCTT TTTGGTCAAA
44401 ACTAATGACA AATTCTGTCC CCTTGTTTGT ATATTTTAAC TTAGTGAGAC
44451 AGGAAACATT TATTCTATAG AAGACTTTTA AAATGTAGTT TAAACAAGTT
44501 GACACATGCT TACTGGTTAA TGAAATGTGC ATCAACCCAC TCCAAACACC
44551 ACTAATTTGA CATGAACTAA CAATTAACTT TTCTTACTCA CTGTCAAAAG
44601 TATATCATTC TGCCTTAACT TAACGCTTTA CCTTCTAAAT AAAATTTAAT
44651 CTTTTAAATA AGTTTTTCTG CTATGTTTTC CTTGCATATG TCTTAAATTT
44701 CTTCTTTCGT CTTTGCTCAC TGAAGAGCAT TTTCTCCCAC ATTCTAGTGA
44751 CTACCAGGGT TTGTAAGCCT AGAGCACCAT CCTTCATTCT ATCTAGCAGC
44801 AGTTGAGAAT AATAACAGCC ATATTTCTAT ATATGGAGCT CCTCCAAAGG
44851 CCTAGCCTGC ATTAAGCTTG TTAATTCTTA CCACAGCCTA GGTATTACTT
44901 TTGTTTTACA AGTGAGCAAA CTGAGGCTAG AAAAGAGGAA ATGACTTCAC
44951 ACATGTTATG TAGCAAGTAC TTGACAGAGC TAGGATTCAA GCCCCCTGAT
45001 CTGTTTGATT CTAAAGCCCG CACGTTTTCC ACCACAGGGC ACACAGTCCC
45051 AAACCATTTT ACTTAAACAC AGTTTGTGTG TGTGTGTGTG TGTGTGTGTG
45101 TGTGTGTGTG TGTGTGTTGT TTTTTTGATG TACCTCTTTG AGCCACCCAT
45151 GCATTTTTGG AGTTTCTTGC TAATTTTAAT TTTTTGTAAT TATGTTTCTC
45201 TATTTAGATG TTTAAATCCA TGAGGCGTAA ACTTTAAAGT TTCATGCCTT
45251 ATATTAATCC TTTATAGTCC ACCAAAAATG AAACTTTTTT CTTCCTTTTT
45301 TGGAGTGGAC ATGTAGTCAC TGCCTTTTTG GAGAATGCTT CTTTAGTTTG
45351 AAGCTTTCTT TATTGGACTA AAATTACTTT CCAATTAAAA TTTAACTCAG
45401 CAAATATTTA CTGAATACTT GCCATGTGCT AGCTAAAGAT AAACAATGTC
45451 TTGAGGGCAT GAAAGTGAAT GAGATACCTG GCCTTAAGGA GCTCTTTTAT
45501 ATTCTAGGTC AACAGAAAAA CATGTAAATA GTATCTATAA TCACTGCCCC
45551 AAGATGATGC TCCCAGTGCC CAAGGCCTTA TTGTACATTT CATTTAACTA
45601 AGTGTGTTAA AATCAAATTC TAAATGTAGA ATTTTTCCTA GGTATGCCTT
45651 GCAATAGCTC ATTATTCCCA GCCAACAGAC CTCCAGCTAC TCTTTGCATT
45701 TGAATATGTT GGGAAAAAAT ACCACAATTC AGGTAAATAT GAAAATATTA
45751 AATATTGTGA CTAATTTTAC ATGTGTAAAT TTTACTCTTA TGTTTACCGG
45801 AAGCCTCCAA GTACATGAGC TTTAATGATT GTAGAATTAC TAGCTTCATA
45851 CCTTAGAGAA GTAAGCACTA CATGCTAAAA GAGCCAATAG TTTGTCAGAT
45901 TATTTCTTGA CAAGTTACCA GGAAGAACCT TTAATGCTAT GAATATGGGC
45951 TTATAAGTTA TGTCAGATAT TTAATCTCCA GTCACTGGCT TGTATTTTAT
46001 GATGAAGAAT ATATAACCCA CCCTTTTTAA TTGATAGCTT GAGTTAAAGT
46051 AATCTTATCT TTTAAGAAAA CTGGCAGAAA ACTAAAAGAT ATATTAAAAG
46101 CATAATCTTT TCTGGCAAGG TGTGATTTCA TGCAAAAGCT AAAGTGATTA
46151 AAAACTTTTT GTGGACTTCA TTAAGATTCT CAGAATACTG AGTTTCTATT
46201 TCTGAGTAAT ACTGATGAAA GGAAGATGAG CATTTTTCCA AGGACAAGTA
46251 TATTCTAGAC AGCTTTTGTG AAAGTAAATA GTTTTGTCTA TATATCTGAC
46301 AGTCATGACA TGACCAGGGA AGATTCCAGA TGATCATGCA ATTCTGTACA
46351 TTCTGTTTCG TACAAATGTA ATTTTAATAA ACAATTTTTA AAAATATCTT
46401 GATAGAGAAA AACAAAGAGC CGTGTCTCCT GTTAGCCCCA TTGTCAGTTA
46451 GTGACTGCAA GTCAGTTAAC TGAGCGAAGC CTGTGTTCTT TTATTTAAGC
46501 AAGAAAAATA AATCAGCTGT GTATTTATAA TGAAAAATCC ATTCACCCAG
46551 CATGCTCTGG GCCATACAAA TTATTAATTG TACTGAAATT TTATATTTTG
46601 TTACCACGAA ACATGGTAGT AATTTAAATA ACTGGCATAA TAAAAGTATA
46651 TTCCAGCAAC ACTATATTGT AAATACATTA AAATGTATCA GTGTACGGTA
46701 TCTGAAGATG CATGTGTATA AGTAAATTTT CCTTAGTTTA AAAGATAACT
46751 ACCTTTCTGT TAAGCACTGA GAGGACCAAA AAAAAAAAAA AAAGAAAATA
46801 CAGTAGAGAT AATATATGAA AATAATGCTT TGCAGAGCAG CTTTTATCAT
46851 ACAGTATTAT ATTTATAGAA ATTGTATAAC AAAAGTATTT GTAACTTAAT
46901 TTTTCTTATC GATATATACA TAATTGTAAC TGAGGCTTAA GCAATACAGT
46951 TATTTTTTGA AGTTTATTAA TATTAAGTAA ATTCACTTAC TGTCTAAAAA
47001 TAAAGTATAC AGATCCTGCA CTATTAGGTA AACACTCCTT GGGATCATCG
47051 TCAAGCTACA GAACAGTGAT CAAGGTTATC TTCAATAAGA TCCTCACCCA
47101 GAGTTGCAAG GGTTGTAGGA GTGAGTCTTT GATTCCTGCT CAACTGTTTA
47151 TGATACAGAC CAGTTCTTCA TGCTGCTGTT TTTCCAATAG AAATGATTCA
47201 TTTCAGTTTA CAGATCCATA ACTTCTACAG TAATGTAGTG ACTTGGGCTC
47251 AGCAAAGACA GTAAACTTCA TTATACAGTT GGTAACCTGA TGCCTGCTTC
47301 AGTTACTTTC CACATTTTTC TTCATTCATA CCTTGTGGGC ATCTCTGGTT
47351 TACAGTACTT TAGTTTATCC ACCCATAGGT CTTCTACTAC TGGAATTTTA
47401 AAATCTACAT CATTCAGTTC CACTATTTCT TCTTATATAG CTTATTGATA
47451 AAATTTGATG ATTAATACTG AAAATATTCA GGGATGCTTT TTTATATTAC
47501 ATCCTTCAGA CTCCTCCTTT GACAAGTACC TCATAAACAT AACACTGGCC
47551 ATAGTTTTGT TAAGATTCCT CGTAGGGTAA CATCCTTTAA TATCCTTCCA
```

FIGURE 3N

```
47601 TGCTGTTACA GAAGCATAAA TACTGCATCT TTAAGATCAA AAGGAGCCTG
47651 AAATTTCCAC ACACTGCAGT CAGAATTCAT TAATTTGTGA GTGAAAGATG
47701 CCCACTCATC CACTCTTGAA CTTCTGGATG ACACCTTGAT TCATTGGCTG
47751 GATTAAAGAA GTCCTTTTTG CAGGCAGGTA GGTGACAAAG CTGTTTCCAC
47801 AAATAAGATC CAAAGTTGGA GGAGCTCCCC TGCAGTTATC TGAGAAAATG
47851 ATATTTTAGC TGGCCTTAGT CACTCAGGTT TTCATTCATA TTCAGTATCA
47901 CATGAGGAAA AGCCATCTCT GAAAGGTCCT GCAGTCATCC CAACACTTCT
47951 GTGAATATCC TGGAGTAAAG TAAGATGTGT AGCACCCAGG CTTTGGAACA
48001 TCGCTTTGCA CAAACACCCC AGGAGATATT ACTAGCACAA ACAAGAACAA
48051 TGATTCTGTT TTTTCTCTTT TAACTTTAAA GAAACCATGA GGACTCTGTT
48101 TTCATCAGTC AGATTATTAT TGGGCAAATA ACGTCAAAAA AGTACAGATT
48151 CATCTTTCTT ATAGAATTGA TAAGATGTCA GATTATGCTT CTGGACCAAA
48201 AATATTGAAA GTTTCATGAA GTTATCTGCA GCCTAGTGTC AGCAACTGCT
48251 TCATGACAGA CATCCTGCTT ACAGATGCTG TGATGTAATC TGAAGTTGTA
48301 ATGAAATTTC ACATCAGAAG TTGTACATTT TCAGTGACAT TTAATTTTAT
48351 CCTTTTTATT AACATAGATC TTGTTATTAG ATTTTCCTTA AAATGCCTAT
48401 TTGAAAAACA CAAGGTACAC AATCCATTTG AAACAGTATA GGAATTTTTA
48451 AACTTTGTTG CTTAAGATTC TCAGAATAGC TATAAATGAT TGTTGAATAT
48501 TGGTGGTTCC AGCCAGCTGT ATACATCAGG ATTACTGGAG GAACCTTTAG
48551 AAATGCAGCC ATGTTGGCTC CAGCACAGGT CAGAATCTCC CAGTTAAGAA
48601 CCACTTTGTT GACTCATGCT TTTGAACTGA TTAATACTCA CAGTCCTCTT
48651 TTTACCTTAT TCCTTTGTGA CTTCTAATTT CTGCAGTATC ATCAGAGTGG
48701 TGGGCTTTCT TTTCATATAT TGATGACTTG TATTTTCTGT TGCTTGAAGC
48751 CATTCTAGAT ATCAATTGGC CAATTCAGTG GAAATTATCT AAAATAACCC
48801 CAACAGTATA GGATTAGACT TTTGTACTGT CACAGAAGAT AGCCAAGGTC
48851 AGGAGCATAT AATATCTATT TCACGCTTAG TCTGCTGTGG AGGCATGTCA
48901 TAAAACCTCA GTCAGGTAGC GGTCAGCGGA GCCAGGTCTC CCTGAGATGA
48951 CCCACCTTTC ACTGTGTTGG TCCAGCCCCT CATAGCGATC CACTCATAGA
49001 GCAGGCCACT GGTATCAGGT CTTTTGAACT TTGGAAAGCA TTCAAATTTC
49051 TGGACTATAA AACCAGATTG AGTATACATT ACACATTCTG TAATGAGCTC
49101 TAACTGAAGA TGATATAGAA CATATAAAAG ACCTAGTCCC AGTTGTTTAG
49151 AAAAGTACAG GATTTGAACG AGAGAAATGG CAAAAATAAC AAACGATAGA
49201 GGATCTCACT TTATGCTTAG AAAATATAGA TGTTCTCATT TTACGTTTAG
49251 AAAAATTTGT GTAAGTTAGA TCTTGAAACA AAATTTGGCC AGAGAAACAA
49301 TCTCATAAAC AATAGCACAT TCTTAGCCTA GCTTATTAAA GTCTGCAACC
49351 CAAAACACTA AAAAGTATTC AGTGCTGCTG GACTCAGTCA CCAAACTGTT
49401 TTACATAACT GTTAAAATTT TGAGTGTGTT TTTTATAATT CTTTTTTGGT
49451 GGTGGTGGTT TTATTGTTTG GCTAGGACTG CTGGTTCAGT GTTGAATAGC
49501 AGTAATATTA GCAGGCATAA TTTCACTTCC CGCTTTTAAT GAAGATGCTC
49551 TTAGCTATGT CTTTTTGATA AACACCCTCT ATCCAGTTAA GGAAATTCCC
49601 TTTTATTCCA AACTTGCTAA CGTTGTTGGG TTTTTTTTTT TAAGTCATAA
49651 ACAGGTATCT ATCATATGTT TTTCTGCACT TACAGAGCTA GTCATTCATA
49701 TAGCCTTTTT CGTGTTTAAT GTAGTCATAT GATGAATTAC TTAGATTTTC
49751 TAATATTGAA TAGCTTTCTT TGTTTTGGTG CACTGGAACA CTGTATAGAT
49801 TGGGCTTTGC CAAAAATTCC ATATGCAGGT TTTGTGTTCT GGAGAGATCA
49851 TAACTCCTAA GTCTTCCTTC TCACAGACAC GCTTTTTAGT TGTGTTACTC
49901 CAGAGAAGGC CCTGAGATGG AGTGGGACTC TAGGATGTGG GCTTAGAATG
49951 AGCATTTTAC TATCTATCTA TCTATCTATC TGTCTGTCTA TCTATCTATC
50001 TGTCTATTTA TTTTTGAGAC AGAGTCTCGC TGTGTCGCTC AGGCTGGAGT
50051 GCACTGGTAC GATCTCGGCT CACTGCAAGC TCTGCCTGCC AGGTTCACAC
50101 CATCTCCTGC CTCACCCTCC CAAGTAGCTG GGACTACAGG CACGTGCCGC
50151 CACACCCGGC TTATTTTTTT TTTTTTAGTA TTTTTAATAG AGACAGGGTT
50201 TCACCGTGTT AGCCAAGATG GTCTCGATCT CCTGACCTTG TGATCCGCCC
50251 ACCTCGGCCT CCCAAAGTGT TGGGATTACA GGCATGAGCC ACCGCGCCCA
50301 GCAACATTTT ACTTTTTAAT GAGCTTTGTT AAAATCAGAA TCACTGGATA
50351 ATTCTGATAC CACTTAAGAG GAGTCCAAAT TCCTAACATA GCCCCTCCGT
50401 AATCTAGAGC AGCACCGTCC AGTGATGGAA GTAGGGCAGC CACTAGAGCC
50451 ACTAGCCACA TGTGGCTGTT AAGTACTTGA AATGTGGCTA GTGCAACTGA
50501 TGGACTGAAT TTTTAATTTT ATTTAATTTT CATTTCAGTT TAAATTTAAA
50551 TGGGCTTGTG TGGCTAGAAG TTACGTTTTT GGGAAACATA CTAGAGTCTA
50601 GGCCCTATTT GATTTCCCGC CTCTCTTCCA CCACCTGTTG AATCCCTATG
50651 CTCTAGCTGT ATTTAGTTAC TTGATATTAT ACAGTTATAC CATCTTTTTA
50701 AAGTTCTTCT CTGTCTAGCA TGCCTACCTC CTCCTCACCA GCTACCTGGC
50751 AACTTTTGAC TTGTTCCTTA GAACTCTCTT TAGTTGTGGT CAAGTCATGA
50801 AGCTTTTCCT GCCCCGGCCT CTCTCTGCAG CGAGAGTTAG GGGACTTCTC
50851 TTTTGCATCT TCATTGCACT CAGACATCTG GTACTCTGTG ATTATCACAC
50901 TTATTAATGC TCTCAAGATA GAGATAAAAT CTTATTCATC TTTTTGCTCT
50951 CAGGCATTAG CACATGGGGA GTTCTCAGAA AATACCTGTC TTATACCAGG
```

FIGURE 30

```
51001 AATTAATGAA TAATCAGTAG GAATGAGCAT GACATGTTCA TGGGACGTTG
51051 GAGGGTAGTG CATGGCTGCA GAGGAGAATG GGAAATGAAG GTCAGATAAG
51101 TTACGTGAGG GATCTCTAAG GCCAAGAGAA GCCATTTAGG TTTGATTTGG
51151 TTGGAAAATG AGCTTATTGA AAGTTTAAGG CAAGGGACTA GCATCATGAA
51201 CACATCTTTT TAGGGAAGTG TGTCTTGTGG TAAGCTGCTG GCTGGTTTAA
51251 ATGCAGCAGA ATATTCCATT GGGGATGCCA GCTGGGAGAC TTGCCACAGT
51301 TGCAGCCTGC AGCAGAAAGA CCCTGGGCCA GAATGGGTTG TGCCATCTGT
51351 CACCAGATAT TGCCAAGGTA GATCTGGCTG ACTTTGTGGG ACAGCTTGTT
51401 TCTCAATAAT CACTTTGCAG GCACTCTTGA GGCTGTGAGC ATGCTCCCAG
51451 AAGATAGCAT TACTTCTCTC TCAGAGCAGG CTCCTTTCTA AGGAAATGCA
51501 AGTCTAGGCC TGCCCTGCTG TAATCTTCAT GTGGAAACAG CACTCTAGCA
51551 AAGAACAAGG AACCTGATGA GCTTTTCAAA GGAAAATCGA GTAGATACAG
51601 GAAACCAAGA ATTTTCTAAT GAGCAGATAG AAAAGAGCAG GTAGGTGAGA
51651 AGTTGGTATT AGAAAAATTA AAGATTTGAA GGGCTTGAGG ACAGAGATGA
51701 TTGTTGGATG TTTCATTTTT CCAGGCAAAA TATGTGGAGC AAATAATCAA
51751 ATGACATGGA CTTACCCCAC AATTAGGGAC GGAGATGAGG AAGGGTTAGG
51801 AATAGTTTCT GTTAGAATGG TAGGGATGGA AGACAATTGA AAATTAAAGA
51851 GAAAATAAAT GGAGAGGAAA TCTAGGCAGC AGCCATTCTT CATTCTGGGG
51901 GAAGGTGGTC AGGAAAAGGA AGGAAGAAAA ATGTATAGCA TAGTAGCTAG
51951 AGTGGTCCGG CGTGATCAAA GTGTTTTCAA TATCATGTTG ACTGACCTGT
52001 TTACGTTTGA AGGCAGAGAA GATAGAGCCA GTAGAAGGAG AGAAAAATCA
52051 AAGCTGTTTT ACGGAGTTGT GAAAGAGCTG GATAAGGACA AGACTAAATG
52101 AGTTATTTTT AGGCCAGGCG TGGTGGCTCA TGCCTGTAAT CCCAGCACTT
52151 TGGGAGGCCA AGGCAGGTGG GGCACCTGAG GTCAGGAGTT CAAGAGCAGC
52201 CTAGCCAACA TGGTGAAACC CTGTCTCTAT TAAAAATACA AAAATTAGCT
52251 GGACATGGTG CATGGTGGCA GGTGCCTGTA ATCCCAGCTA CTCAAGAGGC
52301 TGAGGCAGGA GAATAGCTTG AACCCGGGGG GCGGAGGTTG CAGTCAGCCG
52351 AGATCATGCC AGTGCATTCC AGCCTGGGCG ACAGAACGAG ACTCCGTCAA
52401 AAAAAAAAAA AGGAGTTATT TTTAAATGGA AAGGGCAAGA CAGTTCTCGG
52451 AGAGACTTGG AAGGTGAAGC AGGTTAGAGA CAGCACATCA GAGTATGCAT
52501 GTGACAGGAG GCTCAGAGAA GAGGGAATGC TGGGGAAAAT GTGACTGTTA
52551 AAATTCATAA TGTTGCTTTT TCCTACAGCA AACAAAATTA ATGGAATTCC
52601 CTCAGGAGAT GGAGGAGGAG GAGGAGGAGG AGGTAATGGA GCTGGTGGTG
52651 GCAGCAGCCA GAAAACTCCA CTCTTTGAAA CTTACTCGGA TTGGGACAGA
52701 GAAATCAAGA GGACAGGTGC TTCCGGGTGG AGAGTTTGTT CTATTAACGA
52751 GGGTTACATG ATATCCACTT GGTAAGTACA ATTTTAGCAA TGTTATATAT
52801 GGCTGGAAGT CACTTCCCTA TGAATAATCA TCAAACTCTG TTGTCATTGA
52851 TGACTTTCAA GTTGTGGTTA ATGGAATATT TGTTTTTAAT AATGTTTTAA
52901 TAAATATTTT ATTTTAAAGA TCAAGGCTTA TTAATATAAA TTACGGTATC
52951 CCTTAAAAGA AGTTGATAGT AATTCCTTAC TGTCATCAGT AGTCAGTGTT
53001 TATTGCATTA TATCTTGTAA CTGGTGTTTT ACAGTTGGTT TGTTCATATC
53051 AGGATCTAAA GTCTTCACAT TGAATTTGCT TAATATGTCT CTTAGGCCTT
53101 TTAATCTACA ACAGTCTCCT CCCACCTCTT TTTTACCTAC TATTTGTTGA
53151 CAAACCAGGT CATTTGTTCC CTAGAATTTT CCACATTGTA GATATTGCTT
53201 GTTTTATCCC CAGGGTGTCC CGTAATGTGT TCCTCTGTCT CTAATATTTC
53251 CTTTAAAATG TTAGCAACAG AGGCTTAATC GGATTCAGGT TCAGTACTTT
53301 TGCAAGAAT GTTTCATTAG GTGGTTCTGT GTTCTCCTGT GGAGTCACAT
53351 CCCATCTCAG GCTGGCTGGC TGTGTCTCTC TCATTGTAAT CCTGACGACC
53401 AGTGGGCTTA GAGGGTGTCA ACCTGATCCA CCCAGTAAAA GTTCCCCTCT
53451 TATATCATGG TTTGAGCTCC CAAAAATAGT TTTGCACTGG GAGGGAGGAT
53501 CATTGCTCAG ATCGTTATTT CACTAAGGAT TGCTATTGTT CACCTTCTAA
53551 TTCTATCATC TTTCTGCTTT TATCGAACTT TTCTCTCACC AGCTCTTTAG
53601 TGCCCTGTAA CACAGTTCGT ACAAGAAAAG CAATATAAAT ATCTACATTT
53651 TCTCCTTTAC TTAACATTTT TCCAAATAGT GAGCTGGTTC CTAGGGGAT
53701 CTTCTAGAAG TGACTAGGAA TTTGTTTTTT TAATTTGTTT AATGTCATTT
53751 AGTTATTATG AATTTTTTGG AATGCCTTAT TTTAAGGTCA TTGAAGTCCT
53801 CATTAGTTCA CGCACATAAG CAGCTTTTTA GAAAAAGGAA GAAAAGCACT
53851 ACTGTGTTAT TACTGGTTAA TCCAGTACCA GGAACTTCTA GTACAGTTCT
53901 AGAAAGGTGC TTTGCAGCAT GTAGCTTGTA TCTTTTTGCT CCCCTGGAAT
53951 TTAAGCTTCA AGGCCAGCAC ACTCTGGTAT ATGTGCTGAG AAACATGTGA
54001 TGGGCTGCC CAGCCACGTC GGGGAAAGAA GGAAGATGTC TTGAGGTGCA
54051 GTGAGCTTGC CCACTAGTAA TTATTGTCTG ATCAGTGTCC TAGAGTCTGA
54101 CTGTGCCTTT TAGGCATGGG GAAAGGTAGA AGAGGGACTT AAGAAGAGAG
54151 CTAAAGCTCC TGGTAGATTT GTGGGGTTTT CTTTTGTTTG CCTGGTGTCC
54201 TTAACCATAG CCTGTCAAGA GAACAAAGGT GGATATATTT TTCAGTGAAC
54251 ACATACATGT TTAATAGTCA TTCTGGAAAA TATTTCTAAT ACCTTCTTTG
54301 GAATTTTCTC ATGCTATAAA TTTAGATTTT TAAGAATTGG TCATATCGCA
54351 CCAATTTTAG ACTAAGAGGT GTAGGATCGT CACTGCCCCC CCATGGTGCC
```

FIGURE 3P

```
54401 CACCATGTGG CTACTAAGTG GGGTGCACAT TAAATGCGGA CAACTTGCTT
54451 AATTATTTAT AGGGTCTGCA GGAGCACACT ATTCCTGCTT TTAGCACAGC
54501 ACTCATATAA TTTTTTTTTT CCCCTCCAGC CTTCCAGAAT ACATTGTAGT
54551 GCCAAGTTCT TTAGCAGACC AAGATCTAAA GATCTTTTCC CATTCTTTTG
54601 TTGGGAGAAG GATGCCAGTA AGTGATTTCT GTTGGATTTT ATGAATGCTG
54651 ACGTCCATTG TTTCTACACA GTGAAGTAAG GATTCTACCT CTCCCCTAGC
54701 TCTGGTGCTG GAGCCACTCT AACGGCAGTG CTCTTGTGCG AATGGCCCTC
54751 ATCAAAGACG TGCTGCAGCA GAGGAAGATT GACCAGAGGT AATTGAGAAA
54801 TGGTCATTGT CACTTTAGAT AGTTTTACTT GTTGTGTAAC TACAGTGAGT
54851 TCCCTACTAA TTGAAAATAA CAAAATGCAT AGTCTTACTA ATTAGTTAGC
54901 ACCATGTTTT ATATAAGAAT TGCCATTTTG AAAAGAATGT GATAATATTA
54951 AAATTAACTG ACATTGGAGT TACACTAAAT ATAATTTAAT TATTTGGTTT
55001 GTAAGACACT TGTGGATCTT ACATTGCTGA CATCTTGCTA TAGCATTTCC
55051 TATAACATAC TTTCAAAGTG CAGTGATATC CAGTTGAGAC ACTTCAGGAT
55101 AAATCAAACT TTTCTTGTAG ATCTGATGTG TCTTATTTAG GTCTACACAT
55151 TTGCAAATAG CCTAGACAGT GCTTTTAATT AGCCACCACA GACGAGTCTG
55201 GCATCATCTG CTGTGGGTCA TAGTAACTCC CCGTCATTAA AGTAGGAGGC
55251 CTTTCTCAGT TGTGCTCATA GCAGTGAGCA ATACTATTGA TCACTCTCTC
55301 CTTAAACCCG CCTGGGCCCT CAGCCTCTGC TCCTCTCCAC TCTCCTGAAG
55351 CTCCTCTTCC TCACTGGCAC TCCGTGCCTT CTGCAGACCC ATCCTCTTCT
55401 CTCCAGACAT TACACAGATT CTAAGGCCGC TTCCTCATGT TCTGTATTCT
55451 TTTCCTAAAG AAGTTTCCCC AAGAATGTGG CTTTAGTGAC CAACACATTT
55501 ATATCTTCAG TCTACCTTGA CTTCTACATG GAGGTCTCAA AGACCCCTTA
55551 AACTCATTAT GTCCAAAACC AAACTCAAGG ATATGGCCTC CATGCCCTCC
55601 CCCAGCCTGC TCTCAGAAAC CGGGGGTCA TCCTGGATGC CTTCCTCTTT
55651 CTTTCCCTTC CCCATCACCA ATCCCTCCTC AGGTTTTCTC ACTTCACTTT
55701 TCAGACACCT TGCAAACCCA TGTGCTTCCA CAAACCCAGC TCCACCTCTG
55751 CCTGTGTGTT ATAAGTGCTA TCATTTCCTC CTTCCATGTC TCCTCCACCC
55801 CTGGGCTCCA GCCCCCTGGA CTTTCCCTGG TGTTTTCAAC CTCCTGACAT
55851 TGTCCAGCGC TCTTCCCTTC TGGACTGCCT TCTTTGCACT CATCTGGGAA
55901 CACTCTCCAC GCTTACCCAC TTGGCACTCC TTGTTTCTTT TTTTTTGAGA
55951 CAGAGTCTCA CTCTGTCACC CATGCTGGAG TGCAGTGGTA CGATCTCGGC
56001 TCCCGGGTTC AAGTGATTAT CATGCCTCAG CCTCCTGAGT AGCTGGGATT
56051 ACAGGCACCC ACCACCACAT CCAGCTGATT TTTGTATTTT TAATAGAGAC
56101 AAGATTTCAC CATGTCGGCC AGGCTGGTCT CGAACTCCTG ACCTCAGGTG
56151 ATCCACCCGC CTCGGCCTAC CGAAGTGCTG GGATTACAGG CGTGAGCCAC
56201 TGCACCCGGC TCACTCATTC TTTATATCTC AATTCAAACA TCATTTCCTC
56251 AAGATAAGCC TTCTCTCCCC TCTAAAGTTT GATCAGACCT CAAAAGTCTA
56301 TGTTCTTAGA GCTCCTGAGT TTTTAACATT TATTTCAGTT TTTAATTATA
56351 TATGTGTGTG TTACAGTTTG ATTACCGCCT GTCGTTTTTA CTCCATGAGA
56401 TGAGGGACTA TGTCTGTTTT GCACACCGTT ATATATTTAG CACCCAGGAA
56451 GCATATATGA TATTTATTCA ATACTTGTTG AATAAATGAG GAGTAAATGA
56501 ACAGATCTTA TAAAACAGGC TTATGGAGCC TCAGAAATTG TGTATCACAG
56551 TCCTTTTTGG TACAGCCAGA GTGTAGGGTT TTTCCACTGT ACCGTAACTG
56601 ACAGAGCCAT ATTCACTGAA GCAAATAACC ATCAAGTGAC CCTCAAATGA
56651 CCTTCAGTTT TCTGGAAAGG AAGGTGACTA TAGTTCACAC GAGTCCGTAT
56701 TCTCTGTGGA TTTTGATTTA CCTGAACTCC ATTTGGAATT AACTGTCTGC
56751 TGTGTCATAC TCCAAGCCTT GTTTTCATTA GCATACATGC TGATGAAGTG
56801 CACAGTTAGG AATTTTGCTG TTAAAGGGAC AATTGTAGCA TTGTTGGGTG
56851 AGAGTTAGTT ATAAAACCTT ATAATCAGTG GCAGTTTCAG TGATTTATTA
56901 AGCTGAAAAT TACTTTAATG CCTTTTGTGT TTTCAGCTAT CCTATTCTTC
56951 ATAAGTAGAA CAGATCCTCT TTTTTGTCCA ACCTCGTCTC CTAACCTTTT
57001 TCCCTCAGGT GTGTCATCTA GCCCCACTGG CCTTCTTTAG GTTTCTCAGC
57051 AGCCATGCTT GTTACCTGCC ACAGGGCCT TGCACTAGCT GCCCTCTGCC
57101 TAGAACATTT TCACCCCAGA TCTTTACATT GCTTCTCTAT TCATTTAGGT
57151 TTCGGCTTCA GTACCATCTT CACAGAGCAG CTGTTTTTCA CCATGTGACC
57201 TAAAGTAGCC TGTAATCTCA TGATTACATC ATCCATGGCA TTCACCACAG
57251 CCCATTTATC TTATCATCTA CCCCACCCCA CGAAGAATGT CAACCCCCCA
57301 CTTGCTTGGG CAACACCAGT AGTAAAATTG GAATGATACA GGGAAGGTTA
57351 GCATAGCCCT TGCACAAAGA TGACATGCAG GTTCATGACA CATTACATAT
57401 TTTAATGAAA TGGGAGCATA TTCTTGTTAT TTAATTTTTA AAAATCAGTT
57451 TATCAAGCAA ATGTACAGCG CCATTTTATT TTTCATGCCT ACATTAAATT
57501 CCATACACAT AAAGGTGCAT AGAGGAAACC TAGAAAGATT GCACCAAAAT
57551 TTTAGAATTC TGAGTGATTT TGTTTTTCTT ATCTTTTCTA GGTGTTTTTA
57601 AACATTCCAC ACTAATTTAT ATTACTTTTT CTATTCAGGA AAAAAAAAAA
57651 CAACAGCAGG GTTTTGTTTT GTTTTTTTAA AGTGGTGTGG AAGTTACCCA
57701 TTGAATATAG ATGGGAATCC CAGTCCTGGC TGTTTCCTTT GAAAAGATCT
57751 AGAGACCCCA TGGCACATAT TTATAGTAGC CCATTCTCTC CTAAGAATAG
```

FIGURE 3Q

```
57801 AGGAAGGGTG GGAGGAATTT TGGTGAATGT CTGTACTTGC AGTTTATCCT
57851 ACAGCAAATC GTTAAGACTG TGGGAATAGG TGCTTTGCAT TCTCTAGAGC
57901 TGGAGAATGT GCATCTGGTT TGCCATCCTT CTGTCTACAT CATGTGGAAA
57951 GATGTGGGAG TGTAGGGTCT CCTTAATCTA AATGCAGTGC TGCCCCGCCC
58001 CCCCCTTGGC AGTGTTTCTG TTTCCCAGGC AAGTGTTCCA ATGGATGTGC
58051 TTTATTTTCT CCCATCAGAA ATAAGGGAAT GAGCCCGGGC GCGGTGGCTC
58101 ACGCCTGTAA TCCCAGCACT TTGGGAGGCC AAGGGGGGTG AATCACAAGG
58151 TCAGGAGTTT GAGACCAGCC TGGCCAACAT GGTGAAACCC CGCCTCTACT
58201 AAAAATACAG AAATTTAGCC AGGTGTGGTG GCGGGTGCCT GTAATCCCAA
58251 CTACTCGGGA GGGTGAGGCA GGAGAATCGC TTGAACCCGG GAGGGGGAGG
58301 TTGCAGTGAG CCGAGATGGT GCCACTGCAC TCCAGCCTGG GCGACAGTAT
58351 GAGACTCCGT CTCAAAAAGA AAAAGAAGGA AATGATCTAA TTTGTTCTGT
58401 GCACTGCACG TGGGGGTGGC AGTGAGGTGA ATGGCAGCAT TCTGCAGTAG
58451 TCAAAGCCAG ATGGGTGGGA GAAGTTGGGT GCTAAGAGGG AAACAAAGTT
58501 TACCTGTCTT CTCCTTGATT TCACTCTCAG TTTTATGAGA ATACAGAAAA
58551 ATCATGCAGA GAAACCTGAT GGAATAGTCT CTAAAACTAA AAAATAAGAT
58601 AAGCAATGGT TCTGTCTTAA AAAAAAAAAA GTAAACTCCA TGAAGGCAGA
58651 GACCTTACCT GTCTCATTCC TCTCTCTATC CCCTGGTCTA TAGTAAGGGT
58701 TAAATAAATA TATGCTGAAA TGAATGAGTA ATGACTAAAG TATTTTTGTC
58751 TTTATTAGGA TTTGTAATGC AATAACTAAA AGTCACCCAC AGAGAAGTGA
58801 TGTTTACAAA TCAGATTTGG ATAAGACCTT GCCTAATATT CAAGAAGTAC
58851 AGGCAGCATT TGTAAAACTG AAGCAGCTAT GCGTTAATGG TAATTTCATT
58901 CTTATTTCAT ATATATAATG AACACAGGAT ACAGAGTTGC ATGAGATGTC
58951 AGGAAAAGTG ATGTTCTTAA AAATGTAGAA ATAGATATAT TTAAGGAGTC
59001 TATGGAACTA TTTGTACAAA TTATATATTA TTGTATGAGA ACTTCAGAAC
59051 CTCCTAAGGA ATTAAGTTTA AACTACTTTT TGTTTTAGAG GGGGAAAAAT
59101 GAGTGTATTA AATTTCCTTC AGATGATGAA AGGTATAGGA GAATACTTTT
59151 ATAAAAGCAT TTGCTGAGTA GAACACTGTA TTACCTTACA GACAAACTTA
59201 TTAAGATTGT AATACATACA GTTATACTTT GAGATAGGTG ACTTGACATG
59251 GGTATCAAAC AGCTGTGTTA TATCTGTAGC ATCAGAATTC TGATATATCT
59301 GAGCAAACGT ACCAGGTGGC TTTCATGTGT CCTGCGGGAT GAGTCACATG
59351 AAAGCATCTT TGGTGTAATG TGGGTCCTCC TCAAGAGATC CTCTAAGTCA
59401 CCAGGGAGTC AGCAAAGGCA GCCTTGCAGC AGATCTTGAG CAATGAGTAA
59451 GCACTTCCCT GGGGGAGGGC CTTGCAGGGG CGGGGCAGGG GCAAGTTGTT
59501 GAAAAAACTA GTGTCCTGAA TGATTATGTG CACTCTGGGC AGGGCAGTGA
59551 GGATGCCTGT CCTCATGCAG TGGCTAGCCC TCGGCCACGT GAGCCATGCA
59601 CAGAGGCACC ACTGGCAGCA GGGGTGGGGC AGGGAAGCAG GAGGGCAAGG
59651 CTTGCAGTGA GAAAGCCAAG GGCTAGGGCC TGGGCAGCTG ACCTCACAGG
59701 TCAGGAGGGC CAGGATCAAG GCATAGGCTG AGCAGGGACG GCTGGAATTC
59751 TTAGCTGTTG GGAGTCAGAG TTGGTTGGAC TCCAAGATTT CCCTGAAAGA
59801 GCGAGAGAGA AGATGATGGA GCCCCAGGGG AATGCTTTGT TTTGCTTTGT
59851 TACAGAATTG TAATGTCTTC TTAAATGCTT ATTCCATGTT ATTAAAGTGA
59901 AAATGCATGA TATTTACTTA AAGCTAACTT TTAAATATTA GAAACTGATG
59951 TATCTCTTTA CTCTGATAGG GATCGTATAA AATAAAAAGT AAAAATGTGT
60001 ATGTATATAA TTTATTACAG AGCCTTTTGA AGAAACTGAA GAGAAATGGT
60051 TATCTTCACT GGAAAATACT CGATGGTTAG AATATGTAAG GTTTGTACTT
60101 CTTTACTTTC TTTTCCTTTA ACTTTTTATT TTGAGATAAC TACAGACTCA
60151 CTGGAGGTAC AAAAATAGCA CAGAGGGCCA TGTACTTACT CTTCATCCAA
60201 CTTCCCCCAA TAGTAACATC TCGTAACTAG AGTACAGCAT CCAAACCAGG
60251 AAGCTGACAC TGGGACACTG GATAGCTCTT ACTCACCAGT TCATACATGC
60301 TGTCGTCTGT GTGCATGCCC TTAACACAGC TGTGCGATTT TATCACGTGT
60351 GTAGGTTCAC GTAACCACCA CCACAGGGAG ATACAGACCT GTTCCATGAC
60401 AAGGCTCCCC TGTGCTAGCC TTCTTATAGG TGCACCCTCA TCGCCATCTG
60451 TGTCTGTTGA CTACCACTAA TCTCTTCTCA ATCTCTATAG TTTTGTCATA
60501 AGTCAACCCC TTCCTTTTCA TAAAGGGTTT ATGAATTTCC CTGATGAAAA
60551 AGTACAAAAT GAGGCCAGGC GTGGTGGCTC ATGCCTGTAA TCCCAGCACT
60601 TTGGGAGGCC AAGGCGGGTG GCTCACCTGA GGTCAGGAGT TCAAGACCAG
60651 CCTGGCCAAC ATGGTGAAAC CTTGTCTCTG CTAAAAATAC AAAAATTAGC
60701 CAAGCATGGT GGCACGCACC TGTAGTCCCA GCTACTCAGG AGGCTGAGGC
60751 AGGAGAATCA CTTGAACCTG GGAGGCAGAG GTTGCATTGA GTCAAGATCA
60801 CGCCACTGCA CTGCAGCCTG GGTGATAGAG CAAGTCTCCA TCTCAAAAAA
60851 AAAAATTTAC AAAGTGGGGC CGGTTGTGGT AGCTCATGCC AGTAATTCCA
60901 AAGCTCTGGG GAGGAAGATC ACTTGAGGCC AGTAGTTCAC AACCAGCCTG
60951 AGCAACACAG TGAGACCCCA TCTCCACAAA AAAGTTGGAA ACTAGCCAGG
61001 CATGGTGGCA TGTGCCTGCT GTCCTAGGGA GCCTGAGGCA GGAGGATCAC
61051 TTGAGGCCAG GAGTTCACAA CCAGCCGAGG AACATAGTGA GATGCCCATC
61101 TCCACAAAAA AATTTTAAAA CTAGGCAGGC ATGGTGGCTC GTGCCTGTGG
61151 TCCTAGCTGC TCAGGAGGTG GAGGCAGGAG GATCACTTGA GGCCAGGAGT
```

FIGURE 3R

```
61201 TCAGGGTTAC AATGAGCTGT GATATGCCAC TGCACTCTAG TGTGGGTGAC
61251 AAAATGAGAG CCTGTCTCTT AAAAAGAAAA CAAAAATTAC AAAATATACT
61301 CCTTTGAGAA ATCGTATAAG TAACTAAAGA AACTTTACGG TAATGCGAAA
61351 GCTATGTGCA TTCAGTAGAA AGCAGTCAAT CCTCTCTTGT GATGCTGAGT
61401 AGCAGCAGGG AGCCACAGCT GCCAGTCAGC CACACAGTCT CAGTTTAGGG
61451 TATTTTCAGC TTACAGTGGG TTATCATGGG TCATGAGTTA TGGGAATATC
61501 ATGATCAGAG AGCATCTGTA AAGTGAGAAA TTAGATTTGC TTGATTTCAA
61551 GTACTTTATG TATTTGTAGT GGAAATTTGA TTTTTAACAC TGCTTTTCCT
61601 TTTCTCTCTT CAGGGCATTC CTTAAGCATT CAGCAGAACT TGTATACATG
61651 CTAGAAAGCA AACATCTCTC TGTAGTCCTA CAAGGTAACT AAAGTAACTC
61701 CTGAAAGCAC CATGACCACC ATACCAGCCA GCCTTGGTTT ACTGCTTGTC
61751 CCCATTCAAG TAAATCACAT CAGTTTTAGC TATTTCTTAT TTACTACAGT
61801 ACCATCAAAT ACATTACAGA TTTTGCACAT CATTTGAGTA AAACAGTGGC
61851 ACAGGCTGGG CGCAGTGGCT GAAGCCTGTA ATCCCAGACT TTGGGAGGTC
61901 GAGGCGGGCG GATCACTTGA GGTCAGAAGT TTGAGATCAG CCTGGCCAAC
61951 GTGGTGAAAC CTTGTCTCTA CTAAAAATAC AAAAATTAGT CAGGAGTGGT
62001 GGTGTGCGCC TGTAGTCTCA GCTACTCGGG AGGCCGAGGC AGGAGTATCA
62051 CTTGAACCTA GGAGGCGGAG GTTGCAGTGA GCAGAGATCG CACCACTGCA
62101 CTCCAGCCTG GGCAACACAG CAAGACTCAA AAAAAAAATA AATAAAAACC
62151 AGTGGCACAA GGACTGCAAA TAGAAGAATA GAAAGTAGTC CAGTTTTTAC
62201 CCTTTATTAA ATTATCCTTC CTATTTTATG GGAAGGGTGG GTCCCATCCC
62251 CTAATGGATT AATACTTAGT GTTAATTTTG ACAGGGCATT CTCTCTCTGT
62301 AATTTTGCTG TCTAATTTGT ACAAATTTGT TTTAGTTTAA ATACCTTCTG
62351 GCTCATGCTA GATTATGACT CTAAGGAAGC AGTTTGAGAT GAAGAAATTT
62401 AGACTGAACT GCTGAATAGC TAGTAATGTA ATATTTGGTA GGAATAAACG
62451 GTGATGTAAA AATCTTTCAG TTAAGCAAAG GATAATTACA TATTAAATAA
62501 CTTACAGCTA ATAGAATTTG TAAGTTTGCA GATAAAGTTC AATAGACTAA
62551 AAACTACCTT CGTATAATAC AGTAGTAGGT CCTTTGTACC CATGGCTTCC
62601 CCATCTGTGG TCAACCAACC CAGGACTGAA AATATTGGCG GGGGAAAGCT
62651 TTGGCCGTAA TGAACATGAA CAGACTTTTT TTTTGTTGTC ATTATTCTCT
62701 AAACAGTATA GTATAACAAC TGTTTACATA GCATTTACAT TGTATTAGGT
62751 GTTATAAGTA ATCTAGAGGT AACTTAAAGT GTACAGGAGG ATGTGCATAG
62801 GTTATATGCA AATATTAACA TCATTTTATA TCCAGGACTT AAGCATTTGT
62851 GGATCTTGGT ATCCAAAGGA GGCCCTGGAA TGAGTTCCCC ATGGATACTG
62901 AGGGAAGACT ATATACTCAT GTTGCATAGT ATATGAATAC AAAATGTTGC
62951 TTAAGCTTGC AGAAGTACTT TTTTTTTTTT TGAGATGGAG TTTCGCTCCT
63001 GTCACCTAGG CTGGAGTGCA GTGGAACGAT CTCAGCTCAC TGCAACCTCC
63051 ACCTCCTGGG TTCAAGCGAT TCTCCTGCTT CAGCCTCCCA AGTAGCTGGG
63101 ATTACAAGCA TGCACCACCA CGCCCGGCTA ATTTTTGTAT TTTTACTAGA
63151 GATGGGGTTT CACCTTGTTG GCCAGGCTGC TCTCGAACTC CTGCCCTCAG
63201 GTGGTCTGCC CACCTCAGCC TCCCAAAGTG CTAGGATTAT AGGCGTGAGC
63251 CACCGTGCCT GGCCAGGCTT GCAGAAGTAC ATTTAACAAC TGCCAAACTT
63301 GATTGACTTT AACAAGGCAA AAATCTTTAA GACTCTTAGA AAAAAATCAA
63351 ATAGTAATGT GTCATATAAA GTAATCCTGA ACTGATACAG TCAGAGTGTG
63401 TGTTTAACTC ACAAATGCAT GCAGAGCCTA ATAATCACAA TTTCTCTCAT
63451 CCAGTGGGTG TTCTCATCGT ATTGGAGAAC CCTACTCATC CTCCATTTCT
63501 CCATGCATTT GTAATAGAAA AGGCCTCAGA AGTAGCACTG AACCTTCATT
63551 TTACTAGCAT TTTTATATAC GTTTATTTTT AAACAGTTTG TTAAAAATTT
63601 ACATACTATG GAATTCACCC ATTTTTAATT TGTAATTCAG TAAATTTTAG
63651 TAAATATACA GAGTTCTAGTT TTGGAAATTT TTCATCACCC CAAAAGTCCC
63701 AGCTCCAGGC AGCCACTAAT CTTTCTGTCT CTAGATTTTC CCTTTCTGGG
63751 CATTTCATAT AAATGGAATC ATACAATATG TGGCCTTTTG CCGCTGGCTT
63801 CTTTCATTCA ACATACATGT TTTTGAGGTT CATTCATGTA GTGTGTATCA
63851 GCAATCTTTT CCTTTTTATT TCTGAATTGT ATTCCACTGT TTGTAAATGC
63901 ATTTTGCTTA CCCATTTACC TGTTGATGGA CATTTGGGTT GTTTCCACTT
63951 TGTGGCTGTT ATGAATTATG CTGCTTCATT TATTTAGATC TTTCATTTTA
64001 TCAGCAGTGT TTTATTATGT AAGTCTTATA TTTATTTTGT TAAATCTCTT
64051 AAGTATTTTA TTTTTATGTC ACTGTGAATA TAATTGTTAA TTTCATTTTC
64101 AGGTTTACTA TGTACTCAGA TTGTTGTGTA CAGAATTTCT GTAACCTTAC
64151 TGACCTCATT TATTAATTCT AGTAGTTATT TTGTGGATTC CGTAGGAGTT
64201 TTTACATACA GGATCATATT GTCTTCAAAG ACAGTTTTTA CCTTTTTCTT
64251 TCTGATCTGA ATGCCTTTTA TTTTCTTTTT CTTGCCTAAT TGCTCTGGCT
64301 AGATTCTCCA GTTCAATGAG ATGGAGAAGT GTAGAGAACA GACATCCTTA
64351 TCATCTTCCT GATCTTAGGG AGAGAGTATC CAGTCTTTCA CCAGTGAAAT
64401 GGGAATAACA TTAATTGTAG GTTTTTGTGG ATGTCTCTGA TCAGTTTAAA
64451 TATGTTTACT TTTATTCCTA ATCAGGAATG AAGGTAGAAT TGTATCAGAT
64501 GCTTTTTCCG CATCTAATGA GATAATCGTG TTGGTTTTGT CCTTTATTAC
64551 TGTGGTACGT TACTACAATT GACAGATGTT AAACCAACTT TGCATTCCTG
```

FIGURE 3S

```
64601 GATAATTTGG TTTACTCATA TTTTTATTGA TTTTTACATC TGTAATCATA
64651 AGGGATATTG GTCAATAGTT GTCTTCTGAT TTCCCTGGCT GACTTTGATA
64701 GCGTGGCAAT TCTGGCCTTA TTGGAAAGGA CAACAACTAT AAAAGACAGG
64751 AGGGAATCGT TTGCCACAGC TTCAGTTGGT AGTGAACAGT CCCACTCTCC
64801 CCATTCACTT CTCAGTATTG CCATGTGGCC TGTCAGTAGA AAGATTACCT
64851 TATACTTAAT ACCTTGACAA AAGAGCAGTA GAATGGAGTC TAGACGGATT
64901 TTCTACCACA AACCATTCGA ATGTAAAAAG TATGAGTGAT GAGCTTCTAT
64951 TATCTGGCAA ATATCCATGT ATAAAGACC ATCTCCTATT AAATGCTAAT
65001 TTAGTTTATC TACAAGTCTG TAATATTTTA GAGTTGCTGG AATCCAGTAA
65051 AATTTCCTTA TACAGATTTG GAAGGCAGCC TAGGTGTGCA GAATACTAAA
65101 TTATCTAGTT TACCTTTCCT TCCCTTTCTC TCTCAGCATT TTTCTATGTT
65151 GTAATCATTT TCTTTCCATT TTATTAACAG AGGAGGAAGG AAGAGACTTG
65201 AGCTGTTGTG TAGCTTCTCT TGTTCAAGTG ATGCTGGATC CCTATTTTAG
65251 GACAATTACT GGATTTCAGA GTCTGATACA GAAGGAGTGG GTCATGGCAG
65301 GATATCAGTT TCTAGACAGA TGCAACCATC TAAAGAGATC AGAGAAAGAG
65351 GTAACAAAAT CTTGATGCCT TTTTATCAGT CTTTAAGGAT ACACAAAATA
65401 AAATTTGTGT CATTAAAAGA TGAAGGGGCT TTTAAAAAAT ACTGTATTTA
65451 GTACAACTTA ATTTCCTTAG TCCAAAGCTA ACTAATGGAT TAGAGTTCAA
65501 ATTGATGTAC TTATTATAAA GATTATGCTA ACTATGAAGG TGAAATTTTT
65551 AAAAGTTGTC TATTGAATTT GTCTAAGTGG AAAACTACTG AAAAAATTCT
65601 GAATAAAATA CTGAAAAACA GATAACAAGC ACATTGGCTA TTTTGAAAAA
65651 TCACTTTTGG AATATCATAT TTTCTTAAAA TGGGATACAT AGGTTAAGAT
65701 GAAAAGTTTG AGAGGGCCAC CTTTGCAACA GCTGTGGAGT TAGTGGCTGC
65751 CTCGGATCTC TAGTTAGGCT GCGGAAGGCC TTACAAATAT CTTACCGGCC
65801 AGGCAGGTCA GTCAGATCAG TTTTTAGAAG GTTGTTTCAG AGAGCGCCAT
65851 TTGACTTGTG GTGTCTCATA AAAAATAGTG GTCACCCGCT ACTGCACTTG
65901 GGGACACACC ACGTGACCTA GGCTCATCCC AAAGTGTTTT CTGAAATATG
65951 GGGATGTTTT CTGGATGCTG AGCCTACAGG ATCAACCAAA CATTAGAGAA
66001 GTTTGGTTGA TGGTTTTGTT TTGTTATATA ATCTAAAGAA TTGTTTCTAA
66051 GACATGCTTA AACACATATT TTGCTCTTCC CCCTTCATAT AGTGGCAACC
66101 CGCTCAACTG TGTGCTTTGC TGTTTCAACT TGTTACATGT ACTGGGCAAA
66151 TAAGGGTTGT GATGTTTATC ACGGTTGAAT GTTACTTCTT GGGTTTGATA
66201 GATGTGTATA GCTCAGCTTA GAAGGCAAGT GTTTTAGGCT TCGATGTTTT
66251 CTCATTCATC TCTTCTTTAA CATCAGCAGT ACATTTTGAA GTAAATGTGA
66301 ACGGCTGAAG GATAACATTA AATGATCCCA TTGTCTCTTT GTATTTGCCA
66351 GTCTCCTTTA TTTTTGCTAT TCTTGGATGC CACCTGGCAG CTGTTAGAAC
66401 AATATCCTGC AGCTTTTGAG TTCTCCGAAA CCTACCTGGC AGTGTTGTAT
66451 GACAGCACCC GGATCTCACT GTTTGGCACC TTCCTGTTCA ACTCCCCTCA
66501 CCAGCGAGTG AAGCAAAGCA CGGTAAGCAA CCCTGTGGCT GTGGCTACGT
66551 TTTCCCTGTT TTTACAACTT TATCGAGGCA TAATTGAAGT ATAATTCACT
66601 GCCTATTTAA AATCTTATGA TTTAAAATTC TTACTGCCAT TTTCAGCTGA
66651 AATTTCTGAA TGGATTATTT TGAAGACACA AAAATCTAGG AAATTATTTT
66701 TATGAATGAA CATTTTTTGT TTTACTCTAA TGTAAATGTT TTGTAGTAAA
66751 CCCCTTTAAA GATGTAAATT ACTTTAACCA CCTTAAATGT CATGCTTTTG
66801 TATTTATATT TCACATTTGG GCTATTGGGT AGTAAAAAAC AAAAGCCCTG
66851 TTACACGACA TTTATTTCCT AGGTCAGTAG GATAAAAAGT TGTACAAAAC
66901 AAGATTATTT TCCTTCACGA GTTTGAAGTT TCTGGTCACA ATTCATTGAT
66951 GTAGAGGATT TATGACTAAG CAGGGTCTCA AGCCAAACTT GAAACCATTC
67001 TGAACCAAAG TGCCATTTCA CCCACCTCGA ACCAACAACA GAAGCTGACA
67051 AATGCCGTGG AGACCATTGA GAGAAACAGA AAGGGGCAGC TCTTGTGGAC
67101 CTTCAGGAAG CCTTTCTAGG AAGAGGATTG CCCTCATAGT GAGCTCCGGG
67151 GTCTTCAGCC TCAGCCGTAA GGCCCTGGGC TAGGCAGTGT GACCTAGGGA
67201 GCGGGAAACC TGAGTTCTGG CCCTGGTCTG GGAAAAGTGC TAGGCCCATG
67251 TTCCACTCAG GCTTCAGCCT GAGAGTCCAG GTTGCTAACC TGTAAAATGG
67301 ATCTGTCAAA CTAACACTTA TGCCTTTAGT CTCATTGTAT GAGGTGAAAC
67351 ATTTTGTAAA CTGTGAATCA TTATGCAAAT TTTCCTAAAG ACATATGAAT
67401 TATTCTGGAT TTGTTGGTAT AAAAGACAAA ACACACTGGT CAGTTAAGGA
67451 GCTGATTTTA TTTAGGCTAT TGCAGGAGGG AGAACTTAAT TAATGGGCAT
67501 CCCAAAGAAA AGGACAAGGC CTGGGATTTT ATAGTCAGAA GACAGGGGAA
67551 TCAGGAGGGA GGGCAGTCTC AGTCCACAGG AGCCAGTTCT CAGGACACAA
67601 AAGGCAGGAG AGATTGTCCA GCATTGCCAC TTTTGGGGAA CCCAGGGCTC
67651 AAAGAAACTC AACACCGTCA GCCTGTCTCT ACAAAAAATA CAAAAATTAG
67701 CCAGACATGG TGGTGCGCAC CTGTGGTCCC AGCTACTGGG GAGGCTGAGG
67751 TGGGAGGATG GCTTAAGCCC AGGAGGCAGA GATTGCAGTG AGCTGAGACT
67801 GTGCCACTGC ACTCCAGCCT GGGTGATAGA GCCAGAGTCT GTCCCCTGCC
67851 CACCCCACCA GGAAAGTTTG ACCTTTCCAG ATACTGTGCT GAGAACCAGT
67901 GATACAGGCT TAGAGGCTCC TGAGGCATGG AACGCTCATT TGTTCCTAAA
67951 ATACATGCTC TCCCAGTTGC TTGTTTTTAT TTTTCGTCAC CATAATCATT
```

FIGURE 3T

```
68001 CTTGGGGCCC CTCTCTGCCT CGAGCTAGGC TTTCCCCCTG GCCTTGTTTG
68051 CCTCCTTCAG CTCTTCCCCA TTGTCTCCCG TCACTACCCC GTGCGCACAC
68101 AGTGTGAGCC TGCAAAAGGT GCGTGAGGCG AGGACAAAGA CTTTGGGGTC
68151 TGGGGACTGG GCAGTGCATG GGTGGGTATC TGCCTGGAGG ACTCCCAGCC
68201 CCCAGACACC ACTGCCTCTG CTGCTTGGCT GATGCTGTGT GTGCGGACAG
68251 ACTTCTCACC AGGAATGAAC ATTACTGAAT TGTATTGAGG GAGCTGTAAA
68301 AAATACTTTC TACAAGTATT TCCTCTGCTT TCCCTGTTCA TGTTCTAGTG
68351 CTCTTTTTAA TTTGGCTCTT TCAAAAGCCT TTTCTGACAA ATACTAACAT
68401 GAATCCCCCT CTCCCTTCCT CCCTAGCAGG AACTGGTCAT TGTCTAAGGG
68451 TCGTGATTCT TAACCGTTCT CAGCCCCTTC CACACAGGCA AAAGCCCAAA
68501 GCATTTCTTC CTTTTTTTTC CATTCTGAGG CCACCTTAGG TGCTAGTGGC
68551 CAGGTAGTGT TTATAGAAAA TCTGGTCTCT CTTGGGATAA ATATTTTTAA
68601 TTTTTACCTT TTAAAAAAGA GAACATCTTT TTTTTTTTTT TTAAGACAGT
68651 TTGGCTCTGT CACCCAGGCT GGAGTACAGT GGTACAATAT CAGCTCACTG
68701 CAACCTCTGC CTCCTGGGTC AAGCACTGC TCTCGCCTCA ACCACCTGAG
68751 TAGCTAGGAC TGCAGGCGCA TGCCACCACG CCTAGCTAAT TTTTTGTATTT
68801 TTTTGTAGAG TCAGGGTTTC GCCATGTTGC CCAGTCTGGT CTTGAACTCC
68851 TGGACTCAAG CAATCCGCCC ACCTCAGCTT CCCAAAGTAC TGGGATTACA
68901 GGCGTGAGCC ACCGTGCTTG GCCAAGAGGA CATTTTCTAT ATACTTACTG
68951 AAGGGCCATT AAAACACGTT TGGGTTCATG TTTTACTAGA TTTCAGCTCT
69001 TAACAGTGTT TGAAGCAAAT GGATTGTTTT TAATCCATGT ACATGATGAA
69051 ATGTCAAGTA ACTAAAATTT TTTTTTTTTT TTTTTGAGA CAGAGTCTTG
69101 CTCTATCACC CAGGCTGGAG CACAGTGGCA TGATCTCGGC TCACTGCAAC
69151 CTCTGCCTTC CAGGTTCAGG TGATTCTCCT GCCACAGCCT CCCGAGTAGC
69201 TGGGACTACA GGTGCACACC ACCATGCCTG GCTAATTTTT GTATTTTTAG
69251 TAGAGACGGG GTTTCACCAT ATTGGCCAGG CTGGTCTTGA ACTCCTGACC
69301 TCGTGATCCG CCTGCCTTCG GCCTCCCAAA GTGCTGGGAT TACAGGCATG
69351 AGTCACCACT GCGCCTGGCC AAAACTGTTA AGAGTATGTG TATTTGGTGC
69401 TTAATGAATT TTTACTTATT TGAAATAGAA AATTTTGTAA AACTTTACAA
69451 AATGCCCTGT GCTGTTACAC AGCTTAGCCA TTTCTTGATG ATTCAAGCCG
69501 CCACTGTGCC AGGGAATGCC ACCTGGCTGT GATGTAGTCA TGGCCTCCTG
69551 ACTGCTATAT TCTTGTCCTA ATAACATTCA TTGTTTGCCT TTTTAATAAT
69601 TTCCAAATAA ATTCTTGGGG GTTTTTTTTT GGTAGAAAAT TTGGAGAGTA
69651 CTGAAAGGTA CAGAACAAAG AATCAGACAT TTCCCATCAT CCAGCGACTT
69701 TGTGTCTGGA GTTATTTCCT CCAGCGAACT GTTGTGTATA CACTGCTGTG
69751 GTAGCCTGCT GCCATCAATC AGCTGAGATG AGAGTCCTTT CTCCACATTG
69801 CTAAATGTGA CTGTGCTTCA TAGAAATGGT CTGGGCTGCC TTCCAGAGGA
69851 GCTCCATGTC TTCCTCACAA TGCCGTGGTT GGCTGTCACC CTGTAGCCTT
69901 GTGTTGCCTC AGTTTACTGT GGTGGGAAGC CAGATAACTA GGCTGCACCC
69951 GCCCAGAGTC CGGGCTAGAG GTGGACTCCT GTGAAGGAGG GGTCTCCTGT
70001 GTACATGGTC TCCATGGTTT TAGCCACATG CTAGGACCAC AGGGAGTTGA
70051 TCCCTTCCTT CCTACCCTGA GTCTGTGGTC TGTGATTTGA GATCACTGGC
70101 TCAGTGAAGT GTAGCTCCCC ACTTACGAAG TAAGTTATAA AATTGGTGGC
70151 AGTGATTTCC ATCCAAAGAT TTTGTTAATC CACTTACCAA CAGGTAACTA
70201 CTTAAATGTA CTGACCGTGT GCTCATAAAA GTAAAATACT GTAATTATAG
70251 AAATAAATTC AACATGTTTA AGACTTTCTA GTATCATGTT AGTGAAACTT
70301 CTCTTAATAA CATTCTTATT GCCCAAAGGG CACGGCTTCC TTGGGGTCCT
70351 AAGGCAGAGG GCACCTGAAA AGCACACTCC TTGTTCATGG GGACTGTGGG
70401 GCCCTCTGAG CTCAAAGGCC AGGAGCGTCT CCTCTCTTGA AGTGAAAGTG
70451 CCACTCTGGT GGGTTTTGAG GGCTGCAGTA CAGAACATTT AACCTGTGTA
70501 ATGATGAGTG GCTCATCTGA AAAAAGGCAT TCATGAGAGA ATCTTTAGTT
70551 TTGCAAATAT TTATTTATTT ATTTTGCAGG AATTTGCTAT AAGCAAAAAC
70601 ATCCAATTGG GTGATGAGAA GGGCTTAAAA TTCCCCTCTG TTTGGGACTG
70651 GTCTCTCCAG TTTACAGCAA AGGATCGCAC CCTTTTCCAT AACCCCTTCT
70701 ACATTGGAAA GAGCACACCT TGTATACAGA ATGGCTCCGT GAAGTCTTTT
70751 AAACGGACAA AGGTAAATCA CAGCTAACAA AACGTGATGT TGGCTCACAC
70801 GTAACCAAAC ACCTCTTTTT CAGAACAGAG AGCGTTAAAA GTAAAGGCAC
70851 TTCCAAGAGT AACACTGCTA ATGCGGGTTT CTGAGGGGTC ATTCCCTTTT
70901 TAACTCAAAT GACTGTATCC CAGCTTTCTT CCTGGTGTCT GAGGCCCACA
70951 AAGTCTCAGT ACCTGAGAGT GGGCAGATTG CAGCTTTGAG CCTGCAAGCC
71001 TGATTTACTA AAGCCCCATT TATCCATTTC TTGATGATTC AAGCCGCCAC
71051 TGTGGCAGGG AATGCCGCCT GGCTGTGATG TAGTCATGGC CTCCTGACTG
71101 CTATATTCTT GTCCTAATAA CATTCATTGT TTGCCTTTTT AATAATTCCC
71151 AAATAAATTC TTGGGATTTT TTTTGGTAGA AAATTGCAG ACTACTGAAA
71201 GGTACAGAAC AAAGAATCAG ACATTTGGCC TCCTGACTGC CTCTGTTCAG
71251 TTTGCCATTG TTCTTGATAG AATCGGCCAG GTCTAGTGTT TTTTCTAGCC
71301 CGTCTTAGAA CTTATCCTTA AGCAAATTAG TGGATAGGAG GTACTCTCAT
71351 CCCGCCCCCA TTCAGGCTGA TAGTAACAGC CTAGGTAGAG TCAACACATA
```

FIGURE 3U

```
71401 AAAAAGTGTA ATTCCAGGGG AGGAGGATTA GAATAAGGAC ACAAAGGAAG
71451 GGAGGAAAAT GTTCTTTGAG GCTGAAATTC CATTAATTTT TCATAGTATT
71501 GAGTTTATAT TTGCCATTGC ATCCTTCAAT CTTTCTAAAA AGGGAATCCC
71551 CGGAACATAA TAAAATCTCT TCTGTATAGA AAAGCTACAG CTCCACACTA
71601 AGAGGAATGC CGTCTGCCTT AAAGAATGGA ATCATCAGTG ACCAAGAATT
71651 ACTTCCAAGG AGAAATTCAT TGATATTAAA ACCAAAGCCA GATCCAGCTC
71701 AGCAAACCGA CAGCCAGAAC AGTGATACGG AGCAGTATTT TAGAGAATGG
71751 TTTTCCAAAC CCGCCAACCT GCACGGTGTT ATTCTGCCAC GTGTCTCTGG
71801 AACACACATA AAACTGTGGA AACTGTGCTA CTTCCGCTGG GTTCCCGAGG
71851 CCCAGATCAG CCTGGGTGCT CCATCACAGC CTTTCACAAG CTCTCCCTCC
71901 TGGCTGATGA AGTCGACGTA CTGAGCAGGA TGCTGCGGCA ACAGCGCAGT
71951 GGCCCCCTGG AGGCCTGCTA TGGGGAGCTG GCCAGAGCA GGATGTACTT
72001 CAACGCCAGC GGCCCTCACC ACACCGACAC CTCGGGGACA CCGGAGTTTC
72051 TCTCCTCCTC ATTTCCATTT TCTCCTGTAG GGAATCTGTG CAGACGAAGC
72101 ATTTTAGGAA CACCATTAAG CAAATTTTA AGTGGGGCCA AAATATGGTT
72151 GTCTACTGAG ACATTAGCAA ATGAAGACTA AAATAGGGTG TTTTCTGAAC
72201 ATTTTGAGGG AAGCTGTCAA CTTTTTTCCT CTGAATTAAC ATTGCTAACC
72251 TAGGCGTTTG AATCTCTAAT AACTTTATAT GTAAGAATAA TAGTTGGAAT
72301 TTGCACTAAT ATTTAAAAAC ATGTTGAATC ATGCTTCTTT CACACTTATT
72351 TTAAGAGAGA TGTAAATTTT GTTCCTGTCC TCTTTCTGTC ATTACAGGTC
72401 TGGCTCTTGT AACCGTGATC AAACTGTTCA TGTTGTCTGC TACATTTTTG
72451 TCTCCATCCA TTTTTCCTAC CACCTCCTGA AGGCTATCTG ATAGTCAGTC
72501 ACATTAGCAC CCCAGGCAGC AGACAAGCAG AAAGTTAGGA AATTTGTGTT
72551 TCGTGTCATT TTTAGGAGCA TCTGATAAAA CCTCCAGCAG GTTTTAGGAA
72601 GTATTCATGT ATTTTTCTGG TTACTTTCTG TCGTCTCTAA TTGAACTCAC
72651 CTGATGAAGG TTCAGTGTTC TGGGGCCAGA ATTTATGATT TTAGATCACC
72701 TTCTTTGGAA CCTTAGATCA CTGTGTTTTG AAATCATGAG TTTGCTTTTA
72751 ACTTCATAGG GTCAACTTTA AAATGATATG CACTGTTAAT TTTAAAGCAT
72801 TTGCTGCAGA TAATTAAACT TAGAAGTGCC TTTGACTTTA GGATACAAAT
72851 ATTACAGAAG AAAATATAAT TTCACTTTTT AAAATTGGGG TGGGAAAATC
72901 CCATTGCATA TTTGAAATAG GCTTTTCATA CTAAGCTTCA TAGCCAGGAG
72951 TCCCCAGAGT CTTGTTCCTC TGAAAGCCAC TGGGGAGTGG CCTCTGGGGT
73001 GCTGATTCCA CAGAGGTGTA TGCTGTAGAC AGGAGAGTGC CATCTATGCC
73051 AAAACTCGCC CTCAAAAACA AACAAGGCTT GCTGGGAGGC GTGCTGGGCT
73101 TGGCCATCAG TATTTCCAGT GTGGTAAACT ATTGCTGGCA CTTCCCCCTG
73151 GAAATAACTA ATGAGGTTAC GAGTTGGGCA CCTGCACAGA TGTCCTTCTC
73201 TCATAGTTCC TAATGCTTAG GAATAGAGGA GAAATAAAAA AATGGATTCT
73251 CTCAAAACAC TGCCATTTGA ATAGCGACAG AAGTGCTCCC CCAGCCCCCA
73301 ACTTTGGACA GCAAAGTTGA GGAGAATGAG CAGACACAGT TGTTTGCTTG
73351 ATCTGAATCT CTCTAAAGTA AAGTATTTCC AAACTGTGTG ACAAGAGCCT
73401 ACCTACCACT GTAGCGGTCA AAGCTGAAGC TTCTTACAGC AGTGAAACGG
73451 GGCACCACCT CCCCCACACT CCTCATTCCC CGCTTAAAAC ATGGATACTT
73501 TCAAATTTGA CTGTTTCTTA AACTGCCATC CTAAGATATG GAAAATTTTT
73551 ATAGTAAAGT GTCTAGTTAG CTTATTTCCT TTTCTAAAAC AAGTGTTTTC
73601 AAGATAACTG TATTTTACCT TTATATGTAC TGAATAGCTG TTTCTTTTTG
73651 AATTATTTGC CTTTTAAAAT TTGATAATGT CTCTGGATAT AACAGGACAG
73701 GAGTTCTTAA AAAATATCTT AAGAAATTCA CTTTATGGGT AAACCCAAGG
73751 TTTTTGCCAA CTTGTTGCCT AGAAAATAAG GGCTAGTTTC AGTTTATACA
73801 AATAGAATTA TTAAACATTT TACAGTCCTT GATTAGAAAC CAGACCCAAT
73851 CTCCTTATAA CACCACAGCG TATCCTGCCA TTGACAGTGT AATCACAATT
73901 CTCCCTTTTT CATTTAGCTG CTTTTTTATT ATTACTAAAT GTTTTGGATT
73951 GAGCATTTTT CCCTCTGTAA TTTTCTTCCT TCACGTTTAT TTTAACTCTT
74001 GTAGTATTTT ATTGTTGTTA ATTTACAAGT TTAAAAATAT TAGGTACTAT
74051 TAATAATGGT TAAAAATAGA AAAATGCATA TTTTTGTATG ATAATCAAAT
74101 GTAAAATACT TTTATTTTTG CTGGACAGTT GTTATATCAT GATTATTGTG
74151 CTACAGTTTA TTGTGCATAA TATGAAAAAC AACTATGACA GCCTTCAGTC
74201 GGGCCAGGGT GAAGCTGCTT ATACCACCTC TGCCGTCAGA GGGACATGTG
74251 GTGACAGCAA TGGTGTGGCT GCACAGGGCA CACTAGAGAG AGCTCAGCAC
74301 CCCTGCTGCC CGCCAGCAGA GCCCGTGCTG AGGGAATGCC GCACAGATGC
74351 TGATGCACTG GGTGAAATTT CTAGTATTGA ACGTAAAGGT GTACAGTGTC
74401 TTGCTGTTAT TTTATGATGG AAACTGATTT TGAAACCAAA AATAGCTAAC
74451 TAACTTTATT TAAGGAAAGG ATATTAATTT GTACTAACAG AGGGTGAAAG
74501 CTGTTCACAT TTGTCAACAA AATCTGCTTG CTGCAGTAGT AACCTCAAGT
74551 GGTTAAAACT TGATTTCCCG AGAAAACTAA AACCTTTGTG CCTAAAATTG
74601 ATGACTTGAG TTCAAGTGGG ATGACAAGA AGATGTGTTA TCTTGTTGTT
74651 CAACAGTATT GAATGTGAAG GAAATTTTGA TGGCTTAATA AAATTCCACA
74701 GCGACTGTTT GTTGTTGTCA GTATGAAATC ATCTACTGGA ACACAGTGAT
74751 TGATAGAAGA GGTGAAGGCA TCTTCTCCTA CCCATACTTC TGTGTCATCC
```

FIGURE 3V

```
74801 ATGGGATGTT TCTGCTTGCC CTCTAAAGCC AGGTAGTGAT CAGTAACTTT
74851 TTTTAACAGC AATTCGGAAG TGGCTAAAGT TAAAGCCATG TGGATATTGA
74901 TAGATCATGC CCTAACTGGT CCTTCCATTC AATAAATAAA TATAAAAACT
74951 GGGGAGTAAT ATTCCCCCAA GAAGGCTTCA AAGAAGTCAA GAGACAGACT
75001 GGGGTTCCAG TCCCTGACTC CCGGGCCTGG CGCATGGATA AATCACCTTT
75051 CTACCACACC CCCTTGCCCA GCCTGAGACC CTCCCACAAT GGTGATGAGC
75101 AGCCGATTTG ACTGTACTGT CAACAGAGAA AATACCCCTA TCTAGTTATT
75151 AGGGATGGTC CCAGGGAGAT GGACAATGAA GGACAACTGC CTCTGATAAA
75201 GACTTCATTC CTTTCATGAT CCGGGCCCAA TCAGTAGAAC AAGCATTTAC
75251 ATGTTATAAA TCAACACAAC TTCATGAGAA TGTTTTGATT CCTAAAGAAA
75301 TTGGAATTTC AACTGTTTCA GCCCTTCTTA GATAATCATA AAAGTTTAAC
75351 AGCTAAATGT GTATAGGGCA GTAAAGAAAA ACTTAATTCA AGAATCTCGG
75401 TTTCCCATAT AATTAATTAC TTGAAGGAAA CACTGGTTAT GCTAGTTTTT
75451 AAATTTTTTT TTTTTTGAGA CAGAGTCTCG CTCTGTCTCC CAGGCTGGAG
75501 TGCAGTGGTG CAATCTCGGC TCACTGCAAG CTCCACCTCC CGGGTTCACG
75551 CCATCCTCCT GCCTCAGCCT CCTGAGTAGC TGGGACCACA GGCGTGTGCC
75601 ACCAAGCCCA CCCAATTTTT TGTATTTTTA GTAGAGATGG GTTTCACCAT
75651 GTTGGCCAGG ATGGTCTCGA TCTCTTGACC TCATGATGCG CCTGCCTCGC
75701 TCAGCCTCCC AAAGTGCTGG GATTACAGGC ATGAGCCACT GTGCCCAGCC
75751 ACTACTTTTT TATAAAAAAA ACCTAAAGAT GAATCATCAC TTGTTTTTGA
75801 GTTTTCCAGC TTTTTGCACA TCTAATCATA TAGATGCATC CAGCTCCAAT
75851 AATGGTCAAC AAAATTTTTC TCTTTTAAAA AAGTTCATTA TGAGCTGGGT
75901 ACAGTGGCTC AATGCCTGTA ATCCCCAGCA CTTTGGGAGG CCAAGGTGAG
75951 TAGGTCAGTT GAGGTCAGAA GTTCCAGACC AACCTGGCCA ACCAACATGG
76001 TGAAACCCCG TCTCTACTAA AAATACAAAA TTTAGCCAGG CGTGGTGGCG
76051 CACACCTGTA GTCCCAGCTA CTGGGGACCC TGAGGCAGGA GAATCACTTG
76101 AACCTAGCAG GCGGAGGTTG CAGTGAGCCG AGATCACACC ACTGCACTCC
76151 AGCCTGGGTG ACAGAGCGAG ACTCTGTCTC AAAAAAAAAA AAAAAAAAAA
76201 AAGTTTATTA CCCACTGTGT GGAATCAATG AGTGTATTCA AGCAAACACT
76251 GTTTTGTGAT ATGCAGACAC TGTAAAATGA CAAGTCAAAC TATCAGGTTT
76301 ATAATGCACG ATAACAAAAT TAAATAAAAC ATGTTTTATA CTCTTGAAAA
76351 TCTTACATTA ATGTATGACC AAATATCCCC AATTCCATAC CTTTTAGCTA
76401 AGGCTTTGGC TCTTAGCTCC AACTGCAACC ACATGGCAGA CTTCTACTTC
76451 AGCCCCCAGC TTCTGCAGTT CAGCCAGTCA GATCATCTGC TTATGTGAAA
76501 GACGATCATT GGGGCCTTTA ACTTCCACCA GCTGGAAAAG AAATTTTTAA
76551 AAGTTGTTAT TAGTATCTTA CTGAATGAAA AGCCATTCAA GTAAGTTGTA
76601 GTTGTCACTG ACAACTATTT AAATGGCTCT TCTGCTCTCT CACTGTATTT
76651 GTAAGTGTAA CACAAATATA CGGATGGTCC TTCACTTACA ATGGTTCACC
76701 TTAGGATTTT TTGACTTAAA AATGGTGCAA AAGTGATATA CATTCAACAG
76751 AAACCATACT CTGAGTGTTG ATCTTTTCCC AGTATGATAC TCCATGCTGG
76801 GCAGCAGCAG TGAGCCACAG CTCCAGTCA GCCACATGAT CATGAGGATA
76851 ACCAGTACTC TACGGTTTGC AGTGAACTAC ATGATCTGCC CAACTGTAGG
76901 CTAATGCACA CATTCTGAGC ACATTTAAGG TAGGCTAAGC TAAGCTATGA
76951 GGTTTGGTGG GATAAATATG TTAAATGCAT TTTCAACTTA ACAATATTTT
77001 CAGTTGATGT GTAGGATTTA TCAGGACATA AGGCCATCAT AAGTTGAGAA
77051 GCGTCTGTAT GTAGCTAAGA AATTTATTCA GAAATTCTTC TATTCTGTAG
77101 AAACTAGACA GTTCTTCACA GAGGATGAGT AAACTGATTC TTAGTATAGC
77151 AAATGAAAAA TTGTTTTAAA GCATGCACTG GATTTTACTT CCTTGCTTAA
77201 AACCCTCCGA TTACTCTGTT ACATTTTCAA TTAAATCTAA CCTTCTTGCC
77251 ATGACCAGTC TCTTCCCTAC CCCAAGGCCC TCACTTCCAC TTGCTACTTG
77301 CTGTTCCCGC TGCCTGGGAC ATTTCTCCCT GTTCTTGACA TGCCTGACTT
77351 CTTACCTTTC AATGCTCAGC TTAAACTGAT CTGGAGAGGT CACAGCTCTA
77401 AGTATATCCT CCCTATGCAC TTCTTTCATG GCATTCATAA GATAAAAATA
77451 TATACTACAT GTCATCTTCA TGAAGGCAAG AATTGTGTGT TTTGTTCACT
77501 ACACATCACT AGACTTGAAG ACACAGCAAT AAAAACTATA GGTAAAATAT
77551 AGAAAAAAAT TGTTTAAATA CAGCATTTAG CAGCCTAAGG GACATTTAAT
77601 TAGAGTCCCC AAAGGAACGA GAAAAAAAA TACTTAAAGA AAAAATGGCC
77651 AAAAATTTTC CAAATTTGAT GAAAACAGTA AACCCAAAGA TTGAAGAAAA
77701 TCAATGAATC CCAGGCACAC AAATGTAACG GCACCCTAGG AAATATCACA
77751 ACTGTATAAT CAGGGGATAT AGTCAAAGCA GCCAGAATTT TTAAAGCCAG
77801 AGGAAAAAAA AAGATTCTCT GATTGGAAAC CATGCTAGTT AGAAGACAGT
77851 AGACTAATAT TTTTAAAGTA TTGAAAAATA ACTGTCAACA TAAAATTCAT
77901 TGCACGGAGA AAATATCTTT CAAAACAAA GGTGAAATAA AGGCTAAGAC
77951 ATACAAAACC TAAATACAGC CATCCCTCAG TATCCATGGG GGACTGATTC
78001 AAGGACCCCC TCTGTTACCA AAATCCATGG ATGCTCAAGT CCCTGATATA
78051 AAATGGCATC GCATCTGCAT ATTCTAGCAC ATCTTCTCAT ATACTTTAAA
78101 TCATCTCTAC TTATAATACC TAATATAAAT GCTATGAAAA TAGTTGTTAT
78151 GCTGTATTTT TATTTGATTT GTTTATTGTT GTAGTTACTT TTTATTGTTT
```

FIGURE 3W

```
78201  TTCTTTTTTC  CAAATACTTT  CAGTCCATGG  TTGCATCTAC  AGAAGCAGAA
78251  ACCATGGATA  CAGAGGGCTA  ACTACTGTAA  TTCATTACTA  GCAGAACTTC
78301  TAGACATGGA  AATTTTTTCT  TTTTCTTTTT  TTCTTTTTTT  TTGAGACAAG
78351  GTCTCACTCT  GTTGCCCAGG  CTGGTATACA  GTGGTATGAT  CTCAGCACAC
78401  TGCAGCCTTG  ACCTCCCAGC  CTCAAGCAGT  TCTCTCACCT  CAGCCTCCCA
78451  AGCAGCTGGG  ACTACAAGTG  CACACCACCA  CACCCAGCTA  ATTTGTTTAT
78501  CGTTTTGTAG  AGATGAGGTC  TCACTGTGTT  TGCCCAAGCT  GGTCTCCAAC
78551  TCCTGAGCCC  AAGCAATCCG  CCCACCTCAG  CCTCCCAAAG  TGCTGGAATT
78601  ACAGGCGTGA  AAGGAAATTC  TTCAAGCAGG  AGAATGAGAC  TACACAGAAA
78651  CCTGGATCTA  CACAAAAGAA  TAGCAAGCAC  TGGAAATGCT  ATGTACATGA
78701  GTAAATACAG  ACTCATTAAT  CAACTGTAGA  AAGCAAAAAT  AATATGTTAT
78751  AGAACATATA  ACACGTAGAA  GTAAAATATA  TGAAAACACC  ACAAAGGCTG
78801  GAAGGGAAGA  TATATATTAT  TGAAAGGTTC  TTTTTACTCT  AAAGTGTGTA
78851  TCACCTGAAG  GTGGATAAGT  TTAAGATATA  TAATATACTA  ACGCAACCAC
78901  TTCAACACAA  TGAACAGTTA  CAGCTAACAA  GCCAGCAAAG  CTATCAAATG
78951  CAATCTTTAA  AAATAAGACA  GGGCCAGGCA  CTGTGGCTCA  TGCCTGCAAT
79001  CCCAACACTA  AGAGACCACG  GCAGGTGAAC  TGCTTGAGCC  TGGGGATTTG
79051  AGATCAGCCT  GGGCAACATG  GTGGAACCCC  ATCTCTAAAA  AATACAAAAA
79101  CCACAAAAAT  TAGCCAGGCA  TGGTGGCGTG  CACCTGTGGT  TCCAGCTACT
79151  CAGGAAAAAG  ACAAGGGACA  AAAGAGTTCT  GAGACAAAGA  GAAAATAAGT
79201  ATCAGGATTT  AAAGCTAAGG  ATATCAATAA  TCAAATTAAA  TGTAAATGTT
79251  CCAAACACCC  CATTAAAAGA  CAGAGGTTAA  GTTGGATTCA  AAAGTAAGAC
79301  CCAACTATAT  GATGCCTACA  GGAAATCCAC  ATTAAAAATA  AGATAAAACA
79351  GGTCAAAAGT  AAAAGAATGG  AAAAATGTAT  CATGTTAACA  TTAAAAAAAA
79401  GAAGGCTGAA  GTGGCTACAT  GTTGACAATA  TCGGACAAAG  TTGATTTCAG
79451  AGCAAAGATT  ACCAGGTGTA  AAGGGGGGGT  CACTGCATAA  TGATAAAAGG
79501  GTAGACTCAT  GAAGAGGACA  TGACAGTCCT  AAAAGTCTAT  GCGTCTTATA
79551  ACAGACCTTC  AAAATACATG  AAGCAAATAG  TGATAGAAAC  GCAAGAAGAA
79601  ATACACAAAT  TGGCTGGGCA  CGGTATACTC  TCAGCATTTT  GGGAGGCCAA
79651  CGTGGAGCCC  AGGAGTTTGA  GACCAGCCTG  GGCAACATGG  TGGAACCCCA
79701  TCTCTACAAA  AAATAAAAAA  AATCAGCTGG  GCATGATGGT  GCATGCCTAT
79751  AGTTCGGGCT  ACTCAACAGG  CTGAGGCAGA  AGAATTGCTT  GAGCCTGGGA
79801  GATCAAGGCT  GCAGCGATCC  AGGATCGCAC  TGCCACTACA  CTCCAGCCTA
79851  GGTGATAGTG  AGAGTCTGTC  TCAAAAAACA  AAAACAAAAA  AAAAAGAAA
79901  AGAAATACCA  CAATTATAAT  CAGAGATATC  AATATTCTCT  CAATAATTTA
79951  TAGAACAAGT  AAATAAGAAA  TCAGTAAGGA  CACAGACAAC  TTAAACAACA
80001  CTATCAACCA  ACTTGACCTA  ATTGACATTT  AAAAATACTG  CCCACAACAA
80051  ATGCTAAACA  CACATTCTTT  TCAAGTACAA  ACAGAATATT  CACCAGGGAA
80101  TACCATATTC  TGGACCATAA  AACAAGTCTC  AACAAATTTA  GTGGGATTCA
80151  AATCATACAA  AATATGTCCT  CTGAATACAA  TGGAGTTAAA  TTACAAATCA
80201  ATAGCAGAAA  GATACCTGAA  AATCTCTCAA  GTGTTTGGAA  ATGTAAATGA
80251  CTCACTTCTA  AATAAGCCAA  GGATCAAAGA  AGAGTCAAAA  GGGAAATCAG
80301  AAAGTATTGT  GAACTGAATG  AAAATGAAAA  CAACTACTAA  ATTTGTGAGG
80351  TTCAGATAAA  GCAGCACTGA  GAAGGAAATT  TGGAGCACTA  CCTAACTCTA
80401  TTAGAAAAGA  AGTTCTCAAA  GCAATCACCA  TAGCTTCCAC  CTTGAGAAAC
80451  TAGGAAATAA  AAAAACAAAT  GAAACCAAAA  GCTGATTCTT  CGAGAAAATC
80501  AGTAAATTGA  TAAACCTCCT  GCCAGACTCA  TTAGGGAAAA  AAGAGAAAGA
80551  ACACAAATTA  CCAATATCAA  GAATAAGAGC  ATGACAGAGA  TAAAGATTCT
80601  ACAGATATTA  AAATACAGTA  AGAAATACAT  GGCCGTGTGC  GGTGGCTCAC
80651  ACCCTGTAAT  CCCAGCACTT  TGGGAGGCCA  AGGTGGGCAG  ATCTGAAGCC
80701  AGGAGTTCAA  GACCAGCCTG  GCCAACATGG  CAAAACCTCA  TCTCTACTAA
80751  AAATACAAAA  AAAAAAAAAA  ATTATCCAGG  CATGGTGGTG  CACAGCTGTA
80801  ATCCCAGCTA  CTAGGGAGGC  TGAGGCACGA  GAATCACTTG  AACCCAGGAG
80851  GCGGAAGTTG  CAGTGAGCTA  ACTCACGCTA  CTACACTCCA  GTCTGGGCGA
80901  CAGAGCGAGA  CTCCATCTCA  AAAAAAAAAA  AAAAGAAAAG  AAACAAATAT
80951  AAACAACTTT  AAGACAATAC  TTAAATGAAA  TGGACAAATT  CCTTGAAAGA
81001  CACAAACTAG  CAAAGCGCAA  TCAAGAAGAA  ACAGATAATA  TGAACAGCCT
81051  TATGTTGTTT  AAAAATAAAT  TTAATTTATA  GCTTTAAATT  TTCCTCCCCC
81101  CAAAATCTCC  AGGCCCATAC  TGCTTCACTG  GGGAATTCTA  TCAAATGTTT
81151  AGGGAATAAT  ACTAATTCTA  CACCAACTAT  TCCATCCCAC  TCTGATGCTG
81201  GTATGACTCT  GAAACCAAAA  CCCAACAAAG  AGATAATAAG  AAAAGAAAAG
81251  TACAGCTCAA  TATCCTTCAT  GAACATATAT  GCAAAAATTC  TTAATATTTT
81301  ACAAAATCAA  CTCCCATTTT  TGCTGATCAA  AATAATGCTG  TTAAGATACC
81351  AATTCCTCTC  AGATTGGTCT  ACAGATTCAA  AGGAATTCCA  ATTAAAATCT
81401  CAGCTGGCTT  TTTTTTTTTT  TTTTTTTTTG  AGATGGAGTC  TTGCTCTGTC
81451  GCCCAGGCTG  GAGGGCAGTG  GTGCCATCTC  GGCTCTTGAC  AACCTCCACC
81501  TCCTGGGTTC  AAGCGATTCT  CCTGCCTCAG  CCTCCCAAGT  AGCTGGGACT
81551  ACAGGCGCCC  GCCACCACAC  CCGGCTAATT  TTTTGTATTT  TTAGTAGAGA
```

FIGURE 3X

```
81601 CGGGGTTTCA CCATGTTAGC CAGGATGGTC TCAATCTCCT GACCTCGTGA
81651 TCCGCCCACC TCTGTCTCCC AAAGTGCTGG GATTACAGGT GTGAGCCACC
81701 GTACCCGGCC TCAGCTGGCT TTTTTTTTTC TTGGAAACTT AAAATTTGAT
81751 GTTATAATTC AAATAAAAAT GCAAAAGAGC CAGAACAACT TTGAAAAACA
81801 AGTCATTATA GGACTTACAC TACCTGACTC CAAGATGTAT CTAAAGCTAC
81851 AATAATCAAG AAATACAGAC AAACAGATCA ATGGAACCGA AGAGTATATA
81901 GAAACAGACC CACATATATA TGGGTTACTG ATTTTTGACA AAGATACAGA
81951 GGGAATTCAG TGGAGGAAGC ATGGTCTTCT TGACACATGG AGCTGGAACA
82001 AGTGGATATC CACACACCAC AAATGAATTC CAGTGCATGC CCCACACTGT
82051 ATACAAATGG CGTCTCAAAT GATCATAAAA CTGAATGTAA AACCTAAAAC
82101 TATAACACTT CTAGAAGAAA ACAAAGGAGA AACTCTTTGT GACCTTGGAT
82151 TAGGCAAGTA TTTCTGACAT GTGACACCAA AAGCATGATC CACTAGAGAA
82201 CAAATAAGTT GGATTTTGTC AAACTTTGAA ACCTCTGCTC TTCAAAAGAC
82251 ACTATTAAGA AAATGAAAAG ACAAGCCATA GACTGGGATG AAATGTCACT
82301 GATAAAGGAC TTGTATCCAG GATATATAAT TTTTTAATCT CAAAACTCAA
82351 TAATGAGAAA ACAAATCACC AGTGATGGGC AGCAGGGCTG GGCTAGTGGA
82401 CAGCGTTCAA GGAAGTGTTC ACTCTCTGAG CTTTTTAAAA AATTTTTTGT
82451 GGGTACATAG TAGATGTATA TATTTATGGG GTACATGAGA TGTTTTGATA
82501 CAGGCATGCA ATGTGAACTA AGCACATCAA GGGGAATGGG GTATCTGTCC
82551 CCTCAAGCAT TTATCCTTTG AGTTACAAAC CATTATACTC TTTAAGTCAT
82601 TTTAAAATGT ACAATTATCG GTAAGCTTCT AAAATAGCTC CTGGTGTCCA
82651 CACCCGTTGT GACCCCCTCC CTTTGAGTGT CAGCTGGACT AGAGACTCGT
82701 TCCTAACCAC AGAATACAGC AGGAGTGATG GAACATCATG TCCACATCAA
82751 GTCATAAGAG ATGGAGCTCT GTCTTGCTCA CACTCTGGGG CTCCTCTCAC
82801 CCGCCTGCTC TGATGAAGCC AGTCGCAGGG GACAGGCCCA CAGGAACCCA
82851 GGCCCTCGGC CCAAAAGCTC TCAAGGAATT CAATCTTGCC AACAGCCACT
82901 CAAGAAATGC TACTTGTGG CCTCTGATTC AGTTGCTAAT AAGGTTACCA
82951 ACAGGACTTT CCATTCTGCC TCAACTGACC TTAAAGTGAC GGCTCTGGGA
83001 GTTCCACACC ACCAGGTCGG GGAGGCCCCC TCGACAGTGT CGAAAGTCAG
83051 CAGCCAGGTG CCTGCACACA CCACTGAGCA CAGGGCCCCC CAGGCAGGAG
83101 ACAAGATCCT GAACACAAAA CACAGGACAG TTAGCCACTT CCCTCGTGAC
83151 AGAGAATGGA AATAGGCTCC AGGGATCACG AGACGGAGAA AAGCTCAGTG
83201 TATATGTAAT TCAGTGCACA TGGACCCCAG GCCCACCATG CGCTGTTCTG
83251 CTGCTTGTAC CAGAGCTGCA GAGCCATGGC TGGAATCCCA CTGGCAAGTG
83301 GTGGGAGACT GGTCCTCCTG TGGTCAGTTT CCAGGCTTCT GCAGCGTGGC
83351 CATGCTGGGG AGCGCTGAGG AAGAGGGATG TGGAGGATGC ACTCAGGAAC
83401 GCGACAGCAT GGCCTCATAG AGGGCAGCAG TTGAAGGAAC ACAGAAGGTA    (SEQ ID NO:3)
```

CHROMOSOME MAP POSITION:
Chromosome 15

ALLELIC VARIANTS (SNPs):
DNA

| Position | Major | Minor |
|---|---|---|
| 85 | T | C |
| 1614 | A | G |
| 2648 | T | G |
| 6773 | A | G |
| 8144 | A | G |
| 9488 | A | C |
| 9730 | A | G |
| 10317 | A | C |
| 10391 | T | C |
| 10682 | T | A |
| 11633 | - | T |
| 12054 | G | A |
| 12938 | C | G |
| 13719 | G | A |
| 14333 | T | - |
| 14753 | A | G |
| 14831 | - | A T |
| 15157 | G | A |
| 16242 | G | A |
| 16698 | A | G |
| 17152 | A | G |
| 17624 | T | - A |
| 18268 | - | G |

FIGURE 3Y

| | | |
|---|---|---|
| 18786 | A | G |
| 18813 | - | A C |
| 22061 | A | G |
| 22205 | C | T |
| 22527 | A | G |
| 22876 | A | G |
| 23351 | G | A |
| 23821 | G | A |
| 25487 | C | T |
| 30858 | C | T |
| 31014 | A | C |
| 31437 | C | T |
| 35341 | G | A T |
| 35346 | A | G |
| 36164 | G | A |
| 36620 | A | G |
| 37074 | A | G |
| 37546 | T | - A |
| 38190 | - | G |
| 38708 | A | G |
| 38735 | - | A C |
| 41983 | A | G |
| 42127 | C | T |
| 42449 | A | G |
| 42798 | A | G |
| 43273 | G | A |
| 43743 | G | A |
| 45407 | C | T |
| 45985 | T | C |
| 46198 | A | G |
| 46793 | - | A |
| 46923 | - | A |
| 47851 | A | G |
| 48875 | G | T |
| 50844 | A | C |
| 51267 | C | T |
| 54073 | A | G |
| 54206 | C | G |
| 54488 | C | T |
| 54511 | T | - |
| 56070 | T | A |
| 57119 | G | C |
| 58184 | G | A |
| 58210 | A | G |
| 59015 | T | C |
| 59201 | T | C |
| 60695 | G | A |
| 61592 | A | G |
| 62577 | G | A |
| 62580 | C | T |
| 62596 | C | G |
| 62682 | G | T |
| 64509 | C | T |
| 64898 | A | G |
| 67072 | A | G |
| 67283 | T | C |
| 67432 | C | T |
| 68079 | C | T |
| 69067 | T | A |
| 69122 | G | A |
| 69951 | A | G |
| 70498 | G | A |
| 70850 | C | G |
| 70874 | C | T |
| 70923 | A | G |
| 71276 | G | A |
| 74663 | G | A |
| 74598 | T | C |

FIGURE 3Z

| | | |
|---|---|---|
| 81794 | A | G |
| 81752 | - | T |
| 81652 | G | T C |
| 81899 | T | C |
| 82828 | G | C |

Context:

DNA
Position

85       AAAAACAGAAAAATGGGTGAAGCAGGACAAAACAGTGACATTAGAGCCAAAAGCAGGGGG
TAGGCAATAACACCAAACATACAG
[T,C]
GTAGTCAAGGGCATCAGGGTCTGAGAAGAGGTTATAAAACTAGTTCTACGGACTGAATTG
TGTTCCTCCAAAATGCTAATGTTGAAACCCTAACCCCTGGTATGGCTACATTTGGAGATT
TTAGGAGGTAATTAAAGTTAAATAAGGTAGTAAGAGTGGGGCTCTAATCTGATAGGATTA
GCGTCCTTACAAGAAGAGACATCAAGAGATCCCAGAGAGCATGTTATATACCCTCCCCGC
ACTGTGTGAGGACATGGTGAGATGGCAGCCATCTGCAAATCCGGCAGAGAGCCCTCACCT

1614    CCAAAATCTGCTCCAGTCAGAATTACCGTAAGAGCTCAGAAGTGACCTGTGCTTGGCGGC
ACCGGCCCACTTTCCCAGTGCCGGTTCCTCGCATCCTGGGCGCAGACGGGGTGACCGCCT
GACCCCTGGACCCGAGTCACCTTTCCCTGCCCTGAGCTCCTCCTTGAGAGCTTCAAAACA
ATGCTCGCCCAGGCCGGAGGGCGAAGTCGGCCCATGTGTAAGTCAAGGGAACTGTCCCAG
GACTGCAGCCCGGCCAGAAGACGCCCCGCGCCGCCGTCCCAGGCAGCCACCGCTGCCGCC
[A,G]
TGGCCCCCGCAGGCCGCCGTAGGCCCCCGCGGGCCGCCTGACCCCTGCGGGCCGCCGTAG
AAGGACCCTCCAGAGGCCGCGCTCTTGAGATGGCCGTCGGGCTCCGCTCCCCGCGGGGCC
CCGGCTGAGGGCCCGCCAGCGGGCACCTGGCGCCACCGCTGCGTTCCGGCACTAGCACGG
GACACGGTCAGGGAGCGGCGGGCCGCGGCCTTGCGCGCGCCGTCTCTCGGGGCGGGGCAC
CGGGCCCCTTCCGGGGATGGGCCCCGGCGCCCGCGTCGGCCTGGCTGTGCCCGGCCCCTC

2648    CTGCCCGAAGTTCTGTCGTCCGTAGTTTTGCGGAGTGTTGAGGCCCAGGGGAGCCTTGGG
AGCTGGGGTTTTCTTTAGTTTCCAACCCATCGACCCTCCCTCCTATGACCGCCAGCATGA
TTGCAGCGCTTGGGGTCACTGGTCGAGGCGGTTACCCGTCTGTCATAAATGTGAACACCT
GGAAGCGACACTGGCAGTTTAAACATTTTTTATTATTAGGCTTCCAAGTCGATAATGAGC
AGATCTTAAAAACAGCTCAGTTAATATGCGAAAGAATTTAAATGGGGGGCTGTGTGTCTT
[T,G]
CGCATGTGTCATCACTTAGAAAACAACATTTGCTGTAGCATTTTACGGAGGGTGGGGGGA
TTGAGATTTTGATTTATTTTGCTAATGTATTTCAGACTGACGATAAGATCAATTCGGAAC
CGAAGATTAAAAAACTGGAGCCAGTCCTTTTGCCAGGTAAACATTAGTTAGGATTCTAAC
AGATACTTTAGCAACGTATTTTGGTTTAAGATTATTCTGCCGACTAGTATCATGTGGTTA
ACTTCCCTTCTCTCATTAAACTTTCTCCAGTTAAAAGTCTAGTGACTGAGAGGAGAAAAA

6773    CTTAAACTGTTACCTTACCCAGGCACACACACAGACTAACTTTCAGATTTAGGAGTAAAG
GGAAGACTGTGTTATTTTATGCCAGACATTTCAAGAGATTTATGTCGGAGCCTGGAATTG
AAATAGAGTACTCTGTCAAAGTAGTCAGCTTTTGTGTAGGCTTTCTCTTTATCTTCCTCT
CATTATGTGAATTTCATTCTTTCAGTGATTATATTGTATATGTAAAATCACTCCAATA
CTTGAAAACTGAGTTTGACTTTTAAAGTGTGTGTGTGTATATATGTTTGTGTTCCAGTAT
[A,G]
TATTTGTTAAGAGCATGTAATGCCAGACTCTGTCCTGTTTAGCTGCTGGACTGGTGGATC
GGTTCGGTGAGGATGTGAGTATCTCCTGGGTGCCAGGTCTGTCCTGGATAGCGAGAATGC
TGGAGGTGTCATGTGCCTGTATCGCAGAAAGGCGTGGGGTGAGCCCTAAGCTGCCTGTTG
ACAAGGTAGAAGACTGTGACCTGGATCACTGGTACCCAGATTCCAGCCAGGGCCTGGTAT
CAGATTTGGATGAAGTTTTTACCAGCCCTTGGTCAAAGTGAGAAAATTAAGAAAAGTGCA

8144    ATGTTGTTAGGTTGGTACTAAGGGAAGAGGTCCTCTTTGGTAATGCTGCAAGTGGCCACA
GTTCCAGAAGAATCTGTTGAAAAGAGTGAAGAACCCCAAGGAAGTGCACTAATGTGTGTT
GAAGTCCCTGGGTTTCATTGTCCTTGCAGGCCAGGTGACACAAAAGCCTTGTATTCTTCT
TTTTGCTAAGCTATTACCAGGCATGTTTCTGAACATACTTTGAACGAGGATCCTTAACTA
ATATAGCTTGCAGATTAATCATCATAACAGTCTTGTCAGCTAGGATACCAGTTTATCTCC
[A,G]
TTTGACAGATGTGAAAACTATAGTTTGCTGAGGTTAAGTAACTTGCCCAGTGTCACACAG
CTAGCAAGGCAGAAGCCAGAGTTCTCTGTCCAGCTCCCAGGCTGTGCCACTAACTGCTAAG
TAGCACGGCCCACCTGGCTGCACTGGTGACACTAGGGTACAGATTTATGCTTTGGAACTG
TTGGGGAGTAGATTGGATGTCAGCCTAGAGGGAGTTCTCTAGTGAAGTAAAAAGAGCTCT
GTCCTTGTCTTTGCCCTTTTCACAACAGTGACAGATTTTGACCCAGCGTGCAGAAGAACT

9488    GTTGTTAATTCCTTAAAGGCAAAGACTTTATCTTTCAAGTGTTTTATGTAATTCCTTTTT

FIGURE 3AA

```
              GTAGGTAGGCTTCATAAATGATTGTAGACTGATTTTTGTAGTATTTTAATTTGTGAATGC
              ATTGTTTTTGAAAGACCAAAGGACTTGTAACACACCCTCAGAACAGTGAACAGTGTAACT
              GTACTATCTTAGCATTAGCTTTATACCTTACCCGTAGAGCCTTAGGAATGTTTGGAGCTG
              TCCATTCCTTAGGCTTTTGCTGCAGTACCTTAGGCCAGCATTTTCTTACCCCTCCAAACT
              [A,C]
              CTCACTATCGTTGTCAACACCGTTCATGAACCTCCATAAATAAAATCCTACTTAAGCAGG
              ATAAAATCCAAATTCTTTAACCTTGTAATTTGCTAACACTGTACCTCACTGACTTCATTT
              CTCAGTATTTCCCAATATTGATATTTGCTTCAATCATGCCGCTTCCTTGGTCTCTTCCAG
              ATGCCTTATTCCTTATTTAGGACCTTGTTACTGTTATTATCACACATTCTCTACTATCTC
              AATGCTCTTCTTCCTTCAAGATTTCATTCTACAATTTTTCCTGAGATCGGCACTATACCC

9730     CATTCCTTAGGCTTTTGCTGCAGTACCTTAGGCCAGCATTTTCTTACCCCTCCAAACTAC
              TCACTATCGTTGTCAACACCGTTCATGAACCTCCATAAATAAAATCCTACTTAAGCAGGA
              TAAAATCCAAATTCTTTAACCTTGTAATTTGCTAACACTGTACCTCACTGACTTCATTTC
              TCAGTATTTCCCAATATTGATATTTGCTTCAATCATGCCGCTTCCTTGGTCTCTTCCAGA
              TGCCTTATTCCTTATTTAGGACCTTGTTACTGTTATTATCACACATTCTCTACTATCTCA
              [A,G]
              TGCTCTTCTTCCTTCAAGATTTCATTCTACAATTTTTCCTGAGATCGGCACTATACCCTT
              CCTCCTGCCCCATCCTATCCTGAGTGCTACTCACTGGACTTGGTACTTGCTTTTTTACAT
              TGTGTGTTAGTACCAGCATTAAAGATTTGTGTTTATCTTCCACATAGTTTCAATTTCCTG
              TGATAACTTTTGAGCCACTTTAATTCCTGAATTTACCTAAAGCTAGGGTGACCAGCTTGT
              CCCAGTTTGCTTGAGACTGTCCTGGTTTTAGTGCTAAAAATACCACATCCCAGGGAAACC

10317     ATCCCAGGGAAACCCCTCTGTCCCAGACAAACTGGGGCAGTCACCCTACTGTTAAAAGCC
              CAAGTTAAGTTATGCTTTTGGCCTCTACACATCCCACAGGTTAATTAGCCACGTGTGCCG
              TGAGACTTTGCCTTAAACTGTGTTCCAACCTAAAATGTATGGGAAACATTATTTCTGTCC
              ATCAAACGTGATGAATTTCTAAATGTATAAGGTGTTAGGAAAGATAATACAACATGGTTT
              TGAGGTCCTCAGGGAGTTAAAAACTTTCCTAGCCATATCATTTGGAGGTTTATTAACTGT
              [A,C]
              ATTGCATTTCCCTTCTTATTTATATTTACAGATGAAAGGGTCTTGAGAAAATAAACTTGG
              ATTTCTTGATTTCTTCCCAGGTGTTAGTAGAAACCTTTGGCTCATCATCCTCTAATTTAG
              AAGGTTTTTGCTTACCGCACACTGAAGCTAATTTCCTGCTTTTTCTGGCTTCATGAGGCT
              TCCTTGTGGCATCCTGGGAAGTGCTTGGTGCTGTAAATGGTCCCACCGTGGCTGATGGCA
              TAGCACAGAGCTGGGAGAGAGGAGTCTGGTGGGTTCTCACAAGCAGGCCAGCCAGCCGTC

10391     CTTTTGGCCTCTACACATCCCACAGGTTAATTAGCCACGTGTGCCGTGAGACTTTGCCTT
              AAACTGTGTTCCAACCTAAAATGTATGGGAAACATTATTTCTGTCCATCAAACGTGATGA
              ATTTCTAAATGTATAAGGTGTTAGGAAAGATAATACAACATGGTTTTGAGGTCCTCAGGG
              AGTTAAAAACTTTCCTAGCCATATCATTTGGAGGTTTATTAACTGTAATTGCATTTCCCT
              TCTTATTTATATTTACAGATGAAAGGGTCTTGAGAAAATAAACTTGGATTTCTTGATTTC
              [T,C]
              TCCCAGGTGTTAGTAGAAACCTTTGGCTCATCATCCTCTAATTTAGAAGGTTTTTGCTTA
              CCGCACACTGAAGCTAATTTCCTGCTTTTTCTGGCTTCATGAGGCTTCCTTGTGGCATCC
              TGGGAAGTGCTTGGTGCTGTAAATGGTCCCACCGTGGCTGATGGCATAGCACAGAGCTGG
              GAGAGAGGAGTCTGGTGGGTTCTCACAAGCAGGCCAGCCAGCCGTCTCTAGCACACCACC
              CTTTTACTGCATAAAAAGCACAGGCGTATAGTCTCCCTGAAAACTTCAGATCCTCTAGAG

10682     CTTGATTTCTTCCCAGGTGTTAGTAGAAACCTTTGGCTCATCATCCTCTAATTTAGAAGG
              TTTTTGCTTACCGCACACTGAAGCTAATTTCCTGCTTTTTCTGGCTTCATGAGGCTTCCT
              TGTGGCATCCTGGGAAGTGCTTGGTGCTGTAAATGGTCCCACCGTGGCTGATGGCATAGC
              ACAGAGCTGGGAGAGAGGAGTCTGGTGGGTTCTCACAAGCAGGCCAGCCAGCCGTCTCTA
              GCACACCACCCTTTTACTGCATAAAAAGCACAGGCGTATAGTCTCCCTGAAAACTTCAGA
              [T,A]
              CCTCTAGAGCTTTGAAGCTTTTATTCGGAGTTTTCTCTTCAAGGTCACTTAATTTAACAT
              GTGAACAAGAGCAGTCTCAGTACCTTCTTTTTATATATCCTATCTGGGAAGAGGCCACTT
              TGTGTCTTCTTTTTCTTCCCTGTGTATAAGCTAGTTTTCTGGCCCACAGTGTTTCAGTGC
              ATGGCAGGAGCTTATGACAGCTCCTCTTCAGCATTCCTTTTTTTTAAAATTATGAACAAA
              TGACTTACGTGAGCAGACAGCTGTGCTACATGATCCAAATATTTTAAAGACTGGTTCTGC

11633     AGGATAGAGTTAATGTGAACTCTTCAGCCAGCTTCCGCTAATGTTAATAGCTTATGTAAC
              CTTGGTGAATTTAGCTCAACTGAGAAACCAACAATACTATTAGCTAAACTGCAGGTTTTA
              TTCGTATTTCCCTAGTTTTTTCCACAAATGTTCTTTACCTGTTTCAGGTTCACATCCAGGA
              TACTACATAGCATTTAGTTGTCGTGTCTCCTTATTCTCAATGTCTCAGTCTGTGACAGCT
              TTTTCATCTCATCTTTCAAGACCTTGACGTGTTTTTTTCTATTGAATTTGATTTTCTTTT
              [-,T]
              TTTCTTTTTCTTTTCTTTTTTTTTTGAGATGGAGTCTTGTTCTGTCACCCAGGCTGGAG
              TGCAGTGGCGTGATCTCCGCTCACCGCAACCTCCAGCTCCCGAGTTTGAGCGATTCTCCT
              GCCTCAGCCTGTTGAGTAGCTGGGAGTACAGGTGCGCACCACCAGGCCCAGCTAATTTTT
```

FIGURE 3BB

```
        TGTGTTTTTAGTAGAGACGGGGTTTTACCATGTTGGCCAGGCTGGTTTCGAACTCCTGAC
        CTCAAGTGATCTGCCTGCCTCAGCCTCCCAAAGTGCTAAGATTACAGGCATGAGAATGAG
12054   GCCTCAGCCTGTTGAGTAGCTGGGAGTACAGGTGCGCACCACCAGGCCCAGCTAATTTTT
        TGTGTTTTTAGTAGAGACGGGGTTTTACCATGTTGGCCAGGCTGGTTTCGAACTCCTGAC
        CTCAAGTGATCTGCCTGCCTCAGCCTCCCAAAGTGCTAAGATTACAGGCATGAGAATGAG
        ATTTTTATTTTGCCTCAAATAATACATATTAAAGCTCTTTAAACATAGAAATATACTACT
        ACAAAAGGAAAAATTTTATAATTACTAGATTTCTGTTCTAACAAACCACCCCCTAGAAAC
        [G,A]
        TCATCAAATTGACTTAAAAATGTAGACGTAATTTCAGACTTAGAGAAAAGTTGCAAATAA
        CAGAAGAATCTGTGGATACCCTTTCCTTAGATTCCCCAATAAAACCTTGACGCTTTGGAA
        GATTATTATTCAGGTAGTGTCTTGTAGTATGCCTCTTGGTTTGGATTTGTCCGATGTTTT
        CTTTTGATTAAGCAGAGGTTATGGATTTTGGGAAAGACCCACAGAGGTGGTATCCTTTGC
        CCTTGTGTCATGTGAGCAGGCACAAGACATCAACATGATTGGTTATTGGTGAGGTTAACC
12938   ATGCATGTTGCACACAGCAGTCATTCAGTCTATGACATTGAGTCCATGATAGTTTCTTGA
        TCTTTACTGTAATGTTCTAATCATGATTTTGTTTCCTTATTCCTCCTACATTTATTAATT
        GGAATTCTTCTGTGAGGAAGATTTGTCTCTTCTCCGCCATTTATTTATTTATTATTCAGT
        CATCTGTTGACAACAGTATGGATTCACAGATACTTTTTAATTTACTTTCTAATCCGGCAT
        TTTTGTTATTTCTTTTGTTGCTCAGATTGTTCCAGCTTTGGCCATTGAGAGTTATTTCAT
        [C,G]
        TTGGCTCTTGTATCCTTTGGAAATGCCGTCCCCCCGCTTTTCTTCACCCCCACTTCCATA
        TTTTCTGGTATTCTGGCATTACCAGAGGCTACAGACTCATCTTCTGTTTCCCCTGCCCCA
        GCCTTGGAATCAGCCATTTCTCTAAAGAGCCCTAGTTCTTTTTATTGGAAAATGGTATTT
        TAAAAGCAAGAGCTGGGTACTGAGTGTGTATGTTGTTGCTGGAGCGTCACTGCTTTTAGC
        ACTTTCAGAGGGCAGAGCTAGAAAACATACACACATGTACCAACCCAGGTGTACACACAT
13719   TGTAGCTCATTGGTGAGAAAGGGATCTTTTGACTTGACTTGCATGGACACATTCTAGTAG
        GAAGGTTGTCTGTCCTCATCACTCCTGTGAGTGGTCCTCTAGAGCTCTTTGAAATGGCTA
        CAACATTGCAGATCAAAAACACCTGCTTTTCAGGTGCTTCACTTCTCACCTTTCAGATGG
        GACATGCCCAGTTGTGTCTTCTAAACCTTGTTTCAGATAATTTTAAGAGTTGTCGCTTCA
        GTAACTATCTCTAACACAGGGATCAGCAAACCTTTTCTGTGAAGTGCAGTAAATATTTTA
        [G,A]
        GCTTTGCGGACCATAAGGTATTTGTTTCAAGTACTCAGCTCTGTCTTTGTCCTGTGAAAG
        CAGCCATAGATGGCACATGAACAAATGAGTATGGCTATGTCTTACTAAAATTTCATTTAC
        AAAAACAAGGTTTTGTATTTGGCCCGTGGGCCATGGTTTACCATCCGTTGGACCCATTAA
        GTATATTCTCCTCCTCTTCTTTGTCTCATTCTCACTGCGTTCATAGGCTTGATACGTTAA
        CATTCGTGCATCAGTAAAAGAATCTGGCTTCTAGAGAAGAAGGGCTGTCCATGGGCGTTT
14333   AGTTTGTTTATGGTACTAGTGTGGCCACAAGGCTCTGCCACACAAGCTCTGTCTCTTCCT
        TCCTGTTATTACTTCTGCTTCCCTTCTCAGGAACCTGAAATCATATGGTAGTTTGTTTGT
        TTAAGTGATTTTTTTTTTTGAGATGGAGTCTAGCTCTGTTGCCCAGTCTGGAGTGCACTG
        CAACCTCCACCTCCTGGGTTCAAGCAGTTCTCCTGCCTCAGCCTCCCAAGTAGCTGGGGC
        TACAGGTGCGCACCACCACGCCTGGCGCACCACCACGCCTGGCTAAATTTTTTTTTTTTT
        [T,-]
        AATAGAGATGGGTTTCACCATGTTGGCTCAGGTGGTCTCAAACTGACTTCAGGTGATCCA
        CCCGCCTCAGCCAAAGTGTTGGGATTATAGATGTGAGCCACCACGCCCAGCCTTTAAGTG
        AATTTTTATTTGAGTATAACATGCATAACAAGTTTGTGTGGATCATAAGTCTTAGAAGTG
        GATGAATTTTTGTAGCAAGGTTTGAAGAGTCTGTTTTTAGATGAGTTTGCTAAGGTGGCA
        CAGTATGTGATGATTCCGTGTAAAGAAGTCATTGTTACAGGGCTGTGTCCTCTATCTGAA
14753   GAATTTTTATTTGAGTATAACATGCATAACAAGTTTGTGTGGATCATAAGTCTTAGAAGT
        GGATGAATTTTTGTAGCAAGGTTTGAAGAGTCTGTTTTTAGATGAGTTTGCTAAGGTGGC
        ACAGTATGTGATGATTCCGTGTAAAGAAGTCATTGTTACAGGGCTGTGTCCTCTATCTGA
        ACTGGCATGGTTAGTTTAGTTGTTTAAATTGAGGGCCTGCTTACAATTCATATCTAAGAT
        TTACTGGAGAGGAGAAAGGGTTGAGTATTCAGTGGCCCAGAATCTGATATGGGAATTGGT
        [A,G]
        AGGTTTATGTTCAAGGAGCCAAAGAAGATTTAAATTTTATGTATTTGAATTACTCAGTGC
        GTCTATATATATATATTTGGTCATCTTAAATTTTTTTTCTCGTTAGAATTCAGTTAAG
        GCCAATATTTGAACTTTAATAAGTTTTGGTACTTGCTACACTGCAGTACATTTAATTGTA
        TGTAATTATAGGGAAAGACTATGGGAATTGAAGTCAGAACACTTGGTTATAAGTGCGAAG
        TCCACTACTTCTTTTTAAGATCTTAGGAAAGTGATTTAACCTCTTTGGGTGCAAATCCTT
14831   AGGTTTGAAGAGTCTGTTTTTAGATGAGTTTGCTAAGGTGGCACAGTATGTGATGATTCC
        GTGTAAAGAAGTCATTGTTACAGGGCTGTGTCCTCTATCTGAACTGGCATGGTTAGTTTA
        GTTGTTTAAATTGAGGGCCTGCTTACAATTCATATCTAAGATTTACTGGAGAGGAGAAAG
        GGTTGAGTATTCAGTGGCCCAGAATCTGATATGGGAATTGGTAAGGTTTATGTTCAAGGA
        GCCAAAGAAGATTTAAATTTTATGTATTTGAATTACTCAGTGCGTCTATATATATATATA
```

FIGURE 3CC

```
                [-,A,T]
                TTGGTCATCTTAAATTTTTTTTCTCGTTAGAATTCAGTTAAGGCCAATATTTGAACTTTA
                ATAAGTTTTGGTACTTGCTACACTGCAGTACATTTAATTGTATGTAATTATAGGGAAAGA
                CTATGGGAATTGAAGTCAGAACACTTGGTTATAAGTGCGAAGTCCACTACTTCTTTTTAA
                GATCTTAGGAAAGTGATTTAACCTCTTTGGGTGCAAATCCTTTATCTGTGTATTAAGGAA
                ACCATCTGCCTTCCTCACCTTACAGGTTGTTGAAAGAATCAGACAGGACAGATGTCCTAT

15157           GTTAGAATTCAGTTAAGGCCAATATTTGAACTTTAATAAGTTTTGGTACTTGCTACACTG
                CAGTACATTTAATTGTATGTAATTATAGGGAAAGACTATGGGAATTGAAGTCAGAACACT
                TGGTTATAAGTGCGAAGTCCACTACTTCTTTTTAAGATCTTAGGAAAGTGATTTAACCTC
                TTTGGGTGCAAATCCTTTATCTGTGTATTAAGGAAACCATCTGCCTTCCTCACCTTACAG
                GTTGTTGAAAGAATCAGACAGGACAGATGTCCTATTTATAGCTCTTTAATGCATATGTAG
                [G,A]
                CAAGCAGTGGCAGTTCTGTGACTCTTCTCTAACTTACATATCATTTACCCAAACAGCCCT
                TATCTTCCAGCCAGCTTGGCTGCTTAGCCATATTGAATTACTAGTTTCTCTTATCTAGAA
                CAACTTCTGCCCAACTCATGGTGGACAGAACCAAGTGTCATGAAGTGATTTTATTCATTC
                TTGCATTCAGCACTCTTTTCACAGGCACCTACCCTGTGCCAGACACTGTTCTAGGCACTA
                ACATTTCAGCAGTGAATAAAGTCAGTCCATCTTCTACCCTCATGGAGCATATAATCCTGA

16242           TTCTTCATGAATTGGTAGGAGTTTGGAGTTTGTCAGCAAACATTCTATCGGGCTAAAGGT
                TTTTATAATGAAAGAAATAGGCAAAGTGGATCAGTACACTCACTTTTCTACCATTGACCC
                TGGAGACAGATGGCTTAAAATGTTCTGCGTCTAGTTGACTTTTAGATCTTGAAATTAAGG
                TTTAATGATGACCAAGCTTTAAATAAATTGTAGAAAAGTATTCTTTCAAAAGTACATTAT
                AACTTTTATATTGGTTTCTTATATTTATTTCTTTTAATCTTTTCTTTTAACTCAAACTAC
                [G,A]
                TTTTAAGGTTTTGTTGCCTACTAAGTTATAATCTGAGTGCAGAAGGAAACTTGATTTGGC
                TTTATGGAATACATTTTACATTCAGTGAAGCTGAGCTCTGTTTCTCATTCCTTACAAAAG
                GAATCAAAGGCATTGGTTTGAGAGATCAAGTCATGTGTTAATAAAACACAAATATTCCAT
                CAAGTAATACTCTGAAGGAGCAGGTGTAGTTTATTTCTTCTCCAGAAAGTCTTCCAGCAG
                ATAAATAATGAGAGGTAGTATGGCATAGGAAAAAAGTACACTGAAGTCAGCCTTTCTGGT

16698           TGTTAATAAAACACAAATATTCCATCAAGTAATACTCTGAAGGAGCAGGTGTAGTTTATT
                TCTTCTCCAGAAAGTCTTCCAGCAGATAAATAATGAGAGGTAGTATGGCATAGGAAAAAA
                GTACACTGAAGTCAGCCTTTCTGGTTCAACCAGCTCAGACCCCTGAGCTATTTTTGCCTC
                AGTTTTACGCCTTGGAGAACAATGCCTTGTCATTACTATTCACTTTATGACCATACAGTG
                CCTGGCACCTGGTGGGCAATTGGTGAATGTTTTCACTATCCTCATCCTTGCCCTCATGAA
                [A,G]
                CACTCCTTCTAGGTCCCACAAAGACCGTTGGTATTTTATGACAAAGTACCTTACAAATAT
                TTTTCTTTTTTTAAAGGAGAAATTGTCGTAAATGAAGTCAATTTTGTGAGAAAATGCATT
                GCAACAGACACAAGCCAGTACGATTTGTGGGGAAAGCTGATATGCAGTAACTTCAAAATC
                TCCTTTATTACAGATGACCCAATGCCATTACAGGTGTGTTTTATTAGTACACTGTTTCAT
                TCTATCAGGCTTTCAACTCTAAGTGGTACATATTATTATATAAAACATAGGTATGGAAAA

17152           AAGCTGATATGCAGTAACTTCAAAATCTCCTTTATTACAGATGACCCAATGCCATTACAG
                GTGTGTTTTATTAGTACACTGTTTCATTCTATCAGGCTTTCAACTCTAAGTGGTACATAT
                TATTATATAAAACATAGGTATGGAAAAGTTATAGTAGAAGTATTAGGTAATGCAATGTTT
                GGGATAAATTATATTAAGATTTAAAGTAAAGTTTAAGAAGAATGTTGGAACTTGCTAGAG
                GAGTATTAGTGAGAGGATTGTAAGTCACCTTGCTTTATTTATCCTCTGTGATCGTTCATT
                [A,G]
                TATGTCCTTTTCATTAAGGAAGTTATTCCCTCTGTTGCAGATCTTTTAACCTGCTTATAA
                AAATGACATAAAGAGAAAAGGTTGTTTGCTAAATGATTTTATAAATGCCACACATTTTAG
                TGATTTCATAGGTTTTTTTGTTGTTGGGTTTTTGATTTTTTTTGTTTTGAGCCTGGATCTC
                GCTCTGTCTTGTCTCCCAGGCTGGAGTGCAGTGGCATGATGTCGGCTCACTGCAACCTCT
                GTCTGCTTCCTGGGCTCAAGCTATCCTGCCACCTCAGCCTCCTGAGTAGCTGGGACTACA

17624           CTGGATCTCGCTCTGTCTTGTCTCCCAGGCTGGAGTGCAGTGGCATGATGTCGGCTCACT
                GCAACCTCTGTCTGCTTCCTGGGCTCAAGCTATCCTGCCACCTCAGCCTCCTGAGTAGCT
                GGGACTACAGGTGCATGCCACCACTCCCGGCTAACTGTTGTATTTTTTTGTAGAGATGGG
                GTTTTGTTATGATGCCCGGATTGGTCTTGAACTTCTGAGCCCAAGCAATCTGCCTGCCTC
                CCCCTCCCAAAGTGCCAGAGTACAGGCCACTGCACCCAGCTACCTTTTTTTTTTTTTTTT
                [T,-,A]
                AACTAATTAGAGTTATTTTCCTAAAAAGTTAAATTCTAATTTCTAGGAAGAGTGAAGAAT
                AGTATCGATTTAAAAATTTTCAGTAGCCCTCTTGCTATTTTATGTTCTTACTGGAAAGTA
                ATAGTTCCATGTAATTTTGGTTTTTTAGAAGTTCAGGCATTCATTTGATTAACTTAAAAAC
                CCTGGACTTTTCTGTCAGCCATTTTGTATTTTGTTTTATAAAGTATTATACACACTTACC
                CCTAGATCTTTCTTTATAGTAATTGTTCTTTAATGAAATATTGGTATATGAACTGTAAAC

18268           TGTAGTCACTCACTAATTTACCATAATTATTATACTGTACAAATATTTATTGTACTGTAT
```

FIGURE 3DD

```
         ATTTGTGTGTTCATTACAGTCTTATGTAGGTATATTTAGACTAAATTTAAGGCACTTAAA
         GATACCCACTGTGTAGGGACAGTAGCTTATTTGGATATAGGCTTGTGTGTTTCTCTTTGT
         TTTTAGCTTCATAATGATCATTGGCCCCAGACTTCACTGTAAATGAGAAGCAGATACCTG
         GAACAGCTTAAATCCAGTACCACTATTAGGAAAAAGTAAACCAGTGCCCTACTGACAGCA
         [-,G]
         ATTGATAGTGTTAACTACGTCCTTAGTTTGAACATGCAAAACCTTTTCTAATGGTTTTTA
         TTTCTAGTAGACTTTGTGCTTTAAAAAGATAGTTATTTTGCACTTTAAAATCTTCAGTGT
         GAAAATCAAACATGATTTTACCCACTTAAAATCTGATGACCTAAGAGCCCTTTTTTCTTT
         AATATGTTGTGGCCAGCTTATCCAGATCTAGACATGCAAATGCTTGCTGGTAAGGTGATT
         GATGATATTCCCTATCTTAGGTATTATAATAAGATTGTTGTGTACATTTTAACCTAATTT

18786    AAATGCTTGCTGGTAAGGTGATTGATGATATTCCCTATCTTAGGTATTATAATAAGATTG
         TTGTGTACATTTTAACCTAATTTCTATCTGTCAACATTGGAATGGCCCTAGCTACCTAGA
         CAAAAGCTTTTTGTGCTTTTTAGAGATAACTGTCACAGTTTATCATCACAGTTTAAGGCT
         TATACTACCATTGTGAGATTATTGGGAAAAGAATTAATATGAACATAATTTTTTATTCCA
         GAAATTCCATTACAGAAACCTTCTTCTTGGTGAACACGATGTCCCTTTAACATGTATTGA
         [A,G]
         CAAATTGTCACAGGTACGTAGTATTCCGTACATACTCTAAAAGTCAATTCCACTCTGGAA
         GTATTATTTGAAAAGTCATACCTCTCAAAATACTTGGATTGGCGTTTTATTTCTGTAAGT
         TTACTTTTGCCGTTTTTTTGAGTCCCGGGAACATAAAGAGGGATATGTTAATAAATTATT
         TTAAAAGGAAGATATAAAATGTATAACTTTTCATAGTTTCTAGGTTTTTTGTCCTCTTTT
         TAATTAAAATTAATCATTAAATGTATCTAGATGGTGGTTTTATGCAAATAATCATTTAAA

18813    ATATTCCCTATCTTAGGTATTATAATAAGATTGTTGTGTACATTTTAACCTAATTTCTAT
         CTGTCAACATTGGAATGGCCCTAGCTACCTAGACAAAAGCTTTTTGTGCTTTTTAGAGAT
         AACTGTCACAGTTTATCATCACAGTTTAAGGCTTATACTACCATTGTGAGATTATTGGGA
         AAAGAATTAATATGAACATAATTTTTTATTCCAGAAATTCCATTACAGAAACCTTCTTCT
         TGGTGAACACGATGTCCCTTTAACATGTATTGAACAAATTGTCACAGGTACGTAGTATTC
         [-,A,C]
         GTACATACTCTAAAAGTCAATTCCACTCTGGAAGTATTATTTGAAAAGTCATACCTCTCA
         AAATACTTGGATTGGCGTTTTATTTCTGTAAGTTTACTTTTGCCGTTTTTTTTGAGTCCCG
         GGAACATAAAGAGGGATATGTTAATAAATTATTTTAAAAGGAAGATATAAAATGTATAAC
         TTTTCATAGTTTCTAGGTTTTTTGTCCTCTTTTTAATTAAAATTAATCATTAAATGTATC
         TAGATGGTGGTTTTATGCAAATAATCATTTAAAATATCTTCCAAAGCAAAGTTAAAACCA

22061    CCTTCTGGTTGTCTTGTTGGTGTTGTTTCAATTGTATTATGACAAAATTAGATTGCTTTG
         GGCACTTGTACTCATTAATATTCATCCTCATTATCCTCGAGCTGTCACAGGAAAATAGTG
         ATATTTGGGAAAGGTCTGTATAAAGAAAGAAGGAATTTGATGGTGCAGAATTGGACATCT
         AACCTCATAGCAACTTAGAACCACCATTTTCTTTTGCAGAACCTTTGCTCAAAACTGAAG
         GGCAAAATAATAAAGGTTGTTTTTAATGATTTATCTATATATCTGTCTGTGTAGATAAAG
         [A,G]
         TAAATATATAGATACACATGAGTGACAAGTGAAATACATGCCTTTTGTCTCCACTTTGTT
         CTCTGATTAGTGGGTTGTGAATCACTTCTTCAGGAATACTTTATAGAAGTGAATTCCATT
         CATCTGATTAAGGAACAAGTTGGCCTTTTCATGAACTGTCATTTTTGACTTGAATCTGGT
         ACTGTTTTTTGGTGGCTTTCAGGCCACAGAAATAAACCACTTTTGTTTGCAAATGAGATA
         GAACTTAATGAGGTTTGAGTGTTTCCTGGATTTGAGTTTCTTCAGTACTGCACCCCAGGT

22205    GAAAGAAGGAATTTGATGGTGCAGAATTGGACATCTAACCTCATAGCAACTTAGAACCAC
         CATTTTCTTTTGCAGAACCTTTGCTCAAAACTGAAGGGCAAAATAATAAAGGTTGTTTTT
         AATGATTTATCTATATATCTGTCTGTGTAGATAAAGATAAATATATAGATACACATGAGT
         GACAAGTGAAATACATGCCTTTTGTCTCCACTTTGTTCTCTGATTAGTGGGTTGTGAATC
         ACTTCTTCAGGAATACTTTATAGAAGTGAATTCCATTCATCTGATTAAGGAACAAGTTGG
         [C,T]
         CTTTTCATGAACTGTCATTTTTGACTTGAATCTGGTACTGTTTTTTGGTGGCTTTCAGGC
         CACAGAAATAAACCACTTTTGTTTGCAAATGAGATAGAACTTAATGAGGTTTGAGTGTTT
         CCTGGATTTGAGTTTCTTCAGTACTGCACCCCAGGTGATCTTAGGAAAGAAACCATCCAC
         TGTGGGTACTTCTGGCTTCTGTCCAGAGAAGATTATCAGCTTTGGTCCAAAAATTGATTT
         AAAAGTAGTTTACTTCTTTTTCTCCAATAAAATATTTGCCATAATTTAATGTCTTTAATA

22527    TGACTTGAATCTGGTACTGTTTTTTGGTGGCTTTCAGGCCACAGAAATAAACCACTTTTG
         TTTGCAAATGAGATAGAACTTAATGAGGTTTGAGTGTTTCCTGGATTTGAGTTTCTTCAG
         TACTGCACCCCAGGTGATCTTAGGAAAGAAACCATCCACTGTGGGTACTTCTGGCTTCTG
         TCCAGAGAAGATTATCAGCTTTGGTCCAAAAATTGATTTAAAAGTAGTTTACTTCTTTTT
         CTCCAATAAAATATTTGCCATAATTTAATGTCTTTAATACCAACATTTTCTTCATTTCCT
         [A,G]
         TGGTAGCCAGGACAAATGAAGTATTTCAGATCTTTCAAAAACTCTTAGGATGAAAGGTAG
         GAATTTGGACTTAGGTTTTTAAAATAGTGTGTATGTAAAAGTGCAAAGAATGGGGCCCTG
         GCTTTCTCTTCTCGGAGTGTTCCACAGTAACAACATGAAGACAATCCAGGTACACAAGTT
```

FIGURE 3EE

```
            TGTATGTGCCTTAGTCTGTGTGTCCAAAGAGGCCTCTTACTTAGGTCATATGAACATAAG
            TTATACACTTGAAATTCACTACTGAAAAACAATGTATTTAGTTCGAGTTCTGCCACCCCA

22876       GATGAAAGGTAGGAATTTGGACTTAGGTTTTTAAAATAGTGTGTATGTAAAAGTGCAAAG
            AATGGGGCCCTGGCTTTCTCTTCTCGGAGTGTTCCACAGTAACAACATGAAGACAATCCA
            GGTACACAAGTTTGTATGTGCCTTAGTCTGTGTGTCCAAAGAGGCCTCTTACTTAGGTCA
            TATGAACATAAGTTATACACTTGAAATTCACTACTGAAAAACAATGTATTTAGTTCGAGT
            TCTGCCACCCCAAAAAAAATCAACGAGTAATTCAACTGACTTGCAGTTTTACAATATTTTT
            [A,G]
            TAGACTTCTTTCAGCGTAGATGCTTTTGGACATACTCATTTGTTTCCTAACCTGATGTGA
            TATTGTGCTATTTTTAAGGGGCTTTTAAAAAATACGCTGTGTTGGGTTTTGCCTTGAAAA
            TAGGCTTTATTTCTTTTTTGCCTCATGGCCACAAAAAAAGGATGTCCATGATCAATGATC
            TGTGAATTTCTTTTCTGTAAACAGAAAGAGCATGTAACTGCTTTCTAATTGTTTTGGAGA
            ATGTGATAGACATTAGTATTATTATTATTGGCTTGGAGCATTTTCCTTAATATGTTGGTA

23351       ATGATCTGTGAATTTCTTTTCTGTAAACAGAAAGAGCATGTAACTGCTTTCTAATTGTTT
            TGGAGAATGTGATAGACATTAGTATTATTATTATTGGCTTGGAGCATTTTCCTTAATATG
            TTGGTAACTACTTTTGTCAGTGAATATTAGTGTAGCCACTGTTGGACACAGAGCACCGTC
            AGAAAGCTACTGAAGTGGTGCTGCAAAGTGCAGACATCTTCAGATCTTTACTCAAGTCTG
            TGCAGAGAGGTCTTTCTTGGTCTCCTTCTCTACTTTTTAGCCTGTCTCCCTCTTCTCACT
            [G,A]
            TAACACTTCATATTCCCCTTCCCTGCTCTATTATTTTTCTCTTTTAGCATTCATAGTTAT
            CTAACTTTCTGTATTTTTTCTCTTTATCTTGTTTAGTGTCTGTCTTCCCACTAGAATGTA
            AGCTTCATGAGGACAGGGATTAGTGTCTGTTTTGTTCACTGCATCTCTAGGGCTTACAAC
            ATTGTAGGTACTCAGTAAATATTTGTTAAATCAATGTGAAATGTGTCATTTATCCTTAAG
            GAATTGACCTTCATGGTAGAAGTGTAACAGAACCACCTATATCCTACTTTTCATCCACAT

23821       GGGCTTACAACATTGTAGGTACTCAGTAAATATTTGTTAAATCAATGTGAAATGTGTCAT
            TTATCCTTAAGGAATTGACCTTCATGGTAGAAGTGTAACAGAACCACCTATATCCTACTT
            TTCATCCACATCATAACTATTATGTGAATACCTTGGAAGTAAAGCAAAATAAGCACTTAA
            CTAAAGAGACGCTTTATATTGAAACTGTTGTTCTGGGTTTCTGGAATTAGTACTCTGAAA
            TTGGCTCCCTCTAGGAAGGCTTGTGAAGAGAGTAGTGTTGAACAGACATGACAGTTTCCA
            [G,A]
            GAAAGCATAGTTGGCTAAGAGGAGTAGGATTTTCCAAGCAAAGAGTGTGACAGTGGAGAT
            GGCTGGGGCTAAGTCAGGCAGAATGTGTTCAAACCTGTTTTTCTCTGACCTGAGATTGCG
            GAGGGAATATTGGGAAGGTATAGTTACCTGGTGAGGAGAGCCAGTTTTGTGAAGAATCAA
            GAATGAGGAGATTTAATTTGTTATGCAGATGTCTGGGAACCACAGCAGATTATCAGGAGA
            GCAAAATTGTTAGTCAGAATTACATCGTTAGAAGGTAATCCTTAAGTTTTGTAGATTTCT

25487       TGTGTGTGTGTTGTTTTTTTGATGTACCTCTTTGAGCCACCCATGCATTTTTGGAGTTTC
            TTGCTAATTTTAATTTTTTGTAATTATGTTTCTCTATTTAGATGTTTAAATCCATGAGGC
            GTAAACTTTAAAGTTTCATGCCTTATATTAATCCTTTATAGTCCACCAAAAATGAAACTT
            TTTTCTTCCTTTTTTGGAGTGGACATGTAGTCACTGCCTTTTTGGAGAATGCTTCTTTAG
            TTTGAAGCTTTCTTTATTGGACTAAAATTACTTTCCAATTAAAATTTAACTCAGCAAATA
            [C,T]
            TTACTGAATACTTGCCATGTGCTAGCTAAAGATAAACAATGTCTTGAGGGCATGAAAGTG
            AATGAGATACCTGGCCTTAAGGAGCTCTTTTATATTCTAGGTCAACAGAAAAACATGTAA
            ATAGTATCTATAATCACTGCCCCAAGATGATGCTCCCAGTGCCCAAGGCCTTATTGTACA
            TTTCATTTAACTAAGTGTGTTAAAATCAAATTCTAAATGTAGAATTTTTCCTAGGTATGC
            CTTGCAATAGCTCATTATTCCCAGCCAACAGACCTCCAGCTACTCTTTGCATTTGAATAT

30858       CAGTGATGGAAAGTAGGGCAGCCCACTAGAAGCCACTAGCCACATGTGGCTGTTAAGTAC
            TTGAAATGTGGCTAGTGCAAACTGATGGACTGAATTTTTAATTTTATTTAATTTTCATTT
            CAGTTTAAATTTAAATGGGCTTGTGTGGCTAGAAGTTACGTTTTTGGGAAACATACTAGA
            GTCTAGGCCCTATTTGATTTCCCGCCTCTCTTCCACCACCTGTTGAATCCCTATGCTCTA
            GCTGTATTTAGTTACTTGATATTATACAGTTA
            [C,T]
            ACCATCTTTTTAAAGTTCTTCTCTGTCTAGCATGCCTACCTCCTCCTCACCAGCTACCTG
            GCAACTTTTGACTTGTTCCTTAGAACTCTCTTTAGTTGTGGTCAAGTCATGAAGCTTTTC
            CTGCCCCGGCCTCTCTCTGCAGCGAGAGTTAGGGGACTTCTCTTTTGCATCTTCATTGCA
            CTCAGACATCTGGTACTCTGTGATTATCACACTTATTAATGCTCTCAAGATAGAGATAAA
            ATCTTATTCATCTTTTTTGCTCTCAGGCATTAG

31014       ATTTAAATGGGCTTGTGTGGCTAGAAGTTACGTTTTTGGGAAACATACTAGAGTCTAGGC
            CCTATTTGATTTCCCGCCTCTCTTCCACCACCTGTTGAATCCCTATGCTCTAGCTGTATT
            TAGTTACTTGATATTATACAGTTATACCATCTTTTTAAAGTTCTTCTCTGTCTAGCATGC
            CTACCTCCTCCTCACCAGCTACCTGGCAACTTTTGACTTGTTCCTTAGAACTCTCTTTAG
            TTGTGGTCAAGTCATGAAGCTTTTCCTGCCCCGGCCTCTCTCTGCAGCGAGAGTTAGGGG
```

FIGURE 3FF

```
                [A,C]
                CTTCTCTTTTGCATCTTCATTGCACTCAGACATCTGGTACTCTGTGATTATCACACTTAT
                TAATGCTCTCAAGATAGAGATAAAATCTTATTCATCTTTTTGCTCTCAGGCATTAGCACA
                TGGGGAGTTCTCAGAAAATACCTGTCTTATACCAGGAATTAATGAATAATCAGTAGGAAT
                GAGCATGACATGTTCATGGGACGTTGGAGGGTAGTGCATGGCTGCAGAGGAGAATGGGAA
                ATGAAGGTCAGATAAGTTACGTGAGGGATCTCTAAGGCCAAGAGAAGCCATTTAGGTTTG

31437       GGGAGTTCTCAGAAAATACCTGTCTTATACCAGGAATTAATGAATAATCAGTAGGAATGA
                GCATGACATGTTCATGGGACGTTGGAGGGTAGTGCATGGCTGCAGAGGAGAATGGGAAAT
                GAAGGTCAGATAAGTTACGTGAGGGATCTCTAAGGCCAAGAGAAGCCATTTAGGTTTGAT
                TTGGTTGGAAAATGAGCTTATTGAAAGTTTAAGGCAAGGGACTAGCATCATGAACACATC
                TTTTTAGGGAAGTGTGTCTTGTGGTAAGCTGCTGGCTGGTTTAAATGCAGCAGAATATTC
                [C,T]
                ATTGGGGATGCCAGCTGGGAGACTTGCCACAGTTGCAGCCTGCAGCAGAAAGACCCTGGG
                CCAGAATGGGTTGTGCCATCTGTCACCAGATATTGCCAAGGTAGATCTGGCTGACTTTGT
                GGGACAGCTTGTTTCTCAATAATCACTTTGCAGGCACTCTTGAGGCTGTGAGCATGCTCC
                CAGAAGATAGCATTACTTCTCTCTCAGAGCAGGCTCCTTTCTAAGGAAATGCAAGTCTAG
                GCCTGCCCTGCTGTAATCTTCATGTGGAAACAGCACTCTAGCAAAGAACAAGGAACCTGA

35341       TGGTAAAACCCCGCCTCTACTAAAAATACAAAAATTTAGCCAGGTGTGGTGGCGGGTGCC
                TGTAATCCCAACTACTCGGGAGGGTGAGGCAGGAGAATCGCTTGAACCCGGGAGGGGGAG
                GTTGCAGTGAGCCGAGATGGTGCCACTGCACTCCAGCCTGGGCGACAGTATGAGACTCCG
                TCTCAAAAAGAAAAAGAAGGAAATGATCTAATTTGTTCTGTGCACTGCACGTGGGGGTGG
                CAGTGAGGTGAATGGCAGCATTCTGCAGTAGTCAAAGCCAGATGGGTGGGAGAAGTTGGG
                [G,A,T]
                GCTAAGAGGGAAACAAAGTTTACCTGTCTTCTCCTTGATTTCACTCTCAGTTTTATGAGA
                ATACAGAAAAATCATGCAGAGAAACCTGATGGAATAGTCTCTAAAACTAAAAAATAAGAT
                AAGCAATGGTTCTGTCTTAAAAAAAAAAAAGTAAACTCCATGAAGGCAGAGACCTTACCT
                GTCTCATTCCTCTCTATCCCCTGGTCTATAGTAAGGGTTAAATAAATATATGCTGAAA
                TGAATGAGTAATGACTAAAGTATTTTTGTCTTTATTAGGATTTGTAATGCAATAACTAAA

35346       AAACCCCGCCTCTACTAAAAATACAAAAATTTAGCCAGGTGTGGTGGCGGGTGCCTGTAA
                TCCCAACTACTCGGGAGGGTGAGGCAGGAGAATCGCTTGAACCCGGGAGGGGGAGGTTGC
                AGTGAGCCGAGATGGTGCCACTGCACTCCAGCCTGGGCGACAGTATGAGACTCCGTCTCA
                AAAAGAAAAAGAAGGAAATGATCTAATTTGTTCTGTGCACTGCACGTGGGGGTGGCAGTG
                AGGTGAATGGCAGCATTCTGCAGTAGTCAAAGCCAGATGGGTGGGAGAAGTTGGGTGCTA
                [A,G]
                GAGGGAAACAAAGTTTACCTGTCTTCTCCTTGATTTCACTCTCAGTTTTATGAGAATACA
                GAAAAATCATGCAGAGAAACCTGATGGAATAGTCTCTAAAACTAAAAAATAAGATAAGCA
                ATGGTTCTGTCTTAAAAAAAAAAAAGTAAACTCCATGAAGGCAGAGACCTTACCTGTCTC
                ATTCCTCTCTATCCCCTGGTCTATAGTAAGGGTTAAATAAATATATGCTGAAATGAAT
                GAGTAATGACTAAAGTATTTTTGTCTTTATTAGGATTTGTAATGCAATAACTAAAAGTCA

36164       TTCTTCATGAATTGGTAGGAGTTTGGAGTTTGTCAGCAAACATTCTATCGGGCTAAAGGT
                TTTTATAATGAAAGAAATAGGCAAAGTGGATCAGTACACTCACTTTTCTACCATTGACCC
                TGGAGACAGATGGCTTAAAATGTTCTGCGTCTAGTTGACTTTTAGATCTTGAAATTAAGG
                TTTAATGATGACCAAGCTTTAAATAAATTGTAGAAAAGTATTCTTTCAAAAGTACATTAT
                AACTTTTATATTGGTTTCTTATATTTATTTCTTTTAATCTTTTCTTTTAACACAAACTAC
                [G,A]
                TTTTAAGGTTTTGTTGCCTACTAAGTTATAATCTGAGTGCAGAAGGAAACTTGATTTGGC
                TTTATGGAATACATTTTACATTCAGTGAAGCTGAGCTCTGTTTCTCATTCCTTACAAAAG
                GAATCAAAGGCATTGGTTTGAGAGGATCAAGTCATGTGTTAATAAAACACAAATATTCCAT
                CAAGTAATACTCTGAAGGAGCAGGTGTAGTTTATTTCTTCTCCAGAAAGTCTTCCAGCAG
                ATAAATAATGAGAGGTAGTATGGCATAGGAAAAAAGTACACTGAAGTCAGCCTTTCTGGT

36620       TGTTAATAAAACACAAATATTCCATCAAGTAATACTCTGAAGGAGCAGGTGTAGTTTATT
                TCTTCTCCAGAAAGTCTTCCAGCAGATAAATAATGAGAGGTAGTATGGCATAGGAAAAAA
                GTACACTGAAGTCAGCCTTTCTGGTTCAACCAGCTCAGACCCCTGAGCTATTTTTGCCTC
                AGTTTTACGCCTTGGAGAACAATGCCTTGTCATTACTATTCACTTTATGACCATACAGTG
                CCTGGCACCTGGTGGGCAATTGGTGAATGTTTTCACTATCCTCATCCTTGCCCTCATGAA
                [A,G]
                CACTCCTTCTAGGTCCCACAAAGACCGTTGGTATTTTATGACAAAGTACCTTACAAATAT
                TTTTCTTTTTTTAAAGGAGAAATTGTCGTAAATGAAGTCAATTTTGTGAGAAAATGCATT
                GCAACAGACACAAGCCAGTACGATTTGTGGGGAAAGCTGATATGCAGTAACTTCAAAATC
                TCCTTTATTACAGATGACCCAATGCCATTACAGGTGTGTTTTATTAGTACACTGTTTCAT
                TCTATCAGGCTTTCAACTCTAAGTGGTACATATTATTATATAAAACATAGGTATGGAAAA

37074       AAGCTGATATGCAGTAACTTCAAAATCTCCTTTATTACAGATGACCCAATGCCATTACAG
```

FIGURE 3GG

```
        GTGTGTTTTATTAGTACACTGTTTCATTCTATCAGGCTTTCAACTCTAAGTGGTACATAT
        TATTATATAAAACATAGGTATGGAAAAGTTATAGTAGAAGTATTAGGTAATGCAATGTTT
        GGGATAAATTATATTAAGATTTAAAGTAAAGTTTAAGAAGAATGTTGGAACTTGCTAGAG
        GAGTATTAGTGAGAGGATTGTAAGTCACCTTGCTTTATTTATCCTCTGTGATCGTTCATT
        [A,G]
        TATGTCCTTTTCATTAAGGAAGTTATTCCCTCTGTTGCAGATCTTTTAACCTGCTTATAA
        AAATGACATAAAGAGAAAAGGTTGTTTGCTAAATGATTTTATAAATGCCACACATTTTAG
        TGATTTCATAGGTTTTTTTGTTGTTGGGTTTTTGATTTTTTTTGTTTTGAGCCTGGATCTC
        GCTCTGTCTTGTCTCCCAGGCTGGAGTGCAGTGGCATGATGTCGGCTCACTGCAACCTCT
        GTCTGCTTCCTGGGCTCAAGCTATCCTGCCACCTCAGCCTCCTGAGTAGCTGGGACTACA

37546   CTGGATCTCGCTCTGTCTTGTCTCCCAGGCTGGAGTGCAGTGGCATGATGTCGGCTCACT
        GCAACCTCTGTCTGCTTCCTGGGCTCAAGCTATCCTGCCACCTCAGCCTCCTGAGTAGCT
        GGGACTACAGGTGCATGCCACCACTCCCGGCTAACTGTTGTATTTTTTGTAGAGATGGG
        GTTTTGTTATGATGCCCGGCTGGTCTTGAACTTCTGAGCCCAAGCAATCTGCCTGCCTC
        CCCCTCCCAAAGTGCCAGAGTACAGGCCACTGCACCCAGCTACCTTTTTTTTTTTTTTT
        [T,-,A]
        AACTAATTAGTGTTATTTTCCTAAAAAGTTAAATTCTAATTTCTAGGAAGAGTGAAGAAT
        AGTATCGATTTAAAAATTTTCAGTAGCCCTCTTGCTATTTTATGTTCTTACTGGAAAGTA
        ATAGTTCCATGTAATTTTGGTTTTTAGAAGTTCAGGCATTCATTTGATTAACTTAAAAAC
        CCTGGACTTTTCTGTCAGCCATTTTGTATTTTGTTTTATAAAGTATTATACACACTTACC
        CCTAGATCTTTCTTTATAGTAATTGTTCTTTAATGAAATATTGGTATATGAACTGTAAAC

38190   TGTAGTCACTCACTAATTTACCATAATTATTATACTGTACAAATATTTATTGTACTGTAT
        ATTTGTGTGTTCATTACAGTCTTATGTAGGTATATTTAGACTAAATTTAAGGCACTTAAA
        GATACCCACTGTGTAGGGACAGTAGCTTATTGGATATAGGCTTGTGTGTTTCTCTTTGT
        TTTTAGCTTCATAATGATCATTGGCCCCAGACTTCACTGTAAATGAGAAGCAGATACCTG
        GAACAGCTTAAATCCAGTACCACTATTAGGAAAAAGTAAACCAGTGCCCTACTGACAGCA
        [-,G]
        ATTGATAGTGTTAACTACGTCCTTAGTTTGAACATGCAAAACCTTTTCTAATGGTTTTTA
        TTTCTAGTAGACTTTGTGCTTTAAAAAGATAGTTATTTTGCACTTTAAAATCTTCAGTGT
        GAAAATCAAACATGATTTTACCCACTTAAAATCTGATGACCTAAGAGCCCTTTTTTCTTT
        AATATGTTGTGGCCAGCTTATCCAGATCTAGACATGCAAATGCTTGCTGGTAAGGTGATT
        GATGATATTCCCTATCTTAGGTATTATAATAAGATTGTTGTGTACATTTTAACCTAATTT

38708   AAATGCTTGCTGGTAAGGTGATTGATGATATTCCCTATCTTAGGTATTATAATAAGATTG
        TTGTGTACATTTTAACCTAATTTCTATCTGTCAACATTGGAATGGCCCTAGCTACCTAGA
        CAAAAGCTTTTTGTGCTTTTTAGAGATAACTGTCACAGTTTATCATCACAGTTTAAGGCT
        TATACTACCATTGTGAGATTATTGGGAAAAGAATTAATATGAACATAATTTTTTATTCCA
        GAAATTCCATTACAGAAACCTTCTTCTTGGTGAACACGATGTCCCTTTAACATGTATTGA
        [A,G]
        CAAATTGTCACAGGTACGTAGTATTCCGTACATACTCTAAAAGTCAATTCCACTCTGGAA
        GTATTATTTGAAAAGTCATACCTCTCAAAATACTTGGATTGGCGTTTTATTTCTGTAAGT
        TTACTTTTGCCGTTTTTTTTGAGTCCCGGGAACATAAAGAGGGATATGTTAATAAATTATT
        TTAAAAGGAAGATATAAAATGTATAACTTTTCATAGTTTCTAGGTTTTTTGTCCTCTTTT
        TAATTAAAATTAATCATTAAATGTGTCTAGATGGTGGTTTTATGCAAATAATCATTTAAA

38735   ATATTCCCTATCTTAGGTATTATAATAAGATTGTTGTGTACATTTTAACCTAATTTCTAT
        CTGTCAACATTGGAATGGCCCTAGCTACCTAGACAAAAGCTTTTTGTGCTTTTTAGAGAT
        AACTGTCACAGTTTATCATCACAGTTTAAGGCTTATACTACCATTGTGAGATTATTGGGA
        AAAGAATTAATATGAACATAATTTTTTATTCCAGAAATTCCATTACAGAAACCTTCTTCT
        TGGTGAACACGATGTCCCTTTAACATGTATTGAGCAAATTGTCACAGGTACGTAGTATTC
        [-,A,C]
        GTACATACTCTAAAAGTCAATTCCACTCTGGAAGTATTATTTGAAAAGTCATACCTCTCA
        AAATACTTGGATTGGCGTTTTATTTCTGTAAGTTTACTTTTGCCGTTTTTTTTGAGTCCCG
        GGAACATAAAGAGGGATATGTTAATAAATTATTTTAAAAGGAAGATATAAAATGTATAAC
        TTTTCATAGTTTCTAGGTTTTTTGTCCTCTTTTTAATTAAAATTAATCATTAAATGTGTC
        TAGATGGTGGTTTTATGCAAATAATCATTTAAAATATCTTCCAAAGCAAAGTTAAAACCA

41983   CCTTCTGGTTGTCTTGTTGGTGTTGTTTCAATTGTATTATGACAAAATTAGATTGCTTTG
        GGCACTTGTACTCATTAATATTCATCCTCATTATCCTCGAGCTGTCACAGGAAAATAGTG
        ATATTTGGGAAAGGTCTGTATAAAGAAAGAAGGAATTTGATGGTGCAGAATTGGACATCT
        AACCTCATAGCAACTTAGAACCACCATTTTCTTTTGCAGAACCTTTGCTCAAAACTGAAG
        GGCAAAATAATAAAGGTTGTTTTTAATGATTTATCTATATATCTGTCTGTGTAGATAAAG
        [A,G]
        TAAAATATATAGATACACATGAGTGACAAGTGAAATACATGCCTTTTGTCTCCACTTTGTT
        CTCTGATTAGTGGGTTGTGAATCACTTCTTCAGGAATACTTTATAGAAGTGAATTCCATT
        CATCTGATTAAGGAACAAGTTGGCCTTTTCATGAACTGTCATTTTTGACTTGAATCTGGT
```

FIGURE 3HH

```
              ACTGTTTTTTGGTGGCTTTCAGGCCACAGAAATAAACCACTTTTGTTTGCAAATGAGATA
              GAACTTAATGAGGTTTGAGTGTTTCCTGGATTTGAGTTTCTTCAGTACTGCACCCCAGGT

42127         GAAAGAAGGAATTTGATGGTGCAGAATTGGACATCTAACCTCATAGCAACTTAGAACCAC
              CATTTTCTTTTGCAGAACCTTTGCTCAAAACTGAAGGGCAAAATAATAAAGGTTGTTTTT
              AATGATTTATCTATATATCTGTCTGTGTAGATAAAGATAAATATATAGATACACATGAGT
              GACAAGTGAAATACATGCCTTTTGTCTCCACTTTGTTCTCTGATTAGTGGGTTGTGAATC
              ACTTCTTCAGGAATACTTTATAGAAGTGAATTCCATTCATCTGATTAAGGAACAAGTTGG
              [C,T]
              CTTTTCATGAACTGTCATTTTTGACTTGAATCTGGTACTGTTTTTTGGTGGCTTTCAGGC
              CACAGAAATAAACCACTTTTGTTTGCAAATGAGATAGAACTTAATGAGGTTTGAGTGTTT
              CCTGGATTTGAGTTTCTTCAGTACTGCACCCCAGGTGATCTTAGGAAAGAAACCATCCAC
              TGTGGGTACTTCTGGCTTCTGTCCAGAGAAGATTATCAGCTTTGGTCCAAAAATTGATTT
              AAAAGTAGTTTACTTCTTTTTCTCCAATAAAATATTTGCCATAATTTAATGTCTTTAATA

42449         TGACTTGAATCTGGTACTGTTTTTTGGTGGCTTTCAGGCCACAGAAATAAACCACTTTTG
              TTTGCAAATGAGATAGAACTTAATGAGGTTTGAGTGTTTCCTGGATTTGAGTTTCTTCAG
              TACTGCACCCCAGGTGATCTTAGGAAAGAAACCATCCACTGTGGGTACTTCTGGCTTCTG
              TCCAGAGAAGATTATCAGCTTTGGTCCAAAAATTGATTTAAAAGTAGTTTACTTCTTTTT
              CTCCAATAAAATATTTGCCATAATTTAATGTCTTTAATACCAACATTTTCTTCATTTCCT
              [A,G]
              TGGTAGCCAGGACAAATGAAGTATTTCAGATCTTTCAAAAACTCTTAGGATGAAAGGTAG
              GAATTTGGACTTAGGTTTTTAAAATAGTGTGTATGTAAAAGTGCAAAGAATGGGGCCCTG
              GCTTTCTCTTCTCGGAGTGTTCCACAGTAACAACATGAAGACAATCCAGGTACACAAGTT
              TGTATGTGCCTTAGTCTGTGTGTCCAAAGAGGCCTCTTACTTAGGTCATATGAACATAAG
              TTATACACTTGAAATTCACTACTGAAAAACAATGTATTTAGTTCGAGTTCTGCCACCCCA

42798         GATGAAAGGTAGGAATTTGGACTTAGGTTTTTAAAATAGTGTGTATGTAAAAGTGCAAAG
              AATGGGGCCCTGGCTTTCTCTTCTCGGAGTGTTCCACAGTAACAACATGAAGACAATCCA
              GGTACACAAGTTTGTATGTGCCTTAGTCTGTGTGTCCAAAGAGGCCTCTTACTTAGGTCA
              TATGAACATAAGTTATACACTTGAAATTCACTACTGAAAAACAATGTATTTAGTTCGAGT
              TCTGCCACCCCAAAAAAATCAACGAGTAATTCAACTGACTTGCAGTTTTACAATATTTTT
              [A,G]
              TAGACTTCTTTCAGCGTAGATGCTTTTGGACATACTCATTTGTTTCCTAACCTGATGTGA
              TATTGTGCTATTTTTAAGGGGCTTTTAAAAAATACGCTGTGTTGGGTTTTGCCTTGAAAA
              TAGGCTTTATTTCTTTTTTTGCCTCATGGCCACAAAAAAAGGATGTCCATGATCAATGATC
              TGTGAATTTCTTTTCTGTAAACAGAAAGAGCATGTAACTGCTTTCTAATTGTTTTGGAGA
              ATGTGATAGACATTAGTATTATTATTATTGGCTTGGAGCATTTTCCTTAATATGTTGGTA

43273         ATGATCTGTGAATTTCTTTTCTGTAAACAGAAAGAGCATGTAACTGCTTTCTAATTGTTT
              TGGAGAATGTGATAGACATTAGTATTATTATTATTGGCTTGGAGCATTTTCCTTAATATG
              TTGGTAACTACTTTTGTCAGTGAATATTAGTGTAGCCACTGTTGGACACAGAGCACCGTC
              AGAAAGCTACTGAAGTGGTGCTGCAAAGTGCAGACATCTTCAGATCTTTACTCAAGTCTG
              TGCAGAGAGGTCTTTCTTGGTCTCCTTCTCTACTTTTTAGCCTGTCTCCCTCTTCTCACT
              [G,A]
              TAACACTTCATATTCCCCTTCCCTGCTCTATTATTTTTCTCTTTTAGCATTCATAGTTAT
              CTAACTTTCTGTATTTTTTCTCTTTATCTTGTTTAGTGTCTGTCTTCCCACTAGAATGTA
              AGCTTCATGAGGACAGGGATTAGTGTCTGTTTTGTTCACTGCATCTCTAGGGCTTACAAC
              ATTGTAGGTACTCAGTAAATATTTGTTAAATCAATGTGAAATGTGTCATTTATCCTTAAG
              GAATTGACCTTCATGGTAGAAGTGTAACAGAACCACCTATATCCTACTTTTCATCCACAT

43743         GGGCTTACAACATTGTAGGTACTCAGTAAATATTTGTTAAATCAATGTGAAATGTGTCAT
              TTATCCTTAAGGAATTGACCTTCATGGTAGAAGTGTAACAGAACCACCTATATCCTACTT
              TTCATCCACATCATAACTATTATGTGAATACCTTGGAAGTAAAGCAAAATAAGCACTTAA
              CTAAAGAGACGCTTTATATTGAAACTGTTGTTCTGGGTTTCTGGAATTAGTACTCTGAAA
              TTGGCTCCCTCTAGGAAGGCTTGTGAAGAGAGTAGTGTTGAACAGACATGACAGTTTCCA
              [G,A]
              GAAAGCATAGTTGGCTAAGAGGAGTAGGATTTTCCAAGCAAAGAGTGTGACAGTGGAGAT
              GGCTGGGGCTAAGTCAGGCAGAATGTGTTCAAACCTGTTTTTTCTCTGACCTGAGATTGCG
              GAGGGAATATTGGGAAGGTATAGTTACCTGGTGAGGAGAGCCAGTTTTGTGAAGAATCAA
              GAATGAGGAGATTTAATTTGTTATGCAGATGTCTGGGAACCACAGCAGATTATCAGGAGA
              GCAAAATTGTTAGTCAGAATTACATCGTTAGAAGGTAATCCTTAAGTTTTGTAGATTTCT

45407         TGTGTGTGTGTTGTTTTTTGATGTACCTCTTTGAGCCACCCATGCATTTTTGGAGTTTC
              TTGCTAATTTTAATTTTTTGTAATTATGTTTCTCTATTTAGATGTTTAAATCCATGAGGC
              GTAAACTTTAAAGTTTCATGCCTTATATTAATCCTTTATAGTCCACCAAAAATGAAACTT
              TTTTCTTCCTTTTTTGGAGTGGACATGTAGTCACTGCCTTTTTGGAGAATGCTTCTTTAG
              TTTGAAGCTTTCTTTATTGGACTAAAATTACTTTCCAATTAAAATTTAACTCAGCAAATA
```

FIGURE 3II

```
              [C,T]
         TTACTGAATACTTGCCATGTGCTAGCTAAAGATAAACAATGTCTTGAGGGCATGAAAGTG
         AATGAGATACCTGGCCTTAAGGAGCTCTTTTATATTCTAGGTCAACAGAAAAACATGTAA
         ATAGTATCTATAATCACTGCCCCAAGATGATGCTCCCAGTGCCCAAGGCCTTATTGTACA
         TTTCATTTAACTAAGTGTGTTAAAATCAAATTCTAAATGTAGAATTTTTCCTAGGTATGC
         CTTGCAATAGCTCATTATTCCCAGCCAACAGACCTCCAGCTACTCTTTGCATTTGAATAT

45985    AGCTACTCTTTGCATTTGAATATGTTGGGAAAAAATACCACAATTCAGGTAAATATGAAA
         ATATTAAATATTGTGACTAATTTTACATGTGTAAATTTTACTCTTATGTTTACCGGAAGC
         CTCCAAGTACATGAGCTTTAATGATTGTAGAATTACTAGCTTCATACCTTAGAGAAGTAA
         GCACTACATGCTAAAAGAGCCAATAGTTTGTCAGATTATTTCTTGACAAGTTACCAGGAA
         GAACCTTTAATGCTATGAATATGGGCTTATAAGTTATGTCAGATATTTAATCTCCAGTCA
         [T,C]
         TGGCTTGTATTTTATGATGAAGAATATATAACCCACCCTTTTTAATTGATAGCTTGAGTT
         AAAGTAATCTTATCTTTTAAGAAAACTGGCAGAAAACTAAAAGATATATTAAAAGCATAA
         TCTTTTCTGGCAAGGTGTGATTTCATGCAAAAGCTAAAGTGATTAAAAACTTTTTGTGGA
         CTTCATTAAGATTCTCAGAATACTGAGTTTCTATTTCTGAGTAATACTGATGAAAGGAAG
         ATGAGCATTTTTCCAAGGACAAGTATATTCTAGACAGCTTTTGTGAAAGTAAATAGTTTT

46198    GATTATTTCTTGACAAGTTACCAGGAAGAACCTTTAATGCTATGAATATGGGCTTATAAG
         TTATGTCAGATATTTAATCTCCAGTCACTGGCTTGTATTTTATGATGAAGAATATATAAC
         CCACCCTTTTTAATTGATAGCTTGAGTTAAAGTAATCTTATCTTTTAAGAAAACTGGCAG
         AAAACTAAAAGATATATTAAAAGCATAATCTTTTCTGGCAAGGTGTGATTTCATGCAAAA
         GCTAAAGTGATTAAAAACTTTTTGTGGACTTCATTAAGATTCTCAGAATACTGAGTTTCT
         [A,G]
         TTTCTGAGTAATACTGATGAAAGGAAGATGAGCATTTTTCCAAGGACAAGTATATTCTAG
         ACAGCTTTTGTGAAAGTAAATAGTTTTGTCTATATATCTGACAGTCATGACATGACCAGG
         GAAGATTCCAGATGATCATGCAATTCTGTACATTCTGTTTCGTACAAATGTAATTTTAAT
         AAACAATTTTTAAAAATATCTTGATAGAGAAAAACAAAGAGCCGTGTCTCCTGTTAGCCC
         CATTGTCAGTTAGTGACTGCAAGTCAGTTAACTGAGCGAAGCCTGTGTTCTTTTATTTAA

46793    ATTTAAGCAAGAAAAATAAATCAGCTGTGTATTTATAATGAAAAATCCATTCACCCAGCA
         TGCTCTGGGCCATACAAATTATTAATTGTACTGAAATTTTATATTTTGTTACCACGAAAC
         ATGGTAGTAATTTAAATAACTGGCATAATAAAAGTATATTCCAGCAACACTATATTGTAA
         ATACATTAAAATGTATCAGTGTACGGTATCTGAAGATGCATGTGTATAAGTAAATTTTCC
         TTAGTTTAAAAGATAACTACCTTTCTGTTAAGCACTGAGAGGACCAAAAAAAAAAAAAAA
         [-,A]
         GAAAATACAGTAGAGATAATATATGAAAATAATGCTTTGCAGAGCAGCTTTTATCATACA
         GTATTATATTTATAGAAATTGTATAACAAAAGTATTTGTAACTTAATTTTTCTTATCGAT
         ATATACATAATTGTAACTGAGGCTTAAGCAATACAGTTATTTTTTGAAGTTTATTAATAT
         TAAGTAAATTCACTTACTGTCTAAAAATAAAGTATACAGATCCTGCACTATTAGGTAAAC
         ACTCCTTGGGATCATCGTCAAGCTACAGAACAGTGATCAAGGTTATCTTCAATAAGATCC

46923    TTTAAATAACTGGCATAATAAAAGTATATTCCAGCAACACTATATTGTAAATACATTAAA
         ATGTATCAGTGTACGGTATCTGAAGATGCATGTGTATAAGTAAATTTTCCTTAGTTTAAA
         AGATAACTACCTTTCTGTTAAGCACTGAGAGGACCAAAAAAAAAAAAAAAAGAAAATACA
         GTAGAGATAATATATGAAAATAATGCTTTGCAGAGCAGCTTTTATCATACAGTATTATAT
         TTATAGAAATTGTATAACAAAAGTATTTGTAACTTAATTTTTCTTATCGATATATACATA
         [-,A]
         TTGTAACTGAGGCTTAAGCAATACAGTTATTTTTTGAAGTTTATTAATATTAAGTAAATT
         CACTTACTGTCTAAAAATAAAGTATACAGATCCTGCACTATTAGGTAAACACTCCTTGGG
         ATCATCGTCAAGCTACAGAACAGTGATCAAGGTTATCTTCAATAAGATCCTCACCCAGAG
         TTGCAAGGGTTGTAGGAGTGAGTCTTTGATTCCTGCTCAACTGTTTATGATACAGACCAG
         TTCTTCATGCTGCTGTTTTTCCAATAGAAATGATTCATTTCAGTTTACAGATCCATAACT

47851    ATAGTTTTGTTAAGATTCCTCGTAGGGTAACATCCTTTAATATCCTTCCATGCTGTTACA
         GAAGCATAAATACTGCATCTTTAAGATCAAAAGGAGCCTGAAATTTCCACACACTGCAGT
         CAGAATTCATTAATTTGTGAGTGAAAGATGCCCACTCATCCACTCTTGAACTTCTGGATG
         ACACCTTGATTCATTGGCTGGATTAAAGAAGTCCTTTTTGCAGGCAGGTAGGTGACAAAG
         CTGTTTCCACAAATAAGATCCAAAGTTGGAGGAGCTCCCCTGCAGTTATCTGAGAAAATG
         [A,G]
         TATTTTAGCTGGCCTTAGTCACTCAGGTTTTCATTCATATTCAGTATCACATGAGGAAAA
         GCCATCTCTGAAAGGTCCTGCAGTCATCCCAACACTTCTGTGAATATCCTGGAGTAAAGT
         AAGATGTGTAGCACCCAGGCTTTGGAACATCGCTTTGCACAAACACCCCAGGGAGATATTA
         CTAGCACAAACAAGAACAATGATTCTGTTTTTTCTCTTTTAACTTTAAAGAAACCATGAG
         GACTCTGTTTTCATCAGTCAGATTATTATTGGGCAAATAACGTCAAAAAAGTACAGATTC

48875    ACAGGTCAGAATCTCCCAGTTAAGAACCACTTTGTTGACTCATGCTTTTGAACTGATTAA
```

FIGURE 3JJ

```
       TACTCACAGTCCTCTTTTTACCTTATTCCTTTGTGACTTCTAATTTCTGCAGTATCATCA
       GAGTGGTGGGCTTTCTTTTCATATATTGATGACTTGTATTTTCTGTTGCTTGAAGCCATT
       CTAGATATCAATTGGCCAATTCAGTGGAAATTATCTAAAATAACCCCAACAGTATAGGAT
       TAGACTTTTGTACTGTCACAGAAGATAGCCAAGGTCAGGAGCATATAATATCTATTTCAC
       [G,T]
       CTTAGTCTGCTGTGGAGGCATGTCATAAAACCTCAGTCAGGTAGCGGTCAGCGGAGCCAG
       GTCTCCCTGAGATGACCCACCTTTCACTGTGTTGGTCCAGCCCCTCATAGCGATCCACTC
       ATAGAGCAGGCCACTGGTATCAGGTCTTTTGAACTTTGGAAAGCATTCAAATTTCTGGAC
       TATAAAACCAGATTGAGTATACATTACACATTCTGTAATGAGCTCTAACTGAAGATGATA
       TAGAACATATAAAAGACCTAGTCCCAGTTGTTTAGAAAAGTACAGGATTTGAACGAGAGA

50844  ATTTAAATGGGCTTGTGTGGCTAGAAGTTACGTTTTTGGGAAACATACTAGAGTCTAGGC
       CCTATTTGATTTCCCGCCTCTCTTCCACCACCTGTTGAATCCCTATGCTCTAGCTGTATT
       TAGTTACTTGATATTATACAGTTATACCATCTTTTTAAAGTTCTTCTCTGTCTAGCATGC
       CTACCTCCTCCTCACCAGCTACCTGGCAACTTTTGACTTGTTCCTTAGAACTCTCTTTAG
       TTGTGGTCAAGTCATGAAGCTTTTCCTGCCCCGGCCTCTCTCTGCAGCGAGAGTTAGGGG
       [A,C]
       CTTCTCTTTTGCATCTTCATTGCACTCAGACATCTGGTACTCTGTGATTATCACACTTAT
       TAATGCTCTCAAGATAGAGATAAAATCTTATTCATCTTTTTGCTCTCAGGCATTAGCACA
       TGGGGAGTTCTCAGAAAATACCTGTCTTATACCAGGAATTAATGAATAATCAGTAGGAAT
       GAGCAGACATGTTCATGGGACGTTGGAGGGTAGTGCATGGCTGCAGAGGAGAATGGGAA
       ATGAAGGTCAGATAAGTTACGTGAGGGATCTCTAAGGCCAAGAGAAGCCATTTAGGTTTG

51267  GGGAGTTCTCAGAAAATACCTGTCTTATACCAGGAATTAATGAATAATCAGTAGGAATGA
       GCATGACATGTTCATGGGACGTTGGAGGGTAGTGCATGGCTGCAGAGGAGAATGGGAAAT
       GAAGGTCAGATAAGTTACGTGAGGGATCTCTAAGGCCAAGAGAAGCCATTTAGGTTTGAT
       TTGGTTGGAAAATGAGCTTATTGAAAGTTTAAGGCAAGGGACTAGCATCATGAACACATC
       TTTTTAGGGAAGTGTGTCTTGTGGTAAGCTGCTGGCTGGTTTAAATGCAGCAGAATATTC
       [C,T]
       ATTGGGGATGCCAGCTGGGAGACTTGCCACAGTTGCAGCCTGCAGCAGAAAGACCCTGGG
       CCAGAATGGGTTGTGCCATCTGTCACCAGATATTGCCAAGGTAGATCTGGCTGACTTTGT
       GGGACAGCTTGTTTCTCAATAATCACTTTGCAGGCACTCTTGAGGCTGTGAGCATGCTCC
       CAGAAGATAGCATTACTTCTCTCAGAGCAGGCTCCTTTCTAAGGAAATGCAAGTCTAG
       GCCTGCCCTGCTGTAATCTTCATGTGGAAACAGCACTCTAGCAAAGAACAAGGAACCTGA

54073  TGCCTTATTTTAAGGTCATTGAAGTCCTCATTAGTTCACGCACATAAGCAGCTTTTTAGA
       AAAAGGAAGAAAAGCACTACTGTGTTATTACTGGTTAATCCAGTACCAGGAACTTCTAGT
       ACAGTTCTAGAAAGGTGCTTTGCAGCATGTAGCTTGTATCTTTTGCTTCCCCTGGAATTT
       AAGCTTCAAGGCCAGCACACTCTGGTATATGTGCTGAGAAACATGTGATGGGGCTGCCCA
       GCCACGTCGGGGAAAGAAGGAAGATGTCTTGAGGTGCAGTGAGCTTGCCCACTAGTAATT
       [A,G]
       TTGTCTGATCAGTGTCCTAGAGTCTGACTGTGCCTTTTAGGCATGGGGAAAGGTAGAAGA
       GGGACTTAAGAAGAGAGCTAAAGCTCCTGGTAGATTTGTGGGGTTTTCTTTTGTTTGCCT
       GGTGTCCTTAACCATAGCCTGTCAAGAGAACAAAGGTGGATATATTTTTCAGTGAACACA
       TACATGTTTAATAGTCATTCTGGAAAATATTTCTAATACCTTCTTTGGAATTTTCTCATG
       CTATAAATTTAGATTTTTAAGAATTGGTCATATCGCACCAATTTTAGACTAAGAGGTGTA

54206  GGTGCTTTGCAGCATGTAGCTTGTATCTTTTGCTTCCCCTGGAATTTAAGCTTCAAGGCC
       AGCACACTCTGGTATATGTGCTGAGAAACATGTGATGGGGCTGCCCAGCCACGTCGGGGA
       AAGAAGGAAGATGTCTTGAGGTGCAGTGAGCTTGCCCACTAGTAATTATTGTCTGATCAG
       TGTCCTAGAGTCTGACTGTGCCTTTTAGGCATGGGGAAAGGTAGAAGAGGGACTTAAGAA
       GAGAGCTAAAGCTCCTGGTAGATTTGTGGGGTTTTCTTTTGTTTGCCTGGTGTCCTTAAC
       [C,G]
       ATAGCCTGTCAAGAGAACAAAGGTGGATATATTTTTCAGTGAACACATACATGTTTAATA
       GTCATTCTGGAAAATATTTCTAATACCTTCTTTGGAATTTTCTCATGCTATAAATTTAGA
       TTTTTAAGAATTGGTCATATCGCACCAATTTTAGACTAAGAGGTGTAGGATCGTCACTGC
       CCCCCCATGGTGCCCACCATGTGGCTACTAAGTGGGGTGCACATTAAATGCGGACAACTT
       GCTTAATTATTTATAGGGTCTGCAGGAGCACACTATTCCTGCTTTTAGCACAGCACTCAT

54488  TTGCCTGGTGTCCTTAACCATAGCCTGTCAAGAGAACAAAGGTGGATATATTTTTCAGTG
       AACACATACATGTTTAATAGTCATTCTGGAAAATATTTCTAATACCTTCTTTGGAATTTT
       CTCATGCTATAAATTTAGATTTTTAAGAATTGGTCATATCGCACCAATTTTAGACTAAGA
       GGTGTAGGATCGTCACTGCCCCCCATGGTGCCCACCATGTGGCTACTAAGTGGGGTGCA
       CATTAAATGCGGACAACTTGCTTAATTATTTATAGGGTCTGCAGGAGCACACTATTCCTG
       [C,T]
       TTTTAGCACAGCACTCATATAATTTTTTTTTTCCCCTCCAGCCTTCCAGAATACATTGTA
       GTGCCAAGTTCTTTAGCAGACCAAGATCTAAAGATCTTTTCCCATTCTTTTGTTGGGAGA
       AGGATGCCAGTAAGTGATTTCTGTTGGATTTTATGAATGCTGACGTCCATTGTTTCTACA
```

FIGURE 3KK

```
         CAGTGAAGTAAGGATTCTACCTCTCCCCTAGCTCTGGTGCTGGAGCCACTCTAACGGCAG
         TGCTCTTGTGCGAATGGCCCTCATCAAAGACGTGCTGCAGCAGAGGAAGATTGACCAGAG

54511    CCTGTCAAGAGAACAAAGGTGGATATATTTTTCAGTGAACACATACATGTTTAATAGTCA
         TTCTGGAAAATATTTCTAATACCTTCTTTGGAATTTTCTCATGCTATAAATTTAGATTTT
         TAAGAATTGGTCATATCGCACCAATTTTAGACTAAGAGGTGTAGGATCGTCACTGCCCCC
         CCATGGTGCCCACCATGTGGCTACTAAGTGGGGTGCACATTAAATGCGGACAACTTGCTT
         AATTATTTATAGGGTCTGCAGGAGCACACTATTCCTGCTTTTAGCACAGCACTCATATAA
         [T,-]
         TTTTTTTTTTCCCCTCCAGCCTTCCAGAATACATTGTAGTGCCAAGTTCTTTAGCAGACCA
         AGATCTAAAGATCTTTTCCCATTCTTTTGTTGGGAGAAGGATGCCAGTAAGTGATTTCTG
         TTGGATTTTATGAATGCTGACGTCCATTGTTTCTACACAGTGAAGTAAGGATTCTACCTC
         TCCCCTAGCTCTGGTGCTGGAGCCACTCTAACGGCAGTGCTCTTGTGCGAATGGCCCTCA
         TCAAAGACGTGCTGCAGCAGAGGAAGATTGACCAGAGGTAATTGAGAAATGGTCATTGTC

56070    ATCATTTCCTCCTTCCATGTCTCCTCCACCCCTGGGCTCCAGCCCCCTGGACTTTCCCTG
         GTGTTTTCAACCTCCTGACATTGTCCAGCGCTCTTCCCTTCTGGACTGCCTTCTTTGCAC
         TCATCTGGGAACACTCTCCACGCTTACCCACTTGGCACTCCTTGTTTCTTTTTTTTTGAG
         ACAGAGTCTCACTCTGTCACCCATGCTGGAGTGCAGTGGTACGATCTCGGCTCCCGGGTT
         CAAGTGATTATCATGCCTCAGCCTCCTGAGTAGCTGGGATTACAGGCACCCACCACCACA
         [T,A]
         CCAGCTGATTTTTGTATTTTTAATAGAGACAAGATTTCACCATGTCGGCCAGGCTGGTCT
         CGAACTCCTGACCTCAGGTGATCCACCCGCCTCGGCCTACCGAAGTGCTGGGATTACAGG
         CGTGAGCCACTGCACCCGGCTCACTCATTCTTTATATCTCAATTCAAACATCATTTCCTC
         AAGATAAGCCTTCTCTCCCCTCTAAAGTTTGATCAGACCTCAAAAGTCTATGTTCTTAGA
         GCTCCTGAGTTTTTAACATTTTATTTCAGTTTTTAATTATATATGTGTGTGTTACAGTTTG

57119    TGTTAAAGGGACAATTGTAGCATTGTTGGGTGAGAGTTAGTTTATAAAACCTTATAATCAG
         TGGCAGTTTCAGTGATTTATTAAGCTGAAAATTACTTTAATGCCTTTTGTGTTTTCAGCT
         ATCCTATTCTTCATAAGTAGAACAGATCCTCTTTTTTGTCCAACCTCGTCTCCTAACCTT
         TTTCCCTCAGGTGTGTCATCTAGCCCCACTGGCCTTCTTTAGGTTTCTCAGCAGCCATGC
         TTGTTACCTGCCACAGGGCCCTTGCACTAGCTGCCCTCTGCCTAGAACATTTTCACCCCA
         [G,C]
         ATCTTTACATTGCTTCTCTATTCATTTAGGTTTCGGCTTCAGTACCATCTTCACAGAGCA
         GCTGTTTTTCACCATGTGACCTAAAGTAGCCTGTAATCTCATGATTACATCATCCATGGC
         ATTCACCACAGCCCATTTATCTTATCATCTACCCCACCCCACGAAGAATGTCAACCCCCC
         ACTTGCTTGGGCAACACCAGTAGTAAAATTGGAATGATACAGGGAAGGTTAGCATAGCCC
         TTGCACAAAGATGACATGCAGGTTCATGACACATTACATATTTTAATGAAATGGGAGCAT

58184    TTTGCATTCTCTAGAGCTGGAGAATGTGCATCTGGTTTGCCATCCTTCTGTCTACATCAT
         GTGGAAAGATGTGGGAGTGTAGGGTCTCCTTAATCTAAATGCAGTGCTGCCCCGCCCCCC
         CCTTGGCAGTGTTTCTGTTTCCCAGGCAAGTGTTCCAATGGATGTGCTTTATTTTCTCCC
         ATCAGAAATAAGGGAATGAGCCCGGGCGCGGTGGCTCACGCCTGTAATCCCAGCACTTTG
         GGAGGCCAAGGGGGGTGAATCACAAGGTCAGGAGTTTGAGACCAGCCTGGCCAACATGGT
         [G,A]
         AAACCCCGCCTCTACTAAAAATACAGAAATTTAGCCAGGTGTGGTGGCGGGTGCCTGTAA
         TCCCAACTACTCGGGAGGGTGAGGCAGGAGAATCGCTTGAACCCGGGAGGGGGAGGTTGC
         AGTGAGCCGAGATGGTGCCACTGCACTCCAGCCTGGGCGACAGTATGAGACTCCGTCTCA
         AAAAGAAAAAGAAGGAAATGATCTAATTTGTTCTGTGCACTGCACGTGGGGGTGGCAGTG
         AGGTGAATGGCAGCATTCTGCAGTAGTCAAAGCCAGATGGGTGGGAGAAGTTGGGTGCTA

58210    TGCATCGGTTTGCCATCCTTCTGTCTACATCATGTGGAAAGATGTGGGAGTGTAGGGTC
         TCCTTAATCTAAATGCAGTGCTGCCCCGCCCCCCCCTTGGCAGTGTTTCTGTTTCCCAGG
         CAAGTGTTCCAATGGATGTGCTTTATTTTCTCCCATCAGAAATAAGGGAATGAGCCCGGG
         CGCGGTGGCTCACGCCTGTAATCCCAGCACTTTGGGAGGCCAAGGGGGGTGAATCACAAG
         GTCAGGAGTTTGAGACCAGCCTGGCCAACATGGTGAAACCCCGCCTCTACTAAAAATACA
         [A,G]
         AAATTTAGCCAGGTGTGGTGGCGGGTGCCTGTAATCCCAACTACTCGGGAGGGTGAGGCA
         GGAGAATCGCTTGAACCCGGGAGGGGGAGGTTGCAGTGAGCCGAGATGGTGCCACTGCAC
         TCCAGCCTGGGCGACAGTATGAGACTCCGTCTCAAAAAGAAAAAGAAGGAAATGATCTAA
         TTTGTTCTGTGCACTGCACGTGGGGGTGGCAGTGAGGTGAATGGCAGCATTCTGCAGTAG
         TCAAAGCCAGATGGGTGGGAGAAGTTGGGTGCTAAGAGGGAAACAAAGTTTACCTGTCTT

59015    CTGAAATGAATGAGTAATGACTAAAGTATTTTTGTCTTTATTAGGATTTGTAATGCAATA
         ACTAAAAGTCACCCACAGAGAAGTGATGTTTACAAATCAGATTTGGATAAGACCTTGCCT
         AATATTCAAGAAGTACAGGCAGCATTTGTAAAACTGAAGCAGCTATGCGTTAATGGTAAT
         TTCATTCTTATTTCATATATATAATGAACACAGGATACAGAGTTGCATGAGATGTCAGGA
         AAAGTGATGTTCTTAAAAAATGTAGAAATAGATATATTTAAGGAGTCTATGGAACTATTTG
```

FIGURE 3LL

```
                [T,C]
                ACAAATTATATATATTATTGTATGAGAACTTCAGAACCTCCTAAGGAATTAAGTTTAAACTA
                CTTTTTGTTTTAGAGGGGGAAAAATGAGTGTATTAAATTTCCTTCAGATGATGAAAGGTA
                TAGGAGAATACTTTTATAAAAGCATTTGCTGAGTAGAACACTGTATTACCTTACAGACAA
                ACTTATTAAGATTGTAATACATACAGTTATACTTTGAGATAGGTGACTTGACATGGGTAT
                CAAACAGCTGTGTTATATCTGTAGCATCAGAATTCTGATATATCTGAGCAAACGTACCAG

59201           CTTATTTCATATATATAATGAACACAGGATACAGAGTTGCATGAGATGTCAGGAAAAGTG
                ATGTTCTTAAAAATGTAGAAATAGATATATTTAAGGAGTCTATGGAACTATTTGTACAAA
                TTATATATTATTGTATGAGAACTTCAGAACCTCCTAAGGAATTAAGTTTAAACTACTTTT
                TGTTTTAGAGGGGGAAAAATGAGTGTATTAAATTTCCTTCAGATGATGAAAGGTATAGGA
                GAATACTTTTATAAAAGCATTTGCTGAGTAGAACACTGTATTACCTTACAGACAAACTTA
                [T,C]
                TAAGATTGTAATACATACAGTTATACTTTGAGATAGGTGACTTGACATGGGTATCAAACA
                GCTGTGTTATATCTGTAGCATCAGAATTCTGATATATCTGAGCAAACGTACCAGGTGGCT
                TTCATGTGTCCTGCGGGATGAGTCACATGAAAGCATCTTTGGTGTAATGTGGGTCCTCCT
                CAAGAGATCCTCTAAGTCACCAGGGAGTCAGCAAAGGCAGCCTTGCAGCAGATCTTGAGC
                AATGAGTAAGCACTTCCCTGGGGGAGGGCCTTGCAGGGGCGGGGCAGGGGCAAGTTGTTG

60695           CCACTAATCTCTTCTCAATCTCTATAGTTTTGTCATAAGTCAACCCCTTCCTTTTCATAA
                AGGGTTTATGAATTTCCCTGATGAAAAAGTACAAAATGAGGCCAGGCGTGGTGGCTCATG
                CCTGTAATCCCAGCACTTTGGGAGGCCAAGGCGGGTGGCTCACCTGAGGTCAGGAGTTCA
                AGACCAGCCTGGCCAACATGGTGAAACCTTGTCTCTGCTAAAAATACAAAA
                [G,A]
                TTAGCCAAGCATGGTGGCACGCACCTGTAGTCCCAGCTACTCAGGAGGCTGAGGCAGGAG
                AATCACTTGAACCTGGGAGGCAGAGGTTGCATTGAGTCAAGATCACGCCACTGCACTGCA
                GCCTGGGTGATAGAGCAAGTCTCCATCTCAAAAAAAAAAATTTACAAAGTGGGGCCGGTT
                GTGGTAGCTCATGCCAGTAATTCCAAAGCTCTGGGGAGGAAGATCACTTGA

61592           AAATATACTCCTTTGAGAAATCGTATAAGTAACTAAAGAAACTTTACGGTAATGCGAAAG
                CTATGTGCATTCAGTAGAAAGCAGTCAATCCTCTCTTGTGATGCTGAGTAGCAGCAGGGA
                GCCACAGCTGCCAGTCAGCCACACAGTCTCAGTTTAGGGTATTTTCAGCTTACAGTGGGT
                TATCATGGGTCATGAGTTATGGGAATATCATGATCAGAGAGCATCTGTAAAGTGAGAAAT
                TAGATTTGCTTGATTTCAAGTACTTTATGTATTTGTAGTGGAAATTTGATTTTTAACACT
                [A,G]
                CTTTTCCTTTTCTCTCTTCAGGGCATTCCTTAAGCATTCAGCAGAACTTGTATACATGCT
                AGAAAGCAAACATCTCTCTGTAGTCCTACAAGGTAACTAAAGTAACTCCTGAAAGCACCA
                TGACCACCATACCAGCCAGCCTTGGTTTACTGCTTGTCCCCATTCAAGTAAATCACATCA
                GTTTTAGCTATTTCTTATTTACTACAGTACCATCAAATACATTACAGATTTTGCACATCA
                TTTGAGTAAAACAGTGGCACAGGCTGGGCGCAGTGGCTGAAGCCTGTAATCCCAGACTTT

62577           TTTGACAGGGCATTCTCTCTCTGTAATTTTGCTGTCTAATTTGTACAAATTTGTTTTAGT
                TTAAATACCTTCTGGCTCATGCTAGATTATGACTCTAAGGAAGCAGTTTGAGATGAAGAA
                ATTTAGACTGAACTGCTGAATAGCTAGTAATGTAATATTTGGTAGGAATAAACGGTGATG
                TAAAAATCTTTCAGTTAAGCAAAGGATAATTACATATTAAATAACTTACAGCTAATAGAA
                TTTGTAAGTTTGCAGATAAAGTTCAATAGACTAAAAACTACCTTCGTATAATACAGTAGT
                [G,A]
                GGTCCTTTGTACCCATGGCTTCCCCATCTGTGGTCAACCAACCCAGGACTGAAAATATTG
                GCGGGGGAAAGCTTTGGCCGTAATGAACATGAACAGACTTTTTTTTTGTTGTCATTATTC
                TCTAAACAGTATAGTATAACAACTGTTTACATAGCATTTACATTGTATTAGGTGTTATAA
                GTAATCTAGAGGTAACTTAAAGTGTACAGGAGGATGTGCATAGGTTATATGCAAATATTA
                ACATCATTTTATATCCAGGACTTAAGCATTTGTGGATCTTGGTATCCAAAGGAGGCCCTG

62580           GACAGGGCATTCTCTCTCTGTAATTTTGCTGTCTAATTTGTACAAATTTGTTTTAGTTTA
                AATACCTTCTGGCTCATGCTAGATTATGACTCTAAGGAAGCAGTTTGAGATGAAGAAATT
                TAGACTGAACTGCTGAATAGCTAGTAATGTAATATTTGGTAGGAATAAACGGTGATGTAA
                AAATCTTTCAGTTAAGCAAAGGATAATTACATATTAAATAACTTACAGCTAATAGAATTT
                GTAAGTTTGCAGATAAAGTTCAATAGACTAAAAACTACCTTCGTATAATACAGTAGTAGG
                [C,T]
                CCTTTGTACCCATGGCTTCCCCATCTGTGGTCAACCAACCCAGGACTGAAAATATTGGCG
                GGGGAAAGCTTTGGCCGTAATGAACATGAACAGACTTTTTTTTTGTTGTCATTATTCTCT
                AAACAGTATAGTATAACAACTGTTTACATAGCATTTACATTGTATTAGGTGTTATAAGTA
                ATCTAGAGGTAACTTAAAGTGTACAGGAGGATGTGCATAGGTTATATGCAAATATTAACA
                TCATTTTATATCCAGGACTTAAGCATTTGTGGATCTTGGTATCCAAAGGAGGCCCTGGAA

62596           TCTGTAATTTTGCTGTCTAATTTGTACAAATTTGTTTTAGTTTAAATACCTTCTGGCTCA
                TGCTAGATTATGACTCTAAGGAAGCAGTTTGAGATGAAGAAATTTAGACTGAACTGCTGA
                ATAGCTAGTAATGTAATATTTGGTAGGAATAAACGGTGATGTAAAAATCTTTCAGTTAAG
```

FIGURE 3MM

CAAAGGATAATTACATATTAAATAACTTACAGCTAATAGAATTTGTAAGTTTGCAGATAA
AGTTCAATAGACTAAAAACTACCTTCGTATAATACAGTAGTAGGTCCTTTGTACCCATGG
[C,G]
TTCCCCATCTGTGGTCAACCAACCCAGGACTGAAAATATTGGCGGGGGAAAGCTTTGGCC
GTAATGAACATGAACAGACTTTTTTTTTGTTGTCATTATTCTCTAAACAGTATAGTATAA
CAACTGTTTACATAGCATTTACATTGTATTAGGTGTTATAAGTAATCTAGAGGTAACTTA
AAGTGTACAGGAGGATGTGCATAGGTTATATGCAAATATTAACATCATTTTATATCCAGG
ACTTAAGCATTTGTGGATCTTGGTATCCAAAGGAGGCCCTGGAATGAGTTCCCCATGGAT

62682   GTTTGAGATGAAGAAATTTAGACTGAACTGCTGAATAGCTAGTAATGTAATATTTGGTAG
        GAATAAACGGTGATGTAAAAATCTTTCAGTTAAGCAAAGGATAATTACATATTAAATAAC
        TTACAGCTAATAGAATTTGTAAGTTTGCAGATAAAGTTCAATAGACTAAAAACTACCTTC
        GTATAATACAGTAGTAGGTCCTTTGTACCCATGGCTTCCCCATCTGTGGTCAACCAACCC
        AGGACTGAAAATATTGGCGGGGGAAAGCTTTGGCCGTAATGAACATGAACAGACTTTTTT
        [G,T]
        TTGTTGTCATTATTCTCTAAACAGTATAGTATAACAACTGTTTACATAGCATTTACATTG
        TATTAGGTGTTATAAGTAATCTAGAGGTAACTTAAAGTGTACAGGAGGATGTGCATAGGT
        TATATGCAAATATTAACATCATTTTATATCCAGGACTTAAGCATTTGTGGATCTTGGTAT
        CCAAAGGAGGCCCTGGAATGAGTTCCCCATGGATACTGAGGGAAGACTATATACTCATGT
        TGCATAGTATATGAATACAAAATGTTGCTTAAGCTTGCAGAAGTACTTTTTTTTTTTTTG

64509   CAGGATCATATTGTCTTCAAAGACAGTTTTTACCTTTTTCTTTCTGATCTGAATGCCTTT
        TATTTTCTTTTTCTTGCCTAATTGCTCTGGCTAGATTCTCCAGTTCAATGAGATGGAGAA
        GTGTAGAGAACAGACATCCTTATCATCTTCCTGATCTTAGGGAGAGAGTATCCAGTCTTT
        CACCAGTGAAATGGGAATAACATTAATTGTAGGTTTTTGTGGATGTCTCTGATCAGTTTA
        AATATGTTTACTTTTATTCCTAATCAGGAATGAAGGTAGAATTGTATCAGATGCTTTTTC
        [C,T]
        GCATCTAATGAGATAATCGTGTTGGTTTTGTCCTTTATTACTGTGGTACGTTACTACAAT
        TGACAGATGTTAAACCAACTTTGCATTCCTGGATAATTTGGTTTACTCATATTTTTATTG
        ATTTTTACATCTGTAATCATAAGGGATATTGGTCAATAGTTGTCTTCTGATTTCCCTGGC
        TGACTTTGATAGCGTGGCAATTCTGGCCTTATTGGAAAGGACAACAACTATAAAAGACAG
        GAGGGAATCGTTTGCCACAGCTTCAGTTGGTAGTGAACAGTCCCACTCTCCCCATTCACT

64898   CTGGATAATTTGGTTTACTCATATTTTTATTGATTTTTACATCTGTAATCATAAGGGATA
        TTGGTCAATAGTTGTCTTCTGATTTCCCTGGCTGACTTTGATAGCGTGGCAATTCTGGCC
        TTATTGGAAAGGACAACAACTATAAAAGACAGGAGGGAATCGTTTGCCACAGCTTCAGTT
        GGTAGTGAACAGTCCCACTCTCCCCATTCACTTCTCAGTATTGCCATGTGGCCTGTCAGT
        AGAAAGATTACCTTATACTTAATACCTTGACAAAAGAGCAGTAGAATGGAGTCTAGACGG
        [A,G]
        TTTTCTACCACAAACCATTCGAATGTAAAAAGTATGAGTGATGAGCTTCTATTATCTGGC
        AAATATCCATGTATAAAAGACCATCTCCTATTAAATGCTAATTTAGTTTATCTACAAGTC
        TGTAATATTTTAGAGTTGCTGGAATCCAGTAAAATTTCCTTATACAGATTTGGAAGGCAG
        CCTAGGTGTGCAGAATACTAAATTATCTAGTTTACCTTTCCTTCCCTTTCTCTCTCAGCA
        TTTTTCTATGTTGTAATCATTTTCTTTCCATTTTATTAACAGAGGAGGAAGGAAGAGACT

67072   CTTTAACCACCTTAAATGTCATGCTTTTGTATTTATATTTCACATTTGGGCTATTGGGTA
        GTAAAAAACAAAAGCCCTGTTACACGACATTTATTTCCTAGGTCAGTAGGATAAAAAGTT
        GTACAAAACAAGATTATTTTCCTTCACGAGTTTGAAGTTTCTGGTCACAATTCATTGATG
        TAGAGGATTTATGACTAAGCAGGGTCTCAAGCCAAACTTGAAACCATTCTGAACCAAAGT
        GCCATTTCACCCACCTCGAACCAACAACAGAAGCTGACAAATGCCGTGGAGACCATTGAG
        [A,G]
        GAAACAGAAAGGGGCAGCTCTTGTGGACCTTCAGGAAGCCTTTCTAGGAAGAGGATTGCC
        CTCATAGTGAGCTCCGGGGTCTTCAGCCTCAGCCGTAAGGCCCTGGGCTAGGCAGTGTGA
        CCTAGGGAGCGGGAAACCTGAGTTCTGGCCCTGGTCTGGGAAAAGTGCTAGGCCCATGTT
        CCACTCAGGCTTCAGCCTGAGAGTCCAGGTTGCTAACCTGTAAAATGGATCTGTCAAACT
        AACACTTATGCCTTTAGTCTCATTGTATGAGGTGAAACATTTTGTAAACTGTGAATCATT

67283   CCAAACTTGAAACCATTCTGAACCAAAGTGCCATTTCACCCACCTCGAACCAACAACAGA
        AGCTGACAAATGCCGTGGAGACCATTGAGAGAAACAGAAAGGGGCAGCTCTTGTGGACCT
        TCAGGAAGCCTTTCTAGGAAGAGGATTGCCCTCATAGTGAGCTCCGGGGTCTTCAGCCTC
        AGCCGTAAGGCCCTGGGCTAGGCAGTGTGACCTAGGGAGCGGGAAACCTGAGTTCTGGCC
        CTGGTCTGGGAAAAGTGCTAGGCCCATGTTCCACTCAGGCTTCAGCCTGAGAGTCCAGGT
        [T,C]
        GCTAACCTGTAAAATGGATCTGTCAAACTAACACTTATGCCTTTAGTCTCATTGTATGAG
        GTGAAACATTTTGTAAACTGTGAATCATTATGCAAATTTTCCTAAAGACATATGAATTAT
        TCTGGATTTGTTGGTATAAAAGACAAAACACACTGGTCAGTTAAGGAGCTGATTTTATTT
        AGGCTATTGCAGGAGGGAGAACTTAATTAATGGGCATCCCAAAGAAAAGGACAAGGCCTG
        GGATTTTATAGTCAGAAGACAGGGGAATCAGGAGGGAGGGCAGTCTCAGTCCACAGGAGC

FIGURE 3NN

| | |
|---|---|
| 67432 | CCTCATAGTGAGCTCCGGGGTCTTCAGCCTCAGCCGTAAGGCCCTGGGCTAGGCAGTGTG<br>ACCTAGGGAGCGGGAAACCTGAGTTCTGGCCCTGGTCTGGGAAAAGTGCTAGGCCCATGT<br>TCCACTCAGGCTTCAGCCTGAGAGTCCAGGTTGCTAACCTGTAAAATGGATCTGTCAAAC<br>TAACACTTATGCCTTTAGTCTCATTGTATGAGGTGAAACATTTTGTAAACTGTGAATCAT<br>TATGCAAATTTTCCTAAAGACATATGAATTATTCTGGATTTGTTGGTATAAAAGACAAAA<br>[C,T]<br>ACACTGGTCAGTTAAGGAGCTGATTTTATTTAGGCTATTGCAGGAGGGAGAACTTAATTA<br>ATGGGCATCCCAAAGAAAAGGACAAGGCCTGGGATTTTATAGTCAGAAGACAGGGGAATC<br>AGGAGGGAGGGCAGTCTCAGTCCACAGGAGCCAGTTCTCAGGACACAAAAGGCAGGAGAG<br>ATTGTCCAGCATTGCCACTTTTGGGGAACCCA |
| 68079 | GAGATTGCAGTGAGCTGAGACTGTGCCACTGCACTCCAGCCTGGGTGATAGAGCCAGAGT<br>CTGTCCCCTGCCCACCCCACCAGGAAAGTTTGACCTTTCCAGATACTGTGCTGAGAACCA<br>GTGATACAGGCTTAGAGGCTCCTGAGGCATGGAACGCTCATTTGTTCCTAAAATACATGC<br>TCTCCCAGTTGCTTGTTTTTATTTTTCGTCACCATAATCATTCTTGGGGCCCCTCTCTGC<br>CTCGAGCTAGGCTTTCCCCCCTGGCCTTGTTTGCCTCCTTCAGCTCTTCCCCATTGTCTCC<br>[C,T]<br>GTCACTACCCCGTGCGCACACAGTGTGAGCCTGCAAAAGGTGCGTGAGGCGAGGACAAAG<br>ACTTTGGGGTCTGGGGACTGGGCAGTGCATGGGTGGGTATCTGCGTGGAGGACTCCCAGC<br>CCCCAGACACCACTGCCTCTGCTGCTTGGCTGATGCTGTGTGTGCGGACAGACTTCTCAC<br>CAGGAATGAACATTACTGAATTGTATTGAGGGAGCTGTAAAAAATACTTTCTACAAGTAT<br>TTCCTCTGCTTTCCCTGTTCATGTTCTAGTGCTCTTTTTAATTTGGCTCTTTCAAAAGCC |
| 69067 | CGCATGCCACCACGCCTAGCTAATTTTTGTATTTTTTTGTAGAGTCAGGGTTTCGCCATG<br>TTGCCCAGTCTGGTCTTGAACTCCTGGACTCAAGCAATCCGCCCACCTCAGCTTCCCAAA<br>GTACTGGGATTACAGGCGTGAGCCACCGTGCTTGGCCAAGAGGACATTTTCTATATACTT<br>ACTGAAGGGCCATTAAAACACGTTTGGGTTCATGTTTTACTAGATTTCAGCTCTTAACAG<br>TGTTTGAAGCAAATGGATTGTTTTTAATCCATGTACATGATGAAATGTCAAGTAACTAAA<br>[T,A]<br>TTTTTTTTTTTTTTTTTTTGAGACAGAGTCTTGCTCTATCACCCAGGCTGGAGCACAGTG<br>GCATGATCTCGGCTCACTGCAACCTCTGCCTTCCAGGTTCAGGTGATTCTCCTGCCACAG<br>CCTCCCGAGTAGCTGGGACTACAGGTGCACACCACCATGCCTGGCTAATTTTTGTATTTT<br>TAGTAGAGACGGGGTTTCACCATATTGGCCAGGCTGGTCTTGAACTCCTGACCTCGTGAT<br>CCGCCTGCCTTCGGCCTCCCAAAGTGCTGGGATTACAGGCATGAGTCACCACTGCGCCTG |
| 69122 | CCATGTTGCCCAGTCTGGTCTTGAACTCCTGGACTCAAGCAATCCGCCCACCTCAGCTTC<br>CCAAAGTACTGGGATTACAGGCGTGAGCCACCGTGCTTGGCCAAGAGGACATTTTCTATA<br>TACTTACTGAAGGGCCATTAAAACACGTTTGGGTTCATGTTTTACTAGATTTCAGCTCTT<br>AACAGTGTTTGAAGCAAATGGATTGTTTTTAATCCATGTACATGATGAAATGTCAAGTAA<br>CTAAAATTTTTTTTTTTTTTTTTTGAGACAGAGTCTTGCTCTATCACCCAGGCTGGAGC<br>[G,A]<br>CAGTGGCATGATCTCGGCTCACTGCAACCTCTGCCTTCCAGGTTCAGGTGATTCTCCTGC<br>CACAGCCTCCCGAGTAGCTGGGACTACAGGTGCACACCACCATGCCTGGCTAATTTTTGT<br>ATTTTTTAGTAGAGACGGGGTTTCACCATATTGGCCAGGCTGGTCTTGAACTCCTGACCTC<br>GTGATCCGCCTGCCTTCGGCCTCCCAAAGTGCTGGGATTACAGGCATGAGTCACCACTGC<br>GCCTGGCCAAAACTGTTAAGAGTATGTGTATTTGGTGCTTAATGAATTTTTACTTATTTG |
| 69951 | CTGAAAGGTACAGAACAAAGAATCAGACATTTCCCATCATCCAGCGACTTTGTGTCTGGA<br>GTTATTTTCCTCCAGCGAACTGTTGTGTATACACTGCTGTGGTAGCCTGCTGCCATCAATC<br>AGCTGAGATGAGAGTCCTTTCTCCACATTGCTAAATGTGACTGTGCTTCATAGAAATGGT<br>CTGGGCTGCCTTCCAGAGGAGCTCCATGTCTTCCTCACAATGCGGTGGTTGGCTGTCACC<br>CTGTAGCCTTGTGTTGCCTCAGTTTACTGTGGTGGGAAGCCAGATAACTAGGCTGCACCC<br>[A,G]<br>CCCAGAGTCCGGGCTAGAGGTGGACTCCTGTGAAGGAGGGGTCTCCTGTGTACATGGTCT<br>CCATGGTTTTAGCCACATGCTAGGACCACAGGGAGTTGATCCCTTCCTTCCTACCCTGAG<br>TCTGTGGTCTGTGATTTGAGATCACTGGCTCAGTGAAGTGTAGCTCCCCACTTACGAAGT<br>AAGTTATAAAATTGGTGGCAGTGATTTCCATCCAAAGATTTTGTTAATCCACTTACCAAC<br>AGGTAACTACTTAAATGTACTGACCGTGTGCTCATAAAAGTAAAATACTGTAATTATAGA |
| 70498 | CTACTTAAATGTACTGACCGTGTGCTCATAAAAGTAAAATACTGTAATTATAGAAATAAA<br>TTCAACATGTTTAAGACTTTCTAGTATCATGTTAGTGAAACTTCTCTTAATAACATTCTT<br>ATTGCCCAAAGGGCACGGCTTCCTTGGGGTCCTAAGGCAGAGGGCACCTGAAAAGCACAC<br>TCCTTGTTCATGGGGACTGTGGGGCCCTCTGAGCTCAAAGGCCAGGAGCGTCTCCTCTCT<br>TGAAGTGAAAGTGCCACTCTGGTGGGTTTTGAGGGCTGCAGTACAGAACATTTAACCTGT<br>[G,A]<br>TAATGATGAGTGGCTCATCTGAAAAAAGGCATTCATGAGAGAATCTTTAGTTTTGCAAAT<br>ATTTATTTATTTATTTTGCAGGAATTTGCTATAAGCAAAAACATCCAATTGGGTGATGAG |

FIGURE 3OO

```
                AAGGGCTTAAAATTCCCCTCTGTTTGGGACTGGTCTCTCCAGTTTACAGCAAAGGATCGC
                ACCCTTTTCCATAACCCCTTCTACATTGGAAAGAGCACACCTTGTATACAGAATGGCTCC
                GTGAAGTCTTTTAAACGGACAAAGGTAAATCACAGCTAACAAAACGTGATGTTGGCTCAC

70850           TTTGCAAATATTTATTTATTTATTTTGCAGGAATTTGCTATAAGCAAAAACATCCAATTG
                GGTGATGAGAAGGGCTTAAAATTCCCCTCTGTTTGGGACTGGTCTCTCCAGTTTACAGCA
                AAGGATCGCACCCTTTTCCATAACCCCTTCTACATTGGAAAGAGCACACCTTGTATACAG
                AATGGCTCCGTGAAGTCTTTTAAACGGACAAAGGTAAATCACAGCTAACAAAACGTGATG
                TTGGCTCACACGTAACCAAACACCTCTTTTTTCAGAACAGAGAGCGTTAAAAGTAAAGGCA
                [C,G]
                TTCCAAGAGTAACACTGCTAATGCGGGTTTCTGAGGGGTCATTCCCTTTTTAACTCAAAT
                GACTGTATCCCAGCTTTCTTCCTGGTGTCTGAGGCCCACAAAGTCTCAGTACCTGAGAGT
                GGGCAGATTGCAGCTTTGAGCCTGCAAGCCTGATTTACTAAAGCCCCATTTATCCATTTC
                TTGATGATTCAAGCCGCCACTGTGGCAGGGAATGCCGCCTGGCTGTGATGTAGTCATGGC
                CTCCTGACTGCTATATTCTTGTCCTAATAACATTCATTGTTTGCCTTTTTAATAATTCCC

70874           TTGCAGGAATTTGCTATAAGCAAAAACATCCAATTGGGTGATGAGAAGGGCTTAAAATTC
                CCCTCTGTTTGGGACTGGTCTCTCCAGTTTACAGCAAAGGATCGCACCCTTTTCCATAAC
                CCCTTCTACATTGGAAAGAGCACACCTTGTATACAGAATGGCTCCGTGAAGTCTTTTAAA
                CGGACAAAGGTAAATCACAGCTAACAAAACGTGATGTTGGCTCACACGTAACCAAACACC
                TCTTTTTCAGAACAGAGAGCGTTAAAAGTAAAGGCACTTCCAAGAGTAACACTGCTAATG
                [C,T]
                GGGTTTCTGAGGGGTCATTCCCTTTTTAACTCAAATGACTGTATCCCAGCTTTCTTCCTG
                GTGTCTGAGGCCCACAAAGTCTCAGTACCTGAGAGTGGGCAGATTGCAGCTTTGAGCCTG
                CAAGCCTGATTTACTAAAGCCCCATTTATCCATTTCTTGATGATTCAAGCCGCCACTGTG
                GCAGGGAATGCCGCCTGGCTGTGATGTAGTCATGGCCTCCTGACTGCTATATTCTTGTCC
                TAATAACATTCATTGTTTGCCTTTTTAATAATTCCCAAATAAATTCTTGGGATTTTTTTT

70923           GCTTAAAATTCCCCTCTGTTTGGGACTGGTCTCTCCAGTTTACAGCAAAGGATCGCACCC
                TTTTCCATAACCCCTTCTACATTGGAAAGAGCACACCTTGTATACAGAATGGCTCCGTGA
                AGTCTTTTAAACGGACAAAGGTAAATCACAGCTAACAAAACGTGATGTTGGCTCACACGT
                AACCAAACACCTCTTTTTCAGAACAGAGAGCGTTAAAAGTAAAGGCACTTCCAAGAGTAA
                CACTGCTAATGCGGGTTTCTGAGGGGTCATTCCCTTTTTAACTCAAATGACTGTATCCCA
                [A,G]
                CTTTCTTCCTGGTGTCTGAGGCCCACAAAGTCTCAGTACCTGAGAGTGGGCAGATTGCAG
                CTTTGAGCCTGCAAGCCTGATTTACTAAAGCCCCATTTATCCATTTCTTGATGATTCAAG
                CCGCCACTGTGGCAGGGAATGCCGCCTGGCTGTGATGTAGTCATGGCCTCCTGACTGCTA
                TATTCTTGTCCTAATAACATTCATTGTTTGCCTTTTTAATAATTCCCAAATAAATTCTTG
                GGATTTTTTTTGGTAGAAAATTTGCAGACTACTGAAAGGTACAGAACAAAGAATCAGACA

71276           GATTGCAGCTTTGAGCCTGCAAGCCTGATTTACTAAAGCCCCATTTATCCATTTCTTGAT
                GATTCAAGCCGCCACTGTGGCAGGGAATGCCGCCTGGCTGTGATGTAGTCATGGCCTCCT
                GACTGCTATATTCTTGTCCTAATAACATTCATTGTTTGCCTTTTTAATAATTCCCAAATA
                AATTCTTGGGATTTTTTTTGGTAGAAAATTTGCAGACTACTGAAAGGTACAGAACAAAGA
                ATCAGACATTTGGCCTCCTGACTGCCTCTGTTCAGTTTGCCATTGTTCTTGATAGAATCG
                [G,A]
                CCAGGTCTAGTGTTTTTTCTAGCCCGTCTTAGAACTTATCCTTAAGCAAATTAGTGGATA
                GGAGGTACTCTCATCCCGCCCCCATTCAGGCTGATAGTAACAGCCTAGGTAGAGTCAACA
                CATAAAAAAGTGTAATTCCAGGGGAGGAGGATTAGAATAAGGACACAAAGGAAGGGAGGA
                AAATGTTCTTTGAGGCTGAAATTCCATTAATTTTTCATAGTATTGAGTTTATATTTGCCA
                TTGCATCCTTCAATCTTTCTAAAAAGGGAATCCCCGGAACATAATAAAATCTCTTCTGTA

74663           AAAACCTTTGTGCCTAAAATTGATGACTTGAGTTCAAGTGGGATGAGCAAGAAGATGTGT
                TATCTTGTTGTTCAACAGTATTGA
                [G,A]
                TGTGAAGGAAATTTTGATGGCTTAATAAAATTCCACAGCGACTGTTTGTTGTTGTCAGTA
                TGAAATCATCTACTGGAACACAGT

74598           AAAACCTTTGTGCCTAAAA
                [T,C]
                TGATGACTTGAGTTCAAGT

81794           CTCCACCTCCTGGGTTCAAGCGATTCTCCTGCCTCAGCCTCCCAAGTAGCTGGGACTACA
                GGCGCCCGCCACCACACCCGGCTAATTTTTTGTATTTTTAGTAGAGACGGGGTTTCACCA
                TGTTAGCCAGGATGGTCTCAATCTCCTGACCTCGTGATCCGCCCACCTCTGTCTCCCAAA
                GTGCTGGGATTACAGGTGTGAGCCACCGTACCCGGCCTCAGCTGGCTTTTTTTTTTTCTTG
                GAAACTTAAAATTTGATGTTATAATTCAAATAAAAATGCAAAAGAGCCAGAACAACTTTG
                [A,G]
```

FIGURE 3PP

```
         AAAACAAGTCATTATAGGACTTACACTACCTGACTCCAAGATGTATCTAAAGCTACAATA
         ATCAAGAAATACAGACAAACAGATCAATGGAACCGAAGAGTATATAGAAACAGACCCACA
         TATATATGGGTTACTGATTTTTGACAAAGATACAGAGGGAATTCAGTGGAGGAAGCATGG
         TCTTCTTGACACATGGAGCTGGAACAAGTGGATATCCACACACCACAAATGAATTCCAGT
         GCATGCCCCACACTGTATACAAATGGCGTCTCAAATGATCATAAAACTGAATGTAAAACC

81752    CTCCACCTCCTGGGTTCAAGCGATTCTCCTGCCTCAGCCTCCCAAGTAGCTGGGACTACA
         GGCGCCCGCCACCACACCCGGCTAATTTTTTGTATTTTTAGTAGAGACGGGGTTTCACCA
         TGTTAGCCAGGATGGTCTCAATCTCCTGACCTCGTGATCCGCCCACCTCTGTCTCCCAAA
         GTGCTGGGATTACAGGTGTGAGCCACCGTACCCGGCCTCAGCTGGCTTTTTTTTTTTCTTG
         GAAACTTAAAATTTGATG
         [-,T]
         TATAATTCAAATAAAAATGCAAAAGAGCCAGAACAACTTTGAAAAACAAGTCATTATAGG
         ACTTACACTACCTGACTCCAAGATGTATCTAAAGCTACAATAATCAAGAAATACAGACAA
         ACAGATCAATGGAACCGAAGAGTATATAGAAACAGACCCACATATATATGGGTTACTGAT
         TTTTGACAAAGATACAGAGGGAATTCAGTGGAGGAAGCATGGTCTTCTTGACACATGGAG
         CTGGAACAAGTGGATATC

81652    CTCCACCTCCTGGGTTCAAGCGATTCTCCTGCCTCAGCCTCCCAAGTAGCTGGGACTACA
         GGCGCCCGCCACCACACCCGGCTAATTTTTTGTATTTTTAGTAGAGACGGGGTTTCACCA
         TGTTAGCCAGGATGGTCTCAATCTCCTGACCTCGTGAT
         [G,T,C]
         CGCCCACCTCTGTCTCCCAAAGTGCTGGGATTACAGGTGTGAGCCACCGTACCCGGCCTC
         AGCTGGCTTTTTTTTTTCTTGGAAACTTAAAATTTGATGTTATAATTCAAATAAAAATGC
         AAAAGAGCCAGAACAACTTTGAAAAACAAGTCATTATA

81899    GACGGGGTTTCACCATGTTAGCCAGGATGGTCTCAATCTCCTGACCTCGTGATCCGCCCA
         CCTCTGTCTCCCAAAGTGCTGGGATTACAGGTGTGAGCCACCGTACCCGGCCTCAGCTGG
         CTTTTTTTTTTTCTTGGAAACTTAAAATTTGATGTTATAATTCAAATAAAAATGCAAAGA
         GCCAGAACAACTTTGAAAAACAAGTCATTATAGGACTTACACTACCTGACTCCAAGATGT
         ATCTAAAGCTACAATAATCAAGAAATACAGACAAACAGATCAATGGAACCGAAGAGTATA
         [T,C]
         AGAAACAGACCCACATATATATGGGTTACTGATTTTTGACAAAGATACAGAGGGAATTCA
         GTGGAGGAAGCATGGTCTTCTTGACACATGGAGCTGGAACAAGTGGATATCCACACACCA
         CAAATGAATTCCAGTGCATGCCCCACACTGTATACAAATGGCGTCTCAAATGATCATAAA
         ACTGAATGTAAAACCTAAAACTATAACACTTCTAGAAGAAAACAAAGGAGAAACTCTTTG
         TGACCTTGGATTAGGCAAGTATTTCTGACATGTGACACCAAAAGCATGATCCACTAGAGA

82828    CAAGGGGAATGGGGTATCTGTCCCCTCAAGCATTTATCCTTTGAGTTACAAACCATTATA
         CTCTTTAAGTCATTTTAAAATGTACAATTATCGGTAAGCTTCTAAAATAGCTCCTGGTGT
         CCACACCCGTTGTGACCCCCTCCCTTTGAGTGTCAGCTGGACTAGAGACTCGTTCCTAAC
         CACAGAATACAGCAGGAGTGATGGAACATCATGTCCACATCAAGTCATAAGAGATGGAGC
         TCTGTCTTGCTCACACTCTGGGGCTCCTCTCACCCGCCTGCTCTGATGAAGCCAGTCGCA
         [G,C]
         GGGACAGGCCCACAGGAACCCAGGCCCTCGGCCCAAAAGCTCTCAAGGAATTCAATCTTG
         CCAACAGCCACTCAAGAAATGCCTACTTGTGGCCTCTGATTCAGTTGCTAATAAGGTTAC
         CAACAGGACTTTCCATTCTGCCTCAACTGACCTTAAAGTGACGGCTCTGGGAGTTCCACA
         CCACCAGGTCGGGGAGGCCCCCTCGACAGTGTCGAAAGTCAGCAGCCAGGTGCCTGCACA
         CACCACTGAGCACAGGGCCCCCCAGGCAGGAGACAAGATCCTGAACACAAAACACAGGAC
```

FIGURE 3QQ

SEQUENCE LISTING

```
<160> NUMBER OF SEQ ID NOS: 11

<210> SEQ ID NO 1
<211> LENGTH: 4458
<212> TYPE: DNA
<213> ORGANISM: Human

<400> SEQUENCE: 1
gagagcttta cgcccggagg cgtcggcgct gccactggcc cgcgacggga acggggcgaa      60
aaggcggcgg caccatgttc tccctcaagc cgcccaaacc caccttcagg tcctacctcc     120
tgccaccgcc ccagactgac gataagatca attcggaacc gaagattaaa aaactggagc     180
cagtcctttt gccaggagaa attgtcgtaa atgaagtcaa ttttgtgaga aaatgcattg     240
caacagacac aagccagtac gatttgtggg gaaagctgat atgcagtaac ttcaaaatct     300
cctttattac agatgaccca atgccattac agaaattcca ttacagaaac cttcttcttg     360
gtgaacacga tgtcccttta acatgtattg aacaaattgt cacagtaaac gaccacaaga     420
ggaagcagaa agtcctaggc cccaaccaga aactgaaatt taatccaaca gagttaatta     480
```

-continued

```
tttattgtaa agatttcaga attgtcagat ttcgctttga tgaatcaggt cccgaaagtg      540
ctaaaaaggt atgccttgca atagctcatt attcccagcc aacagacctc cagctactct      600
ttgcatttga atatgttggg aaaaaatacc acaattcagc aaacaaaatt aatggaattc      660
cctcaggaga tggaggagga ggaggaggag gaggtaatgg agctggtggt ggcagcagcc      720
agaaaactcc actctttgaa acttactcgg attgggacag agaaatcaag aggacaggtg      780
cttccgggtg gagagtttgt tctattaacg agggttacat gatatccact tgccttccag      840
aatacattgt agtgccaagt tctttagcag accaagatct aaagatcttt tcccattctt      900 ttgtttgggag aaggatgcca ctctggtgct ggagccactc taacggcagt gctcttgtgc      960
gaatggccct catcaaagac gtgctgcagc agaggaagat tgaccagagg atttgtaatg     1020
caataactaa aagtcaccca cagagaagtg atgtttacaa atcagatttg ataagacct      1080 tgcctaatat tcaagaagta caggcagcat ttgtaaaact gaagcagcta tgcgttaatg     1140 agcctttga agaaactgaa gagaaatggt tatcttcact ggaaaatact cgatggttag      1200
aatatgtaag ggcattcctt aagcattcag cagaacttgt atacatgcta gaaagcaaac     1260
atctctctgt agtcctacaa gaggaggaag gaagagactt gagctgttgt gtagcttctc      1320
ttgttcaagt gatgctggat ccctatttta ggacaattac tggatttcag agtctgatac     1380
agaaggagtg ggtcatggca ggatatcagt ttctagacag atgcaaccat ctaaagagat     1440
cagagaaaga gtctcctta ttttttgctat tcttggatgc cacctggcag ctgttagaac      1500
aatatcctgc agcttttgag ttctccgaaa cctacctggc agtgttgtat gacagcaccc     1560
ggatctcact gtttggcacc ttcctgttca actcccctca ccagcgagtg aagcaaagca     1620
cggaatttgc tataagcaaa aacatccaat tgggtgatga aagggctta aaattcccct     1680 ctgtttggga ctggtctctc cagtttacag caaaggatcg cacccttttc cataacccct     1740
tctacattgg aaagagcaca ccttgtatac agaatggctc cgtgaagtct tttaaacgga     1800
caaagaaaag ctacagctcc acactaagag gaatgccgtc tgccttaaag aatggaatca     1860
tcagtgacca agaattactt ccaaggagaa attcattgat attaaaacca agccagatc      1920 cagctcagca aaccgacagc cagaacagtg atacggagca gtatttaga gaatggtttt      1980 ccaaacccgc caacctgcac ggtgttattc tgccacgtgt ctctggaaca cacataaaac     2040
tgtggaaact gtgctacttc cgctgggttc ccgaggccca gatcagcctg ggtggctcca     2100
tcacagcctt tcacaagctc tccctcctgg ctgatgaagt cgacgtactg agcaggatgc     2160
tgcggcaaca gcgcagtggc cccctggagg cctgctatgg ggagctgggc cagagcagga     2220
tgtacttcaa cgccagcggc cctcaccaca ccgacacctc ggggacaccg gagtttctct     2280
cctcctcatt tccatttct cctgtaggga atctgtgcag acgaagcatt ttaggaacac     2340
cattaagcaa attttaagt gggggccaaaa tatggttgtc tactgagaca ttagcaaatg    2400
aagactaaaa tagggtgttt tctgaacatt tgagggaag ctgtcaactt ttttcctctg     2460
aattaacatt gctaacctag gcgtttgaat ctctaataac tttatatgta agaataatag     2520
ttggaatttg cactaatatt taaaaacatg ttgaatcatg cttctttcac acttatttta     2580
agagagatgt aaattttgtt cctgtcctct ttctgtcatt acaggtctgg ctcttgtaac     2640
cgtgatcaaa ctgttcatgt tgtctgctac attttttgtct ccatccattt ttcctaccac     2700
ctcctgaagg ctatctgata gtcagtcaca ttagcagccc caggcagcag acaacaggaa     2760
agttaggaaa tttgtgtttc gtgtcatttt taggagcatc tgataaaacc tccagcaggt     2820
```

-continued

```
tttaggaagt attcatgtat ttttctggtt actttctgtc atctctaatt gaactcacct    2880
gatgaaggtt cagtgttctg gggccagaat ttatgatttt agatcacctt ctttggaacc    2940
ttagatcact gtgttttgaa atcatgagtt tgcttttaac ttcatagggt caactttaaa    3000
atgatatgca ctgttaattt taaagcattt gctgcagata attaaactta gaagtgcctt    3060
tgactttagg atacaaatat tacagaagaa aatataattt cactttttaa aattggggtg    3120
ggaaaatccc attgcatatt tgaataggc ttttcatact aagcttcata gccaggagtc     3180
cccagagtct tgttcctctg aaagccactg gggagtggcc tctggggtgc tgattccaca    3240
gaggtgtatg ctgtagacag gagagtgcca tctatgccaa aactcgccct caaaaacaaa    3300
caaggcttgc tgggaggcgt gctgggcttg gccatcagta tttccagtgt ggtaaactat    3360
tgctggcact tcccctgga  aataactaat gaggttacga gttgggcacc tgcacagatg     3420
tccttctctc atagttccta atgcttagga atagaggaga aataaaaaaa tggattctct    3480
caaaacactg ccatttgaat agcgacagaa gtgctccccc agcccccaac tttggacagc    3540
aaagttgagg agaatgagca gacacagttg tttgcttgat ctgaatctct ctaaagtaaa    3600
gtatttccaa actgtgtgac aagagcctac ctaccactgt agcggtcaaa gctgaagctt    3660
cttacagcag tgaaacgggg caccacctcc cccacactcc tcattccccg cttaaaacat    3720
ggatactttc aaatttgact gtttcttaaa ctgccatcct aagatatgga aaattttat     3780 agtaaagtgt ctagttagct tatttccttt tctaaaacaa gtgttttcaa gataactgta    3840 ttttacctt  atatgtactg aatagctgtt tcttttgaa  ttatttgcct tttaaaattt    3900
gataatgtct ctggatataa caggacagga gttcttaaaa aatatcttaa gaaattcact    3960
ttatgggtaa acccaaggtt tttgccaact tgttgcctag aaaataaggg ctagtttcag    4020
tttatacaaa tagaattatt aaacatttta cagtccttga ttagaaacca gacccaatct    4080
ccttataaca ccacagcgta tcctgccatt gacagtgtaa tcacaattct ccctttttca    4140
tttagctgct ttttattat  tactaaatgt tttggattga gcattttcc  ctctgtaatt    4200 ttcttccttc acgtttattt tattttaact cttgtagtat tttattgttg ttaatttaca    4260
agtttaaaaa tattaggtac tattaataat ggttaaaaat agaaaaatgc atattttgt     4320 atgataatca aatgtaaaat acttttattt ttgctggaca gttgttatat catgattatt    4380
gtgctacagt ttattgtgca taatatgaaa aacaactatg acagccttca gtcgggccag    4440
ggtgaagctg cttatacc                                                  4458
```

<210> SEQ ID NO 2
<211> LENGTH: 777
<212> TYPE: PRT
<213> ORGANISM: Human

<400> SEQUENCE: 2

Met Phe Ser Leu Lys Pro Pro Lys Pro Thr Phe Arg Ser Tyr Leu Leu
1               5                   10                  15

Pro Pro Pro Gln Thr Asp Asp Lys Ile Asn Ser Glu Pro Lys Ile Lys
            20                  25                  30

Lys Leu Glu Pro Val Leu Leu Pro Gly Glu Ile Val Val Asn Glu Val
        35                  40                  45

Asn Phe Val Arg Lys Cys Ile Ala Thr Asp Thr Ser Gln Tyr Asp Leu
    50                  55                  60

Trp Gly Lys Leu Ile Cys Ser Asn Phe Lys Ile Ser Phe Ile Thr Asp
65                  70                  75                  80

```
Asp Pro Met Pro Leu Gln Lys Phe His Tyr Arg Asn Leu Leu Leu Gly
            85                  90                  95

Glu His Asp Val Pro Leu Thr Cys Ile Glu Gln Ile Val Thr Val Asn
           100                 105                 110

Asp His Lys Arg Lys Gln Lys Val Leu Gly Pro Asn Gln Lys Leu Lys
           115                 120                 125

Phe Asn Pro Thr Glu Leu Ile Ile Tyr Cys Lys Asp Phe Arg Ile Val
130                 135                 140

Arg Phe Arg Phe Asp Glu Ser Gly Pro Glu Ser Ala Lys Lys Val Cys
145                 150                 155                 160

Leu Ala Ile Ala His Tyr Ser Gln Pro Thr Asp Leu Gln Leu Leu Phe
           165                 170                 175

Ala Phe Glu Tyr Val Gly Lys Lys Tyr His Asn Ser Ala Asn Lys Ile
           180                 185                 190

Asn Gly Ile Pro Ser Gly Asp Gly Gly Gly Gly Gly Gly Gly Gly Asn
           195                 200                 205

Gly Ala Gly Gly Ser Ser Gln Lys Thr Pro Leu Phe Glu Thr Tyr
           210                 215                 220

Ser Asp Trp Asp Arg Glu Ile Lys Arg Thr Gly Ala Ser Gly Trp Arg
225                 230                 235                 240

Val Cys Ser Ile Asn Glu Gly Tyr Met Ile Ser Thr Cys Leu Pro Glu
           245                 250                 255

Tyr Ile Val Val Pro Ser Ser Leu Ala Asp Gln Asp Leu Lys Ile Phe
           260                 265                 270

Ser His Ser Phe Val Gly Arg Arg Met Pro Leu Trp Cys Trp Ser His
           275                 280                 285

Ser Asn Gly Ser Ala Leu Val Arg Met Ala Leu Ile Lys Asp Val Leu
290                 295                 300

Gln Gln Arg Lys Ile Asp Gln Arg Ile Cys Asn Ala Ile Thr Lys Ser
305                 310                 315                 320

His Pro Gln Arg Ser Asp Val Tyr Lys Ser Asp Leu Asp Lys Thr Leu
           325                 330                 335

Pro Asn Ile Gln Glu Val Gln Ala Ala Phe Val Lys Leu Lys Gln Leu
           340                 345                 350

Cys Val Asn Glu Pro Phe Glu Glu Thr Glu Glu Lys Trp Leu Ser Ser
           355                 360                 365

Leu Glu Asn Thr Arg Trp Leu Glu Tyr Val Arg Ala Phe Leu Lys His
370                 375                 380

Ser Ala Glu Leu Val Tyr Met Leu Glu Ser Lys His Leu Ser Val Val
385                 390                 395                 400

Leu Gln Glu Glu Glu Gly Arg Asp Leu Ser Cys Val Ala Ser Leu
           405                 410                 415

Val Gln Val Met Leu Asp Pro Tyr Phe Arg Thr Ile Thr Gly Phe Gln
           420                 425                 430

Ser Leu Ile Gln Lys Glu Trp Val Met Ala Gly Tyr Gln Phe Leu Asp
           435                 440                 445

Arg Cys Asn His Leu Lys Arg Ser Glu Lys Glu Ser Pro Leu Phe Leu
450                 455                 460

Leu Phe Leu Asp Ala Thr Trp Gln Leu Leu Glu Gln Tyr Pro Ala Ala
465                 470                 475                 480

Phe Glu Phe Ser Glu Thr Tyr Leu Ala Val Leu Tyr Asp Ser Thr Arg
           485                 490                 495

Ile Ser Leu Phe Gly Thr Phe Leu Phe Asn Ser Pro His Gln Arg Val
```

-continued

```
                 500              505              510
Lys Gln Ser Thr Glu Phe Ala Ile Ser Lys Asn Ile Gln Leu Gly Asp
            515                  520                  525
Glu Lys Gly Leu Lys Phe Pro Ser Val Trp Asp Trp Ser Leu Gln Phe
        530                  535                  540
Thr Ala Lys Asp Arg Thr Leu Phe His Asn Pro Phe Tyr Ile Gly Lys
545                  550                  555                  560
Ser Thr Pro Cys Ile Gln Asn Gly Ser Val Lys Ser Phe Lys Arg Thr
                565                  570                  575
Lys Lys Ser Tyr Ser Ser Thr Leu Arg Gly Met Pro Ser Ala Leu Lys
            580                  585                  590
Asn Gly Ile Ile Ser Asp Gln Glu Leu Leu Pro Arg Arg Asn Ser Leu
                595                  600                  605
Ile Leu Lys Pro Lys Pro Asp Pro Ala Gln Gln Thr Asp Ser Gln Asn
610                  615                  620
Ser Asp Thr Glu Gln Tyr Phe Arg Glu Trp Phe Ser Lys Pro Ala Asn
625                  630                  635                  640
Leu His Gly Val Ile Leu Pro Arg Val Ser Gly Thr His Ile Lys Leu
                645                  650                  655
Trp Lys Leu Cys Tyr Phe Arg Trp Val Pro Glu Ala Gln Ile Ser Leu
                660                  665                  670
Gly Gly Ser Ile Thr Ala Phe His Lys Leu Ser Leu Leu Ala Asp Glu
            675                  680                  685
Val Asp Val Leu Ser Arg Met Leu Arg Gln Gln Arg Ser Gly Pro Leu
        690                  695                  700
Glu Ala Cys Tyr Gly Glu Leu Gly Gln Ser Arg Met Tyr Phe Asn Ala
705                  710                  715                  720
Ser Gly Pro His His Thr Asp Thr Ser Gly Thr Pro Glu Phe Leu Ser
                725                  730                  735
Ser Ser Phe Pro Phe Ser Pro Val Gly Asn Leu Cys Arg Arg Ser Ile
                740                  745                  750
Leu Gly Thr Pro Leu Ser Lys Phe Leu Ser Gly Ala Lys Ile Trp Leu
            755                  760                  765
Ser Thr Glu Thr Leu Ala Asn Glu Asp
        770                  775

<210> SEQ ID NO 3
<211> LENGTH: 83450
<212> TYPE: DNA
<213> ORGANISM: Human
<220> FEATURE:
<221> NAME/KEY: misc_feature
<222> LOCATION: (1)...(83450)
<223> OTHER INFORMATION: n = A,T,C or G

<400> SEQUENCE: 3
aaaaacagaa aaatgggtga agcaggacaa aacagtgaca ttagagccaa aagcaggggg      60
taggcaataa caccaaacat acagcgtagt caagggcatc agggtctgag aagaggttat     120
aaaactagtt ctacggactg aattgtgttc ctccaaaatg ctaatgttga aaccctaacc     180
cctggtatgg ctcatttggg agattttagg aggtaattaa agttaaataa ggtagtaaga     240
gtgggctct aatctgatag gattagcgtc cttacaagaa gagacatcaa gagatcccag      300
agagcatgtt atataccctc cccgcactgt gtgaggacat ggtgagatgg cagccatctg     360
caaatccggc agagagccct cacctgtctg cctgccacaa gttaggcaga tccctacctt     420
```

-continued

| | |
|---|---|
| gccaacacct ggatcttgga cttcctatac tccagaattg tgagaaatta atgtctgctc | 480 |
| tttaagccat caacctgtgg tattttgtta tggcagcctg agcagactaa tacaaccaga | 540 |
| tatttgggaa atgccataaa atttagtgtt aagacaataa taaatgctgg aaatagagtt | 600 |
| tttccacttt tcagttgtat ggtcacatat tagaattgca gatcctaaga aaacctgtac | 660 |
| agaaaaaccc aaatcacaga gtcatttaag tgtaaagaaa aagccaatta ttgcttaaag | 720 |
| agtatttgta gaaaatatcc gttgaatata gaggaataac agcatattca taaaaatttt | 780 |
| ttaaaaagtg tgcacgacag tgattttaac acttctaatc caatgaaact aacattttaa | 840 |
| agtacaatta tggccaggca cggtgcctca tgcccatagt cccggctact tgagaggcta | 900 |
| aggcacgtgg atcacttgag cccaggaggt ggaggcagca gtgagccctg atcatgccac | 960 |
| tgcacttcag cccaggtgat ggtgtgagac cctgactcta aaaatacaa ttatggttac | 1020 |
| ggttcttggg cagagtggaa ttcaaacagg ttaacctgaa agatcagtag ggttctaaat | 1080 |
| ccaggataaa ttattttcag aaaaagaata acttttttgaa tctttattta aattgttaaa | 1140 |
| tgttcctgtg agtaacactc atcagcgtga ttgtgactgg tatggctgca tggaagcttc | 1200 |
| cctgtggcat taatcataaa atgctggatt ggggtttgat tcttcaaggt ataagaagga | 1260 |
| cctagtctca agtaatagat tcaccaaaat gtaacaccac tagcccctc ccaccaaaat | 1320 |
| ctgctccagt cagaattacc gtaagagctc agaagtgacc tgtgcttggc ggcaccggcc | 1380 |
| cactttccca gtgccggttc ctcgcatcct gggcgcagac ggggtgaccg cctgaccct | 1440 |
| ggacccgagt caccttccc tgccctgagc tcctccttga gagcttcaaa acaatgctcg | 1500 |
| cccaggccgg agggcgaagt cggcccatgt gtaagtcaag ggaactgtcc caggactgca | 1560 |
| gccccggccag aagacgcccc gcgccgccgt cccaggcagc caccgctgcc gccatggccc | 1620 |
| ccgcaggccg ccgtaggccc cgcgggccg cctgacccct gcgggccgcc gtagaaggac | 1680 |
| cctccagagg ccgcgctctt gagatggccg tcgggctccg ctccccgcgg ggccccggct | 1740 |
| gagggcccgc cagcgggcac ctggcgccac cgctgcgttc cggcactagc acgggacacg | 1800 |
| gtcagggagc ggcgggccgc ggccttgcgc gcgccgtctc tcggggcggg gcaccggggcc | 1860 |
| ccttccgggg atgggccccg gcgcccgcgt cggcctggct gtgcccggcc cctccccgct | 1920 |
| cgggcgggcg ctgcgccgta tccccgcccg tcagtccgcc cggctcggct ggccgcagaa | 1980 |
| agggcctggg cggccgcact gagagcttta cgcccggagg cgtcggcgct gccactggcc | 2040 |
| cgcgacggga acgggcgaa aaggcggcgg caccatgttc tccctcaagc cgcccaaacc | 2100 |
| caccttcagg tcctacctcc tgccaccgcc ccaggtaaac aaccctcc cgcgagcgcc | 2160 |
| cgactctcct ctgcgcttcc gtggagcctc caggccgacc cccgggaact ggaggacccc | 2220 |
| aggaggctgc gcgcgtctcc ctgcccacag cagcgcggct gcctgattcc cggcgccgcg | 2280 |
| aaatgcgcct tctcgggagc ccccactggc tcggcgaaaa cttgtaaaac tcttctgcag | 2340 |
| ccattctctg cccgaagttc tgtcgtccgt agttttgcgg agtgttgagg cccaggggag | 2400 |
| ccttgggagc tggggttttc tttagtttcc aacccatcga ccctccctcc tatgaccgcc | 2460 |
| agcatgattg cagcgcttgg ggtcactggt cgaggcggtt accgtctgt cataaatgtg | 2520 |
| aacacctgga agcgacactg gcagtttaaa cattttttat tattaggctt ccaagtcgat | 2580 |
| aatgagcaga tcttaaaaac agctcagtta atatgcgaaa gaatttaaat gggggctgt | 2640 |
| gtgtctttcg catgtgtcat cacttagaaa acaacatttg ctgtagcatt ttacggaggg | 2700 |
| tgggggatt gagattttga tttatttgc taatgtattt cagactgacg ataagatcaa | 2760 |
| ttcggaaccg aagattaaaa aactggagcc agtccttttg ccaggtaaac attagttagg | 2820 |

-continued

```
attctaacag atactttagc aacgtatttt ggtttaagat tattctgccg actagtatca    2880
tgtggttaac ttcccttctc tcattaaact ttctccagtt aaaagtctag tgactgagag    2940
gagaaaaagg aactgtcaag aatgtcatta cctcatttcc ttttttgtct cccgaatttc    3000
tttttgaaaa gatgtatatg tttaattgct tgggtagtaa aagtactctt tgctgacgtg    3060
tttgccactt attgcattaa tgattaatca ttttaatgca ttttgatagt ataaaaagac    3120
gcctttatta tgtgtgtgtc tctataccaa taacagagct tagtgaactt tgaattactt    3180
gcttggcaat tgttttttga agttgtcagc tgtatttgca aatttgcttg tttcagttta    3240
gaaccaggct tttcccagca gagacactta attgacattt ggggccagat aattcatagt    3300
tggacgggca ggctgtcctg tgtatagcaa caaagatggc ctccacccac tagatgccag    3360
tagtagtacc cttatccccc accacctagt tgcgacctag ttgccacacc aaaatgccac    3420
cagtcattgc caatttttttt ttgtcccccta cctctggggg acaaaaatct cacagttgag    3480
aatcactgct ttagaacaaa atttgctata ggtgacctta gagatggaag tagggattgg    3540
tggtagaaag gggtttgttt tagagcatac agaatattgg tatggtattt tgaattgtat    3600
aacaattgta taataattag gaaaagtcag ttgtttaatg cgattattag gggaagtagc    3660
cagatactta ggaaagcctg ttttaaacct gaaatcggcc gggcacggtg gctcatgcct    3720
gtaatcccag cactttggga ggccgaggcg ggtggatcac gtggtcaaga gaccgagacc    3780
atcctggcta cacggtgaaa accccgtctc tactaaaaat acaaaaaaaa ttagccaggc    3840
atggtggcgg gcgcctgtag tcccagctac tcgggaggct gaggcaggag aatggcatga    3900
actcgggagg cggagcttgc agtgagccga gatcctgcca ctgcagtcca gcctgggcgg    3960
cagagtgaga caccgtctca aaaaaaaaa aaaacctgaa atcaaatact agtttgtgtg    4020
gctactatca gcattgtaaa atctgactca ttacttaaag ccaaatcggt aaaataatta    4080
gaattttgta ggtaaaaatt gaacaaatgt ggaaacttta aaattttaaa tattatatag    4140
ggacaaaata ttaaaaacac caaactttgg ttccatatga aagtttaaaa agtgtttttt    4200
aaactttact atgggagtca taaatatttt cccttgattt tgttagtgct tttcactcaa    4260
cagtgtgtac taattaatca tttgtacttt tcctcagagt gaacagtaga attactaagt    4320 aaccctttgct ccctgtgtgc tctgtttttag tcttagtcac tctgagcatt taaaatgcag    4380
ggacgaggaa acagtactca tcttgaatga gtgcctatga gctattgaac tttgacttcg    4440
tttactctga acaggcctgg ttcttaggct ttgattcctc cactctgcat actatgattt    4500
cacactcaga aacaacatgg tcttagctgt aaatgtcagt gcttgctttt taatttttta    4560 aaatttttt taaattttt tttttttttt tttgagacag agtctcactc ttacttgggc    4620
tggagtgcag tggcgtgatc tcggctcact gcaacctctg cctcccaggt tcaagcgatt    4680
ctcctgcctc tgtctcccaa gtagctggga ttacaggagc ccaccaccac acctggctaa    4740 ttttttcgtat ttttagtaga atgggggttt ctccatgttg gccaggctgg tcttgaactc    4800
ctgccctcag gtgatccgcc cgccttggcc tcccaaagtg ctgggattac aggcgtgagc    4860
cactggcgcc tggccacttt tttaaaatta gcttttaaat ttaagatatg tgctaagaaa    4920
aggtgttact aagtatgcat aaacttgaag aactttctca ctgagggtta tcaattctat    4980
aaaatggcta aaagtcagag ttttctgggg aagttgtaaa ccaagtttct gactgtgctt    5040
ttcttgtccc agaaatggca gctaaattcc gtattatttt tagagaaatt ctaaaagagc    5100
tgtaacacta agtctgaacc ttttagttgc ccattaagga attctctgac ctgtgttaat    5160
```

-continued

```
ttttattgca ttggcggcca aatcatagct gaaatctgta catgcataca tgacggctct    5220
atcacccagc attctgtttg tacctgactt atccttaccc aacatttagc cggtcctgaa    5280
ttaggatgtc ttttgccccc ttcctctccc cttctgttct taccctctca ttctggcctt    5340
cctgcaccca tcctggctgt gttctgtctg gctgccctgt tgtggtctct gtttcctgct    5400
ttacctcgcc tgtcacatct ctcactgcta ccatttgctc tttgttggcc tgtagcctac    5460
tgctctaccc atgaaatctg gaagacaagt ggaaagttac cgaactattg gtgatctaaa    5520
gacctagact aggctagagc ttttactaag agggagtgaa taatatagtt cttgcctttg    5580
tgactatcag aatcaataga aaacctggcc acatcacnnn nnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnntgttggg ggtgggggat gagggaaggg    5880
agagcattag gacaaatacc taatgcgtgc ggggcttgaa attcccggcg tcatccctaa    5940
agacggggtt gatgggtgca gcaaaccagc atggcacgta tatacctatg taacaaacct    6000
gcacattctg cacatgtatc ccagaactta aaaaaaaaaa taaaaaaaga attaattgtt    6060
agagatatgg tattgcatgc tttgctttgg cataatgcct tgggtccaag ggtatcctac    6120
ttcagttgcc caaagtttga acttctaatt caataagcag atgaaaatta gaacacaaaa    6180
tgagttgttt atttgtgtgc tgtcaccatg tgcactgttg gaacttaagc ctaatttcaa    6240
aatgatcctc atcttttatt aagtaaagaa aacagaagaa aatgactagt aatttaattt    6300
agattgtggt ttatgttagt aattttcagc tttcctgata catgaaactc tgagatgggt    6360
attgtgccta cttcaacttt gtggtcttga tgtctcacaa agtgccagga atgtggtaga    6420
cactgagatg tttactgagg gactgaacga aaggacctct cagaccacct ggcttaaact    6480
gttaccttac ccaggcacac acacagacta actttcagat ttaggagtaa agggaagact    6540
gtgttatttt atgccagaca tttcaagaga tttatgtcgg agcctggaat tgaaatagag    6600
tactctgtca aagtagtcag cttttgtgta ggctttctct ttatcttcct ctcattatgt    6660
gaatttcatt ctttcagtga ttatattgta tatgtgtaaa atcactccaa tacttgaaaa    6720
ctgagtttga cttttaaagt gtgtgtgtgt atatatgttt gtgttccagt atatatttgt    6780
taagagcatg taatgccaga ctctgtcctg tttagctgct ggactggtgg atcggttcgg    6840
tgaggatgtg agtatctcct gggtgccagg tctgtcctgg atagcgagaa tgctggaggt    6900
gtcatgtgcc tgtatcgcag aaaggcgtgg ggtgagccct aagctgcctg ttgacaaggt    6960
agaagactgt gacctggatc actggtaccc agattccagc cagggcctgg tatcagattt    7020
ggatgaagtt tttaccagcc cttggtcaaa gtgagaaaat taagaaaagt gcagttttct    7080
ttaataaaga taaatttatt tgatttaaaa gattgtcttt tattctgaga ttatgttctt    7140
ctaacttact tggaatagat actttttttg ttaaatgttg gtgataatag ctgtagcttt    7200
aaaaaagttt ttaagttaac aaaattaaaa agttaaaaac tctttattgg tcctttaaat    7260
tagttttgca ctatacctgg tttgaatct aaactagaac ctactagatg agattattat    7320
aatactatag atacaatttt gtgagcactc acacagagaa cattaattat tttgtctgcc    7380
taggagtact gccatttttt tgtttgtgtt ttgagacagg gtctcgctct gtcacccagt    7440
ttggactgta gtggtgtgat cacggcttac tgcagcttca acctcctggg ctcgagtgat    7500
cctcacagct cagcctccca gtagctagg actacagacg tgcgccacca cacctggcta    7560
```

```
atttttgtat tttttgtgga gatggggtcc aactatattg cccaggctgg tttcgaactc   7620
ctgggctcaa gcaattggct caccttggcc tcccaaagtg ttgggattat agccgtgagc   7680
caccacaccc agccccttc  caccatcctc tgaaaaatgc atcctccctc ttttgacaaa   7740
ttatcctttc ctgactaact ccacccaacc ttgggttcca gtgtggccag caaggttaat   7800
aacccaccct ggactgcaag catgaacaca gtctgcctc  tggatgttgt taggttggta   7860
ctaagggaag aggtcctctt tggtaatgct gcaagtggcc acagttccag aagaatctgt   7920
tgaaaagagt gaagaacccc aaggaagtgc actaatgtgt gttgaagtcc ctgggtttca   7980
ttgtccttgc aggccaggtg acacaaaagc cttgtattct tcttttgct  aagctattac   8040 caggcatgtt tctgaacata ctttgaacga ggatccttaa ctaatatagc ttgcagatta   8100
atcatcataa cagtcttgtc agctaggata ccagtttatc tccatttgac agatgtgaaa   8160
actatagttt gctgaggtta agtaacttgc ccagtgtcac acagctagca aggcagagcc   8220
agagttctct gtccagctcc caggctgtgc cactaactgc taagtagcac ggcccacctg   8280
gctgcactgg tgacactagg gtacagattt atgctttgga actgttgggg agtagattgg   8340
atgtcagcct agagggagtt ctctagtgaa gtaaaaagag ctctgtcctt gtctttgccc   8400
ttttcacaac agtgacagat tttgacccag cgtgcagaag aactttcaga gaatttcagc   8460
tgccagaaaa tggaatgtct tagggaggta gtggacttcc tgttgctggc tgtgccgaag   8520
cacagtctgg tgaaatgcca gcagcttgt  attgaggatg taagatttgc agtgagtggg   8580
gcttgatggc ctttgctctc ttctcacccc agggcatgct cttttttaag ggagaagagt   8640
tgaaatgcca agactaacga taatgaattt gttctgcagg tattgagtgt gtgcttgatg   8700
cagtttggca gaagggtaaa atgctgagga gatgggatcc tgttcttaga cagtttcagt   8760
tcactggaga gatgcttcag tagaggagag aaaaagtagt aagagctcag aggaaggtca   8820
cctaagccag atttggagta gggcagggt  gtcaagaaag atctctggaa acaaatgctt   8880
gtgctctgaa tcttgagtgc ccgttgagcc tgggccctg  tgctgaggct gtgcgtcagc   8940
tcagttcttt cccctgttcg catctacagt gctcacagca ctttcattct tgagattaac   9000
tattagataa tgaatgcagt gattgtcaga gtcttttgta atcggatcag aaaagcatac   9060
aaccatgggc catctgggaa atgaaaatag ccattgttgt atagatgtct tgtttatttt   9120
ttacaagctc actggcccgt actgttcttg tttttctgtct caccatacgt cttatttcct   9180
cagttgggtt gttaattcct taaaggcaaa gactttatct ttcaagtgtt ttatgtaatt   9240 ccttttttgta ggtaggcttc ataaatgatt gtagactgat ttttgtagta ttttaatttg   9300
tgaatgcatt gtttttgaaa gaccaaagga cttgtaacac accctcagaa cagtgaacag   9360
tgtaactgta ctatcttagc attagcttta taccttaccc gtagagcctt aggaatgttt   9420
ggagctgtcc attccttagg cttttgctgc agtaccttag gccagcattt tcttaccccct  9480 ccaaactact cactatcgtt gtcaacaccg ttcatgaacc tccataaata aaatcctact   9540
taagcaggat aaaatccaaa ttctttaacc ttgtaatttg ctaacactgt acctcactga   9600
cttcatttct cagtatttcc caatattgat atttgcttca atcatgccgc ttccttggtc   9660
tcttccagat gccttattcc ttatttagga ccttgttact gttattatca cacattctct   9720
actatctcaa tgctcttctt ccttcaagat ttcattctac aatttttcct gagatcggca   9780
ctatacccct cctcctgccc catcctatcc tgagtgctac tcactggact tggtacttgc   9840
ttttttacat tgtgtgttag taccagcatt aaagatttgt gtttatcttc cacatagttt   9900
```

```
caatttcctg tgataacttt tgagccactt taattcctga atttacctaa agctagggtg    9960
accagcttgt cccagtttgc ttgagactgt cctggtttta gtgctaaaaa taccacatcc   10020
cagggaaacc cctctgtccc agacaaactg gggcagtcac cctactgtta aaagcccaag   10080
ttaagttatg cttttggcct ctacacatcc cacaggttaa ttagccacgt gtgccgtgag   10140
actttgcctt aaactgtgtt ccaacctaaa atgtatggga acattattt ctgtccatca    10200
aacgtgatga atttctaaat gtataaggtg ttaggaaaga taatacaaca tggttttgag   10260
gtcctcaggg agttaaaaac tttcctagcc atatcatttg gaggtttatt aactgtaatt   10320
gcatttccct tcttatttat atttacagat gaaagggtct tgagaaaata aacttggatt   10380
tcttgatttc ttcccaggtg ttagtagaaa cctttggctc atcatcctct aatttagaag   10440
gttttttgctt accgcacact gaagctaatt tcctgctttt tctggcttca tgaggcttcc   10500
ttgtggcatc ctgggaagtg cttggtgctg taaatggtcc caccgtggct gatggcatag   10560
cacagagctg ggagagagga gtctggtggg ttctcacaag caggccagcc agccgtctct   10620
agcacaccac ccttttactg cataaaaagc acaggcgtat agtctccctg aaaacttcag   10680
atcctctaga gctttgaagc ttttattcgg agttttctct tcaaggtcac ttaatttaac   10740
atgtgaacaa gagcagtctc agtaccttct ttttatatat cctatctggg aagaggccac   10800
tttgtgtctt cttttttcttc cctgtgtata agctagtttt ctggcccaca gtgtttcagt   10860
gcatggcagg agcttatgac agctcctctt cagcattcct tttttttaaa attatgaaca   10920
aatgacttac gtgagcagac agctgtgcta catgatccaa atattttaaa gactggttct   10980
gcatgaacaa aatttagcat tatcaaataa aactcatgtc actaactcga cacttaatta   11040
ttgtaatagg aagacccaat tgtagcatat cctcagaagt gcccttcttt tctttcttct   11100
tccctgtat ccctctgtac ttctgttctt tgctctcttc caagggctca tttccattct    11160
gtaagaaaag gctgtgtggc gcttaaaaga ccctggccca gagagtcctt ctttcacttt   11220
tttttttcttt tttctttttt ttggctgttg ttaatgttgt gtctcttgtt tatttttcttc   11280
tttagtagtt ttatttttgga atgaatttga atttgtaaga gttgtacaaa agaggataga   11340
gttaatgtga actcttcagc cagcttccgc taatgttaat agcttatgta accttggtga   11400
atttagctca actgagaaac caacaatact attagctaaa ctgcaggttt tattcgtatt   11460
tccctagttt ttccacaaat gttctttacc tgtttcaggt tcacatccag gatactacat   11520
agcatttagt tgtcgtgtct ccttattctc aatgtctcag tctgtgacag cttttttcatc   11580
tcatctttca agaccttgac gtgtttttttt ctattgaatt tgattttctt tttttttcttt  11640
ttcttttctt ttttttttg agatggagtc ttgttctgtc acccaggctg gagtgcagtg   11700
gcgtgatctc cgctcaccgc aacctccagc tcccgagttt gagcgattct cctgcctcag   11760
cctgttgagt agctgggagt acaggtgcgc accaccaggc ccagctaatt ttttgtgttt   11820
ttagtagaga cggggttta ccatgttggc caggctggtt tcgaactcct gacctcaagt    11880
gatctgcctg cctcagcctc ccaaagtgct aagattacag gcatgagaat gagattttta   11940
ttttgcctca aataatacat attaaagctc tttaaacata gaaatatact actacaaaag   12000
gaaaaatttt ataattacta gatttctgtt ctaacaaacc acccctaga aacgtcatca    12060
aattgactta aaaatgtaga cgtaatttca gacttagaga aaagttgcaa ataacagaag   12120
aatctgtgga taccctttcc ttagattccc caataaaacc ttgacgcttt ggaagattat   12180
tattcaggta gtgtcttgta gtatgcctct tggtttggat ttgtccgatg ttttcttttg   12240
attaagcaga ggttatggat tttgggaaag acccacagag gtggtatcct ttgcccttgt   12300
```

-continued

```
gtcatgtgag caggcacaag acatcaacat gattggttat tggtgaggtt aacctcgatc   12360
acttcaggtt aaagtgatat ctgtcaggtt tctcctctag aaagtgactg tttttccttt   12420
tctgtactgt ttgttagaaa caaatcacta agtgcagccc acattcaagg gattgggaat   12480
taagctccac ttcctggaga gaggagaatc acgaatttat gggcatacct taaaactacc   12540
acagtaatta gtcaatactt ttgggaagat agctttgtgc ttatacaaat aacctgtttc   12600
tccttaaagt ttggctctct gaatttagca ttcatcaatg catgttgcac acagcagtca   12660
ttcagtctat gacattgagt ccatgatagt ttcttgatct ttactgtaat gttctaatca   12720
tgattttgtt tccttattcc tcctacattt attaattgga attcttctgt gaggaagatt   12780
tgtctcttct ccgccattta tttatttatt attcagtcat ctgttgacaa cagtatggat   12840
tcacagatac tttttaattt actttctaat ccggcatttt tgttatttct tttgttgctc   12900
agattgttcc agctttggcc attgagagtt atttcatctt ggctcttgta tccttttggaa   12960 atgccgtccc cccgcttttc ttcaccccca cttccatatt ttctggtatt ctggcattac   13020
cagaggctac agactcatct tctgtttccc ctgccccagc cttggaatca gccatttctc   13080
taaagagccc tagttctttt tattggaaaa tggtatttta aaagcaagag ctgggtactg   13140
agtgtgtatg ttgttgctgg agcgtcactg cttttagcac tttcagaggg cagagctaga   13200
aaacatacac acatgtacca acccaggtgt acacacatct gttactgcat gtctatttgt   13260
atatttatta aggcaagcat aagttcattc tgctatctca aactcttaat ctagcccctc   13320
ggggttcatt tccaaattct tgcttttgct ttttgttgat ggagtatggg cagtacagca   13380
gttaaacctg gtttccatat ttactttctg ctgagtgctg tagctcattg gtgagaaagg   13440
gatcttttga cttgacttgc atggacacat tctagtagga aggttgtctg tcctcatcac   13500
tcctgtgagt ggtcctctag agctctttga aatggctaca acattgcaga tcaaaaacac   13560
ctgcttttca ggtgcttcac ttctcacctt tcagatggga catgcccagt tgtgtcttct   13620
aaaccttgtt tcagataatt ttaagagttg tcgcttcagt aactatctct aacacaggga   13680
tcagcaaacc ttttctgtga agtgcagtaa atattttagg ctttgcggac cataaggtat   13740
ttgtttcaag tactcagctc tgtctttgtc ctgtgaaagc agccatagat ggcacatgaa   13800
caaatgagta tggctatgtc ttactaaaat ttcatttaca aaaacaaggt tttgtatttg   13860
gcccgtgggc catggtttac catccgttgg acccattaag tatattctcc tcctcttctt   13920
tgtctcattc tcactgcgtt cataggcttg atacgttaac attcgtgcat cagtaaaaga   13980
atctggcttc tagagaagaa gggctgtcca tgggcgtttg actcctaaat acagtttgtt   14040
tatggtacta gtgtggccac aaggctctgc cacacaagct ctgtctcttc cttcctgtta   14100
ttacttctgc ttcccttctc aggaacctga aatcatatgg tagtttgttt gtttaagtga   14160
tttttttttt tgagatggag tctagctctg ttgcccagtc tggagtgcac tgcaacctcc   14220
acctcctggg ttcaagcagt tctcctgcct cagcctccca gtagctggg ctacaggtg   14280 cgcaccacca cgcctggcgc accaccacgc ctggctaaat ttttttttt tttaatagag   14340 atgggtttca ccatgttggc tcaggtggtc tcaaactgac ttcaggtgat ccacccgcct   14400
cagccaaagt gttgggatta tagatgtgag ccaccacgcc cagcctttaa gtgaattttt   14460
atttgagtat aacatgcata acaagtttgt gtggatcata agtcttagaa gtggatgaat   14520
ttttgtagca aggtttgaag agtctgtttt tagatgagtt tgctaaggtg gcacagtatg   14580
tgatgattcc gtgtaaagaa gtcattgtta cagggctgtg tcctctatct gaactggcat   14640
```

| | |
|---|---|
| ggttagttta gttgtttaaa ttgagggcct gcttacaatt catatctaag atttactgga | 14700 |
| gaggagaaag ggttgagtat tcagtggccc agaatctgat atgggaattg gtaaggttta | 14760 |
| tgttcaagga gccaaagaag atttaaattt tatgtatttg aattactcag tgcgtctata | 14820 |
| tatatatata tttggtcatc ttaaattttt tttctcgtta gaattcagtt aaggccaata | 14880 |
| tttgaacttt aataagtttt ggtacttgct acactgcagt acatttaatt gtatgtaatt | 14940 |
| atagggaaag actatgggaa ttgaagtcag aacacttggt tataagtgcg aagtccacta | 15000 |
| cttctttta agatcttagg aaagtgattt aacctctttg ggtgcaaatc ctttatctgt | 15060 |
| gtattaagga aaccatctgc cttcctcacc ttacaggttg ttgaaagaat cagacaggac | 15120 |
| agatgtccta tttatagctc tttaatgcat atgtaggcaa gcagtggcag ttctgtgact | 15180 |
| cttctctaac ttacatatca tttacccaaa cagcccttat cttccagcca gcttggctgc | 15240 |
| ttagccatat tgaattacta gtttctctta tctagaacaa cttctgccca actcatggtg | 15300 |
| gacagaacca agtgtcatga agtgatttta ttcattcttg cattcagcac tcttttcaca | 15360 |
| ggcacctacc ctgtgccaga cactgttcta ggcactaaca tttcagcagt gaataaagtc | 15420 |
| agtccatctt ctaccctcat ggagcatata atcctgaggg taatgcaggc attaatttaa | 15480 |
| aaatatataa atataattgt agctatcatg agtgctggaa atacaatgct tcgatatgtg | 15540 |
| aatgtaaact agataggaag attttttttaa agaggcattc cctagacagt ggttggacta | 15600 |
| aggtagaaga aaagaatatt ccatgaaatg ggaagaagca tggtcccatg agggattaat | 15660 |
| aggccaccac tgtgggcaga gcagtgaggg tgaggaaggc tggtagctgg ctgggtatgc | 15720 |
| agggctccca gccatgagag ggaggcttgt cttcaaagtg gaagttaact caagctgttg | 15780 |
| gcactgtgaa tttgacatga gcagatttta ggtaaatgtt aaggggcagt tactaaaact | 15840 |
| agccttgtac attttttaaga acttcgaata aaagttattg cagctcaaat ttgttataac | 15900 |
| ctatttgtta aagagaggat tgttttgaga ctatagttcc attcttcatg aattggtagg | 15960 |
| agtttggagt ttgtcagcaa acattctatc gggctaaagg ttttttataat gaaagaaata | 16020 |
| ggcaaagtgg atcagtacac tcactttttct accattgacc ctggagacag atggcttaaa | 16080 |
| atgttctgcg tctagttgac ttttagatct tgaaattaag gtttaatgat gaccaagctt | 16140 |
| taaataaatt gtagaaaagt attctttcaa aagtacatta taactttttat attggttttct | 16200 |
| tatatttatt tcttttaatc ttttcttttta actcaaacta cgttttaagg ttttgttgcc | 16260 |
| tactaagtta taatctgagt gcagaaggaa acttgatttg gctttatgga atacattta | 16320 |
| cattcagtga agctgagctc tgtttctcat tccttacaaa aggaatcaaa ggcattggtt | 16380 |
| tgagagatca agtcatgtgt taataaaaca caaatattcc atcaagtaat actctgaagg | 16440 |
| agcaggtgta gtttatttct tctccagaaa gtcttccagc agataaataa tgagaggtag | 16500 |
| tatggcatag gaaaaaagta cactgaagtc agcctttctg gttcaaccag ctcagacccc | 16560 |
| tgagctattt ttgcctcagt tttacgcctt ggagaacaat gccttgtcat tactattcac | 16620 |
| tttatgacca tacagtgcct ggcacctggt gggcaattgg tgaatgtttt cactatcctc | 16680 |
| atccttgccc tcatgaaaca ctccttctag gtcccacaaa gaccgttggt attttatgac | 16740 |
| aaagtacctt acaaatattt ttcttttttt aaaggagaaa ttgtcgtaaa tgaagtcaat | 16800 |
| tttgtgagaa aatgcattgc aacagacaca agccagtacg atttgtgggg aaagctgata | 16860 |
| tgcagtaact tcaaaatctc ctttattaca gatgacccaa tgccattaca ggtgtgtttt | 16920 |
| attagtacac tgtttcattc tatcaggctt tcaactctaa gtggtacata ttattatata | 16980 |
| aaacataggt atggaaaagt tatagtagaa gtattaggta atgcaatgtt tgggataaat | 17040 |

```
tatattaaga tttaaagtaa agtttaagaa gaatgttgga acttgctaga ggagtattag    17100
tgagaggatt gtaagtcacc ttgctttatt tatcctctgt gatcgttcat tatatgtcct    17160
tttcattaag gaagttattc cctctgttgc agatctttta acctgcttat aaaaatgaca    17220
taaagagaaa aggttgtttg ctaaatgatt ttataaatgc cacacatttt agtgatttca    17280 taggttttt  tgttgttggg ttttgattt ttttgttttg agcctggatc tcgctctgtc     17340
ttgtctccca ggctggagtg cagtggcatg atgtcggctc actgcaacct ctgtctgctt    17400
cctgggctca agctatcctg ccacctcagc ctcctgagta gctgggacta caggtgcatg    17460
ccaccactcc cggctaactg ttgtattttt ttgtagagat ggggttttgt tatgatgccc    17520
ggattggtct tgaacttctg agcccaagca atctgcctgc ctcccctcc  caaagtgcca    17580 gagtacaggc cactgcaccc agctaccttt ttttttttt  tttaaactaa ttagagttat    17640
tttcctaaaa agtaaaattc taatttctag gaagagtgaa gaatagtatc gatttaaaaa    17700
ttttcagtag ccctcttgct attttatgtt cttactggaa agtaatagtt ccatgtaatt    17760 ttggtttta  gaagttcagg cattcatttg attaacttaa aaaccctgga cttttctgtc    17820
agccattttg tattttgttt tataaagtat tatacacact taccctaga  tctttcttta    17880 tagtaattgt tctttaatga aatattggta tatgaactgt aaactttaa  atttaaggat    17940 ctaatagttt agtgtaagta tatttcatgt agtcactcac taatttacca taattattat    18000
actgtacaaa tatttattgt actgtatatt tgtgtgttca ttacagtctt atgtaggtat    18060
atttagacta aatttaaggc acttaaagat acccactgtg tagggacagt agcttatttg    18120
gatataggct tgtgtgtttc tctttgtttt tagcttcata atgatcattg gccccagact    18180
tcactgtaaa tgagaagcag ataccgtgaa cagcttaaat ccagtaccac tattaggaaa    18240
aagtaaacca gtgccctact gacagcagat tgatagtgtt aactacgtcc ttagtttgaa    18300
catgcaaaac ctttcctaat ggttttatt tctagtagac tttgtgcttt aaaaagatag     18360
ttattttgca ctttaaaatc ttcagtgtga aaatcaaaca tgattttacc cacttaaaat    18420
ctgatgacct aagagccctt ttttctttaa tatgttgtgg ccagcttatc cagatctaga    18480
catgcaaatg cttgctggta aggtgattga tgatattccc tatcttaggt attataataa    18540
gattgttgtg tacatttaa  cctaatttct atctgtcaac attggaatgg ccctagctac    18600
ctagacaaaa gctttttgtg cttttagag  ataactgtca cagtttatca tcacagttta    18660
aggcttatac taccattgtg agattattgg gaaaagaatt aatatgaaca taattttta    18720 ttccagaaat tccattacag aaaccttctt cttggtgaac acgatgtccc tttaacatgt    18780
attgaacaaa ttgtcacagg tacgtagtat tccgtacata ctctaaaagt caattccact    18840
ctggaagtat tatttgaaaa gtcataccct tcaaaatact tggattggcg ttttatttct    18900
gtaagtttac ttttgccgtt tttttgagtc ccgggaacat aaagagggat atgttaataa    18960
attattttaa aaggaagata taaaatgtat aacttttcat agtttctagg tttttttgtcc   19020 tctttttaat taaaattaat cattaaatgt atctagatgg tggttttatg caaataatca    19080
tttaaaatat cttccaaagc aaagttaaaa ccaaccccca agttctagga attacaagta    19140
tgaaacattc tagacaagca gagctcaaat gttgggtgac cttccaatta ttttcactaa    19200
gaatttgtat taaagggtga gtaacaaata actgttacgc attttatttt ctctattttt    19260
ttttcttttt tagtaaacga ccacaagagg aagcagaaag tcctaggccc caaccagaaa    19320
ctgaaattta atccaacaga gttaattatt tattgtaaag atttcagaat tgtcagattt    19380
```

-continued

```
cgctttgatg aatcaggtcc cgaaagtgct aaaaaggtaa tactgttaag gtttatcaag     19440
ttctgggttc tgtactgtgt ttactgattt caattccgta tggcagtttt catttctcaa     19500
ttgctcagat gttttttagg ggaagttatc agacatcttc ttaagtaaag tcaaagccaa     19560
gaatattaat agaactattt tcttggattg gtttatggct gttttaaagt gttctatata     19620
acttttatc agcttctcaa atattaaaga ctcttacgtg gaaattagca ttttttaca      19680
taaagatcat tacttgtcag tttcttggtt aaaaggttga aaagttggtg atatactgta    19740
attaaggttt ggttaggctt ttaattcagt actgcagaac tttaccaaca aactgtaagc    19800
tagacttatg ttacataaga tttaggtaaa tatataatta cgggaaaggc ctagtaatta    19860
ttagtggttt aaagaaatat tatgaattga gtgacactca acaggggcaa cacaaagcta    19920
gtaactttt aactgcctta ttttccacg gccttccaga taatgactta ttaccctact      19980
tgtaagagtc aagggcatgt tttccatgtt ttgctttgcc agaggagtga agctggtaga    20040
cctaatatgg cccccgttcc agtctgtgct gcagcaaatg cagagtcaca gactttccag   20100
taggaagctt gcgcgtgtgt atgggaatag ggcaacagta tcttagtata ataggacgtg    20160
gctttctctc agaatggagg cagtctttgc accaccaagc aatgagtgcc tttgttttcc    20220
atggttagtc aactgactgc agtaaatctt ctgttgatac caaaacaagg ctggcaaaaa    20280
tactgtaagg cagctgtctt catatacttt ggtgaagagg tggtagattt gttttagat    20340
tgagaaccaa cagtttcttc acaggaaggc aagcaggaga tgaatatatg aaaatacatc    20400
tgaaaatatg tgactgtcta gcagagtaga gtggttgtag gctcctctat gggtaaaagt   20460
tttcaaatgg tctgtataac catctctcag caagctgcat tattgaaaat tcaactagat   20520
aactcttaaa gcctctttca cctgttcgat tgtgctgttt tgattttgg cattttacta    20580
atttaaagtg cctattatat agaaggactt tagaattcat gatgtattag actgtacata   20640
aaatatttca gacaggttaa ttcctcaagc ttatttatat ttgtaattta attgatcaaa   20700
gcatcaaaga cctgcttatg aaaaccttaa gatgtgtagc atctcaagat tagggacatc    20760
acagaacttg ctagattgag ttaggacagc atattcctaa ggaagaaatt gatgcaattg   20820
accggatctc tttcggaaag ttcaattctc cctcttttac tgtattttc agtttacact    20880
attttaatga gtggaaataa taattatttg gcctagttct tgaaccatct gtagtacttg   20940
ttggtcattt ttcatgttga ggcagtgtgc taaattttgc aagtagaaag aagggtaaga   21000
tgcagtttct tgccctagag aacttaaatc tagtgaagaa gataaagcat gaacaaatga   21060
aaagtaatgg tacaaagtgg cagcataaaa tcaactacac aaatagttga tttccagatg   21120
aacagagcat aataagtgct gtggaaattc agaatatccc ctatgtgttg tgctgctggt   21180
tcatgaagag ggccttacta aaccgtctgc acaaaacaag ccagtccctc atatgccctt   21240
tcctaagacc aagtttcaga caaaaatctt ttccccagta tcctaaaata taaaaagcat   21300
gtgagtctct gtcttttgta tagccacggg ggttgcaggg caggggaggg tgcaggaaaa   21360
aaaaatagat gcaatgagaa tataaatagt tttttggga tttacgcatt tcaaacaggg    21420
ttaagttgta tatggctacc aaagcttgac ggctttgtga gttaaaaaca aaaattatgg   21480
catattcttt tatttcaagt gaaagttttt catctaaaat tcggtagcag ttaggaaatt   21540
atggctcatt tttacctcct ggaagcttgg aatactgttt tctctggaaa atgctttgct   21600
attttatcag ttgctttaaa atgatgaaat gcatgtttgg agttctctgg tgggtaaacc   21660
gttgattcat tttgaaatac ctaagccatt tatgttttg ttttgaaaaa tgaaattcaa     21720
gaatactaaa ttggttcaca ttttgttaaa tgttctgaac ccttctggtt gtcttgttgg   21780
```

```
tgttgtttca attgtattat gacaaaatta gattgctttg ggcacttgta ctcattaata   21840
ttcatcctca ttatcctcga gctgtcacag gaaaatagtg atatttggga aaggtctgta   21900
taaagaaaga aggaatttga tggtgcagaa ttggacatct aacctcatag caacttagaa   21960
ccaccatttt cttttgcaga acctttgctc aaaactgaag ggcaaaataa taaaggttgt   22020
ttttaatgat ttatctatat atctgtctgt gtagataaag ataaatatat agatacacat   22080
gagtgacaag tgaaatacat gccttttgtc tccactttgt tctctgatta gtgggttgtg   22140
aatcacttct tcaggaatac tttatagaag tgaattccat tcatctgatt aaggaacaag   22200
ttggcctttt catgaactgt cattttttgac ttgaatctgg tactgttttt tggtggcttt   22260
caggccacag aaataaaacca cttttgtttg caaatgagat agaacttaat gaggtttgag   22320
tgtttcctgg atttgagttt cttcagtact gcaccccagg tgatcttagg aaagaaacca   22380
tccactgtgg gtacttctgg cttctgtcca gagaagatta tcagctttgg tccaaaaatt   22440
gatttaaaag tagtttactt ctttttctcc aataaaatat ttgccataat ttaatgtctt   22500
taataccaac attttcttca tttcctgtgg tagccaggac aaatgaagta tttcagatct   22560
ttcaaaaact cttaggatga aaggtaggaa tttggactta ggttttttaaa atagtgtgta   22620 tgtaaaagtg caaagaatgg ggccctggct ttctcttctc ggagtgttcc acagtaacaa   22680
catgaagaca atccaggtac acaagtttgt atgtgcctta gtctgtgtgt ccaaagaggc   22740
ctcttactta ggtcatatga acataagtta tacacttgaa attcactact gaaaacaat   22800 gtatttagtt cgagttctgc caccccaaaa aaatcaacga gtaattcaac tgacttgcag   22860
ttttacaata tttttataga cttctttcag cgtagatgct tttggacata ctcatttgtt   22920
tcctaacctg atgtgatatt gtgctatttt taaggggctt ttaaaaaata cgctgtgttg   22980
ggttttgcct tgaaaatagg ctttatttct tttttgcctc atggccacaa aaaaaggatg   23040
tccatgatca atgatctgtg aatttctttt ctgtaaacag aaagagcatg taactgcttt   23100
ctaattgttt tggagaatgt gatagacatt agtattatta ttattggctt ggagcatttt   23160
ccttaatatg ttggtaacta cttttgtcag tgaatattag tgtagccact gttggacaca   23220
gagcaccgtc agaaagctac tgaagtggtg ctgcaaagtg cagacatctt cagatcttta   23280
ctcaagtctg tgcagagagg tcttcttgg tctccttctc tactttttag cctgtctccc   23340
tcttctcact gtaacacttc atattcccct tccctgctct attatttttc tcttttagca   23400
ttcatagtta tctaactttc tgtatttttt ctctttatct tgtttagtgt ctgtcttccc   23460
actagaatgt aagcttcatg aggacaggga ttagtgtctg ttttgttcac tgcatctcta   23520
gggcttacaa cattgtaggt actcagtaaa tatttgttaa atcaatgtga aatgtgtcat   23580
ttatccttaa ggaattgacc ttcatggtag aagtgtaaca gaaccaccta tatcctactt   23640
ttcatccaca tcataactat tatgtgaata ccttggaagt aaagcaaaat aagcacttaa   23700
ctaaagagac gctttatatt gaaactgttg ttctgggttt ctggaattag tactctgaaa   23760
ttggctccct ctaggaaggc ttgtgaagag agtagtgttg aacagacatg acagtttcca   23820
agaaagcata gttggctaag aggagtagga ttttccaagc aaagagtgtg acagtggaga   23880
tggctggggc taagtcaggc agaatgtgtt caaacctgtt tttctctgac ctgagattgc   23940
ggagggaata ttgggaaggt atagttacct ggtgaggaga gccagttttg tgaagaatca   24000
agaatgagga gatttaattt gttatgcaga tgtctgggaa ccacagcaga ttatcaggag   24060
agcaaaattg ttagtcagaa ttcatcgtt agaaggtaat ccttaagttt tgtagatttc   24120
```

```
tagaatgtaa ggaagctctc agaggtgcca taaggtgagt atggcctaag gatgtggcta    24180
tggcagtgta gcaaaatgga caactatgaa aaatgtctag agaaaagtgc aacatagctt    24240
atcaacggtg cccaaacaaa taggaaggat gagaactttt tcaagctaca gatttcagta    24300
gttttgctgc tagaaatgct ttaaggaaaa ctgttaaaaa gattaggaat gggaatatag    24360
ataaccggct cctaaatttt gcaagtggga ccgtcataga aagctctcct ataggtattg    24420
agaaatcgag ataccacgta agtttcaaga agcagttttt tttttctttt tggtcaaaac    24480
taatgacaaa ttctgtcccc ttgtttgtat attttaactt agtgagacag gaaacattta    24540
ttctatagaa gacttttaaa atgtagttta aacaagttga cacatgctta ctggttaatg    24600
aaatgtgcat caacccactc caaacaccac taatttgaca tgaactaaca attaactttt    24660
cttactcact gtcaaaagta tatcattctg ccttaactta acgctttacc ttctaaataa    24720
aatttaatct tttaaataag tttttctgct atgttttcct tgcatatgtc ttaaatttct    24780
tctttcgtct ttgctcactg aagagcattt tctcccacat tctagtgact accagggttt    24840
gtaagcctag agcaccatcc ttcattctat ctagcagcag ttgagaataa taacagccat    24900
atttctatat atggagctcc tccaaaggcc tagcctgcat taagcttgtt aattcttacc    24960
acagcctagg tattactttt gtttttacaag tgagcaaact gaggctagaa aagaggaaat    25020
gacttcacac atgttatgta gcaagtactt gacagagcta ggattcaagc ccctgatct    25080 gtttgattct aaagcccgca cgttttccac cacagggcac acagtcccaa accatttttac    25140 ttaaacacag tttgtgtgtg tgtgtgtgtg tgtgtgtgtg tgtgtgtgtg tgtgtgttgt    25200 tttttttgatg tacctctttg agccacccat gcattttttgg agtttcttgc taatttttaat    25260 tttttgtaat tatgtttctc tatttagatg tttaaatcca tgaggcgtaa actttaaagt    25320
ttcatgcctt atattaatcc tttatagtcc accaaaaatg aaacttttt cttccttttt    25380 tggagtggac atgtagtcac tgccttttg gagaatgctt ctttagtttg aagctttctt    25440
tattggacta aaattacttt ccaattaaaa tttaactcag caaatactta ctgaatactt    25500
gccatgtgct agctaaagat aaacaatgtc ttgagggcat gaaagtgaat gagatacctg    25560
gccttaagga gctcttttat attctaggtc aacagaaaaa catgtaaata gtatctataa    25620
tcactgcccc aagatgatgc tcccagtgcc caaggcctta ttgtacattt catttaacta    25680
agtgtgttaa aatcaaattc taaatgtaga atttttccta ggtatgcctt gcaatagctc    25740
attattccca gccaacagac ctccagctac tctttgcatt tgaatatgtt gggaaaaaat    25800
accacaattc aggtaaatat gaaatatta aatattgtga ctaattttac atgtgtaaat    25860
tttactctta tgtttaccgg aagcctccaa gtacatgagc tttaatgatt gtagaattac    25920
tagcttcata ccttagagaa gtaagcacta catgctaaaa gagccaatag tttgtcagat    25980
tatttcttga caagttacca ggaagaacct ttaatgctat gaatatgggc ttataagtta    26040
tgtcagatat ttaatctcca gtcactggct tgtattttat gatgaagaat atataaccca    26100
ccctttttaa ttgatagctt gagttaaagt aatcttatct tttaagaaaa ctggcagaaa    26160
actaaaagat atattaaaag cataatcttt tctggcaagg tgtgatttca tgcaaaagct    26220
aaagtgatta aaaactttt gtggacttca ttaagattct cagaatactg agtttctatt    26280
tctgagtaat actgatgaaa ggaagatgag catttttcca aggacaagta tattactaga    26340
cagcttttgt gaaagtaaat agttttgtct atatatctga cagtcatgac atgaccaggg    26400
aagattccag atgatcatgc aannnnnnnn nnnnnnnnnn nnnnnnnnnn nnnnnnnnnn    26460
nnnnnnnnnn nnnnnnnnnn nnnnnnnnnn nnnnnnnnnn nnnnnnnnnn nnnnnnnnnn    26520
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 26580 |
| nnnnnnnnnn | nnnnnnnnnn | nnnnnnnnnn | nnnnnnnnnn | nnnnnnnnnn | nnnnnnnnnn | 26640 |
| nnnnnnnnnn | nnnnnnnnnn | nnnnnnnnnn | nnnnnnnnnn | nnnnnnnnnn | nnnnnnnnnn | 26700 |
| nnnnnnnnnn | nnnnnnnnnn | nnnnnnnnnn | nnnnnnnnnn | nnnnnnnnnn | nnnnnnnnnn | 26760 |
| nnnnnnnnnn | nnnnnnnnnn | nnnnnnnnnn | nnnnnnnnnn | nnnnnnnnnn | nnnnnnnnnn | 26820 |
| nnnnnnnnnn | nnnnnnnnnn | nnnnnnnnnn | nnnnnnnnnn | nnnnnnnnnn | nnnnnnnnnn | 26880 |
| nnnnnnnnnn | nnnnnnnnnn | nnnnnnnnnn | nnnnnnnnnn | nnnnnnnnnn | nnnnnnnnnn | 26940 |
| nnnnnnnnnn | nnnnnnnnnn | nnnnnnnnnn | nnnnnnnnnn | nnnnnnnnnn | nnnnnnnnnn | 27000 |
| nnnnnnnnnn | nnnnnnnnnn | nnnnnnnnnn | nnnnnnnnnn | nnnnnnnnnn | nnnnnnnnnn | 27060 |
| nnnnnnnnnn | nnnnnnnnnn | nnnnnnnnnn | nnnnnnnnnn | nnnnnnnnnn | nnnnnnnnnn | 27120 |
| nnnnnnnnnn | nnnnnnnnnn | nnnnnnnnnn | nnnnnnnnnn | nnnnnnnnnn | nnnnnnnnnn | 27180 |
| nnnnnnnnnn | nnnnnnnnnn | nnnnnnnnnn | nnnnnnnnnn | nnnnnnnnnn | nnnnnnnnnn | 27240 |
| nnnnnnnnnn | nnnnnnnnnn | nnnnnnnnnn | nnnnnnnnnn | nnnnnnnnnn | nnnnnnnnnn | 27300 |
| nnnnnnnnnn | nnnnnnnnnn | nnnnnnnnnn | nnnnnnnnnn | nnnnnnnnnn | nnnnnnnnnn | 27360 |
| nnnnnnnnnn | nnnnnnnnnn | nnnnnnnnnn | nnnnnnnnnn | nnnnnnnnnn | nnnnnnnnnn | 27420 |
| nnnnnnnnnn | nnnnnnnnnn | nnnnnnnnnn | nnnnnnnnnn | nnnnnnnnnn | nnnnnnnnnn | 27480 |
| nnnnnnnnnn | nnnnnnnnnn | nnnnnnnnnn | nnnnnnnnnn | nnnnnnnnnn | nnnnnnnnnn | 27540 |
| nnnnnnnnnn | nnnnnnnnnn | nnnnnnnnnn | nnnnnnnnnn | nnnnnnnnnn | nnnnnnnnnn | 27600 |
| nnnnnnnnnn | nnnnnnnnnn | nnnnnnnnnn | nnnnnnnnnn | nnnnnnnnnn | nnnnnnnnnn | 27660 |
| nnnnnnnnnn | nnnnnnnnnn | nnnnnnnnnn | nnnnnnnnnn | nnnnnnnnnn | nnnnnnnnnn | 27720 |
| nnnnnnnnnn | nnnnnnnnnn | nnnnnnnnnn | nnnnnnnnnn | nnnnnnnnnn | nnnnnnnnnn | 27780 |
| nnnnnnnnnn | nnnnnnnnnn | nnnnnnnnnn | nnnnnnnnnn | nnnnnnnnnn | nnnnnnnnnn | 27840 |
| nnnnnnnnnn | nnnnnnnnnn | nnnnnnnnnn | nnnnnnnnnn | nnnnnnnnnn | nnnnnnnnnn | 27900 |
| nnnnnnnnnn | nnnnnnnnnn | nnnnnnnnnn | nnnnnnnnnn | nnnnnnnnnn | nnnnnnnnnn | 27960 |
| nnnnnnnnnn | nnnnnnnnnn | nnnnnnnnnn | nnnnnnnnnn | nnnnnnnnnn | nnnnnnnnnn | 28020 |
| nnnnnnnnnn | nnnnnnnnnn | nnnnnnnnnn | nnnnnnnnnn | nnnnnnnnnn | nnnnnnnnnn | 28080 |
| nnnnnnnnnn | nnnnnnnnnn | nnnnnnnnnn | nnnnnnnnnn | nnnnnnnnnn | nnnnnnnnnn | 28140 |
| nnnnnnnnnn | nnnnnnnnnn | nnnnnnnnnn | nnnnnnnnnn | nnnnnnnnnn | nnnnnnnnnn | 28200 |
| nnnnnnnnnn | nnnnnnnnnn | nnnnnnnnnn | nnnnnnnnnn | nnnnnnnnnn | nnnnnnnnnn | 28260 |
| nnnnnnnnnn | nnnnnnnnnn | nnnnnnnnnn | nnnnnnnnnn | nnnnnnnnnn | nnnnnnnnnn | 28320 |
| nnnnnnnnnn | nnnnnnnnnn | nnnnnnnnnn | nnnnnnnnnn | nnnnnnnnnn | nnnnnnnnnn | 28380 |
| nnnnnnnnnn | nnnnnnnnnn | nnnnnnnnnn | nnnnnnnnnn | nnnnnnnnnn | nnnnnnnnnn | 28440 |
| nnnnnnnnnn | nnnnnnnnnn | nnnnnnnnnn | nnnnnnnnnn | nnnnnnnnnn | nnnnnnnnnn | 28500 |
| nnnnnnnnnn | nnnnnnnnnn | nnnnnnnnnn | nnnnnnnnnn | nnnnnnnnnn | nnnnnnnnnn | 28560 |
| nnnnnnnnnn | nnnnnnnnnn | nnnnnnnnnn | nnnnnnnnnn | nnnnnnnnnn | nnnnnnnnnn | 28620 |
| nnnnnnnnnn | nnnnnnnnnn | nnnnnnnnnn | nnnnnnnnnn | nnnnnnnnnn | nnnnnnnnnn | 28680 |
| nnnnnnnnnn | nnnnnnnnnn | nnnnnnnnnn | nnnnnnnnnn | nnnnnnnnnn | nnnnnnnnnn | 28740 |
| nnnnnnnnnn | nnnnnnnnnn | nnnnnnnnnn | nnnnnnnnnn | nnnnnnnnnn | nnnnnnnnnn | 28800 |
| nnnnnnnnnn | nnnnnnnnnn | nnnnnnnnnn | nnnnnnnnnn | nnnnnnnnnn | nnnnnnnnnn | 28860 |

-continued

```
nnnnnnnnnn nnnnnnnnnn nnnnnnnnnn nnnnnnnnnn nnnnnnnnnn nnnnnnnnnn    28920
nnnnnnnnnn nnnnnnnnnn nnnnnnnnnn nnnnnnnnnn nnnnnnnnnn nnnnnnnnnn    28980
nnnnnnnnnn nnnnnnnnnn nnnnnnnnnn nnnnnnnnnn nnnnnnnnnn nnnnnnnnnn    29040
nnnnnnnnnn nnnnnnnnnn nnnnnnnnnn nnnnnnnnnn nnnnnnnnnn nnnnnnnnnn    29100
nnnnnnnnnn nnnnnnnnnn nnnnnnnnnn nnnnnnnnnn nnnnnnnnnn nnnnnnnnnn    29160
nnnnnnnnnn nnnnnnnnnn nnnnnnnnnn nnnnnnnnnn nnnnnnnnnn nnnnnnnnnn    29220
nnnnnnnnnn nnnnnnnnnn nnnnnnnnnn nnnnnnnnnn nnnnnnnnnn nnnnnnnnnn    29280
nnnnnnnnnn nnnnnnnnnn nnnnnnnnnn nnnnnnnnnn nnnnnnnnnn nnnnnnnngt    29340
nnnnnnnnnn nnnnnnnnnn nnnnnnnnnn nnnnnnnnnn nnnnnnnnnn nnnnnnnnnn    29400
nnnnnnnnnn nnnnnnnnnn nnnnnnnnnn nnnnnnnnnn nnnnnnnnnn nnnnnnnnnn    29460
nnnnnnnnnn nnnnnnnnnn nnnnnnnnnn nnnnnnnnnn nnnnnnnnnn nnnnnnnnnn    29520
nnnnnnnnnn nnnnnnnnnn nnnnnnnnnn nnnnnnnnnn nnnnnannnn nnnnnnnnnn    29580
nnnnnnnnnn nnnnnnnnnn nnnnnnnnnn nnnnnnnnnn nnnnnnnnnn nnnnnnnnnn    29640
nnnnnnnnnn nnnnnnnnnn nnnnnnnnnn nnnnnnnnnn nnnnnnnnnn nnnnnnnnnn    29700
nnnnnnnnnn nnnnnnnnnn nnnnnnnnnn nnnnnnnnnn nnnnnnnntt nnnnnnnnnn    29760
nnnnnnnnnn nnnnnnnnnn nnnnnnnnnn nnnnnnnnnn nnnnnnnnnn nnnnnnnnnn    29820
nnnnnnnnnn nnnnnnnnnn nnnnnnnnnn nnnnnnnnnn nnnnnnnnnn nnnnnnnnnn    29880
nnnnnnnnnn nnnnnnnnnn nnnnnnnnnn nnnnnnnnnn nnnnnnnnnn nnnnnnnnnn    29940
nnnnnnnnnn nnnnnnnnnn nnnnnnnnnn nnnnnnnnnn nnnnnnnnnn nnnnnnnnnn    30000
nnnnnnnnnn nnnnnnnnnn nnnnnnnnnn nnnnnnnnnn nnnnnnnnnn nnnnnnnnnn    30060
nnnnnnnnnn nnnnnnnnnn nnnnnnnnnn nnnnnnnnnn nnnnnnnnnn nnnnnnnnnn    30120
nnnnnnnnnn nnnnnnnnnn nnnnnnnnnn nnnnnnnnnn nnnnnnnnnn nnnnnnnnnn    30180
nnnnnnnnnn nnnnnnnnnn nnnnnnnnnn nnnnnnnnnn nnnnnnnnnn nnnnnnnnnn    30240
nnnnnnnnnn nnnnnnnnnn nnnnnnnnnn nnnnnnnnnn nnnnnnnnnn nnnnnnnnnn    30300
nnnnnnnnnn nnnnnnnnnn nnnnnnnnnn nnnnnnnnnn nnnnnnnnnn nnnnnnnnnn    30360
nnnnnnnnnn nnnnnnnnnn nnnnnnnnnn nnnnnnnnnn nnnnnnnnnn nnnnnnnnnn    30420
nnnnnnnnnn nnnnnnnnnn nnnnnnnnnn nnnnnnnnnn nnnnnnnnnn nnnnnnnnnn    30480
nnnnnnnnnn nnnnnnnnnn nnnnnnnnnn nnnnnnnnnn nnnnnnnnnn nnnnnnnnnn    30540
nnnnnnnnnn nnnnnnnnnn nnnnnnnnnn nnnnnnnnnn nnnncagtg atggaaagta    30600 gggcagccca ctagaagcca ctagccacat gtggctgtta agtacttgaa atgtggctag    30660
tgcaaactga tggactgaat ttttaatttt atttaatttt catttcagtt taaatttaaa    30720
tgggcttgtg tggctagaag ttacgttttt gggaaacata ctagagtcta ggccctattt    30780
gatttcccgc ctctcttcca ccacctgttg aatccctatg ctctagctgt atttagttac    30840
ttgatattat acagttatac catcttttta agttcttct ctgtctagca tgcctacctc    30900
ctcctcacca gctacctggc aacttttgac ttgttcctta gaactctctt tagttgtggt    30960
caagtcatga agcttttcct gccccggcct ctctctgcag cgagagttag gggacttctc    31020
ttttgcatct tcattgcact cagacatctg gtactctgtg attatcacac ttattaatgc    31080
tctcaagata gagataaaat cttattcatc tttttgctct caggcattag cacatgggga    31140
gttctcagaa aatacctgtc ttataccagg aattaatgaa taatcagtag gaatgagcat    31200
gacatgttca tgggacgttg gagggtagtg catggctgca gaggagaatg ggaaatgaag    31260
```

```
gtcagataag ttacgtgagg gatctctaag gccaagagaa gccatttagg tttgatttgg    31320
ttggaaaatg agcttattga aagtttaagg caagggacta gcatcatgaa cacatctttt    31380
tagggaagtg tgtcttgtgg taagctgctg gctggtttaa atgcagcaga atattccatt    31440
ggggatgcca gctgggagac ttgccacagt tgcagcctgc agcagaaaga ccctgggcca    31500 gaatggggttg tgccatctgt caccagatat tgccaaggta gatctggctg actttgtggg    31560
acagcttgtt tctcaataat cactttgcag gcactcttga ggctgtgagc atgctcccag    31620
aagatagcat tacttctctc tcagagcagg ctcctttcta aggaaatgca agtctaggcc    31680
tgccctgctg taatcttcat gtggaaacag cactctagca agaacaagg aacctgatga     31740 gcttttcaaa ggaaaatcga gtagatacag gaaaccaaga attttctaat gagcagatag    31800
aaaagagcag gtaggtgaga agttggtatt agaaaatta aagatttgaa gggcttgagg     31860
acagagatga ttgttggatg tttcattttt ccaggcaaaa tatgtggagc aaataatcaa    31920
atgacatgga cttaccccac aattagggac ggagatgagg aagggttagg aatagtttct    31980
gttagaatgg tagggatgga agacaattga aaattaaaga gaaataaat ggagaggaaa     32040 tctaggcagc agccattctt cattctgggg gaaggtggtc aggaaaagga aggaagaaaa    32100
atgtatagca tagtagctag agtggtccgg cgtgatcaaa gtgttttcaa tatcatgttg    32160
actgacctgt ttacgtttga aggcagagaa gatagagcca gtagaaggag agaaaaatca    32220
aagctgtttt acggagttgt gaaagagctg gataaggaca agactaaatg agttattttt    32280
aggccaggca tggtggctca tgcctgtaat cccagcactt tgggaggcca aggcaggtgg    32340
ggcacctgag gtcaggagtt caagagcagc ctggccaaca tggtgaaacc ctgtctctat    32400
taaaaataca aaaattagct ggacatggtg catggtggca ggtgcctgta atcccagcta    32460
ctcaagaggc tgaggcagga gaatagcttg aacccgggggg gcggaggttg cagtcagccg    32520
agatcatgcc agtgcattcc agcctgggcg acagaacgag actccgtcaa aaaaaaaaa    32580 aggagttatt tttaaatgga aagggcaaga cagttactcg gagagacttg gaaggtgaag    32640
caggttagag acagcacatc agagtatgca tgtgacagga ggctcagaga agagggaatg    32700
ctggggaaaa tgtgactgtt aaaattcata atgttgcttt ttcctacagc aaacaaaatt    32760
aatggaattc cctcaggaga tggaggagga ggaggaggag gaggtaatgg agctggtggt    32820
ggcagcagcc agaaaactcc actctttgaa acttactcgg attgggacag agaaatcaag    32880
aggacaggtg cttccgggtg gagagtttgt tctattaacg agggttacat gatatccact    32940
tggtaagtac aatttagca atgttatata tggctggaag tcacttccct atgaataatc     33000
atcaaactct gttgtcattg atgactttca agttgtggtt aatggaatat ttgttttaa    33060 taatgtttta ataaatattt tattttaaag atcaaggctt attaatataa attacggtat    33120
cccttaaaag aagttgatag taattcctta ctgtcatcag tagtcagtgt ttattgcatt    33180
atatcttgta actggtgttt tacagttggt ttgttcatat caggatctaa agtcttcaca    33240
ttgaatttgc ttaatatgtc tcttaggcct tttaatctac aacagtctcc tcccacctct    33300
tttttaccta ctatttgttg acaaaccagg tcatttgttc cctagaattt tccacattgt    33360
agatattgct tgttttatcc ccagggtgtc ccgtaatgtg ttcctctgtc tctaatattt    33420
cctttaaaat gttagcaaca gaggcttaat cggattcagg ttcagtactt ttggcaagaa    33480
tgtttcatta ggtggttctg tgttctcctg tggagtcaca tcccatctca ggctggctgg    33540
ctgtgtctct ctcattgtaa tcctgacgac cagtgggctt agagggtgtc aacctgatcc    33600
```

-continued

```
acccagtaaa agttcccctc ttatatcatg gtttgagctc ccaaaaatag ttttgcactg    33660
ggagggagga tcattgctca gatcgttatt tcactaagga ttgctattgt tcaccttcta    33720
attctatcat ctttctgctt ttatcgaact tttctctcac cagctcttta gtgccctgta    33780
acacagttcg tacaagaaaa gcaatataaa tatctacatt ttctccttta cttaacattt    33840
ttccaaatag tgagctggtt ccctagggga tctttctaga agtgactagg aatttgtttt    33900
tttaatttgt ttaatgtcat ttagttatta tgaattttt ggaatgcctt attttaaggt    33960
cattgaagtc ctcattagtt cacgcacata agcagctttt tagaaaaagg aagaaaagca    34020
ctactgtgtt attactggtt aatccagtac caggaacttc tagtacagtt ctagaaaggt    34080
gctttgcagc atgtagcttg tatgcttttg cttccctgg aatttaagct tcaaggccag    34140
cacactctgg tatatgtgct gagaaacatg tgatggggct gccnnnnnnn nnnnnnnnn    34200 nnnnnnnnnn nnnnnnnnnn nnnnnnnnnn nnnnnnnnnn nnnnnnnnnn nnnnnnnnnn    34260
nnnnnnnnnn nnnnnnnnnn nnnnnnnnnn nnnnnnnnnn nnnnnnnnnn nnnnnnnnnn    34320
nnnnnnnnnn nnnnnnnnnn nnnnnnnnnn nnnnnnnnnn nnnnnnnnnn nnnnnnnnnn    34380
nnnnnnnnnn nnnnnnnnnn nnnnnnnnnn nnnnnnnnnn nnnnnnnnnn nnnnnnnnnn    34440
nnnnnnnnnn nnnnnnnnnn nnnnnnnnnn nnnnnnnnnn nnnnnnnnnn nnnnnnnnnn    34500
nnnnnnnnnn nnnnnnnnnn nnnnnnnnnn nnnnnnnnnn nnnnnnnnnn nnnnnnnnnn    34560
nnnnnnnnnn nnnnnnnnnn nnnnnnnnnn nnnnnnnnnn nnnnnnnnnn nnnnnnnnnn    34620
nnnnnnnnnn nnnnnnnnnn nnnnnnnnnn nnnnnnnnnn nnnnnnnnnn nnnnnnnnnn    34680
nnnnnnnnnn nnnnnnnnnn nnnnnnnnnn nnnnnnnnnn nnnnnnnnnn nnnnnnnnnn    34740
nnnnnnnnnn nnnnnnnnnn nnnnnnnnnn nnnnnnnnnn nnnnnnnnnn nnnnnnnnnn    34800
nnnnnnnnnn nnnnnnnnnn nnnnnnnnnn nnnnnnnnnn nnnnnnnnnn nnnnnnnnnn    34860
nnnnnnnnnn nnnnnnnnnn nnnnnnnnnn nnnnnnnnnn nnnnnnnnnn nnnnnnnnnn    34920
nnnnnnnnnn nnnnnnnnnn nnnnnnnnnn nnnnnnnnnn nnnnnnnnnn nnnnnnnnnn    34980
nnnnnnnnnn nnnnnnnnnn nnnnnnnnnn nnnnnnnnnn nnnnnnnnnn nnnnnnnnnn    35040
tggtaaaacc ccgcctctac taaaaataca aaaatttagc caggtgtggt ggcgggtgcc    35100
tgtaatccca actactcggg aggtgaggc aggagaatcg cttgaacccg ggaggggag    35160 gttgcagtga gccgagatgg tgccactgca ctccagcctg ggcgacagta tgagactccg    35220
tctcaaaaag aaaagaagg aaatgatcta atttgttctg tgcactgcac gtggggtgg    35280 cagtgaggtg aatggcagca ttctgcagta gtcaaagcca gatgggtggg agaagttggg    35340
tgctaagagg gaaacaaagt ttacctgtct tctccttgat ttcactctca gttttatgag    35400
aatacagaaa aatcatgcag agaaacctga tggaatagtc tctaaaacta aaaataaga    35460 taagcaatgg ttctgtctta aaaaaaaaaa agtaaactcc atgaaggcag agaccttacc    35520
tgtctcattc ctctctctat ccctggtct atagtaaggg ttaaataaat atatgctgaa    35580
atgaatgagt aatgactaaa gtattttgt ctttattagg atttgtaatg caataactaa    35640
aagtcaccca cagagaagtg atgtttacaa atcagatttg gataagccct tgcctaatat    35700
tcannnnnnn nnnnnnnnn nnnnnnnnnn nnnnnnnnnn nnnnnnnnn nnnnnnnnnn    35760 nnnnnnnnnn nnnnnnnnnn nnnnnnnnnn nnnnnnnnnn nncagctcaa atttgttata    35820
acctatttgt taaagagagg attgtttttga gactatagtt ccattcttca tgaattggta    35880
ggagtttgga gtttgtcagc aaacattcta tcgggctaaa ggttttttata atgaaagaaa    35940 taggcaaagt ggatcagtac actcactttt ctaccattga ccctggagac agatggctta    36000
```

-continued

```
aaatgttctg cgtctagttg acttttagat cttgaaatta aggtttaatg atgaccaagc    36060
tttaaataaa ttgtagaaaa gtattctttc aaaagtacat tataactttt atattggttt    36120
cttatattta tttctttttaa tcttttcttt taacacaaac tacgttttaa ggttttgttg    36180
cctactaagt tataatctga gtgcagaagg aaacttgatt tggctttatg gaatacattt    36240
tacattcagt gaagctgagc tctgtttctc attccttaca aaaggaatca aaggcattgg    36300
tttgagagat caagtcatgt gttaataaaa cacaaatatt ccatcaagta atactctgaa    36360
ggagcaggtg tagtttattt cttctccaga aagtcttcca gcagataaat aatgagaggt    36420
agtatggcat aggaaaaaag tacactgaag tcagcctttc tggttcaacc agctcagacc    36480
cctgagctat ttttgcctca gttttacgcc ttggagaaca atgccttgtc attactattc    36540
actttatgac catacagtgc ctggcacctg gtgggcaatt ggtgaatgtt ttcactatcc    36600
tcatccttgc cctcatgaaa cactccttct aggtcccaca agaccgttg gtattttatg    36660 acaaagtacc ttacaaatat ttttcttttt ttaaaggaga aattgtcgta aatgaagtca    36720
attttgtgag aaaatgcatt gcaacagaca caagccagta cgatttgtgg ggaaagctga    36780
tatgcagtaa cttcaaaatc tcctttatta cagatgaccc aatgccatta caggtgtgtt    36840
ttattagtac actgtttcat tctatcaggc tttcaactct aagtggtaca tattattata    36900
taaaacatag gtatggaaaa gttatagtag aagtattagg taatgcaatg tttgggataa    36960
attatattaa gatttaaagt aaagtttaag aagaatgttg gaacttgcta gaggagtatt    37020
agtgagagga ttgtaagtca ccttgcttta tttatcctct gtgatcgttc attatatgtc    37080
cttttcatta aggaagttat tccctctgtt gcagatcttt taacctgctt ataaaaatga    37140
cataaagaga aaaggttgtt tgctaaatga ttttataaat gccacacatt ttagtgattt    37200
cataggtttt tttgttgttg ggttttttgat tttttttgttt tgagcctgga tctcgctctg    37260
tcttgtctcc caggctggag tgcagtggca tgatgtcggc tcactgcaac ctctgtctgc    37320
ttcctgggct caagctatcc tgccacctca gcctcctgag tagctgggac tacaggtgca    37380
tgccaccact cccggctaac tgttgtattt ttttgtagag atgggggttttt gttatgatgc    37440 ccggattggt cttgaacttc tgagcccaag caatctgcct gcctccccct cccaaagtgc    37500
cagagtacag gccactgcac ccagctacct tttttttttt tttttaaact aattagtgtt    37560
attttcctaa aaagttaaat tctaatttct aggaagagtg aagaatagta tcgatttaaa    37620
aattttcagt agccctcttg ctattttatg ttcttactgg aaagtaatag ttccatgtaa    37680
ttttggtttt tagaagttca ggcattcatt tgattaactt aaaaaccctg acttttctg    37740 tcagccattt tgtattttgt tttataaagt attatacaca cttacccta gatctttctt    37800 tatagtaatt gttctttaat gaaatattgg tatatgaact gtaaacttttt aaatttaagg    37860 atctaatagt ttagtgtaag tatatttcat gtagtcactc actaatttac cataattatt    37920
atactgtaca aatatttatt gtactgtata tttgtgtgtt cattacagtc ttatgtaggt    37980
atatttagac taaatttaag gcacttaaag atacccactg tgtagggaca gtagcttatt    38040
tggatatagg cttgtgtgtt tctctttgtt tttagcttca taatgatcat tggccccaga    38100
cttcactgta aatgagaagc agatacctgg aacagcttaa atccagtacc actattagga    38160 aaagtaaac cagtgcccta ctgacagcag attgatagtg ttaactacgt ccttagtttg    38220
aacatgcaaa accttttcta atggttttta tttctagtag actttgtgct ttaaaaagat    38280
agttattttg cactttaaaa tcttcagtgt gaaaatcaaa catgatttta cccacttaaa    38340
```

```
atctgatgac ctaagagccc ttttttcttt aatatgttgt ggccagctta tccagatcta    38400
gacatgcaaa tgcttgctgg taaggtgatt gatgatattc cctatcttag gtattataat    38460
aagattgttg tgtacatttt aacctaattt ctatctgtca acattggaat ggccctagct    38520
acctagacaa aagcttttg tgcttttag agataactgt cacagtttat catcacagtt     38580
taaggcttat actaccattg tgagattatt gggaaaagaa ttaatatgaa cataattttt    38640
tattccagaa attccattac agaaaccttc ttcttggtga acacgatgtc cctttaacat    38700
gtattgagca aattgtcaca ggtacgtagt attccgtaca tactctaaaa gtcaattcca    38760
ctctggaagt attatttgaa aagtcatacc tctcaaaata cttggattgg cgttttattt    38820
ctgtaagttt acttttgccg ttttttgag tcccgggaac ataaagaggg atatgttaat     38880
aaattatttt aaaaggaaga tataaaatgt ataactttc atagtttcta ggtttttgt      38940 cctcttttta attaaaatta atcattaaat gtgtctagat ggtggtttta tgcaaataat    39000
catttaaaat atcttccaaa gcaaagttaa aaccaacccc caagttctag gaattacaag    39060
tatgaaacat tctagacaag cagagctcaa atgttgggtg accttccaat tatttttcact   39120 aagaatttgt attaaagggt gagtaacaaa taactgttac gcatttttatt ttctctatt    39180 tttttttcttt tttagtaaac gaccacaaga ggaagcagaa agtcctaggc cccaaccaga   39240
aactgaaatt taatccaaca gagttaatta tttattgtaa agatttcaga attgtcgat    39300 ttcgctttga tgaatcaggt cccgaaagtg ctaaaaaggt aatactgtta aggtttatca    39360
agttctgggt tctgtactgt gtttactgat ttcaattccg tatggcagtt ttcatttctc    39420
aattgctcag atgtttttta ggggaagtta tcagacatct tcttaagtaa agtcaaagcc    39480
aagaatatta atagaactat tttcttggat tggtttatgg ctgttttaaa gtgttctata    39540
taacttttta tcagcttctc aaatattaaa gactcttacg tggaaattag catttttta    39600 cataaagatc attacttgtc agtttcttgg ttaaaaggtt gaaagttgg tgatatactg    39660 taattaaggt ttggttaggc ttttaattca gtactgcaga actttaccaa caaactgtaa    39720
gctagactta tgttacataa gatttaggta aatatataat tacgggaaag gcctagtaat    39780
tattagtggt ttaaagaaat attatgaatt gagtgacact caacaggggc aacacaaagc    39840
tagtaacttt ttaactgcct tatttttcca cggccttcca gataatgact tattacccta    39900
cttgtaagag tcaagggcat gttttccatg ttttgctttg ccagaggagt gaagctggta    39960
gacctaatat ggccccgtt ccagtctgtg ctgcagcaaa tgcagagtca cagacttcc    40020 agtaggaagc ttgcgcgtgt gtatgggaat agggcaacag tatcttagta ataggacg     40080 tggctttctc tcagaatgga ggcagtcttt gcaccaccaa gcaatgagtg cctttgtttt    40140
ccatggttag tcaactgact gcagtaaatc ttctgttgat accaaaacaa ggctggcaaa    40200
aatactgtaa ggcagctgtc ttcatatact ttggtgaaga ggtggtagat ttgttttag    40260 attgagaacc aacagtttct tcacaggaag gcaagcagga gatgaatata tgaaaataca    40320
tctgaaaata tgtgactgtc tagcagagta gagtggttgt aggctcctct atgggtaaaa    40380
gttttcaaat ggtctgtata accatctctc agcaagctgc attattgaaa attcaactag    40440
ataactctta aagcctcttt cacctgttcg attgtgctgt ttgtgatttt ggcattttac    40500
taatttaaag tgcctattat atagaaggac tttagaattc atgatgtatt agactgtaca    40560
taaaatattt cagacaggtt aattcctcaa gcttatttat atttgtaatt taattgatca    40620
aagcatcaaa gacctgctta tgaaaacctt aagatgtgta gcatctcaag attagggaca    40680
tcacagaact tgctagattg agttaggaca gcatattcct aaggaagaaa ttgatgcaat    40740
```

```
tgaccggatc tctttcggaa agttcaattc tccctctttt actgtatttt tcagtttaca   40800
ctattttaat gagtggaaat aataattatt tggcctagtt cttgaaccat ctgtagtact   40860
tgttggtcat ttttcatgtt gaggcagtgt gctaaatttt gcaagtagaa agaagggtaa   40920
gatgcagttt cttgccctag agaacttaaa tctagtgaag aagataaagc atgaacaaat   40980
gaaaagtaat ggtacaaagt ggcagcataa aatcaactac acaaatagtt gatttccaga   41040
tgaacagagc ataataagtg ctgtggaaat tcagaatatc ccctatgtgt tgtgctgctg   41100
gttcatgaag agggccttac taaaccgtct gcacaaaaca agccagtccc tcatatgccc   41160
tttcctaaga ccaagtttca gacaaaaatc ttttccccag tatcctaaaa tataaaaagc   41220
atgtgagtct ctgtcttttg tatagccacg ggggttgcag ggcaggggag ggtgcaggaa   41280
aaaaaaatag atgcaatgag aatataaata gttttttttgg gatttacgca tttcaaacag   41340
ggttaagttg tatatggcta ccaaagcttg acggctttgt gagttaaaaa caaaaattat   41400
ggcatattct tttatttcaa gtgaaaagtt ttcatctaaa attcggtagc agttaggaaa   41460
ttatggctca ttttttacctc ctggaagctt ggaatactgt tttctctgga aaatgctttg   41520
ctattttatc agttgcttta aaatgatgaa atgcatgttt ggagttctct ggtgggtaaa   41580
ccgttgattc attttgaaat acctaagcca tttatgtttt tgttttgaaa aatgaaattc   41640
aagaatacta aattggttca cattttgtta aatgttctga acccttctgg ttgtcttgtt   41700
ggtgttgttt caattgtatt atgacaaaat tagattgctt tgggcacttg tactcattaa   41760
tattcatcct cattatcctc gagctgtcac aggaaaatag tgatatttgg gaaaggtctg   41820
tataaagaaa gaaggaattt gatggtgcag aattggacat ctaacctcat agcaacttag   41880
aaccaccatt ttcttttgca gaacctttgc tcaaaactga agggcaaaat aataaaggtt   41940
gtttttaatg atttatctat atatctgtct gtgtagataa agataaatat atagatacac   42000
atgagtgaca agtgaaatac atgccttttg tctccacttt gttctctgat tagtgggttg   42060
tgaatcactt cttcaggaat actttataga agtgaattcc attcatctga ttaaggaaca   42120
agttggcctt ttcatgaact gtcattttttg acttgaatct ggtactgttt tttggtggct   42180
ttcaggccac agaaataaac cacttttgtt tgcaaatgag atagaactta atgaggtttg   42240
agtgtttcct ggatttgagt ttcttcagta ctgcaccccca ggtgatctta ggaaagaaac   42300
catccactgt gggtacttct ggcttctgtc cagagaagat tatcagcttt ggtccaaaaa   42360
ttgatttaaa agtagtttac ttcttttttct ccaataaaat atttgccata atttaatgtc   42420
tttaatacca acattttctt catttcctgt ggtagccagg acaaatgaag tatttcagat   42480
cttttcaaaaa ctcttaggat gaaaggtagg aatttggact taggttttta aaatagtgtg   42540
tatgtaaaag tgcaaagaat ggggcccctgg ctttctcttc tcggagtgtt ccacagtaac   42600
aacatgaaga caatccaggt acacaagttt gtatgtgcct tagtctgtgt gtccaaagag   42660
gcctcttact taggtcatat gaacataagt tatacacttg aaattcacta ctgaaaaaca   42720
atgtatttag ttcgagttct gccaccccaa aaaaatcaac gagtaattca actgacttgc   42780
agttttacaa tatttttata gacttctttc agcgtagatg cttttggaca tactcatttg   42840
tttcctaacc tgatgtgata ttgtgctatt tttaagggggc ttttaaaaaa tacgctgtgt   42900
tgggttttgc cttgaaaata ggctttattt cttttttgcc tcatggccac aaaaaaagga   42960
tgtccatgat caatgatctg tgaatttctt ttctgtaaac agaaagagca tgtaactgct   43020
ttctaattgt tttggagaat gtgatagaca ttagtattat tattattggc ttggagcatt   43080
```

```
ttccttaata tgttggtaac tacttttgtc agtgaatatt agtgtagcca ctgttggaca    43140
cagagcaccg tcagaaagct actgaagtgg tgctgcaaag tgcagacatc ttcagatctt    43200
tactcaagtc tgtgcagaga ggtctttctt ggtctccttc tctacttttt agcctgtctc    43260
cctcttctca ctgtaacact tcatattccc cttccctgct ctattatttt tctcttttag    43320
cattcatagt tatctaactt tctgtatttt ttctctttat cttgtttagt gtctgtcttc    43380
ccactagaat gtaagcttca tgaggacagg gattagtgtc tgttttgttc actgcatctc    43440
tagggcttac aacattgtag gtactcagta aatatttgtt aaatcaatgt gaaatgtgtc    43500
atttatcctt aaggaattga ccttcatggt agaagtgtaa cagaaccacc tatatcctac    43560
ttttcatcca catcataact attatgtgaa taccttggaa gtaaagcaaa ataagcactt    43620
aactaaagag acgctttata ttgaaactgt tgttctgggt ttctggaatt agtactctga    43680
aattggctcc ctctaggaag gcttgtgaag agagtagtgt tgaacagaca tgacagtttc    43740
caagaaagca tagttggcta agaggagtag gattttccaa gcaaagagtg tgacagtgga    43800
gatggctggg gctaagtcag gcagaatgtg ttcaaacctg tttttctctg acctgagatt    43860
gcggagggaa tattgggaag gtatagttac ctggtgagga gagccagttt tgtgaagaat    43920
caagaatgag gagatttaat ttgttatgca gatgtctggg aaccacagca gattatcagg    43980
agagcaaaat tgttagtcag aattacatcg ttagaaggta atccttaagt tttgtagatt    44040
tctagaatgt aaggaagctc tcagaggtgc cataaggtga gtatggccta aggatgtggc    44100
tatggcagtg tagcaaaatg gacaactatg aaaaatgtct agagaaaagt gcaacatagc    44160
ttatcaacgg tgcccaaaca aataggaagg atgagaactt tttcaagcta cagatttcag    44220
tagttttgct gctagaaatg ctttaaggaa aactgttaaa aagattagga atgggaatat    44280
agataaccgg ctcctaaatt ttgcaagtgg gaccgtcata gaaagctctc ctataggtat    44340
tgagaaatcg agataccacg taagtttcaa gaagcagttt ttttttttctt tttggtcaaa    44400 actaatgaca aattctgtcc ccttgtttgt atattttaac ttagtgagac aggaaacatt    44460
tattctatag aagactttta aaatgtagtt taaacaagtt gacacatgct tactggttaa    44520
tgaaatgtgc atcaacccac tccaaacacc actaatttga catgaactaa caattaactt    44580
ttcttactca ctgtcaaaag tatatcattc tgccttaact taacgctttta ccttctaaat    44640 aaaatttaat ctttaaata agttttctg ctatgttttc cttgcatatg tcttaaattt    44700
cttctttcgt ctttgctcac tgaagagcat tttctcccac attctagtga ctaccagggt    44760
ttgtaagcct agagcaccat ccttcattct atctagcagc agttgagaat aataacagcc    44820
atatttctat atatggagct cctccaaagg cctagcctgc attaagcttg ttaattctta    44880
ccacagccta ggtattactt ttgttttaca agtgagcaaa ctgaggctag aaaagaggaa    44940
atgacttcac acatgttatg tagcaagtac ttgacagagc taggattcaa gccccctgat    45000
ctgtttgatt ctaaagcccg cacgttttcc accacagggc acacagtccc aaaccatttt    45060
acttaaacac agtttgtgtg tgtgtgtgtg tgtgtgtg tgtgtgtgtg tgtgtgttgt    45120 tttttgatg tacctctttg agccacccat gcatttttgg agtttcttgc taatttaat    45180 tttttgtaat tatgtttctc tatttagatg tttaaatcca tgaggcgtaa actttaaagt    45240
ttcatgcctt atattaatcc tttatagtcc accaaaaatg aaactttttt cttccttttt    45300
tggagtggac atgtagtcac tgccttttg gagaatgctt ctttagtttg aagctttctt    45360
tattggacta aaattacttt ccaattaaaa tttaactcag caaatatttta ctgaatactt    45420 gccatgtgct agctaaagat aaacaatgtc ttgagggcat gaaagtgaat gagatacctg    45480
```

-continued

```
gccttaagga gctcttttat attctaggtc aacagaaaaa catgtaaata gtatctataa    45540
tcactgcccc aagatgatgc tcccagtgcc caaggcctta ttgtacattt catttaacta    45600
agtgtgttaa aatcaaattc taaatgtaga attttcctta ggtatgcctt gcaatagctc    45660
attattccca gccaacagac ctccagctac tctttgcatt tgaatatgtt gggaaaaaat    45720
accacaattc aggtaaatat gaaaatatta aatattgtga ctaattttac atgtgtaaat    45780
tttactctta tgtttaccgg aagcctccaa gtacatgagc tttaatgatt gtagaattac    45840
tagcttcata ccttagagaa gtaagcacta catgctaaaa gagccaatag tttgtcagat    45900
tatttcttga caagttacca ggaagaacct ttaatgctat gaatatgggc ttataagtta    45960
tgtcagatat ttaatctcca gtcactggct tgtattttat gatgaagaat atataaccca    46020
cccttttttaa ttgatagctt gagttaaagt aatcttatct tttaagaaaa ctggcagaaa    46080
actaaaagat atattaaaag cataatcttt tctggcaagg tgtgatttca tgcaaaagct    46140
aaagtgatta aaaactttttt gtggacttca ttaagattct cagaatactg agtttctatt    46200
tctgagtaat actgatgaaa ggaagatgag cattttttcca aggacaagta tattctagac    46260
agcttttgtg aaagtaaata gttttgtcta tatatctgac agtcatgaca tgaccaggga    46320
agattccaga tgatcatgca attctgtaca ttctgtttcg tacaaatgta attttaataa    46380
acaatttttta aaaatatctt gatagagaaa acaaagagc cgtgtctcct gttagcccca    46440
ttgtcagtta gtgactgcaa gtcagttaac tgagcgaagc ctgtgttctt ttatttaagc    46500
aagaaaaata aatcagctgt gtatttataa tgaaaaatcc attcacccag catgctctgg    46560
gccatacaaa ttattaattg tactgaaatt ttatattttg ttaccacgaa acatggtagt    46620
aatttaaata actggcataa taaaagtata ttccagcaac actatattgt aaatacatta    46680
aaatgtatca gtgtacggta tctgaagatg catgtgtata agtaaatttt ccttagttta    46740
aaagataact acctttctgt taagcactga gaggaccaaa aaaaaaaaaa aaagaaaata    46800
cagtagagat aatatatgaa aataatgctt tgcagagcag cttttatcat acagtattat    46860
atttatagaa attgtataac aaaagtatttt gtaacttaat ttttcttatc gatatataca    46920
taattgtaac tgaggcttaa gcaatacagt tatttttttga agtttattaa tattaagtaa    46980
attcacttac tgtctaaaaa taaagtatac agatcctgca ctattaggta aacactcctt    47040
gggatcatcg tcaagctaca gaacagtgat caaggttatc ttcaataaga tcctcaccca    47100
gagttgcaag ggttgtagga gtgagtcttt gattcctgct caactgttta tgatacagac    47160
cagttcttca tgctgctgtt tttccaatag aaatgattca tttcagttta cagatccata    47220
acttctacag taatgtagtg acttgggctc agcaaagaca gtaaacttca ttatacagtt    47280
ggtaacctga tgcctgcttc agttactttc cacattttttc ttcattcata ccttgtgggc    47340
atctctggtt tacagtactt tagtttatcc acccataggt cttctactac tggaattttta    47400
aaatctacat cattcagttc cactatttct tcttatatag cttattgata aaatttgatg    47460
attaatactg aaaatattca gggatgcttt tttatattac atccttcaga ctcctccttt    47520
gacaagtacc tcataaacat aacactggcc atagtttttgt taagattcct cgtagggtaa    47580
catccttttaa tatccttcca tgctgttaca gaagcataaa tactgcatct ttaagatcaa    47640
aaggagcctg aaatttccac acactgcagt cagaattcat taatttgtga gtgaaagatg    47700
cccactcatc cactcttgaa cttctggatg acacctgat tcattggctg gattaaagaa    47760
gtcctttttg caggcaggta ggtgacaaag ctgtttccac aaataagatc caaagttgga    47820
```

-continued

```
ggagctcccc tgcagttatc tgagaaaatg atatttagc tggccttagt cactcaggtt    47880
ttcattcata ttcagtatca catgaggaaa agccatctct gaaaggtcct gcagtcatcc    47940
caacacttct gtgaatatcc tggagtaaag taagatgtgt agcacccagg ctttggaaca    48000
tcgctttgca caaacacccc aggagatatt actagcacaa caagaacaa tgattctgtt    48060 ttttctcttt taactttaaa gaaaccatga ggactctgtt ttcatcagtc agattattat    48120
tgggcaaata acgtcaaaaa agtacagatt catctttctt atagaattga taagatgtca    48180
gattatgctt ctggaccaaa aatattgaaa gtttcatgaa gttatctgca gcctagtgtc    48240
agcaactgct tcatgacaga catcctgctt acagatgctg tgatgtaatc tgaagttgta    48300
atgaaatttc acatcagaag ttgtacattt tcagtgacat ttaattttat cctttttatt    48360
aacatagatc ttgttattag attttcctta aaatgcctat ttgaaaaaca caaggtacac    48420
aatccatttg aaacagtata ggaatttta aactttgttg cttaagattc tcagaatagc    48480
tataaatgat tgttgaatat tggtggttcc agccagctgt atacatcagg attactggag    48540
gaacctttag aaatgcagcc atgttggctc agcacaggt cagaatctcc cagttaagaa    48600
ccactttgtt gactcatgct tttgaactga ttaatactca cagtcctctt tttaccttat    48660
tcctttgtga cttctaattt ctgcagtatc atcagagtgg tgggcttct tttcatatat    48720 tgatgacttg tattttctgt tgcttgaagc cattctagat atcaattggc caattcagtg    48780
gaaattatct aaaataaccc caacagtata ggattagact tttgtactgt cacagaagat    48840
agccaaggtc aggagcatat aatatctatt tcacgcttag tctgctgtgg aggcatgtca    48900
taaaacctca gtcaggtagc ggtcagcgga gccaggtctc cctgagatga cccacctttc    48960
actgtgttgg tccagcccct catagcgatc cactcataga gcaggccact ggtatcaggt    49020
cttttgaact ttggaaagca ttcaaatttc tggactataa aaccagattg agtatacatt    49080
acacattctg taatgagctc taactgaaga tgatatagaa catataaaag acctagtccc    49140
agttgtttag aaaagtacag gatttgaacg agagaaatgg caaaaataac aaacgataga    49200
ggatctcact ttatgcttag aaaatataga tgttctcatt ttacgtttag aaaaatttgt    49260
gtaagttaga tcttgaaaca aaatttggcc agagaaacaa tctcataaac aatagcacat    49320
tcttagccta gcttattaaa gtctgcaacc caaaacacta aaaagtattc agtgctgctg    49380
gactcagtca ccaaaactgt ttacataact gttaaaattt tgagtgtgtt ttttataatt    49440 ctttttggt ggtggtggtt ttattgtttg gctaggactg ctggttcagt gttgaatagc    49500
agtaatatta gcaggcataa tttcacttcc cgcttttaat gaagatgctc ttagctatgt    49560 cttttgata aacaccctct atccagttaa ggaaattccc ttttattcca aacttgctaa    49620
cgttgttggg tttttttttt taagtcataa acaggtatct atcatatgtt tttctgcact    49680
tacagagcta gtcattcata tagccttttt cgtgtttaat gtagtcatat gatgaattac    49740
ttagattttc taatattgaa tagctttctt tgttttggtg cactggaaca ctgtatagat    49800
tgggctttgc caaaaattcc atatgcaggt tttgtgttct ggagagatca taactcctaa    49860
gtcttccttc tcacagacac gcttttagt tgtgttactc cagagaaggc cctgagatgg    49920
agtgggactc taggatgtgg gcttagaatg agcattttac tatctatcta tctatctatc    49980
tgtctgtcta tctatctatc tgtctatta tttttgagac agagtctcgc tgtgtcgctc    50040
aggctggagt gcactggtac gatctcggct cactgcaagc tctgcctgcc aggttcacac    50100
catctcctgc ctcaccctcc caagtagctg ggactacagg cacgtgccgc cacacccggc    50160 ttatttttt tttttagta tttttaatag agacagggtt tcaccgtgtt agccaagatg    50220
```

-continued

```
gtctcgatct cctgaccttg tgatccgccc acctcggcct cccaaagtgt tgggattaca    50280
ggcatgagcc accgcgccca gcaacatttt acttttaat gagctttgtt aaaatcagaa     50340
tcactggata attctgatac cacttaagag gagtccaaat tcctaacata gcccctccgt    50400
aatctagagc agcaccgtcc agtgatggaa gtagggcagc cactagagcc actagccaca    50460
tgtggctgtt aagtacttga aatgtggcta gtgcaactga tggactgaat tttaatttt    50520 attaattt  cattcagtt taaatttaaa tgggcttgtg tggctagaag ttacgttttt     50580
gggaaacata ctagagtcta ggccctattt gatttcccgc ctctcttcca ccacctgttg    50640
aatccctatg ctctagctgt attagttac ttgatattat acagttatac catctttta    50700 aagttcttct ctgtctagca tgcctacctc ctcctcacca gctacctggc aacttttgac    50760
ttgttcctta gaactctctt tagttgtggt caagtcatga agcttttcct gccccggcct    50820
ctctctgcag cgagagttag gggacttctc ttttgcatct tcattgcact cagacatctg    50880
gtactctgtg attatcacac ttattaatgc tctcaagata gagataaaat cttattcatc    50940 ttttgctct caggcattag cacatgggga gttctcagaa ataccctgtc ttataccagg    51000
aattaatgaa taatcagtag gaatgagcat gacatgttca tgggacgttg gagggtagtg    51060
catggctgca gaggagaatg ggaaatgaag gtcagataag ttacgtgagg gatctctaag    51120
gccaagagaa gccatttagg tttgatttgg ttggaaaatg agcttattga agtttaagg    51180 caagggacta gcatcatgaa cacatctttt taggaagtg tgtcttgtgg taagctgctg    51240
gctggtttaa atgcagcaga atattccatt ggggatgcca gctgggagac ttgccacagt    51300
tgcagcctgc agcagaaaga ccctgggcca gaatgggttg tgccatctgt caccagatat    51360
tgccaaggta gatctggctg actttgtggg acagcttgtt tctcaataat cactttgcag    51420
gcactcttga ggctgtgagc atgctcccag aagatagcat tacttctctc tcagagcagg    51480
ctcctttcta aggaaatgca agtctaggcc tgccctgctg taatcttcat gtggaaacag    51540
cactctagca aagaacaagg aacctgatga gcttttcaaa ggaaaatcga gtagatacag    51600
gaaaccaaga atttttctaat gagcagatag aaaagagcag gtaggtgaga agttggtatt    51660
agaaaaatta aagatttgaa gggcttgagg acagagatga ttgttggatg tttcatttt    51720 ccaggcaaaa tatgtggagc aaataatcaa atgacatgga cttaccccac aattagggac    51780
ggagatgagg aagggttagg aatagttct gttagaatgg tagggatgga agacaattga    51840
aaattaaaga gaaatataat ggagaggaaa tctaggcagc agccattctt cattctgggg    51900
gaaggtggtc aggaaaagga aggaagaaaa atgtatagca tagtagctag agtggtccgg    51960
cgtgatcaaa gtgttttcaa tatcatgttg actgacctgt ttacgtttga aggcagaaa     52020 gatagagcca gtagaaggag agaaaatca aagctgttt acggagttgt gaaagagctg     52080
gataaggaca agactaaatg agttattt aggccaggcg tggtggctca tgcctgtaat    52140
cccagcactt tgggaggcca aggcaggtgg ggcacctgag gtcaggagtt caagagcagc    52200
ctagccaaca tggtgaaacc ctgtctctat taaaaataca aaaattagct ggacatggtg    52260
catggtggca ggtgcctgta atcccagcta ctcaagaggc tgaggcagga gaatagcttg    52320
aacccggggg gcgaggttg cagtcagccg agatcatgcc agtgcattcc agcctgggcg    52380
acagaacgag actccgtcaa aaaaaaaaaa aggagttatt tttaaatgga aagggcaaga    52440
cagttctcgg agagacttgg aaggtgaagc aggttagaga cagcacatca gagtatgcat    52500
gtgacaggag gctcagagaa gagggaatgc tggggaaaat gtgactgtta aaattcataa    52560
```

```
tgttgctttt tcctacagca aacaaaatta atggaattcc ctcaggagat ggaggaggag    52620
gaggaggagg aggtaatgga gctggtggtg gcagcagcca gaaaactcca ctctttgaaa    52680
cttactcgga ttgggacaga gaaatcaaga ggacaggtgc ttccgggtgg agagtttgtt    52740
ctattaacga gggttacatg atatccactt ggtaagtaca attttagcaa tgttatatat    52800
ggctggaagt cacttcccta tgaataatca tcaaactctg ttgtcattga tgactttcaa    52860
gttgtggtta atggaatatt tgtttttaat aatgttttaa taaatatttt attttaaaga    52920
tcaaggctta ttaatataaa ttacggtatc ccttaaaaga agttgatagt aattccttac    52980
tgtcatcagt agtcagtgtt tattgcatta tatcttgtaa ctggtgtttt acagttggtt    53040
tgttcatatc aggatctaaa gtcttccacat tgaatttgct aatatgtct cttaggcctt    53100 ttaatctaca acagtctcct cccacctctt ttttacctac tatttgttga caaaccaggt    53160
catttgttcc ctagaatttt ccacattgta gatattgctt gttttatccc cagggtgtcc    53220
cgtaatgtgt tcctctgtct ctaatatttc ctttaaaatg ttagcaacag aggcttaatc    53280
ggattcaggt tcagtacttt tggcaagaat gtttcattag gtggttctgt gttctcctgt    53340
ggagtcacat cccatctcag gctggctggc tgtgtctctc tcattgtaat cctgacgacc    53400
agtgggctta gagggtgtca acctgatcca cccagtaaaa gttcccctct tatatcatgg    53460
tttgagctcc caaaaatagt tttgcactgg gagggaggat cattgctcag atcgttattt    53520
cactaaggat tgctattgtt caccttctaa ttctatcatc tttctgcttt tatcgaactt    53580
ttctctcacc agctctttag tgccctgtaa cacagttcgt acaagaaaag caatataaat    53640
atctacattt tctcctttac ttaacatttt tccaaatagt gagctggttc cctaggggat    53700
cttctagaag tgactaggaa tttgtttttt taatttgttt aatgtcattt agttattatg    53760 aatttttttgg aatgccttat tttaaggtca ttgaagtcct cattagttca cgcacataag    53820
cagcttttta gaaaaaggaa gaaaagcact actgtgttat tactggttaa tccagtacca    53880
ggaacttcta gtacagttct agaaaggtgc tttgcagcat gtagcttgta tcttttgctt    53940
cccctggaat ttaagcttca aggccagcac actctggtat atgtgctgag aaacatgtga    54000
tggggctgcc cagccacgtc ggggaaagaa ggaagatgtc ttgaggtgca gtgagcttgc    54060
ccactagtaa ttattgtctg atcagtgtcc tagagtctga ctgtgccttt taggcatggg    54120
gaaaggtaga agagggactt aagaagagag ctaaagctcc tggtagattt gtgggttttt    54180
cttttgtttg cctggtgtcc ttaaccatag cctgtcaaga gaacaaaggt ggatatattt    54240
ttcagtgaac acatacatgt ttaatagtca ttctggaaaa tatttctaat accttctttg    54300
gaattttctc atgctataaa tttagatttt taagaattgg tcatatcgca ccaattttag    54360
actaagaggt gtaggatcgt cactgccccc ccatggtgcc caccatgtgg ctactaagtg    54420
gggtgcacat taaatgcgga caacttgctt aattatttat agggtctgca ggagcacact    54480
attcctgctt ttagcacagc actcatataa ttttttttttt cccctccagc cttccagaat    54540
acattgtagt gccaagttct ttagcagacc aagatctaaa gatcttttcc cattcttttg    54600
ttgggagaag gatgccagta agtgatttct gttggatttt atgaatgctg acgtccattg    54660
tttctacaca gtgaagtaag gattctacct ctcccctagc tctggtgctg agccactct    54720 aacggcagtg ctcttgtgcg aatggccctc atcaaagacg tgctgcagca gaggaagatt    54780
gaccagaggt aattgagaaa tggtcattgt cactttagat agttttactt gttgtgtaac    54840
tacagtgagt tccctactaa ttgaaaataa caaaatgcat agtcttacta attagttagc    54900
accatgtttt atataagaat tgccattttg aaaagaatgt gataatatta aaattaactg    54960
```

-continued

```
acattggagt tacactaaat ataatttaat tatttggttt gtaagacact tgtggatctt    55020
acattgctga catcttgcta tagcatttcc tataacatac tttcaaagtg cagtgatatc    55080
cagttgagac acttcaggat aaatcaaact tttcttgtag atctgatgtg tcttatttag    55140
gtctacacat ttgcaaatag cctagacagt gcttttaatt agccaccaca gacgagtctg    55200
gcatcatctg ctgtgggtca tagtaactcc ccgtcattaa agtaggaggc ctttctcagt    55260
tgtgctcata gcagtgagca atactattga tcactctctc cttaaacccg cctgggccct    55320
cagcctctgc tcctctccac tctcctgaag ctcctcttcc tcactggcac tccgtgcctt    55380
ctgcagaccc atcctcttct ctccagacat tacacagatt ctaaggccgc ttcctcatgt    55440
tctgtattct tttcctaaag aagtttcccc aagaatgtgg ctttagtgac caacacattt    55500
atatcttcag tctaccttga cttctacatg gaggtctcaa agacccctta aactcattat    55560
gtccaaaacc aaactcaagg atatggcctc catgccctcc cccagcctgc tctcagaaac    55620
cggggggtca tcctggatgc cttcctcttt cttttccttc cccatcacca atccctcctc    55680
aggttttctc acttcacttt tcagacacct tgcaaaccca tgtgcttcca caaacccagc    55740
tccacctctg cctgtgtgtt ataagtgcta tcatttcctc cttccatgtc tcctccaccc    55800
ctgggctcca gccccctgga cttttcctgg tgttttcaac ctcctgacat tgtccagcgc    55860
tcttcccttc tggactgcct tctttgcact catctgggaa cactctccac gcttacccac    55920
ttggcactcc ttgtttcttt tttttgaga cagagtctca ctctgtcacc catgctggag    55980
tgcagtggta cgatctcggc tcccgggttc aagtgattat catgcctcag cctcctgagt    56040
agctgggatt acaggcaccc accaccacat ccagctgatt tttgtatttt taatagagac    56100
aagatttcac catgtcggcc aggctggtct cgaactcctg acctcaggtg atccacccgc    56160
ctcggcctac cgaagtgctg ggattacagg cgtgagccac tgcacccggc tcactcattc    56220
tttatatctc aattcaaaca tcatttcctc aagataagcc ttctctcccc tctaaagttt    56280
gatcagacct caaagtctca tgttcttaga gctcctgagt ttttaacatt tatttcagtt    56340
tttaattata tatgtgtgtg ttacagtttg attaccgcct gtcgttttta ctccatgaga    56400
tgagggacta tgtctgtttt gcacaccgtt atatatttag cacccaggaa gcatatatga    56460
tatttattca atacttgttg aataaatgag gagtaaatga acagatctta taaaacaggc    56520
ttatggagcc tcagaaattg tgtatcacag tccttttttgg tacagccaga gtgtagggtt    56580
tttccactgt accgtaactg acagagccat attcactgaa gcaaataacc atcaagtgac    56640
cctcaaatga ccttcagttt tctggaaagg aaggtgacta tagttcacac gagtccgtat    56700
tctctgtgga ttttgattta cctgaactcc atttggaatt aactgtctgc tgtgtcatac    56760
tccaagcctt gttttcatta gcatacatgc tgatgaagtg cacagttagg aattttgctg    56820
ttaaagggac aattgtagca ttgttgggtg agagttagtt ataaaacctt ataatcagtg    56880
gcagtttcag tgatttatta agctgaaaat tactttaatg ccttttgtgt tttcagctat    56940
cctattcttc ataagtagaa cagatcctct tttttgtcca acctcgtctc ctaacctttt    57000
tccctcaggt gtgtcatcta gccccactgg ccttctttag gtttctcagc agccatgctt    57060
gttacctgcc acagggccct tgcactagct gccctctgcc tagaacattt tcaccccaga    57120
tctttacatt gcttctctat tcatttaggt ttcggcttca gtaccatctt cacagagcag    57180 ctgttttttca ccatgtgacc taaagtagcc tgtaatctca tgattacatc atccatggca    57240
ttcaccacag cccatttatc ttatcatcta ccccacccca cgaagaatgt caacccccca    57300
```

```
cttgcttggg caacaccagt agtaaaattg gaatgataca gggaaggtta gcatagccct   57360
tgcacaaaga tgacatgcag gttcatgaca cattacatat tttaatgaaa tgggagcata   57420
ttcttgttat ttaattttta aaaatcagtt tatcaagcaa atgtacagcg ccattttatt   57480
tttcatgcct acattaaatt ccatacacat aaaggtgcat agaggaaacc tagaaagatt   57540
gcaccaaaat tttagaattc tgagtgattt tgttttcctt atcttttcta ggtgttttta   57600
aacattccac actaatttat attactttt ctattcagga aaaaaaaaa caacagcagg    57660 gttttgtttt gttttttaa agtggtgtgg aagttaccca ttgaatatag atgggaatcc   57720
cagtcctggc tgtttccttt gaaaagatct agagacccca tggcacatat ttatagtagc   57780
ccattctctc ctaagaatag aggaagggtg ggaggaattt tggtgaatgt ctgtacttgc   57840
agtttatcct acagcaaatc gttaagactg tgggaatagg tgctttgcat tctctagagc   57900
tggagaatgt gcatctggtt tgccatcctt ctgtctacat catgtggaaa gatgtgggag   57960
tgtagggtct ccttaatcta aatgcagtgc tgccccgccc cccccttggc agtgtttctg   58020
tttcccaggc aagtgttcca atggatgtgc tttattttct cccatcagaa ataagggaat   58080
gagcccgggc gcggtggctc acgcctgtaa tcccagcact tgggaggcc aagggggtg    58140 aatcacaagg tcaggagttt gagaccagcc tggccaacat ggtgaaaccc cgcctctact   58200
aaaaatacag aaatttagcc aggtgtggtg gcgggtgcct gtaatcccaa ctactcggga   58260
gggtgaggca ggagaatcgc ttgaacccgg gaggggagg ttgcagtgag ccgagatggt    58320
gccactgcac tccagcctgg gcgacagtat gagactccgt ctcaaaaaga aaagaagga   58380 aatgatctaa tttgttctgt gcactgcacg tgggggtggc agtgaggtga atggcagcat   58440
tctgcagtag tcaaagccag atgggtggga gaagttgggg gctaagaggg aaacaaagtt   58500
tacctgtctt ctccttgatt tcactctcag ttttatgaga atacagaaaa atcatgcaga   58560
gaaacctgat ggaatagtct ctaaaactaa aaataagat aagcaatggt tctgtcttaa    58620
aaaaaaaaaa gtaaactcca tgaaggcaga gaccttacct gtctcattcc tctctctatc   58680
ccctggtcta tagtaagggt taaataaata tatgctgaaa tgaatgagta atgactaaag   58740 tattttgtc tttattagga tttgtaatgc aataactaaa agtcacccac agagaagtga    58800
tgtttacaaa tcagatttgg ataagaccct gcctaatatt caagaagtac aggcagcatt   58860
tgtaaaactg aagcagctat gcgttaatgg taatttcatt cttatttcat atatataatg   58920
aacacaggat acagagttgc atgagatgtc aggaaaagtg atgttcttaa aaatgtagaa   58980
atagatatat ttaaggagtc tatggaacta tttgtacaaa ttatatatta ttgtatgaga   59040
acttcagaac ctcctaagga attaagttta aactactttt tgttttagag ggggaaaaat   59100
gagtgtatta aatttccttc agatgatgaa aggtatagga gaatactttt ataaaagcat   59160
ttgctgagta gaacactgta ttaccttaca gacaaactta ttaagattgt aatacataca   59220
gttatacttt gagataggtg acttgacatg ggtatcaaac agctgtgtta tatctgtagc   59280
atcagaattc tgatatatct gagcaaacgt accaggtggc tttcatgtgt cctgcgggat   59340
gagtcacatg aaagcatctt tggtgtaatg tgggtcctcc tcaagagatc ctctaagtca   59400
ccagggagtc agcaaaggca gccttgcagc agatcttgag caatgagtaa gcacttccct   59460 ggggagggc cttgcagggg cggggcaggg gcaagttgtt gaaaaaacta gtgtcctgaa   59520
tgattatgtg cactctgggc agggcagtga ggatgcctgt cctcatgcag tggctagccc   59580
tcggccacgt gagccatgca cagaggcacc actggcagca ggggtggggc agggaagcag   59640
gagggcaagg cttgcagtga gaaagccaag ggctagggcc tggcagctg acctcacagg     59700
```

| | |
|---|---|
| tcaggagggc caggatcaag gcataggctg agcagggacg gctggaattc ttagctgttg | 59760 |
| ggagtcagag ttggttggac tccaagattt ccctgaaaga gcgagagaga agatgatgga | 59820 |
| gccccagggg aatgctttgt tttgctttgt tacagaattg taatgtcttc ttaaatgctt | 59880 |
| attccatgtt attaaagtga aaatgcatga tatttactta aagctaactt ttaaatatta | 59940 |
| gaaactgatg tatctcttta ctctgatagg gatcgtataa aataaaaagt aaaaatgtgt | 60000 |
| atgtatataa tttattacag agccttttga agaaactgaa gagaaatggt tatcttcact | 60060 |
| ggaaaatact cgatggttag aatatgtaag gtttgtactt ctttactttc ttttccttta | 60120 |
| acttttatt ttgagataac tacagactca ctggaggtac aaaaatagca cagagggcca | 60180 |
| tgtacttact cttcatccaa cttcccccaa tagtaacatc tcgtaactag agtacagcat | 60240 |
| ccaaaccagg aagctgacac tgggacactg atagctctt actcaccagt tcatacatgc | 60300 |
| tgtcgtctgt gtgcatgccc ttaacacagc tgtgcgattt tatcacgtgt gtaggttcac | 60360 |
| gtaaccacca ccacagggag atacagacct gttccatgac aaggctcccc tgtgctagcc | 60420 |
| ttcttatagg tgcaccctca tcgccatctg tgtctgttga ctaccactaa tctcttctca | 60480 |
| atctctatag ttttgtcata agtcaacccc ttccttttca taagggtttt atgaatttcc | 60540 |
| ctgatgaaaa agtacaaaat gaggccaggc gtggtggctc atgcctgtaa tcccagcact | 60600 |
| ttgggaggcc aaggcgggtg gctcacctga ggtcaggagt tcaagaccag cctggccaac | 60660 |
| atggtgaaac cttgtctctg ctaaaaatac aaaaattagc caagcatggt ggcacgcacc | 60720 |
| tgtagtccca gctactcagg aggctgaggc aggagaatca cttgaacctg ggaggcagag | 60780 |
| gttgcattga gtcaagatca cgccactgca ctgcagcctg ggtgatagag caagtctcca | 60840 |
| tctcaaaaaa aaaaatttac aaagtggggc cggttgtggt agctcatgcc agtaattcca | 60900 |
| aagctctggg gaggaagatc acttgaggcc agtagttcac aaccagcctg agcaacacag | 60960 |
| tgagacccca tctccacaaa aaagttggaa actagccagg catggtggca tgtgcctgct | 61020 |
| gtcctaggga gcctgaggca ggaggatcac ttgaggccag gagttcacaa ccagccgagg | 61080 |
| aacatagtga gatgcccatc tccacaaaaa aattttaaaa ctaggcaggc atggtggctc | 61140 |
| gtgcctgtgg tcctagctgc tcaggaggtg gaggcaggag gatcacttga ggccaggagt | 61200 |
| tcagggttac aatgagctgt gatatgccac tgcactctag tgtgggtgac aaaatgagag | 61260 |
| cctgtctctt aaaagaaaa caaaaattac aaaatatact cctttgagaa atcgtataag | 61320 |
| taactaaaga aactttacgg taatgcgaaa gctatgtgca ttcagtagaa agcagtcaat | 61380 |
| cctctcttgt gatgctgagt agcagcaggg agccacagct gccagtcagc cacacagtct | 61440 |
| cagtttaggg tattttcagc ttacagtggg ttatcatggg tcatgagtta tgggaatatc | 61500 |
| atgatcagag agcatctgta aagtgagaaa ttagatttgc ttgatttcaa gtactttatg | 61560 |
| tatttgtagt ggaaatttga tttttaacac tgcttttcct tttctctctt cagggcattc | 61620 |
| cttaagcatt cagcagaact tgtatacatg ctagaaagca aacatctctc tgtagtccta | 61680 |
| caaggtaact aaagtaactc ctgaaagcac catgaccacc ataccagcca gccttggttt | 61740 |
| actgcttgtc cccattcaag taaatcacat cagttttagc tatttcttat ttactacagt | 61800 |
| accatcaaat acattacaga ttttgcacat catttgagta aaacagtggc acaggctggg | 61860 |
| cgcagtggct gaagcctgta atcccagact ttgggaggtc gaggcgggcg gatcacttga | 61920 |
| ggtcagaagt ttgagatcag cctggccaac gtggtgaaac cttgtctcta ctaaaaatac | 61980 |
| aaaaattagt caggagtggt ggtgtgcgcc tgtagtctca gctactcggg aggccgaggc | 62040 |

-continued

```
aggagtatca cttgaaccta ggaggcggag gttgcagtga gcagagatcg caccactgca    62100
ctccagcctg ggcaacacag caagactcaa aaaaaaaata aataaaaacc agtggcacaa    62160
ggactgcaaa tagaagaata gaaagtagtc cagtttttac cctttattaa attatccttc    62220
ctattttatg ggaagggtgg gtcccatccc ctaatggatt aatacttagt gttaattttg    62280
acagggcatt ctctctctgt aattttgctg tctaatttgt acaaatttgt tttagtttaa    62340
ataccttctg gctcatgcta gattatgact ctaaggaagc agtttgagat gaagaaattt    62400
agactgaact gctgaatagc tagtaatgta atatttggta ggaataaacg gtgatgtaaa    62460
aatctttcag ttaagcaaag gataattaca tattaaataa cttacagcta atagaatttg    62520
taagtttgca gataaagttc aatagactaa aaactaccct cgtataatac agtagtaggt    62580
cctttgtacc catggcttcc ccatctgtgg tcaaccaacc caggactgaa aatattggcg    62640
ggggaaagct ttggccgtaa tgaacatgaa cagactttt ttttgttgtc attattctct     62700
aaacagtata gtataacaac tgtttacata gcatttacat tgtattaggt gttataagta    62760
atctagaggt aacttaaagt gtacaggagg atgtgcatag gttatatgca aatattaaca    62820
tcattttata tccaggactt aagcatttgt ggatcttggt atccaaagga ggccctggaa    62880
tgagttcccc atggatactg agggaagact atatactcat gttgcatagt atatgaatac    62940
aaaatgttgc ttaagcttgc agaagtactt ttttttttt tgagatggag tttcgctcct     63000
gtcacctagg ctggagtgca gtggaacgat ctcagctcac tgcaacctcc acctcctggg    63060
ttcaagcgat tctcctgctt cagcctccca gtagctggg attacaagca tgcaccacca     63120
cgcccggcta ttttgtat tttactaga gatggggttt caccttgttg gccaggctgc       63180
tctcgaactc ctgcctcag gtggtctgcc cacctcagcc tcccaaagtg ctaggattat      63240
aggcgtgagc caccgtgcct ggccaggctt gcagaagtac atttaacaac tgccaaactt    63300
gattgacttt aacaaggcaa aaatctttaa gactcttaga aaaaaatcaa atagtaatgt    63360
gtcatataaa gtaatcctga actgatacag tcagagtgtg tgtttaactc acaaatgcat    63420
gcagagccta ataatcacaa tttctctcat ccagtgggtg ttctcatcgt attggagaac    63480
cctactcatc ctccatttct ccatgcattt gtaatagaaa aggcctcaga agtagcactg    63540
aaccttcatt ttactagcat ttttatatac gtttattttt aaacagtttg ttaaaaattt    63600
acatactatg gaattcaccc attttaatt tgtaattcag taaattttag taaatataca     63660
gagtctagtt ttgaaatttt ttcatcaccc caaaagtccc agctccaggc agccactaat    63720
ctttctgtct ctagattttc cctttctggg catttcatat aaatggaatc atacaatatg    63780 tggcctttg ccgctggctt ctttcattca acatacatgt ttttgaggtt cattcatgta     63840
gtgtgtatca gcaatctttt ccttttatt tctgaattgt attccactgt tgtaaatgc      63900 attttgctta cccatttacc tgttgatgga catttgggtt gtttccactt tgtggctgtt    63960
atgaattatg ctgcttcatt tatttagatc tttcatttta tcagcagtgt tttattatgt    64020
aagtcttata tttattttgt taaatctctt aagtatttta tttttatgtc actgtgaata    64080
taattgttaa tttcattttc aggtttacta tgtactcaga ttgttgtgta cagaatttct    64140
gtaaccttac tgacctcatt tattaattct agtagttatt ttgtggattc cgtaggagtt    64200
tttacataca ggatcatatt gtcttcaaag acagttttta cctttttctt tctgatctga    64260 atgccttta ttttctttt cttgcctaat tgctctggct agattctcca gttcaatgag       64320
atggagaagt gtagagaaca gacatcctta tcatcttcct gatcttaggg agagagtatc    64380
cagtctttca ccagtgaaat gggaataaca ttaattgtag gttttgtgg atgtctctga     64440
```

```
tcagtttaaa tatgtttact tttattccta atcaggaatg aaggtagaat tgtatcagat   64500 gcttttttccg catctaatga gataatcgtg ttggttttgt cctttattac tgtggtacgt   64560
tactacaatt gacagatgtt aaaccaactt tgcattcctg gataatttgg tttactcata   64620
tttttattga ttttttacatc tgtaatcata agggatattg gtcaatagtt gtcttctgat   64680
ttccctggct gactttgata gcgtggcaat tctggcctta ttggaaagga caacaactat   64740
aaaagacagg agggaatcgt ttgccacagc ttcagttggt agtgaacagt cccactctcc   64800
ccattcactt ctcagtattg ccatgtggcc tgtcagtaga aagattacct tatacttaat   64860
accttgacaa aagagcagta gaatggagtc tagacggatt ttctaccaca aaccattcga   64920
atgtaaaaag tatgagtgat gagcttctat tatctggcaa atatccatgt ataaaagacc   64980
atctcctatt aaatgctaat ttagtttatc tacaagtctg taatatttta gagttgctgg   65040
aatccagtaa aatttcctta tacagatttg gaaggcagcc taggtgtgca gaatactaaa   65100
ttatctagtt tacctttcct tcccttctc tctcagcatt tttctatgtt gtaatcattt   65160
tctttccatt ttattaacag aggaggaagg aagagacttg agctgttgtg tagcttctct   65220
tgttcaagtg atgctggatc cctatttag acaattact ggatttcaga gtctgataca   65280
gaaggagtgg gtcatggcag gatatcagtt tctagacaga tgcaaccatc taaagagatc   65340
agagaaagag gtaacaaaat cttgatgcct ttttatcagt ctttaaggat acacaaaata   65400
aaatttgtgt cattaaaaga tgaaggggct tttaaaaaat actgtattta gtacaactta   65460
atttccttag tccaaagcta actaatggat tagagttcaa attgatgtac ttattataaa   65520
gattatcgta actatgaagg tgaaattttt aaaagttgtc tattgaattt gtctaagtgg   65580
aaaactactg aaaaaattct gaataaaata ctgaaaaaca gataacaagc acattggcta   65640
ttttgaaaaa tcacttttgg aatatcatat tttcttaaaa tgggatacat aggttaagat   65700
gaaaagtttg agagggccac ctttgcaaca gctgtggagt tagtggctgc ctcggatctc   65760
tagttaggct gcggaaggcc ttacaaatat cttaccggcc aggcaggtca gtcagatcag   65820
tttttagaag gttgtttcag agagcgccat ttgacttgtg gtgtctcata aaaaatagtg   65880
gtcacccgct actgcacttg gggacacacc acgtgaccta ggctcatccc aaagtgtttt   65940
ctgaaatatg gggatgtttt ctggatgctg agcctacagg atcaaccaaa cattagagaa   66000
gtttggttga tggttttgtt ttgttatata atctaaagaa ttgtttctaa gacatgctta   66060
aacacatatt ttgctcttcc cccttcatat agtggcaacc cgctcaactg tgtgctttgc   66120
tgtttcaact tgttacatgt actgggcaaa taagggttgt gatgtttatc acggttgaat   66180
gttacttctt gggtttgata gatgtgtata gctcagctta gaaggcaagt gttttaggct   66240
tcgatgtttt ctcattcatc tcttctttaa catcagcagt acattttgaa gtaaatgtga   66300
acggctgaag gataacatta aatgatccca ttgtctcttt gtatttgcca gtctccttta   66360
tttttgctat tcttggatgc cacctggcag ctgttagaac aatatcctgc agcttttgag   66420
ttctccgaaa cctacctggc agtgttgtat gacagcaccc ggatctcact gtttggcacc   66480
ttcctgttca actcccctca ccagcgagtg aagcaaagca cggtaagcaa ccctgtggct   66540
gtggctacgt tttccctgtt tttacaactt tatcgaggca taattgaagt ataattcact   66600
gcctatttaa aatcttatga tttaaaattc ttactgccat tttcagctga aatttctgaa   66660
tggattattt tgaagacaca aaaatctagg aaattatttt tatgaatgaa catttttgt   66720 tttactctaa tgtaaatgtt ttgtagtaaa ccccttaaa gatgtaaatt actttaacca   66780
```

```
ccttaaatgt catgcttttg tatttatatt tcacatttgg gctattgggt agtaaaaaac    66840
aaaagccctg ttacacgaca tttatttcct aggtcagtag gataaaaagt tgtacaaaac    66900
aagattattt tccttcacga gtttgaagtt tctggtcaca attcattgat gtagaggatt    66960
tatgactaag cagggtctca agccaaactt gaaaccattc tgaaccaaag tgccatttca    67020
cccacctcga accaacaaca gaagctgaca atgccgtgg agaccattga gagaaacaga    67080
aagggggcagc tcttgtggac cttcaggaag cctttctagg aagaggattg ccctcatagt    67140
gagctccggg gtcttcagcc tcagccgtaa ggccctgggc taggcagtgt gacctaggga    67200
gcgggaaacc tgagttctgg ccctggtctg ggaaaagtgc taggcccatg ttccactcag    67260
gcttcagcct gagagtccag gttgctaacc tgtaaaatgg atctgtcaaa ctaacactta    67320
tgcctttagt ctcattgtat gaggtgaaac attttgtaaa ctgtgaatca ttatgcaaat    67380
tttcctaaag acatatgaat tattctggat ttgttggtat aaaagacaaa acacactggt    67440
cagttaagga gctgatttta tttaggctat tgcaggaggg agaacttaat taatgggcat    67500
cccaaagaaa aggacaaggc ctgggatttt atagtcagaa gacaggggaa tcaggaggga    67560
gggcagtctc agtccacagg agccagttct caggacacaa aaggcaggag agattgtcca    67620
gcattgccac ttttggggaa cccagggctc aaagaaactc aacaccgtca gcctgtctct    67680
acaaaaaata caaaaattag ccagacatgg tggtgcgcac ctgtggtccc agctactggg    67740
gaggctgagg tgggaggatg gcttaagccc aggaggcaga gattgcagtg agctgagact    67800
gtgccactgc actccagcct gggtgataga gccagagtct gtcccctgcc caccccacca    67860
ggaaagtttg acctttccag atactgtgct gagaaccagt gatacaggct tagaggctcc    67920
tgaggcatgg aacgctcatt tgttcctaaa atacatgctc tcccagttgc ttgtttttat    67980
ttttcgtcac cataatcatt cttggggccc ctctctgcct cgagctaggc tttcccctg    68040
gccttgtttg cctccttcag ctcttcccca ttgtctcccg tcactacccc gtgcgcacac    68100
agtgtgagcc tgcaaaaggt gcgtgaggcg aggacaaaga ctttgggtc tggggactgg    68160
gcagtgcatg ggtgggtatc tgcgtggagg actcccagcc cccagacacc actgcctctg    68220
ctgcttggct gatgctgtgt gtgcggacag acttctcacc aggaatgaac attactgaat    68280
tgtattgagg gagctgtaaa aaatactttc tacaagtatt tcctctgctt tccctgttca    68340
tgttctagtg ctcttttttaa tttggctctt tcaaaagcct tttctgacaa atactaacat    68400
gaatccccct ctcccttcct ccctagcagg aactggtcat tgtctaaggg tcgtgattct    68460
taaccgttct cagccccttc cacacaggca aaagcccaaa gcatttcttc ctttttttc    68520
cattctgagg ccaccttagg tgctagtggc caggtagtgt ttatagaaaa tctggtctct    68580
cttgggataa atatttttaa ttttttacctt ttaaaaaga gaacatcttt tttttttttt    68640
ttaagacagt ttggctctgt cacccaggct ggagtacagt ggtacaatat cagctcactg    68700
caacctctgc ctcctgggtc caagcactgc tctcgcctca accacctgag tagctaggac    68760
tgcaggcgca tgccaccacg cctagctaat ttttgtattt ttttgtagag tcagggtttc    68820
gccatgttgc ccagtctggt cttgaactcc tggactcaag caatccgccc acctcagctt    68880
cccaaagtac tgggattaca ggcgtgagcc accgtgcttg gccaagagga cattttctat    68940
atacttactg aagggccatt aaaacacgtt tgggttcatg ttttactaga tttcagctct    69000
taacagtgtt tgaagcaaat ggattgtttt taatccatgt acatgatgaa atgtcaagta    69060
actaaaattt tttttttttt tttttgaga cagagtcttg ctctatcacc caggctggag    69120
cacagtggca tgatctcggc tcactgcaac ctctgccttc caggttcagg tgattctcct    69180
```

```
gccacagcct cccgagtagc tgggactaca ggtgcacacc accatgcctg gctaattttt   69240 gtattttag tagagacggg gtttcaccat attggccagg ctggtcttga actcctgacc    69300
tcgtgatccg cctgccttcg gcctcccaaa gtgctgggat tacaggcatg agtcaccact   69360
gcgcctggcc aaaactgtta agagtatgtg tatttggtgc ttaatgaatt tttacttatt   69420
tgaaatagaa aattttgtaa aactttacaa aatgccctgt gctgttacac agcttagcca   69480
tttcttgatg attcaagccg ccactgtgcc agggaatgcc acctggctgt gatgtagtca   69540
tggcctcctg actgctatat tcttgtccta ataacattca ttgtttgcct ttttaataat   69600
ttccaaataa attcttgggg gttttttttt ggtagaaaat ttggagagta ctgaaaggta   69660
cagaacaaag aatcagacat ttcccatcat ccagcgactt tgtgtctgga gttatttcct   69720
ccagcgaact gttgtgtata cactgctgtg gtagcctgct gccatcaatc agctgagatg   69780
agagtccttt ctccacattg ctaaatgtga ctgtgcttca tagaaatggt ctgggctgcc   69840
ttccagagga gctccatgtc ttcctcacaa tgcggtggtt ggctgtcacc ctgtagcctt   69900
gtgttgcctc agtttactgt ggtgggaagc cagataacta ggctgcaccc gcccagagtc   69960
cgggctagag gtggactcct gtgaaggagg ggtctcctgt gtacatggtc tccatggttt   70020
tagccacatg ctaggaccac agggagttga tcccttcctt cctaccctga gtctgtggtc   70080
tgtgatttga gatcactggc tcagtgaagt gtagctcccc acttacgaag taagttataa   70140
aattggtggc agtgattccc atccaaagat tttgttaatc cacttaccaa caggtaacta   70200
cttaaatgta ctgaccgtgt gctcataaaa gtaaatact gtaattatag aaataaattc     70260
aacatgttta agactttcta gtatcatgtt agtgaaactt ctcttaataa cattcttatt   70320
gcccaaaggg cacggcttcc ttggggtcct aaggcagagg gcacctgaaa agcacactcc   70380
ttgttcatgg ggactgtggg gccctctgag ctcaaaggcc aggagcgtct cctctcttga   70440
agtgaaagtg ccactctggt gggttttgag ggctgcagta cagaacattt aacctgtgta   70500
atgatgagtg gctcatctga aaaaaggcat tcatgagaga atctttagtt ttgcaaatat   70560
ttatttattt attttgcagg aatttgctat aagcaaaaac atccaattgg gtgatgagaa   70620
gggcttaaaa ttcccctctg tttgggactg gtctctccag tttacagcaa aggatcgcac   70680 cctttttccat aaccccttct acattggaaa gagcacacct tgtatacaga atggctccgt  70740
gaagtctttt aaacggacaa aggtaaatca cagctaacaa aacgtgatgt tggctcacac   70800
gtaaccaaac acctctttt cagaacagag agcgttaaaa gtaaaggcac ttccaagagt    70860
aacactgcta atgcgggttt ctgaggggtc attccctttt taactcaaat gactgtatcc   70920
cagctttctt cctggtgtct gaggcccaca aagtctcagt acctgagagt gggcagattg   70980
cagctttgag cctgcaagcc tgatttacta agcccccatt tatccatttc ttgatgattc   71040
aagccgccac tgtggcaggg aatgccgcct ggctgtgatg tagtcatggc ctcctgactg   71100
ctatattctt gtcctaataa cattcattgt ttgcttttt aataattccc aaataaattc     71160 ttgggattttt ttttggtaga aaatttgcag actactgaaa ggtacagaac aaagaatcag   71220
acatttggcc tcctgactgc ctctgttcag tttgccattg ttcttgatag aatcggccag   71280
gtctagtgtt ttttctagcc cgtcttagaa cttatcctta agcaaattag tggataggag   71340
gtactctcat cccgccccca ttcaggctga tagtaacagc ctaggtagag tcaacacata   71400 aaaagtgta attccagggg aggaggatta gaataaggac acaaaggaag gggaggaaaat   71460 gttctttgag gctgaaattc cattaatttt tcatagtatt gagtttatat ttgccattgc   71520
```

-continued

```
atccttcaat ctttctaaaa agggaatccc cggaacataa taaatctct tctgtataga    71580 aaagctacag ctccacacta agaggaatgc cgtctgcctt aaagaatgga atcatcagtg    71640
accaagaatt acttccaagg agaaattcat tgatattaaa accaaagcca gatccagctc    71700
agcaaaccga cagccagaac agtgatacgg agcagtattt tagagaatgg ttttccaaac    71760
ccgccaacct gcacggtgtt attctgccac gtgtctctgg aacacacata aaactgtgga    71820
aactgtgcta cttccgctgg gttcccgagg cccagatcag cctgggtgct ccatcacagc    71880
ctttcacaag ctctccctcc tggctgatga agtcgacgta ctgagcagga tgctgcggca    71940
acagcgcagt ggcccctgg aggcctgcta tggggagctg ggccagagca ggatgtactt    72000
caacgccagc ggccctcacc acaccgacac ctcggggaca ccggagtttc tctcctcctc    72060
atttccattt tctcctgtag ggaatctgtg cagacgaagc attttaggaa caccattaag    72120 caaatttta agtggggcca aaatatggtt gtctactgag acattagcaa atgaagacta    72180 aaataggtg ttttctgaac attttgaggg aagctgtcaa cttttttcct ctgaattaac    72240
attgctaacc taggcgtttg aatctctaat aactttatat gtaagaataa tagttggaat    72300
ttgcactaat atttaaaaac atgttgaatc atgcttcttt cacacttatt ttaagagaga    72360
tgtaaatttt gttcctgtcc tctttctgtc attacaggtc tggctcttgt aaccgtgatc    72420
aaactgttca tgttgtctgc tacatttttg tctccatcca ttttttcctac cacctcctga    72480 aggctatctg atagtcagtc acattagcac cccaggcagc agacaacagg aaagttagga    72540
aatttgtgtt tcgtgtcatt tttaggagca tctgataaaa cctccagcag ttttaggaa    72600 gtattcatgt atttttctgg ttactttctg tcgtctctaa ttgaactcac ctgatgaagg    72660
ttcagtgttc tggggccaga atttatgatt ttagatcacc ttctttggaa ccttagatca    72720
ctgtgttttg aaatcatgag tttgcttta acttcatagg gtcaacttta aaatgatatg    72780
cactgttaat tttaaagcat ttgctgcaga taattaaact tagaagtgcc tttgacttta    72840
ggatacaaat attacagaag aaaatataat ttcactttt aaaattgggg tgggaaaatc    72900
ccattgcata tttgaaatag cttttcata ctaagcttca tagccaggag tccccagagt    72960
cttgttcctc tgaaagccac tggggagtgg cctctggggt gctgattcca cagaggtgta    73020
tgctgtagac aggagagtgc catctatgcc aaaactcgcc ctcaaaaaca aacaaggctt    73080
gctgggaggc gtgctgggct tggccatcag tatttccagt gtggtaaact attgctggca    73140 cttcccctg gaaataacta atgaggttac gagttgggca cctgcacaga tgtccttctc    73200
tcatagttcc taatgcttag gaatagagga gaaataaaa aatggattct ctcaaaacac    73260
tgccatttga atagcgacag aagtgctccc ccagccccca actttggaca gcaaagttga    73320
ggagaatgag cagacacagt tgtttgcttg atctgaatct ctctaaagta aagtatttcc    73380
aaactgtgtg acaagagcct acctaccact gtagcggtca aagctgaagc ttcttacagc    73440
agtgaaacgg ggcaccacct cccccacact cctcattccc cgcttaaaac atggatactt    73500
tcaaatttga ctgtttctta aactgccatc ctaagatatg gaaattttt atagtaaagt    73560 gtctagttag cttatttcct tttctaaaac aagtgttttc aagataactg tattttacct    73620
ttatatgtac tgaatagctg tttctttttg aattatttgc cttttaaaat ttgataatgt    73680
ctctggatat aacaggacag gagttcttaa aaatatctt aagaaattca ctttatgggt    73740
aaacccaagg tttttgccaa cttgttgcct agaaaataag ggctagtttc agtttataca    73800
aatagaatta ttaaacattt tacagtcctt gattagaaac cagacccaat ctccttataa    73860
caccacagcg tatcctgcca ttgacagtgt aatcacaatt ctcccttttt catttagctg    73920
```

```
cttttttatt attactaaat gttttggatt gagcattttt ccctctgtaa ttttcttcct    73980
tcacgtttat tttaactctt gtagtatttt attgttgtta atttacaagt ttaaaaatat    74040
taggtactat taataatggt taaaaataga aaaatgcata tttttgtatg ataatcaaat    74100
gtaaaatact tttattttg ctggacagtt gttatatcat gattattgtg ctacagttta    74160
ttgtgcataa tatgaaaaac aactatgaca gccttcagtc gggccagggt gaagctgctt    74220
ataccacctc tgccgtcaga gggacatgtg gtgacagcag tggtgtggct gcacagggcg    74280
cactagagag agctcagcac ccctgctgcc cgccagcaga gcccgtgctg agggaatgcc    74340
gcacagatgc tgatgcactg ggtgaaattt ctagtattga acgtaaaggt gtacagtgtc    74400
ttgctgttat tttatgatgg aaactgattt tgaaaccaaa aatagctaac taactttatt    74460
taaggaaagg atattaattt gtactaacag agggtgaaag ctgttcacat tgtcaacaa    74520 aatctgcttg ctgcagtagt aacctcaagt ggttaaaact tgatttcccg agaaaactaa    74580
aacctttgtg cctaaaattg atgacttgag ttcaagtggg atgagcaaga agatgtgtta    74640
tcttgttgtt caacagtatt gaatgtgaag gaaattttga tggcttaata aaattccaca    74700
gcgactgttt gttgttgtca gtatgaaatc atctactgga acacagtgat tgatagaaga    74760
ggtgaaggca tcttctccta cccatacttc tgtgtcatcc atgggatgtt tctgcttgcc    74820
ctctaaagcc aggtagtgat cagtaacttt ttttaacagc aattcggaag tggctaaagt    74880
taaagccatg tggatattga tagatcatgc cctaactggt ccttccattc aataaataaa    74940
tataaaaact ggggagtaat attcccccaa gaaggcttca agaagtcaa gagacagact    75000 ggggttccag tccctgactc ccgggcctgg cgcatggata aatcaccttt ctaccacacc    75060
cccttgccca gcctgagacc ctcccacaat ggtgatgagc agccgatttg actgtactgt    75120
caacagagaa aataccccta tctagttatt agggatggtc ccaggagat ggacaatgaa    75180 ggacaactgc ctctgataaa gacttcattc ctttcatgat ccgggcccaa tcagtagaac    75240
aagcatttac atgttataaa tcaacacaac ttcatgagaa tgttttgatt cctaaagaaa    75300
ttggaatttc aactgtttca gcccttctta gataatcata aaagtttaac agctaaatgt    75360
gtatagggca gtaaagaaaa acttaattca agaatctcgg tttcccatat aattaattac    75420
ttgaaggaaa cactggttat gctagttttt aaatttttt ttttttgaga cagagtctcg    75480
ctctgtctcc caggctggag tgcagtggtg caatctcggc tcactgcaag ctccacctcc    75540
cgggttcacg ccatcctcct gcctcagcct cctgagtagc tgggaccaca ggcgtgtgcc    75600
accaagccca cccaattttt tgtatttta gtagagatgg gtttcaccat gttggccagg    75660
atggtctcga tctcttgacc tcatgatgcg cctgcctcgc tcagcctccc aaagtgctgg    75720
gattacaggc atgagccact gtgcccagcc actacttttt tataaaaaa acctaaagat    75780 gaatcatcac ttgtttttga gttttccagc tttttgcaca tctaatcata tagatgcatc    75840
cagctccaat aatggtcaac aaaattttc tcttttaaaa aagttcatta tgagctgggt    75900
acagtggctc aatgcctgta atccccagca ctttgggagg ccaaggtgag taggtcagtt    75960
gaggtcagaa gttccagacc aacctggcca accaacatgg tgaaacccg tctctactaa    76020 aaatacaaaa tttagccagg cgtggtggcg cacacctgta gtcccagcta ctggggaccc    76080
tgaggcagga gaatcacttg aacctagcag gcggaggttg cagtgagccg agatcacacc    76140
actgcactcc agcctgggtg acagagcgag actctgtctc aaaaaaaaaa aaaaaaaaa    76200 aagtttatta cccactgtgt ggaatcaatg agtgtattca agcaaacact gttttgtgat    76260
```

```
atgcagacac tgtaaaatga caagtcaaac tatcaggttt ataatgcacg ataacaaaat    76320
taaataaaac atgttttata ctcttgaaaa tcttacatta atgtatgacc aaatatcccc    76380
aattccatac cttttagcta aggctttggc tcttagctcc aactgcaacc acatggcaga    76440
cttctacttc agcccccagc ttctgcagtt cagccagcca gatcatctgc ttatgtgaaa    76500
gacgatcatt gggccttta acttccacca gctggaaaag aaattttta aagttgttat      76560 tagtatctta ctgaatgaaa agccattcaa gtaagttgta gttgtcactg acaactattt    76620
aaatggctct tctgctctct cactgtattt gtaagtgtaa cacaaatata cggatggtcc    76680
ttcacttaca atggttcacc ttaggatttt ttgacttaaa aatggtgcaa agtgatata     76740 cattcaacag aaaccatact ctgagtgttg atcttttccc agtatgatac tccatgctgg    76800
gcagcagcag tgagccacag ctcccagtca gccacatgat catgaggata accagtactc    76860
tacggtttgc agtgaactac atgatctgcc caactgtagg ctaatgcaca cattctgagc    76920
acatttaagg taggctaagc taagctatga ggtttggtgg gataaatatg ttaaatgcat    76980
tttcaactta acaatatttt cagttgatgt gtaggattta tcaggacata aggccatcat    77040
aagttgagaa gcgtctgtat gtagctaaga aattattca gaaattcttc tattctgtag     77100
aaactagaca gttcttcaca gaggatgagt aaactgattc ttagtatagc aaatgaaaaa    77160
ttgttttaaa gcatgcactg gattttactt ccttgcttaa aaccctccga ttactctgtt    77220
acattttcaa ttaaatctaa ccttcttgcc atgaccagtc tcttccctac cccaaggccc    77280
tcacttccac ttgctacttg ctgttcccgc tgcctgggac atttctccct gttcttgaca    77340
tgcctgactt cttacctttc aatgctcagc ttaaactgat ctggagaggt cacagctcta    77400
agtatatcct cccatgcac ttctttcatg gcattcataa gataaaaata tatactacat     77460
gtcatcttca tgaaggcaag aattgtgtgt tttgttcact acacatcact agacttgaag    77520
acacagcaat aaaactata ggtaaaatat agaaaaaat tgtttaaata cagcatttag      77580
cagcctaagg gacatttaat tagagtcccc aaaggaacga gaaaaaaaa tacttaaaga     77640 aaaaatggcc aaaaatttc caaatttgat gaaaacagta aacccaaaga ttgaagaaaa     77700
tcaatgaatc ccaggcacac aaatgtaacg gcaccctagg aaatatcaca actgtataat    77760
caggggatat agtcaaagca gccagaattt ttaaagccag aggaaaaaaa aagattctct    77820
gattggaaac catgctagtt agaagacagt agactaatat ttttaaagta ttgaaaaata   77880
actgtcaaca taaaattcat tgcacggaga aaatatcttt caaaaacaaa ggtgaaataa   77940
aggctaagac atacaaaacc taaatacagc catccctcag tatccatggg ggactgattc   78000 aaggacccc tctgttacca aaatccatgg atgctcaagt ccctgatata aaatggcatc    78060
gcatctgcat attctagcac atcttctcat atactttaaa tcatctctac ttataatacc   78120
taatataaat gctatgaaaa tagttgttat gctgtatttt tatttgattt gtttattgtt   78180
gtagttactt tttattgttt tctttttc caaatacttt cagtccatgg ttgcatctac     78240
agaagcagaa accatggata cagagggcta actactgtaa ttcattacta gcagaacttc   78300
tagacatgga aatttttct ttttcttttt ttctttttt ttgagacaag gtctcactct     78360
gttgcccagg ctggtataca gtggtatgat ctcagcacac tgcagccttg acctcccagc   78420
ctcaagcagt tctctcacct cagcctccca agcagctggg actacaagtg cacaccacca   78480
cacccagcta atttgtttat cgttttgtag agatgaggtc tcactgtgtt tgcccaagct   78540
ggtctccaac tcctgagccc aagcaatccg ccccacctcag cctcccaaag tgctggaatt   78600
acaggcgtga aggaaattc ttcaagcagg agaatgagac tacacagaaa cctggatcta    78660
```

```
cacaaaagaa tagcaagcac tggaaatgct atgtacatga gtaaatacag actcattaat   78720
caactgtaga aagcaaaaat aatatgttat agaacatata acacgtagaa gtaaaatata   78780
tgaaaacacc acaaaggctg aagggaaga tatatattat tgaaaggttc tttttactct    78840
aaagtgtgta tcacctgaag gtggataagt ttaagatata taatatacta acgcaaccac   78900
ttcaacacaa tgaacagtta cagctaacaa gccagcaaag ctatcaaatg caatctttaa   78960
aaataagaca gggccaggca ctgtggctca tgcctgcaat cccaacacta agagaccacg   79020
gcaggtgaac tgcttgagcc tggggatttg agatcagcct gggcaacatg gtggaacccc   79080
atctctaaaa aatacaaaaa ccacaaaaat tagccaggca tggtggcgtg cacctgtggt   79140
tccagctact caggaaaaag acaagggaca aaagagttct gagacaaaga gaaataagt    79200 atcaggattt aaagctaagg atatcaataa tcaaattaaa tgtaaatgtt ccaaacaccc   79260
cattaaaaga cagaggttaa gttggattca aaagtaagac ccaactatat gatgcctaca   79320
ggaaatccac attaaaaata agataaaaca ggtcaaaagt aaaagaatgg aaaaatgtat   79380
catgttaaca ttaaaaaaaa gaaggctgaa gtggctacat gttgacaata tcggacaaag   79440
ttgatttcag agcaaagatt accaggtgta aagggggggt cactgcataa tgataaaagg   79500
gtagactcat gaagaggaca tgacagtcct aaaagtctat gcgtcttata acagaccttc   79560
aaaatacatg aagcaaatag tgatagaaac gcaagaagaa atacacaaat tggctgggca   79620
cggtatactc tcagcatttt gggaggccaa cgtggagccc aggagtttga gaccagcctg   79680
ggcaacatgg tggaacccca tctctacaaa aaataaaaaa aatcagctgg gcatgatggt   79740
gcatgcctat agttcgggct actcaacagg ctgaggcaga agaattgctt gagcctggga   79800
gatcaaggct gcagcgatcc aggatcgcac tgccactaca ctccagccta ggtgatagtg   79860
agagtctgtc tcaaaaaaca aaaacaaaaa aaaaagaaa agaaatacca caattataat    79920
cagagatatc aatattctct caataattta tagaacaagt aaataagaaa tcagtaagga   79980
cacagacaac ttaaacaaca ctatcaacca acttgaccta attgacattt aaaaatactg   80040
cccacaacaa atgctaaaca cacattcttt tcaagtacaa acagaatatt caccagggaa   80100
taccatattc tggaccataa aacaagtctc aacaaattta gtgggattca aatcatacaa   80160
aatatgtcct ctgaatacaa tggagttaaa ttacaaatca atagcagaaa gatacctgaa   80220
aatctctcaa gtgttttggaa atgtaaatga ctcacttcta aataagccaa ggatcaaaga   80280
agagtcaaaa gggaaatcag aaagtattgt gaactgaatg aaaatgaaaa caactactaa   80340
atttgtgagg ttcagataaa gcagcactga gaaggaaatt tggagcacta cctaactcta   80400
ttagaaaaga agttctcaaa gcaatcacca tagcttccac cttgagaaac taggaaataa   80460
aaaaacaaat gaaccaaaa gctgattctt cgagaaaatc agtaaattga taaacctcct    80520
gccagactca ttagggaaaa aagagaaaag acacaaatta ccaatatcaa gaataagagc   80580
atgacagaga taaagattct acagatatta aaatacagta agaaatacat ggccgtgtgc   80640
ggtggctcac accctgtaat cccagcactt tgggaggcca aggtgggcag atctgaagcc   80700
aggagttcaa gaccagcctg gccaacatgg caaaacctca tctctactaa aaatacaaaa   80760 aaaaaaaaa attatccagg catggtggtg cacagctgta atcccagcta ctagggaggc   80820
tgaggcacga gaatcacttg aacccaggag gcggaagttg cagtgagcta actcacgcta   80880
ctacactcca gtctgggcga cagagcgaga ctccatctca aaaaaaaaa aaaagaaaag    80940 aaacaaatat aaacaacttt aagacaatac ttaaatgaaa tggacaaatt ccttgaaaga   81000
```

-continued

```
cacaaactag caaagcgcaa tcaagaagaa acagataata tgaacagcct tatgttgttt    81060
aaaaataaat ttaatttata gctttaaatt ttcctccccc caaaatctcc aggcccatac    81120
tgcttcactg gggaattcta tcaaatgttt agggaataat actaattcta caccaactat    81180
tccatcccac tctgatgctg gtatgactct gaaaccaaaa cccaacaaag agataataag    81240
aaaagaaaag tacagctcaa tatccttcat gaacatatat gcaaaaattc ttaatatttt    81300
acaaaatcaa ctcccatttt tgctgatcaa aataatgctg ttaagatacc aattcctctc    81360
agattggtct acagattcaa aggaattcca attaaaatct cagctggctt ttttttttt    81420 ttttttttg agatggagtc ttgctctgtc gcccaggctg gagggcagtg gtgccatctc     81480
ggctcttgac aacctccacc tcctgggttc aagcgattct cctgcctcag cctcccaagt    81540
agctgggact acaggcgccc gccaccacac ccggctaatt ttttgtattt ttagtagaga    81600
cggggtttca ccatgttagc caggatggtc tcaatctcct gacctcgtga tccgcccacc    81660
tctgtctccc aaagtgctgg gattacaggt gtgagccacc gtacccggcc tcagctggct    81720 ttttttttc ttggaaactt aaaatttgat gttataattc aaataaaaat gcaaagagc    81780 cagaacaact ttgaaaaaca agtcattata ggacttacac tacctgactc caagatgtat    81840
ctaaagctac aataatcaag aaatacagac aaacagatca atggaaccga agagtatata    81900
gaaacagacc cacatatata tgggttactg atttttgaca aagatacaga gggaattcag    81960
tggaggaagc atggtcttct tgacacatgg agctggaaca agtggatatc cacacaccac    82020
aaatgaattc cagtgcatgc cccacactgt atacaaatgg cgtctcaaat gatcataaaa    82080
ctgaatgtaa aacctaaaac tataacactt ctagaagaaa acaaaggaga aactctttgt    82140
gaccttggat taggcaagta tttctgacat gtgacaccaa aagcatgatc cactagaaa    82200 caaataagtt ggattttgtc aaactttgaa acctctgctc ttcaaaagac actattaaga    82260
aaatgaaaag acaagccata gactgggatg aaatgtcact gataaaggac ttgtatccag    82320
gatatataat ttttaatct caaaactcaa taatgagaaa acaaatcacc agtgatgggc    82380
agcagggctg ggctagtgga cagcgttcaa ggaagtgttc actctctgag ctttttaaaa    82440
aattttttgt gggtacatag tagatgtata tatttatggg gtacatgaga tgttttgata    82500
caggcatgca atgtgaacta agcacatcaa ggggaatggg gtatctgtcc cctcaagcat    82560
ttatcctttg agttacaaac cattatactc tttaagtcat tttaaaatgt acaattatcg    82620
gtaagcttct aaaatagctc ctggtgtcca cacccgttgt gacccctcc ctttgagtgt    82680 cagctggact agagactcgt tcctaaccac agaatacagc aggagtgatg gaacatcatg    82740
tccacatcaa gtcataagag atggagtctt gtcttgctca cactctgggg ctcctctcac    82800
ccgcctgctc tgatgaagcc agtcgcaggg gacaggccca caggaaccca ggccctcggc    82860
ccaaaagctc tcaaggaatt caatcttgcc aacagccact caagaaatgc ctacttgtgg    82920
cctctgattc agttgctaat aaggttacca acaggacttt ccattctgcc tcaactgacc    82980
ttaaagtgac ggctctggga gttccacacc accaggtcgg ggaggccccc tcgacagtgt    83040
cgaaagtcag cagccaggtg cctgcacaca ccactgagca cagggccccc caggcaggag    83100
acaagatcct gaacacaaaa cacaggacag ttagccactt ccctcgtgac agagaatgga    83160
aataggctcc agggatcacg agacggagaa aagctcagtg tatatgtaat tcagtgcaca    83220
tggaccccag gccaccatg cgctgttctg ctgcttgtac cagagctgca gagccatggc    83280
tggaatccca ctggcaagtg gtgggagact ggtcctcctg tggtcagttt ccaggcttct    83340
gcagcgtggc catgctgggg agcgctgagg aagagggatg tggaggatgc actcaggaac    83400
```

```
gcgacagcat ggcctcatag agggcagcag ttgaaggaac acagaaggta          83450
```

<210> SEQ ID NO 4
<211> LENGTH: 476
<212> TYPE: PRT
<213> ORGANISM: Human

<400> SEQUENCE: 4

| Gly | Glu | Ile | Val | Val | Asn | Glu | Val | Asn | Phe | Val | Arg | Lys | Cys | Ile | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Asp | Thr | Ser | Gln | Tyr | Asp | Leu | Trp | Gly | Lys | Leu | Ile | Cys | Ser | Asn |
|     |     |     | 20  |     |     |     |     | 25  |     |     |     |     | 30  |     |     |

| Phe | Lys | Ile | Ser | Phe | Ile | Thr | Asp | Asp | Pro | Met | Pro | Leu | Gln | Lys | Phe |
|     |     |     | 35  |     |     |     | 40  |     |     |     |     | 45  |     |     |     |

| His | Tyr | Arg | Asn | Leu | Leu | Leu | Gly | Glu | His | Asp | Val | Pro | Leu | Thr | Cys |
|     |     | 50  |     |     |     |     | 55  |     |     |     |     | 60  |     |     |     |

| Ile | Glu | Gln | Ile | Val | Thr | Val | Asn | Asp | His | Lys | Arg | Lys | Gln | Lys | Val |
| 65  |     |     |     |     | 70  |     |     |     |     | 75  |     |     |     |     | 80  |

| Leu | Gly | Pro | Asn | Gln | Lys | Leu | Lys | Phe | Asn | Pro | Thr | Glu | Leu | Ile | Ile |
|     |     |     |     | 85  |     |     |     |     | 90  |     |     |     |     | 95  |     |

| Tyr | Cys | Lys | Asp | Phe | Arg | Ile | Val | Arg | Phe | Arg | Phe | Asp | Glu | Ser | Gly |
|     |     |     |     | 100 |     |     |     |     | 105 |     |     |     |     | 110 |     |

| Pro | Glu | Ser | Ala | Lys | Lys | Val | Cys | Leu | Ala | Ile | Ala | His | Tyr | Ser | Gln |
|     |     |     |     | 115 |     |     |     |     | 120 |     |     |     |     | 125 |     |

| Pro | Thr | Asp | Leu | Gln | Leu | Leu | Phe | Ala | Phe | Glu | Tyr | Val | Gly | Lys | Lys |
|     |     | 130 |     |     |     |     | 135 |     |     |     |     | 140 |     |     |     |

| Tyr | His | Asn | Ser | Ala | Asn | Lys | Ile | Asn | Gly | Ile | Pro | Ser | Gly | Asp | Gly |
| 145 |     |     |     |     | 150 |     |     |     |     | 155 |     |     |     |     | 160 |

| Gly | Gly | Gly | Gly | Gly | Gly | Asn | Gly | Ala | Gly | Gly | Ser | Ser | Gln |
|     |     |     |     | 165 |     |     |     |     | 170 |     |     |     | 175 |

| Lys | Thr | Pro | Leu | Phe | Glu | Thr | Tyr | Ser | Asp | Trp | Asp | Arg | Glu | Ile | Lys |
|     |     |     | 180 |     |     |     |     | 185 |     |     |     |     | 190 |     |     |

| Arg | Thr | Gly | Ala | Ser | Gly | Trp | Arg | Val | Cys | Ser | Ile | Asn | Glu | Gly | Tyr |
|     |     | 195 |     |     |     |     | 200 |     |     |     |     | 205 |     |     |     |

| Met | Ile | Ser | Thr | Cys | Leu | Pro | Glu | Tyr | Ile | Val | Val | Pro | Ser | Ser | Leu |
|     | 210 |     |     |     |     | 215 |     |     |     |     | 220 |     |     |     |     |

| Ala | Asp | Gln | Asp | Leu | Lys | Ile | Phe | Ser | His | Ser | Phe | Val | Gly | Arg | Arg |
| 225 |     |     |     |     | 230 |     |     |     |     | 235 |     |     |     |     | 240 |

| Met | Pro | Leu | Trp | Cys | Trp | Ser | His | Ser | Asn | Gly | Ser | Ala | Leu | Val | Arg |
|     |     |     |     | 245 |     |     |     |     | 250 |     |     |     |     | 255 |     |

| Met | Ala | Leu | Ile | Lys | Asp | Val | Leu | Gln | Gln | Arg | Lys | Ile | Asp | Gln | Arg |
|     |     |     |     | 260 |     |     |     |     | 265 |     |     |     |     | 270 |     |

| Ile | Cys | Asn | Ala | Ile | Thr | Lys | Ser | His | Pro | Gln | Arg | Ser | Asp | Val | Tyr |
|     |     |     |     | 275 |     |     |     |     | 280 |     |     |     |     | 285 |     |

| Lys | Ser | Asp | Leu | Asp | Lys | Thr | Leu | Pro | Asn | Ile | Gln | Glu | Val | Gln | Ala |
|     | 290 |     |     |     |     | 295 |     |     |     |     | 300 |     |     |     |     |

| Ala | Phe | Val | Lys | Leu | Lys | Gln | Leu | Cys | Val | Asn | Glu | Pro | Phe | Glu | Glu |
| 305 |     |     |     |     | 310 |     |     |     |     | 315 |     |     |     |     | 320 |

| Thr | Glu | Glu | Lys | Trp | Leu | Ser | Ser | Leu | Glu | Asn | Thr | Arg | Trp | Leu | Glu |
|     |     |     |     | 325 |     |     |     |     | 330 |     |     |     |     | 335 |     |

| Tyr | Val | Arg | Ala | Phe | Leu | Lys | His | Ser | Ala | Glu | Leu | Val | Tyr | Met | Leu |
|     |     |     |     | 340 |     |     |     |     | 345 |     |     |     |     | 350 |     |

| Glu | Ser | Lys | His | Leu | Ser | Val | Val | Leu | Gln | Glu | Glu | Gly | Arg | Asp |
|     |     |     | 355 |     |     |     |     | 360 |     |     |     |     | 365 |     |

```
Leu Ser Cys Cys Val Ala Ser Leu Val Gln Val Met Leu Asp Pro Tyr
    370                 375                 380

Phe Arg Thr Ile Thr Gly Phe Gln Ser Leu Ile Gln Lys Glu Trp Val
385                 390                 395                 400

Met Ala Gly Tyr Gln Phe Leu Asp Arg Cys Asn His Leu Lys Arg Ser
                405                 410                 415

Glu Lys Glu Ser Pro Leu Phe Leu Phe Leu Asp Ala Thr Trp Gln
            420                 425                 430

Leu Leu Glu Gln Tyr Pro Ala Ala Phe Glu Phe Ser Glu Thr Tyr Leu
        435                 440                 445

Ala Val Leu Tyr Asp Ser Thr Arg Ile Ser Leu Phe Gly Thr Phe Leu
    450                 455                 460

Phe Asn Ser Pro His Gln Arg Val Lys Gln Ser Thr
465                 470                 475

<210> SEQ ID NO 5
<211> LENGTH: 434
<212> TYPE: PRT
<213> ORGANISM: Human

<400> SEQUENCE: 5

Met Pro Leu Gln Lys Phe His Tyr Arg Asn Leu Leu Leu Gly Glu His
1               5                   10                  15

Asp Val Pro Leu Thr Cys Ile Glu Gln Ile Val Thr Val Asn Asp His
            20                  25                  30

Lys Arg Lys Gln Lys Val Leu Gly Pro Asn Gln Lys Leu Lys Phe Asn
        35                  40                  45

Pro Thr Glu Leu Ile Ile Tyr Cys Lys Asp Phe Arg Ile Val Arg Phe
    50                  55                  60

Arg Phe Asp Glu Ser Gly Pro Glu Ser Ala Lys Lys Val Cys Leu Ala
65                  70                  75                  80

Ile Ala His Tyr Ser Gln Pro Thr Asp Leu Gln Leu Leu Phe Ala Phe
                85                  90                  95

Glu Tyr Val Gly Lys Lys Tyr His Asn Ser Ala Asn Lys Ile Asn Gly
            100                 105                 110

Ile Pro Ser Gly Asp Gly Gly Gly Gly Gly Gly Asn Gly Ala
        115                 120                 125

Gly Gly Gly Ser Ser Gln Lys Thr Pro Leu Phe Glu Thr Tyr Ser Asp
    130                 135                 140

Trp Asp Arg Glu Ile Lys Arg Thr Gly Ala Ser Gly Trp Arg Val Cys
145                 150                 155                 160

Ser Ile Asn Glu Gly Tyr Met Ile Ser Thr Cys Leu Pro Glu Tyr Ile
                165                 170                 175

Val Val Pro Ser Ser Leu Ala Asp Gln Asp Leu Lys Ile Phe Ser His
            180                 185                 190

Ser Phe Val Gly Arg Arg Met Pro Leu Trp Cys Trp Ser His Ser Asn
        195                 200                 205

Gly Ser Ala Leu Val Arg Met Ala Leu Ile Lys Asp Val Leu Gln Gln
    210                 215                 220

Arg Lys Ile Asp Gln Arg Ile Cys Asn Ala Ile Thr Lys Ser His Pro
225                 230                 235                 240

Gln Arg Ser Asp Val Tyr Lys Ser Asp Leu Asp Lys Thr Leu Pro Asn
                245                 250                 255

Ile Gln Glu Val Gln Ala Ala Phe Val Lys Leu Lys Gln Leu Cys Val
```

```
                    260                 265                 270
Asn Glu Pro Phe Glu Thr Glu Lys Trp Leu Ser Ser Leu Glu
        275                 280                 285
Asn Thr Arg Trp Leu Glu Tyr Val Arg Ala Phe Leu Lys His Ser Ala
        290                 295                 300
Glu Leu Val Tyr Met Leu Glu Ser Lys His Leu Ser Val Val Leu Gln
305                 310                 315                 320
Glu Glu Glu Gly Arg Asp Leu Ser Cys Cys Val Ala Ser Leu Val Gln
                325                 330                 335
Val Met Leu Asp Pro Tyr Phe Arg Thr Ile Thr Gly Phe Gln Ser Leu
                340                 345                 350
Ile Gln Lys Glu Trp Val Met Ala Gly Tyr Gln Phe Leu Asp Arg Cys
            355                 360                 365
Asn His Leu Lys Arg Ser Glu Lys Glu Ser Pro Leu Phe Leu Leu Phe
            370                 375                 380
Leu Asp Ala Thr Trp Gln Leu Leu Glu Gln Tyr Pro Ala Ala Phe Glu
385                 390                 395                 400
Phe Ser Glu Thr Tyr Leu Ala Val Leu Tyr Asp Ser Thr Arg Ile Ser
                405                 410                 415
Leu Phe Gly Thr Phe Leu Phe Asn Ser Pro His Gln Arg Val Lys Gln
                420                 425                 430
Ser Thr

<210> SEQ ID NO 6
<211> LENGTH: 668
<212> TYPE: PRT
<213> ORGANISM: Human

<400> SEQUENCE: 6

Lys Ala Pro Lys Pro Ser Phe Val Ser Tyr Val Arg Pro Glu Glu Ile
1               5                   10                  15
His Thr Asn Glu Lys Glu Val Thr Glu Lys Glu Val Thr Leu His Leu
                20                  25                  30
Leu Pro Gly Glu Gln Leu Leu Cys Glu Ala Ser Thr Val Leu Lys Tyr
            35                  40                  45
Val Gln Glu Asp Ser Cys Gln His Gly Val Tyr Gly Arg Leu Val Cys
        50                  55                  60
Thr Asp Phe Lys Ile Ala Phe Leu Gly Asp Asp Glu Ser Ala Leu Asp
65                  70                  75                  80
Asn Asp Glu Thr Gln Phe Lys Asn Lys Val Ile Gly Asn Asp Ile
                85                  90                  95
Thr Leu His Cys Val Asp Gln Ile Tyr Gly Val Phe Asp Glu Lys Lys
                100                 105                 110
Lys Thr Leu Phe Gly Gln Leu Lys Lys Tyr Pro Glu Lys Leu Ile Ile
            115                 120                 125
His Cys Lys Asp Leu Arg Val Phe Gln Phe Cys Leu Arg Tyr Thr Lys
        130                 135                 140
Glu Glu Val Lys Arg Ile Val Ser Gly Ile Ile His His Thr Gln
145                 150                 155                 160
Ala Pro Lys Leu Leu Lys Arg Leu Phe Leu Phe Ser Tyr Ala Thr Ala
                165                 170                 175
Ala Gln Asn Asn Thr Val Thr Asp Pro Lys Asn His Thr Val Met Phe
                180                 185                 190
Asp Thr Leu Lys Asp Trp Cys Trp Glu Leu Glu Arg Thr Lys Gly Asn
            195                 200                 205
Met Lys Tyr Lys Ala Val Ser Val Asn Glu Gly Lys Val Cys Glu
        210                 215                 220
Arg Leu Pro Ala Tyr Phe Val Val Pro Thr Pro Leu Pro Glu Glu Asn
225                 230                 235                 240
Val Gln Arg Phe Gln Gly His Gly Ile Pro Ile Trp Cys Trp Ser Cys
                245                 250                 255
His Asn Gly Ser Ala Leu Leu Lys Met Ser Ala Leu Pro Lys Glu Gln
                260                 265                 270
Asp Asp Gly Ile Leu Gln Ile Gln Lys Ser Phe Leu Asp Gly Ile Tyr
            275                 280                 285
Lys Thr Ile His Arg Pro Pro Tyr Glu Ile Val Lys Thr Glu Asp Leu
```

```
                290                 295                 300
Ser Ser Asn Phe Leu Ser Leu Gln Glu Ile Gln Thr Ala Tyr Ser Lys
305                 310                 315                 320
Phe Lys Gln Leu Phe Leu Ile Asp Asn Ser Thr Glu Phe Trp Asp Thr
                325                 330                 335
Asp Ile Lys Trp Phe Ser Leu Leu Glu Ser Ser Trp Leu Asp Ile
                340                 345                 350
Ile Arg Arg Cys Leu Lys Lys Ala Ile Glu Ile Thr Glu Cys Met Glu
                355                 360                 365
Ala Gln Asn Met Asn Val Leu Leu Glu Glu Asn Ala Ser Asp Leu
370                 375                 380
Cys Cys Leu Ile Ser Ser Leu Val Gln Leu Met Met Asp Pro His Cys
385                 390                 395                 400
Arg Thr Arg Ile Gly Phe Gln Ser Leu Ile Gln Lys Glu Trp Val Met
                405                 410                 415
Gly Gly His Cys Phe Leu Asp Arg Cys Asn His Leu Arg Gln Asn Asp
                420                 425                 430
Lys Glu Glu Val Pro Val Phe Leu Leu Phe Leu Asp Cys Val Trp Gln
                435                 440                 445
Leu Val His Gln His Pro Pro Ala Phe Glu Phe Thr Glu Thr Tyr Leu
                450                 455                 460
Thr Val Leu Ser Asp Ser Leu Tyr Ile Pro Ile Phe Ser Thr Phe Phe
465                 470                 475                 480
Phe Asn Ser Pro His Gln Lys Asp Thr Asn Met Gly Arg Glu Gly Gln
                485                 490                 495
Asp Thr Gln Ser Lys Pro Leu Asn Leu Leu Thr Val Trp Asp Trp Ser
                500                 505                 510
Val Gln Phe Glu Pro Lys Ala Gln Thr Leu Leu Lys Asn Pro Leu Tyr
                515                 520                 525
Val Glu Lys Pro Lys Leu Asp Lys Gly Gln Arg Lys Gly Met Arg Phe
                530                 535                 540
Lys His Gln Arg Gln Leu Ser Leu Pro Leu Thr Gln Ser Lys Ser Ser
545                 550                 555                 560
Pro Lys Arg Gly Phe Phe Arg Glu Glu Thr Asp His Leu Ile Lys Asn
                565                 570                 575
Leu Leu Gly Lys Arg Ile Ser Lys Leu Ile Asn Ser Ser Asp Glu Leu
                580                 585                 590
Gln Asp Asn Phe Arg Glu Phe Tyr Asp Ser Trp His Ser Lys Ser Thr
                595                 600                 605
Asp Tyr His Gly Leu Leu Pro His Ile Glu Gly Pro Glu Ile Lys
610                 615                 620
Val Trp Ala Gln Arg Tyr Leu Arg Trp Ile Pro Glu Ala Gln Ile Leu
625                 630                 635                 640
Gly Gly Gly Gln Val Ala Thr Leu Ser Lys Leu Leu Glu Met Met Glu
                645                 650                 655
Glu Val Gln Ser Leu Gln Glu Lys Ile Asp Glu Arg
                660                 665

SEQ ID NO 7
LENGTH: 508
TYPE: PRT
ORGANISM: Human

SEQUENCE: 7

Lys Ala Pro Lys Pro Ser Phe Val Ser Tyr Val Arg Pro Glu Glu Ile
1               5                   10                  15

His Thr Asn Glu Lys Glu Val Thr Glu Lys Glu Val Thr Leu His Leu
                20                  25                  30

Leu Pro Gly Glu Gln Leu Leu Cys Glu Ala Ser Thr Val Leu Lys Tyr
                35                  40                  45

Val Gln Glu Asp Ser Cys Gln His Gly Val Tyr Gly Arg Leu Val Cys
            50                  55                  60

Thr Asp Phe Lys Ile Ala Phe Leu Gly Asp Glu Ser Ala Leu Asp
65                  70                  75                  80

Asn Asp Glu Thr Gln Phe Lys Asn Lys Val Ile Gly Glu Asn Asp Ile
                85                  90                  95

Thr Leu His Cys Val Asp Gln Ile Tyr Gly Val Phe Asp Glu Lys Lys
            100                 105                 110

Lys Thr Leu Phe Gly Gln Leu Lys Lys Tyr Pro Glu Lys Leu Ile Ile
            115                 120                 125
```

-continued

```
His Cys Lys Asp Leu Arg Val Phe Gln Phe Cys Leu Arg Tyr Thr Lys
    130                 135                 140
Glu Glu Glu Val Lys Arg Ile Val Ser Gly Ile Ile His His Thr Gln
145                 150                 155                 160
Ala Pro Lys Leu Leu Lys Arg Leu Phe Leu Phe Ser Tyr Ala Thr Ala
                165                 170                 175
Ala Gln Asn Asn Thr Val Thr Val Pro Lys Asn His Thr Val Met Phe
            180                 185                 190
Asp Thr Leu Lys Asp Trp Cys Trp Glu Leu Glu Arg Thr Lys Gly Asn
        195                 200                 205
Met Lys Tyr Lys Ala Val Ser Val Asn Glu Gly Tyr Lys Val Cys Glu
    210                 215                 220
Arg Leu Pro Ala Tyr Phe Val Val Pro Thr Pro Leu Pro Glu Glu Asn
225                 230                 235                 240
Val Gln Arg Phe Gln Gly His Gly Ile Pro Ile Trp Cys Trp Ser Cys
                245                 250                 255
His Asn Gly Ser Ala Leu Leu Lys Met Ser Ala Leu Pro Lys Glu Gln
            260                 265                 270
Asp Asp Gly Ile Leu Gln Ile Gln Lys Ser Phe Leu Asp Gly Ile Tyr
        275                 280                 285
Lys Thr Ile His Arg Pro Pro Tyr Glu Ile Val Lys Thr Glu Asp Leu
    290                 295                 300
Ser Ser Asn Phe Leu Ser Leu Gln Glu Ile Gln Thr Ala Tyr Ser Lys
305                 310                 315                 320
Phe Lys Gln Leu Phe Leu Ile Asp Asn Ser Thr Glu Phe Trp Asp Thr
                325                 330                 335
Asp Ile Lys Trp Phe Ser Leu Leu Glu Ser Ser Ser Trp Leu Asp Ile
            340                 345                 350
Ile Arg Arg Cys Leu Lys Lys Ala Ile Glu Ile Thr Glu Cys Met Glu
        355                 360                 365
Ala Gln Asn Met Asn Val Leu Leu Leu Glu Glu Asn Ala Ser Asp Leu
    370                 375                 380
Cys Cys Leu Ile Ser Ser Leu Val Gln Leu Met Met Asp Pro His Cys
385                 390                 395                 400
Arg Thr Arg Ile Gly Phe Gln Ser Leu Ile Gln Lys Glu Trp Val Met
                405                 410                 415
Gly Gly His Cys Phe Leu Asp Arg Cys Asn His Leu Arg Gln Asn Asp
            420                 425                 430
Lys Glu Glu His Gln Arg Gln Leu Ser Leu Pro Leu Thr Gln Ser Lys
        435                 440                 445
Ser Ser Pro Lys Arg Gly Phe Phe Arg Glu Glu Thr Asp His Leu Ile
    450                 455                 460
Lys Asn Leu Leu Gly Lys Arg Ile Ser Lys Leu Ile Asn Ser Ser Asp
465                 470                 475                 480
Glu Leu Gln Asp Asn Phe Arg Glu Phe Tyr Asp Ser Trp His Ser Lys
                485                 490                 495
Ser Thr Asp Tyr His Gly Leu Leu Leu Pro His Ile
            500                 505
```

<210> SEQ ID NO 8
<211> LENGTH: 80
<212> TYPE: PRT
<213> ORGANISM: Human

```
<400> SEQUENCE: 8

Ser Asp Glu Leu Gln Asp Asn Phe Arg Glu Phe Tyr Asp Ser Trp His
 1               5                  10                  15

Ser Lys Ser Thr Asp Tyr His Gly Leu Leu Pro His Ile Glu Gly
            20                  25                  30

Pro Glu Ile Lys Val Trp Ala Gln Arg Tyr Leu Arg Trp Ile Pro Glu
        35                  40                  45

Ala Gln Ile Leu Gly Gly Gln Val Ala Thr Leu Ser Lys Leu Leu
    50                  55                  60

Glu Met Met Glu Glu Val Gln Ser Leu Gln Glu Lys Ile Asp Glu Arg
65                  70                  75                  80

<210> SEQ ID NO 9
<211> LENGTH: 638
<212> TYPE: PRT
<213> ORGANISM: Drosophila melanogaster

<400> SEQUENCE: 9

Phe Gly Leu Leu Ser Val Thr Asn Phe Lys Leu Ala Phe Val Pro Leu
 1               5                  10                  15

His Glu Lys Arg Asn Gln Ala Ile Thr Ala Pro Leu Ile Asp Leu Tyr
            20                  25                  30

Gln Glu Asn Thr Tyr Leu Gly Arg Asn Glu Ile Thr Leu Asn Asn Ile
        35                  40                  45

Asp His Ile Tyr Thr Ile Thr Glu Leu Gly Arg Ala Ser Ala Leu
    50                  55                  60

Gln Ala Ala Arg Gly Met Ala Ser His Ala Gly Met Ser Arg Arg Lys
65                  70                  75                  80

Lys Leu Glu Pro Phe Lys Gln Asn Ile Ser Gly Arg Ile Ala Ala
            85                  90                  95

Leu His Ile Val Cys Lys Asn Phe Arg Leu Leu Lys Phe Ala Phe Gln
        100                 105                 110

Gln Gln Asp Ser Lys Met Phe Gly Ala Ser Asp Gln Gly Lys Leu Ile
    115                 120                 125

Ala Ser Ala Leu Val Arg Phe Ala Tyr Pro Met Arg His Asp Leu Ser
130                 135                 140

Phe Ala Tyr Ala His Arg Glu Pro Tyr Tyr Ser Thr Leu Gly Ala Ser
145                 150                 155                 160

Gly Thr Ser Met Tyr Ala Thr Lys Asn Asp Trp Ala Arg Glu Leu Ile
                165                 170                 175

Arg Cys Gly Ala Thr Glu Trp Gln Val Val Ser Cys Ala Ser Val Gln
            180                 185                 190

Leu Leu Gln Asn Pro Leu Gln Ala Gly Lys Tyr Thr Val Pro Pro His
        195                 200                 205

Phe Val Ile Pro Lys Ser Cys Ser Val Asp Arg Phe Leu Asp Leu Ser
    210                 215                 220

Arg Ala Phe Cys Asp Ser Arg Ala Ala Phe Trp Val Tyr Ser Tyr Gly
225                 230                 235                 240

Ser Ser Ala Ala Leu Val Arg Leu Ala Glu Leu Gln Pro Ala Ala Gln
                245                 250                 255

Gln Asp Thr Lys Ser Glu Asn Val Met Leu Glu Leu Val Arg Lys Cys
            260                 265                 270

Asp Ala Gly Arg Gln Leu Lys Leu Leu Gln Leu Thr Asp Arg Leu Pro
        275                 280                 285
```

```
Ser Ile Gln Asp Val Leu Arg Ala Tyr Gln Lys Leu Arg Arg Leu Cys
    290                 295                 300

Thr Pro Glu Thr Pro Glu Lys Phe Met Leu Gln Asp Lys Tyr Leu
305                 310                 315                 320

Gly Leu Leu Glu Lys Thr Asn Trp Leu Phe Tyr Val Ser Leu Cys Leu
                325                 330                 335

Arg Tyr Ala Ser Glu Ala Ser Ala Thr Leu Arg Ser Gly Val Thr Cys
                340                 345                 350

Val Leu Gln Glu Ser Asn Gly Arg Asp Leu Cys Cys Val Ile Ser Ser
                355                 360                 365

Leu Ala Gln Leu Leu Asp Pro His Phe Arg Thr Ile Asp Gly Phe
370                 375                 380

Gln Ser Leu Val Gln Lys Glu Trp Val Ala Leu Glu His Pro Phe Gln
385                 390                 395                 400

Arg Arg Leu Gly His Val Tyr Pro Ala Gln Pro Ala Gly Gly Asn Ala
                405                 410                 415

Glu Leu Phe Asp Ser Glu Gln Ser Pro Val Phe Leu Leu Phe Leu Asp
                420                 425                 430

Cys Val Trp Gln Leu Leu Gln Gln Phe Pro Asp Glu Phe Glu Phe Thr
                435                 440                 445

Gln Thr Tyr Leu Thr Thr Leu Trp Asp Ser Cys Phe Met Pro Ile Phe
                450                 455                 460

Asp Thr Phe Gln Phe Asp Thr Gln Ala Gln Arg Leu Lys Ala Val Thr
465                 470                 475                 480

Asp Ser Gln Leu Val Leu Arg Pro Val Trp Asp Trp Gly Glu Gln Phe
                485                 490                 495

Ser Asp Lys Asp Lys Met Phe Phe Ser Asn Pro Leu Tyr Gln Arg Gln
                500                 505                 510

Arg Gly Asp Leu Gly Ala Gln Ala Ala Val Ala His Arg Arg Ser
                515                 520                 525

Leu Ala Val Gly Ser Lys Gly Ala His Gly Ala Ala Ser Gly Val Thr
                530                 535                 540

Pro Ser Arg Asn Thr Ile Asn Pro Gln Leu Phe Ala Thr Ala Ser Ser
545                 550                 555                 560

Val Pro Gln Asp Arg Tyr Leu Gln Pro Ala His Arg Ile Phe Asp Leu
                565                 570                 575

Gln Val Trp Asp Gln Cys Tyr Tyr Arg Trp Leu Pro Ile Leu Asp Ile
                580                 585                 590

Arg Gly Gly Gly Gln Pro Gln Val Asp Leu Tyr His Arg Leu Leu Leu
                595                 600                 605

Ser Asn Ile Ala Lys Val Gln Arg Cys Leu Asp Tyr Gln Asn Phe Asp
                610                 615                 620

Asp Leu Pro Asp Ala Tyr Tyr Glu Phe Ala Gly Glu Ser Arg
625                 630                 635

<210> SEQ ID NO 10
<211> LENGTH: 458
<212> TYPE: PRT
<213> ORGANISM: Human

<400> SEQUENCE: 10

Glu Pro Pro Leu Leu Pro Gly Glu Asn Ile Lys Asp Met Ala Lys Asp
  1               5                  10                  15

Val Thr Tyr Ile Cys Pro Phe Thr Gly Ala Val Arg Gly Thr Leu Thr
                20                  25                  30
```

-continued

```
Val Thr Asn Tyr Arg Leu Tyr Phe Lys Ser Met Glu Arg Asp Pro Pro
             35                  40                  45

Phe Val Leu Asp Ala Ser Leu Gly Val Ile Asn Arg Val Glu Lys Ile
         50                  55                  60

Gly Gly Ala Ser Ser Arg Gly Glu Asn Ser Tyr Gly Leu Glu Thr Val
65                  70                  75                  80

Cys Lys Asp Ile Arg Asn Leu Arg Phe Ala His Lys Pro Glu Gly Arg
                 85                  90                  95

Thr Arg Arg Ser Ile Phe Glu Asn Leu Met Lys Tyr Ala Phe Pro Val
             100                 105                 110

Ser Asn Asn Leu Pro Leu Phe Ala Phe Glu Tyr Lys Glu Val Phe Pro
         115                 120                 125

Glu Asn Gly Trp Lys Leu Tyr Asp Pro Leu Leu Glu Tyr Arg Arg Gln
130                 135                 140

Gly Ile Pro Asn Glu Ser Trp Arg Ile Thr Lys Ile Asn Glu Arg Tyr
145                 150                 155                 160

Glu Leu Cys Asp Thr Tyr Pro Ala Leu Leu Val Val Pro Ala Asn Ile
                 165                 170                 175

Pro Asp Glu Glu Leu Lys Arg Val Ala Ser Phe Arg Ser Arg Gly Arg
             180                 185                 190

Ile Pro Val Leu Ser Trp Ile His Pro Glu Ser Gln Ala Thr Ile Thr
         195                 200                 205

Arg Cys Ser Gln Pro Met Val Gly Val Ser Gly Lys Arg Ser Lys Glu
         210                 215                 220

Asp Glu Lys Tyr Leu Gln Ala Ile Met Asp Ser Asn Ala Gln Ser His
225                 230                 235                 240

Lys Ile Phe Ile Phe Asp Ala Arg Pro Ser Val Asn Ala Val Ala Asn
                 245                 250                 255

Lys Ala Lys Gly Gly Tyr Glu Ser Glu Asp Ala Tyr Gln Asn Ala
             260                 265                 270

Glu Leu Val Phe Leu Asp Ile His Asn Ile His Val Met Arg Glu Ser
         275                 280                 285

Leu Arg Lys Leu Lys Glu Ile Val Tyr Pro Asn Ile Glu Glu Thr His
         290                 295                 300

Trp Leu Ser Asn Leu Glu Ser Thr His Trp Leu Glu His Ile Lys Leu
305                 310                 315                 320

Ile Leu Ala Gly Ala Leu Arg Ile Ala Asp Lys Val Glu Ser Gly Lys
                 325                 330                 335

Thr Ser Val Val His Cys Ser Asp Gly Trp Asp Arg Thr Ala Gln
             340                 345                 350

Leu Thr Ser Leu Ala Met Leu Met Leu Asp Gly Tyr Tyr Arg Thr Ile
         355                 360                 365

Arg Gly Phe Glu Val Leu Val Glu Lys Glu Trp Leu Ser Phe Gly His
         370                 375                 380

Arg Phe Gln Leu Arg Val Gly His Gly Asp Lys Asn His Ala Asp Ala
385                 390                 395                 400

Asp Arg Ser Pro Val Phe Leu Gln Phe Ile Asp Cys Val Trp Gln Met
                 405                 410                 415

Thr Arg Gln Phe Pro Thr Ala Phe Glu Phe Asn Glu Tyr Phe Leu Ile
             420                 425                 430

Thr Ile Leu Asp His Leu Tyr Ser Cys Leu Phe Gly Thr Phe Leu Cys
         435                 440                 445
```

```
Asn Ser Glu Gln Gln Arg Gly Lys Glu Asn
    450                 455

<210> SEQ ID NO 11
<211> LENGTH: 458
<212> TYPE: PRT
<213> ORGANISM: Human

<400> SEQUENCE: 11

Glu Pro Pro Leu Leu Pro Gly Glu Asn Ile Lys Asp Met Ala Lys Asp
 1               5                  10                  15

Val Thr Tyr Ile Cys Pro Phe Thr Gly Ala Val Arg Gly Thr Leu Thr
                20                  25                  30

Val Thr Asn Tyr Arg Leu Tyr Phe Lys Ser Met Glu Arg Asp Pro Pro
             35                  40                  45

Phe Val Leu Asp Ala Ser Leu Gly Val Ile Asn Arg Val Glu Lys Ile
         50                  55                  60

Gly Gly Ala Ser Ser Arg Gly Glu Asn Ser Tyr Gly Leu Glu Thr Val
 65                  70                  75                  80

Cys Lys Asp Ile Arg Asn Leu Arg Phe Ala His Lys Pro Glu Gly Arg
                 85                  90                  95

Thr Arg Arg Ser Ile Phe Glu Asn Leu Met Lys Tyr Ala Phe Pro Val
            100                 105                 110

Ser Asn Asn Leu Pro Leu Phe Ala Phe Glu Tyr Lys Glu Val Phe Pro
        115                 120                 125

Glu Asn Gly Trp Lys Leu Tyr Asp Pro Leu Leu Glu Tyr Arg Arg Gln
    130                 135                 140

Gly Ile Pro Asn Glu Ser Trp Arg Ile Thr Lys Ile Asn Glu Arg Tyr
145                 150                 155                 160

Glu Leu Cys Asp Thr Tyr Pro Ala Leu Leu Val Val Pro Ala Asn Ile
                165                 170                 175

Pro Asp Glu Glu Leu Lys Arg Val Ala Ser Phe Arg Ser Arg Gly Arg
            180                 185                 190

Ile Pro Val Leu Ser Trp Ile His Pro Glu Ser Gln Ala Thr Ile Thr
        195                 200                 205

Arg Cys Ser Gln Pro Met Val Gly Val Ser Gly Lys Arg Ser Lys Glu
    210                 215                 220

Asp Glu Lys Tyr Leu Gln Ala Ile Met Asp Ser Asn Ala Gln Ser His
225                 230                 235                 240

Lys Ile Phe Ile Phe Asp Ala Arg Pro Ser Val Asn Ala Val Ala Asn
                245                 250                 255

Lys Ala Lys Gly Gly Gly Tyr Glu Ser Glu Asp Ala Tyr Gln Asn Ala
            260                 265                 270

Glu Leu Val Phe Leu Asp Ile His Asn Ile His Val Met Arg Glu Ser
        275                 280                 285

Leu Arg Lys Leu Lys Glu Ile Val Tyr Pro Asn Ile Glu Glu Thr His
    290                 295                 300

Trp Leu Ser Asn Leu Glu Ser Thr His Trp Leu Glu His Ile Lys Leu
305                 310                 315                 320

Ile Leu Ala Gly Ala Leu Arg Ile Ala Asp Lys Val Glu Ser Gly Lys
                325                 330                 335

Thr Ser Val Val Val His Cys Ser Asp Gly Trp Asp Arg Thr Ala Gln
            340                 345                 350

Leu Thr Ser Leu Ala Met Leu Met Leu Asp Gly Tyr Tyr Arg Thr Ile
        355                 360                 365
```

```
Arg Gly Phe Glu Val Leu Val Glu Lys Glu Trp Leu Ser Phe Gly His
    370                 375                 380

Arg Phe Gln Leu Arg Val Gly His Gly Asp Lys Asn His Ala Asp Ala
385                 390                 395                 400

Asp Arg Ser Pro Val Phe Leu Gln Phe Ile Asp Cys Val Trp Gln Met
                405                 410                 415

Thr Arg Gln Phe Pro Thr Ala Phe Glu Phe Asn Glu Tyr Phe Leu Ile
            420                 425                 430

Thr Ile Leu Asp His Leu Tyr Ser Cys Leu Phe Gly Thr Phe Leu Cys
        435                 440                 445

Asn Ser Glu Gln Gln Arg Gly Lys Glu Asn
    450                 455
```

ISOLATED HUMAN PHOSPHATASE PROTEINS, NUCLEIC ACID MOLECULES ENCODING HUMAN PHOPHATASE PROTEINS, AND USES THEREOF

FIELD OF THE INVENTION

The present invention is in the field of phosphatase proteins that are related to the dual specificity phosphatase subfamily, recombinant DNA molecules and protein production. The present invention specifically provides a novel phosphatase splice form and nucleic acid molecules encoding the novel splice form, all of which are useful in the development of human therapeutics and diagnostic compositions and methods.

BACKGROUND OF THE INVENTION

Phosphatase proteins, particularly members of the dual specificity phosphatase subfamily, are a major target for drug action and development. Accordingly, it is valuable to the field of pharmaceutical development to identify and characterize previously unknown members of this subfamily of phosphatase proteins. The present invention advances the state of the art by providing a previously unidentified human phosphatase proteins that have homology to members of the dual specificity phosphatase subfamily.

Protein Phosphatase

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation certain residues on proteins. The phosphorylation state of a protein may affect its conformation and/or enzymic activity as well as its cellular location. The phosphorylation state of a protein is modified through the reciprocal actions of protein phosphatases (PKs) and protein phosphatases (PPs) at various specific amino acid residues.

Protein phosphorylation is the ubiquitous strategy used to control the activities of eukaryotic cells. It is estimated that 10% of the proteins active in a typical mammalian cell are phosphorylated. The high-energy phosphate that confers activation and is transferred from adenosine triphosphate molecules to protein-by-protein phosphatases is subsequently removed from the protein-by-protein phosphatases. In this way, the phosphatases control most cellular signaling events that regulate cell growth and differentiation, cell-to-cell contacts, the cell cycle, and oncogenesis.

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to protein-by-protein phosphatases and are removed from the protein-by-protein phosphatases.

Protein phosphatases function in cellular signaling events that regulate cell growth and differentiation, cell-to-cell contacts, the cell cycle, and oncogenesis. Three protein phosphatase families have been identified as evolutionarily distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein phosphatase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine phosphatases. PP-IIB, or calcineurin (Cn), is a $Ca^{+2}$-activated phosphatase; it is involved in the regulation of such diverse cellular functions as ion channel regulation, neuronal transmission, gene transcription, muscle glycogen metabolism, and lymphocyte activation.

PP-IIC is a $Mg^{++}$-dependent phosphatase which participates in a wide variety of functions including regulating cyclic AMP-activated protein-phosphatase activity, $Ca^{++}$-dependent signal transduction, tRNA splicing, and signal transmission related to heat shock responses. PP-IIC is a monomeric protein with a molecular mass of about 40–45 kDa. One alpha. and several beta. isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318:387–393).

The levels of protein phosphorylation required for normal cell growth and differentiation at any time are achieved through the coordinated action of PKs and PPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235:77–82) and that antibodies capable of blocking the activity of this enzyme can abrogate tumor growth (Drebin et al., 1988, Oncogene 2:387–394). Blocking the signal transduction capability of tyrosine phosphatases such as Flk-1 and the PDGF receptor have been shown to block tumor growth in animal models (Millauer et al., 1994, Nature 367:577; Ueno et al., Science, 252:844–848).

Relatively less is known with respect to the direct role of phosphatases in signal transduction; PPs may play a role in human diseases. For example, ectopic expression of RPTP.alpha. produces a transformed phenotype in embryonic fibroblasts,(Zheng et al., Nature 359:336–339), and overexpression of RPTP.alpha. in embryonal carcinoma cells causes the cells to differentiate into a cell type with neuronal phenotype (den Hertog et al., EMBO J 12:3789–3798). The gene for human RPTP.gamma. has been localized to chromosome 3p21 which is a segment frequently altered in renal and small lung carcinoma. Mutations may occur in the extracellular segment of RPTP.gamma. which renders a RPTP that no longer respond to external signals (LaForgia et al., Wary et al., 1993, Cancer Res 52:478–482). Mutations in the gene encoding PDP1C (also known as HCP, SHP) are the cause of the moth-eaten phenotype in mice that suffer severe immunodeficiency, and systemic autoimmune disease accompanied by hyperproliferation of macrophages (Schultz et al., 1993, Cell 73:1445–1454). PDP1D (also known as Syp or PTP2C) has been shown to bind through SH2 domains to sites of phosphorylation in PDGFR, EGFR and insulin receptor substrate 1 (IRS-1). Reducing the activity of PDP1D by microinjection of anti-PDP1D antibody has been shown to block insulin or EGF-induced mitogenesis (Xiao et al., 1994, J Biol Chem 269:21244–21248).

Myotubularin Dual Specificityv Phosphatases

The novel human protein provided by the present invention is an alternative splice form of a known gene (referred to in Genbank as "hypothetical protein FLJ203 13"; mRNA: gi8923296, protein sequences: gi 11433679 and gi8923297). The alternative splice form of the present invention differs from the art-known protein at both the 5' and 3' ends.

The human protein, and encoding gene, of the present invention is related to dual specificity phosphatases (DSPs) in general, and myotubularin DSPs specifically.

Mutations in myotubularin DSP genes are known to cause X-linked myotubular myopathy, which is a severe congenital muscle disorder (Laporte et al., *Hum Mol Genet* Oct 7, 1998 (11):1703–12). Furthermore, is has been suggested that myotubularin DSP genes are good candidates for other genetic diseases (Laporte et al., *Hum Mol Genet* 1998 Oct;7(11):1703–12).

Other than containing an active tyrosine phosphatase consensus site, myotubularin shares limited homology with other phosphatases. Myotubularin acts on both phosphotyrosine and phosphoserine, and has been shown to hydrolyze a synthetic analog of tyrosine phosphatase in a reaction that can be inhibited by orthovanadate. The myotubularin DSP family is strongly conserved throughout evolution and is the largest known DSP family (Laporte et al., *Hum mol Genet* Oct 7, 1998 (11):1703–12).

The discovery of a new human protein phosphatase and the polynucleotides encoding it satisfies a need in the art by providing new compositions that are useful in the diagnosis, prevention and treatment of biological processes associated with abnormal or unwanted protein phosphorylation.

SUMMARY OF THE INVENTION

The present invention is based in part on the identification of amino acid sequences of a novel human phosphatase splice form that is related to the dual specificity phosphatase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phosphatase activity in cells and tissues that express the phosphatase. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

DESCRIPTION OF THE FIGURE SHEETS

FIG. 1 provides the nucleotide sequence of a cDNA molecule that encodes the phosphatase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

FIG. 2 provides the predicted amino acid sequence of the phosphatase of the present invention. (SEQ ID NO:2) In addition, structure and functional information such as protein family, function, and modification sites is provided where available, allowing one to readily determine specific uses of inventions based on this molecular sequence.

FIG. 3 provides genomic sequences that span the gene encoding the phosphatase protein of the present invention. (SEQ ID NO:3) As illustrated in FIG. 3, the chromosome map position has been determined to be on chromosome 15 and SNPs were identified at 96 different nucleotide positions. Specific uses of the inventions can readily be determined based on the molecular sequence and accompanying chromosome map and SNP information provided in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphatase protein or part of a phosphatase protein and are related to the dual specificity phosphatase subfamily. Utilizing these sequences, additional genomic sequences were assembled and transcript and/or cDNA sequences were isolated and characterized. Based on this analysis, the present invention provides amino acid sequences of a novel human phosphatase splice form that is related to the dual specificity phosphatase subfamily, nucleic acid sequences in the form of transcript sequences, cDNA sequences and/or genomic sequences that encode this phosphatase splice form, nucleic acid variation (allelic information), tissue distribution of expression, and information about the closest art known protein/peptide/domain that has structural or sequence homology to the phosphatase of the present invention.

In addition to being previously unknown, the peptides that are provided in the present invention are selected based on their ability to be used for the development of commercially important products and services. Specifically, the present peptides are selected based on homology and/or structural relatedness to known phosphatase proteins of the dual specificity phosphatase subfamily and the expression pattern observed. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known dual specificity phosphatase family or subfamily of phosphatase proteins.

Specific Embodiments

Peptide Molecules

The present invention provides nucleic acid sequences that encode protein molecules that have been identified as being members of the phosphatase family of proteins and are related to the dual specificity phosphatase subfamily (protein sequences are provided in FIG. 2, transcript/cDNA sequences.are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phosphatase peptides of the present invention, phosphatase peptides, or peptides/proteins of the present invention.

The present invention provides isolated peptide and protein molecules that consist of, consist essentially of, or comprise the amino acid sequences of the phosphatase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphatase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphatase peptide can be purified from cells that naturally express it, purified from cells that have been altered to express it (recombinant), or synthesized using known protein synthesis methods. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. For example, a nucleic acid molecule encoding the phosphatase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphatase peptides of the present invention are the naturally occurring mature proteins. A brief description of how various types of these proteins can be made/isolated is provided below.

The phosphatase peptides of the present invention can be attached to heterologous sequences to form chimeric or fusion proteins. Such chimeric and fusion proteins comprise a phosphatase peptide operatively linked to a heterologous protein having an amino acid sequence not substantially homologous to the phosphatase peptide. "Operatively linked" indicates that the phosphatase peptide and the heterologous protein are fused in-frame. The heterologous protein can be fused to the N-terminus or C-terminus of the phosphatase peptide.

In some uses, the fusion protein does not affect the activity of the phosphatase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphatase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A phosphatase peptide-encoding nucleic acid can be cloned into such an expression vector such that the fusion moiety is linked in-frame to the phosphatase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphatase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (fievereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:–11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score 50, wordlergth=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphatase peptides of the present invention as well as being encoded by the same genetic locus as the phosphatase peptide provided herein. The gene encoding the novel phosphatase protein of the present invention is located on a genome component that has been mapped to human chromosome 15 (as indicated in FIG. 3), which is supported by multiple lines of evidence. such as STS and BAC map data.

Allelic variants of a phosphatase peptide can readily be identified as being a human protein having a high degree (significant) of sequence homology/identity to at least a portion of the phosphatase peptide as well as being encoded by the same genetic locus as the phosphatase peptide provided herein. Genetic locus can readily be determined based on the genomic information provided in FIG. 3, such as the genomic sequence mapped to the reference human. The gene encoding the novel phosphatase protein of the present invention is located on a genome component that has been mapped to human chromosome 15 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphatase peptide encoding nucleic acid molecule under stringent conditions as more fully described below.

FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Paralogs of a phosphatase peptide can readily be identified as having some degree of significant sequence homology/identity to at least a portion of the phosphatase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphatase peptide encoding nucleic acid molecule under moderate to stringent conditions as more fully described below.

Orthologs of a phosphatase peptide can readily be identified as having some degree of significant sequence homology/identity to at least a portion of the phosphatase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphatase peptide encoding nucleic acid molecule under moderate to stringent conditions, as more fully described below, depending on the degree of relatedness of the two organisms yielding the proteins.

Non-naturally occurring variants of the phosphatase peptides of the present invention can readily be generated using recombinant techniques. Such variants include, but are not limited to deletions, additions and substitutions in the amino acid sequence of the phosphatase peptide. For example, one class of substitutions are conserved amino acid substitution. Such substitutions are those that substitute a given amino acid in a phosphatase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphatase peptides can be fully functional or can lack function in one or more activities, e.g. ability to bind substrate, ability to dephosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, *Science* 244:1081–1085 (1989)), particularly using the results provided in FIG. 2. The latter procedure introduces single alanine mutations at every residue in the molecule. The resulting mutant molecules are then tested for biological activity such as phosphatase activity or in assays such as an in vitro proliferative activity. Sites that are critical for binding partner/substrate binding can also be determined by structural analysis such as crystallization, nuclear magnetic resonance or photoaffinity labeling (Smith et al, *J. Mol. Biol.* 224:899–904 (1992); de Vos et a. *Science* 255:306–312 (1992)).

The present invention further provides fragments of the phosphatase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphatase peptide. Such fragments can be chosen based on the ability to retain one or more of the biological activities of the phosphatase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphatase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphatase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formulation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol* 182: 626–646 (1990)) and Rattan et al. (*Ann. N. Y Acad. Sci.* 663:48–62 (1992)).

Accordingly, the phosphatase peptides of the present invention also encompass derivatives or analogs in which a substituted amino acid residue is not one encoded by the genetic code, in which a substituent group is included, in which the mature phosphatase peptide is fused with another compound, such as a compound to increase the half-life of the phosphatase peptide, or in which the additional amino acids are fused to the mature phosphatase peptide, such as a leader or secretory, sequence or a sequence for purification of the mature phosphatase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphatase-effector protein interaction or phosphatase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphatases isolated from humans and their human/mammalian orthologs serve as targets for identifying agents for use in mammalian therapeutic applications, e.g. a human drug, particularly in modulating a biological or pathological response in a cell or tissue that expresses the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. A large percentage of pharmaceutical agents are being developed that modulate the activity of phosphatase proteins, particularly members of the dual specificity phosphatase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Such uses can readily be determined using the information provided herein, that which is known in the art, and routine experimentation.

The proteins of the present invention (including variants and fragments that may have been disclosed prior to the present invention) are useful for biological assays related to phosphatases that are related to members of the dual specificity phosphatase subfamily. Such assays involve any of the known phosphatase functions or activities or properties useful for diagnosis and treatment of phosphatase-related conditions that are specific for the subfamily of phosphatases that the one of the present invention belongs to, particularly in cells and tissues that express the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver.

The proteins of the present invention are also useful in drug screening assays, in cell-based or cell-free systems. Cell-based systems can be native, i.e., cells that normally express the phosphatase, as a biopsy or expanded in cell culture. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. In an alternate embodiment, cell-based assays involve recombinant host cells expressing the phosphatase protein.

The polypeptides can be used to identify compounds that modulate phosphatase activity of the protein in its natural state or an altered form that causes a specific disease or pathology associated with the phosphatase. Both the phosphatases of the present invention and appropriate variants and fragments can be used in high-throughput screens to assay candidate compounds for the ability to bind to the phosphatase. These compounds can be further screened against a functional phosphatase to determine the effect of the compound on the phosphatase activity. Further, these compounds can be tested in animal or invertebrate systems to determine activity/effectiveness. Compounds can be identified that activate (agonist) or inactivate (antagonist) the phosphatase to a desired degree.

Further, the proteins of the present invention can be used to screen a compound for the ability to stimulate or inhibit interaction between the phosphatase protein and a molecule that normally interacts with the phosphatase protein, e.g. a substrate or a component of the signal pathway that the phosphatase protein normally interacts (for example, another phosphatase). Such assays typically include the steps of combining the phosphatase protein with a candidate compound under conditions that allow the phosphatase protein, or fragment, to interact with the target molecule, and to detect the formation of a complex between the protein and the target or to detect the biochemical consequence of the interaction with the phosphatase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphatases or appropriate fragments containing mutations that affect phosphatase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphatase activity. The assays typically involve an assay of events in the signal transduction pathway that indicate phosphatase activity. Thus, the ephosphorylation of a substrate, activation of a protein, a change in the expression of genes hat are up- or down-regulated in response to the phosphatase protein dependent signal ascade cah be assayed.

Any of the biological or biochemical functions mediated by the phosphatase can be sed as an endpoint assay. These include all of the biochemical or biochemical/biological vents described herein, in the references cited herein, incorporated by reference for these ndpoint assay targets, and other functions known to those of ordinary skill in the art or that an be readily identified using the information provided in the Figures, particularly FIG. 2. Specifically, a biological function of a cell or tissues that expresses the phosphatase can be assayed. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver.

Binding and/or activating compounds can also be screened by using chimeric phosphatase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphatase. Accordingly, a different set of signal transduction components is available as an end-point assay for activation. This allows for assays to be performed in other than the specific host cell from which the phosphatase is derived.

The proteins of the present invention are also useful in competition binding assays in methods designed to discover compounds that interact with the phosphatase (e.g. binding partners and/or ligands). Thus, a compound is exposed to a phosphatase polypeptide under conditions that allow the compound to bind or to otherwise interact with the polypeptide. Soluble phosphatase polypeptide is also added to the mixture. If the test compound interacts with the soluble phosphatase polypeptide, it decreases the amount of complex formed or activity from the phosphatase target. This type of assay is particularly useful in cases in which compounds are sought that interact with specific regions of the phosphatase. Thus, the soluble polypeptide that competes with the target phosphatase region is designed to contain peptide sequences corresponding to the region of interest.

To perform cell free drug screening assays, it is sometimes desirable to immobilize either the phosphatase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphatase-binding protein and a candidate compound are incubated in the phosphatase protein-presenting wells and the amount of complex trapped in the well can be quantitated. Methods for detecting such complexes, in addition to those described above for the GST-immobilized complexes, include immunodetection of complexes using antibodies reactive with the phosphatase protein target molecule, or which are reactive with phosphatase protein and compete with the target molecule, as well as enzyme-linked assays which rely on detecting an enzymatic activity associated with the target molecule.

Agents that modulate one of the phosphatases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphatase protein activity identified according to these drug screening assays can be used to treat a subject with a disorder mediated by the kinase pathway, by treating cells or tissues that express the phosphatase. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. These methods of treatment include the steps of administering a modulator of phosphatase activity in a pharmaceutical composition to a subject in need of such treatment, the modulator being identified as described herein.

In yet another aspect of the inventions the phosphatase proteins can be used as "bait proteins" in a two-hybrid assay or three-hybrid assay (see, e.g., U.S. Pat. No. 5,283,317; Zervos et a. (1993) Cell 72:223–232; Madura et al. (1993) *J. Biol Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phosphatase and are involved in phosphatase activity. Such phosphatase-binding proteins are also likely to be involved in the propagation of signals by the phosphatase proteins or phosphatase targets as, for example, downstream elements of a kinase-mediated signaling pathway. Alternatively, such phosphatase-binding proteins are likely to be phosphatase inhibitors.

The two-hybrid system is based on the modular nature of most transcription factors, which consist of separable DNA-binding and activation domains. Briefly, the assay utilizes two different DNA constructs. In one construct, the gene that codes for a phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphatase protein.

This invention further pertains to novel agents identified by the above-described screening assays. Accordingly, it is within the scope of this invention to further use an agent identified as described herein in an appropriate animal model. For example, an agent identified as described herein (e.g., a phosphatase-modulating agent, an antisense phosphatase nucleic acid molecule, a phosphatase-specific antibody, or a phosphatase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphatase proteins of the present invention are also useful to provide a target for diagnosing a disease or predisposition to disease mediated by the peptide.

Accordingly, the invention provides methods for detecting the presence, or levels of, the protein (or encoding mRNA) in a cell, tissue, or organism. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The method involves contacting a biological sample with a compound capable of interacting with the phosphatase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphatase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharinacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2): 254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype.

The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphatase protein in which one or more of the phosphatase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phosphatase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Accordingly, methods for treatment include the use of the phosphatase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphatase proteins. Antibodies can be prepared from any region of the peptide as described herein. However, preferred regions will include those involved in function/activity and/or phosphatase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition.

Antibody detection of circulating fragments of the ftll length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Thus, where a specific protein has been correlated with expression in a specific tissue, antibodies that are specific for this protein can be used to identify a tissue type.

The antibodies are also useful for inhibiting protein function, for example, blocking the binding of the phosphatase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the-sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phosphatase peptide or protein of the present invention (cDNA, transcript and genomic sequence). Such nucleic acid molecules will consist of, consist essentially of, or comprise a nucleotide sequence that encodes one of the phosphatase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphatase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phosphatase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genornic sequence provided in FIG. 3.

A fragment comprises.a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phosphatase protein of the present invention is located on a genome component that has been mapped to human chromosome 15 (as indicated in FIG. 3), which is supported by multiple lines of evidence, such as STS and BAC map data.

FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 96 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phosphatase protein of the present invention is located on a genome component that has been mapped to human chromosome 15 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphatase protein expression relative to normal results.

In vitro techniques for detection of mRNA include Northerri hybridizations and in situ hybridizations. In vitro techniques for detecting DNA includes Southern hybridizations and in situ hybridization.

Probes can be used as a part of a diagnostic test kit for identifying cells or tissues that express a phosphatase protein, such as by measuring a level of a phosphatase-encoding nucleic acid in a sample of cells from a subject e.g., mRNA or genomic DNA, or determining if a phosphatase gene has been mutated. Experimental data as provided in FIG. 1 indicates that the phosphatase proteins of the present invention are expressed in humans in B-cell Burkitt's lymphoma, lymph germinal center B-cells, fetal lung, neural tissue. breast invasive ductal carcinoma, parathyroid tumor, carcinoid lung tissue, and fetal liver/spleen, as indicated by virtual northern blot analysis. In addition, PCR-based tissue screening panels indicate expression in the liver.

Nucleic acid expression assays are useful for drug screening to identify compounds that modulate phosphatase nucleic acid expression.

The invention thus provides a method for identifying a compound that can be used to treat a disorder associated with nucleic acid expression of the phosphatase gene, particularly biological and pathological processes that are mediated by the phosphatase in cells and tissues that express it. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The method typically includes assaying the ability of the compound to modulate the expression of the phosphatase nucleic acid and thus identifying a compound that can be used to treat a disorder characterized by undesired phosphatase nucleic acid expression. The assays can be performed in cell-based and cell-free systems. Cell-based assays include cells naturally expressing the phosphatase nucleic acid or recombinant cells genetically engineered to express specific nucleic acid sequences.

The assay for phosphatase nucleic acid expression can involve direct assay of nucleic acid levels, such as mRNA levels, or on collateral compounds involved in the signal pathway. Further, the expression of genes that are up- or down-regulated in response to the phosphatase protein signal pathway can also be assayed. In this embodiment the regulatory regions of these genes can be operably linked to a reporter gene such as luciferase.

Thus, modulators of phosphatase gene expression can be identified in a method wherein a cell is contacted with a candidate compound and the expression of mRNA determined. The level of expression of phosphatase mRNA in the presence of the candidate compound is compared to the level of expression of phosphatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphatase nucleic acid expression in cells and tissues that express the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Modulation includes both up-regulation (i.e. activation or agonization) or down-regulation (suppression or antagonization) or nucleic acid expression.

Alternatively, a modulator for phosphatase nucleic acid expression can be a small molecule or drug identified using the screening assays described herein as long as the drug or small molecule inhibits the phosphatase nucleic acid expression in the cells and tissues that express the protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

The nucleic acid molecules are also useful for monitoring the effectiveness of modulating compounds on the expression or activity of the phosphatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphatase nucleic acid expression, and particularly in qualitative changes that lead to pathology. The nucleic acid molecules can be used to detect mutations in phosphatase genes and gene expression products such as mRNA. The nucleic acid molecules can be used as hybridization probes to detect naturally occurring genetic mutations in the phosphatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphatase gene associated with a dysftnction provides a diagnostic tool for an active disease or susceptibility to disease when the disease results from overexpression, underexpression, or altered expression of a phosphatase protein.

Individuals carrying mutations in the phosphatase gene can be detected at the nucleic acid level by a variety of techniques. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements. The gene encoding the novel phosphatase protein of the present invention is located on a genome component that has been mapped to human chromosome 15 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of-a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran el al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or anti sense DNA sequences.

Alternatively, mutations in a phosphatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphatase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., PNAS 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphatase gene in an individual in order to select an appropriate compound or dosage regimen for treatment. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphatase gene expression in cells, tissues, and organisms. A DNA antisense nucleic acid molecule is designed to. be complementary to a region of the gene involved in transcription, preventing transcription and hence production of phosphatase protein. An antisense RNA or DNA nucleic acid molecule would hybridize to the mRNA and thus block translation of mRNA into phosphatase protein.

Alternatively, a class of antisense molecules can be used to inactivate mRNA in order to decrease expression of phosphatase nucleic acid. Accordingly, these molecules can treat a disorder characterized by abnormal or undesired phosphatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphatase protein, such as substrate binding.

The nucleic acid molecules also provide vectors for gene therapy in patients containing cells that are aberrant in phosphata-e gene expression. Thus, recombinant cells, which include the patient's cells that have been engineered ex vivo and returned to the patient, are introduced into an individual where the cells produce the desired phosphatase protein to treat the individual.

The invention also encompasses kits for detecting the presence of a phosphatase nucleic acid in a biological sample. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. For example, the kit can comprise reagents such as a labeled or labelable nucleic acid or agent capable of detecting phosphatase nucleic acid in a biological sample; means for determining the amount of phosphatase nucleic acid in the sample; and means for comparing the amount of phosphatase nucleic acid in the sample with a standard. The compound or agent can be packaged in a suitable container. The kit can further comprise instructions for using the kit to detect phosphatase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and rnost preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically exarnined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphatase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphatase gene of the present invention. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al, *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphatase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytornegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such-as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types: such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophosphatase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123(1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using manmalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed, *Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phosphatases, appropriate secretion signals are incorporated into the vector. The signal sequence can be endogenous to the peptides or heterologous to these peptides.

Where the peptide is not secreted into the medium, which is typically the case with phosphatases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance.liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a phosphatase protein or peptide that can be firther purified to produce desired amounts of phosphatase protein or fragments. Thus, host cells containing expression vectors are useful for peptide production.

Host cells are also useful for conducting cell-based assays involving the phosphatase protein or phosphatase protein fragments, such as those described above as well as other formats known in the art. Thus, a recombinant host cell expressing a native phosphatase protein is useful for assaying compounds that stimulate or inhibit phosphatase protein function.

Host cells are also useful for identifying phosphatase protein mutants in which these functions are affected. If the mutants naturally occur and give rise to a pathology, host cells containing the mutations are useful to assay compounds that have a desired effect on the mutant phosphatase protein (for example, stimulating or inhibiting function) which may not be indicated by their effect on the native phosphatase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphatase protein and identifying and evaluating modulators of phosphatase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphatase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the phosphatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut. I. et al. *Nature* 385:810–813 (1997) and PCT International Publication Nos. WO 97/07668 and WO 97/07669. In brief, a cell. e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo phosphatase protein function, including substrate interaction, the effect of specific mutant phosphatase proteins on phosphatase protein function and substrate interaction, and the effect of chimeric phosphatase proteins. It is also possible to assess the effect of null mutations, that is mutations that substantially or completely eliminate one or more phosphatase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amnino acid sequence of SEQ ID NO:2;
   (b) a nucleotide sequence consisting of SEQ ID NO:1;
   (c) a nucleotide sequence consisting of SEQ D NO:3; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence of SEQ ID NO:1.

6. An isolated polynucleotide consisting of the nucleotide sequence of SEQ ID NO:3.

7. The vector of claim 2, wherein said vector is selected from the group consisting of a plasmid, a virus, and a bacteriophage.

8. The vector of claim 2, wherein said isolated nucleic acid molecule is inserted into said vector in proper orientation and correct reading frame such that a polypeptide comprising SEQ ID NO:2 may be expressed by a cell transformed with said vector.

9. The vector of claim 8, wherein said isolated nucleic acid molecule is operatively linked to a promoter sequence.

* * * * *